(12) United States Patent
Chang et al.

(10) Patent No.: US 12,378,318 B2
(45) Date of Patent: *Aug. 5, 2025

(54) PROTEINS BINDING NKG2D, CD16 AND A TUMOR-ASSOCIATED ANTIGEN

(71) Applicant: Dragonfly Therapeutics, Inc., Waltham, MA (US)

(72) Inventors: Gregory P. Chang, Medford, MA (US); Ann F. Cheung, Lincoln, MA (US); Jinyan Du, Waltham, MA (US); Daniel Fallon, Winchester, MA (US); Asya Grinberg, Lexington, MA (US); William Haney, Wayland, MA (US); Bradley M. Lunde, Lebanon, NH (US); Steven O'Neil, Wayland, MA (US); Bianka Prinz, Lebanon, NH (US); Ronnie Wei, Weston, MA (US)

(73) Assignee: DRAGONFLY THERAPEUTICS, INC., Waltham, MA (US)

( * ) Notice: Subject to any disclaimer, the term of this patent is extended or adjusted under 35 U.S.C. 154(b) by 729 days.

This patent is subject to a terminal disclaimer.

(21) Appl. No.: 17/266,966

(22) PCT Filed: Aug. 8, 2019

(86) PCT No.: PCT/US2019/045677
§ 371 (c)(1),
(2) Date: Feb. 8, 2021

(87) PCT Pub. No.: WO2020/033664
PCT Pub. Date: Feb. 13, 2020

(65) Prior Publication Data
US 2022/0153848 A1    May 19, 2022

Related U.S. Application Data

(60) Provisional application No. 62/716,110, filed on Aug. 8, 2018.

(51) Int. Cl.
C07K 16/28 (2006.01)
A61P 35/00 (2006.01)

(52) U.S. Cl.
CPC .......... *C07K 16/2851* (2013.01); *A61P 35/00* (2018.01); *C07K 16/283* (2013.01); *C07K 16/2863* (2013.01); *C07K 2317/31* (2013.01); *C07K 2317/33* (2013.01); *C07K 2317/52* (2013.01); *C07K 2317/565* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,776,427 A | 7/1998 | Thorpe et al. |
| 5,807,706 A | 9/1998 | Carter et al. |
| 5,863,538 A | 1/1999 | Thorpe et al. |
| 5,959,084 A | 9/1999 | Ring et al. |
| 6,036,955 A | 3/2000 | Thorpe et al. |
| 6,129,914 A | 10/2000 | Weiner et al. |
| 6,210,670 B1 | 4/2001 | Berg |
| 6,294,167 B1 | 9/2001 | Lindhofer et al. |
| 6,518,415 B1 | 2/2003 | Armour et al. |
| 6,572,856 B1 | 6/2003 | Taylor et al. |
| 6,737,056 B1 | 5/2004 | Presta |
| 7,112,324 B1 | 9/2006 | Dorken et al. |
| 7,235,641 B2 | 6/2007 | Kufer et al. |
| 7,575,923 B2 | 8/2009 | Dorken et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,820,166 B2 | 10/2010 | Lanzavecchia |
| 7,879,985 B2 | 2/2011 | Urso et al. |
| 7,951,917 B1 | 5/2011 | Arathoon et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,409,577 B2 | 4/2013 | Thompson et al. |
| 8,518,403 B2 | 8/2013 | Hoffmann et al. |

(Continued)

FOREIGN PATENT DOCUMENTS

| | | |
|---|---|---|
| CA | 2990511 A1 | 12/2016 |
| CN | 102378768 A | 3/2012 |

(Continued)

OTHER PUBLICATIONS

Yakes et al. Cabozantinib (XL184), a novel MET and VEGFR2 inhibitor, simultaneously suppresses metastasis, angiogenesis, and tumor growth. Mol Cancer Ther. Dec. 2011;10(12):2298-308. doi: 10.1158/1535-7163.MCT-11-0264. Epub Sep. 16, 2011. (Year: 2011).*

(Continued)

*Primary Examiner* — Anne M. Gussow
*Assistant Examiner* — Brianna K Swartwout
(74) *Attorney, Agent, or Firm* — Fox Rothschild LLP

(57) ABSTRACT

Multi-specific binding proteins that bind NKG2D receptor, CD 16, and a tumor-associated antigen selected from c-MET, KIT, F3, IGF1R, Lewis Y, MUC13, MUC4, MCAM, LRRC32, sialyl-Tn, gpA33, GD3, GM2, EPHA3, TNFRSF10A, TNFSF11, CD74, and PMEL are described, as well as pharmaceutical compositions and therapeutic methods useful for the treatment of cancer.

11 Claims, 23 Drawing Sheets

Specification includes a Sequence Listing.

(56) References Cited

U.S. PATENT DOCUMENTS

| | | | |
|---|---|---|---|
| 8,545,839 B2 * | 10/2013 | Goetsch | C07K 16/2863 424/130.1 |
| 8,592,562 B2 | 11/2013 | Kannan et al. | |
| 8,658,765 B2 | 2/2014 | Martin, Jr. et al. | |
| 8,679,785 B2 | 3/2014 | Carter et al. | |
| 8,759,494 B2 | 6/2014 | Bachmann et al. | |
| 8,784,821 B1 | 7/2014 | Kufer et al. | |
| 8,796,420 B2 | 8/2014 | Martin, Jr. et al. | |
| 8,840,888 B2 | 9/2014 | Nagorsen et al. | |
| 8,931,406 B2 | 1/2015 | Detloff et al. | |
| 9,079,969 B2 | 7/2015 | Martin, Jr. et al. | |
| 9,102,736 B2 | 8/2015 | Hofmeister et al. | |
| 9,127,064 B2 | 9/2015 | Urso et al. | |
| 9,150,656 B2 | 10/2015 | Johnson et al. | |
| 9,150,663 B2 | 10/2015 | Labrijn et al. | |
| 9,200,078 B2 | 12/2015 | Bachmann | |
| 9,248,181 B2 | 2/2016 | De Kruif et al. | |
| 9,248,182 B2 | 2/2016 | De Kruif et al. | |
| 9,273,136 B2 | 3/2016 | Rader et al. | |
| 9,334,331 B2 | 5/2016 | Igawa et al. | |
| 9,447,185 B2 | 9/2016 | Romagne et al. | |
| 9,493,578 B2 | 11/2016 | Lazar et al. | |
| 9,562,109 B2 | 2/2017 | Von Kreudenstein et al. | |
| 9,587,036 B2 | 3/2017 | Kufer et al. | |
| 9,637,557 B2 | 5/2017 | Scheer et al. | |
| 9,683,052 B2 | 6/2017 | Blein et al. | |
| 9,683,053 B2 | 6/2017 | Blein et al. | |
| 9,690,969 B2 | 6/2017 | Okamoto | |
| 9,718,893 B2 | 8/2017 | Jung et al. | |
| 9,951,133 B2 | 4/2018 | Yu et al. | |
| 9,963,513 B2 | 5/2018 | Vu et al. | |
| 10,040,853 B2 | 8/2018 | Spies et al. | |
| 10,047,167 B2 | 8/2018 | Demarest et al. | |
| 10,059,765 B2 | 8/2018 | Velardi et al. | |
| 10,377,827 B2 | 8/2019 | Swanson et al. | |
| 10,421,807 B2 | 9/2019 | Gonzales et al. | |
| 10,526,409 B2 | 1/2020 | Urso et al. | |
| 10,767,760 B2 | 9/2020 | Ando | |
| 11,084,880 B2 | 8/2021 | Brogdon et al. | |
| 11,124,582 B2 | 9/2021 | Ambrogelly et al. | |
| 11,787,864 B2 | 10/2023 | Cheung et al. | |
| 11,834,506 B2 | 12/2023 | Chang et al. | |
| 11,884,733 B2 | 1/2024 | Chang et al. | |
| 11,939,384 B1 | 3/2024 | Chang et al. | |
| 2002/0103345 A1 | 8/2002 | Zhu | |
| 2002/0193569 A1 | 12/2002 | Hanna | |
| 2003/0095965 A1 | 5/2003 | Van Beneden et al. | |
| 2004/0038339 A1 | 2/2004 | Kufer et al. | |
| 2004/0052783 A1 | 3/2004 | Weiner et al. | |
| 2004/0115198 A1 | 6/2004 | Spies et al. | |
| 2005/0037002 A1 | 2/2005 | Velardi et al. | |
| 2005/0054019 A1 | 3/2005 | Michaud et al. | |
| 2005/0058639 A1 | 3/2005 | Gudas et al. | |
| 2005/0158307 A1 | 7/2005 | Spies et al. | |
| 2005/0244416 A1 | 11/2005 | Jung | |
| 2006/0018899 A1 | 1/2006 | Kao et al. | |
| 2006/0235201 A1 | 10/2006 | Kischel | |
| 2007/0004909 A1 | 1/2007 | Johnson et al. | |
| 2007/0071759 A1 | 3/2007 | Shin et al. | |
| 2007/0179086 A1 | 8/2007 | Gliniak et al. | |
| 2007/0190063 A1 | 8/2007 | Bahjat et al. | |
| 2008/0025975 A1 | 1/2008 | Weiner et al. | |
| 2008/0299137 A1 | 12/2008 | Svendsen et al. | |
| 2008/0305105 A1 | 12/2008 | Kufer et al. | |
| 2009/0142352 A1 | 6/2009 | Jackson et al. | |
| 2009/0175867 A1 | 7/2009 | Thompson et al. | |
| 2009/0226399 A1 | 9/2009 | Shitara et al. | |
| 2009/0226429 A1 | 9/2009 | Salcedo et al. | |
| 2009/0226442 A1 | 9/2009 | Huet et al. | |
| 2009/0226466 A1 | 9/2009 | Fong et al. | |
| 2009/0252729 A1 | 10/2009 | Farrington et al. | |
| 2009/0299039 A1 | 12/2009 | Kataoka et al. | |
| 2009/0304693 A1 | 12/2009 | Ghayur et al. | |
| 2009/0304696 A1 | 12/2009 | Lawson et al. | |
| 2010/0009866 A1 | 1/2010 | Prinz et al. | |
| 2010/0055034 A1 | 3/2010 | Martin et al. | |
| 2010/0056764 A1 | 3/2010 | Urso et al. | |
| 2010/0124764 A1 | 5/2010 | Hufton et al. | |
| 2010/0174053 A1 | 7/2010 | Johnson et al. | |
| 2010/0178298 A1 | 7/2010 | Lindhofer | |
| 2010/0256339 A1 | 10/2010 | Bossenmaier et al. | |
| 2010/0260765 A1 | 10/2010 | Barry et al. | |
| 2010/0272718 A1 | 10/2010 | Urso et al. | |
| 2010/0286374 A1 | 11/2010 | Kannan et al. | |
| 2010/0291112 A1 | 11/2010 | Kellner et al. | |
| 2010/0310463 A1 | 12/2010 | Cicortas Gunnarsson et al. | |
| 2011/0008335 A1 | 1/2011 | Velardi et al. | |
| 2011/0020273 A1 | 1/2011 | Chang et al. | |
| 2011/0044980 A1 | 2/2011 | Ghayur et al. | |
| 2011/0054151 A1 | 3/2011 | Lazar et al. | |
| 2011/0150870 A1 | 6/2011 | Rader et al. | |
| 2011/0236374 A1 | 9/2011 | Shitara et al. | |
| 2011/0311535 A1 | 12/2011 | Dranoff et al. | |
| 2012/0014957 A1 | 1/2012 | Ghayur et al. | |
| 2012/0058082 A1 | 3/2012 | Kaplan et al. | |
| 2012/0058906 A1 | 3/2012 | Smider et al. | |
| 2012/0093823 A1 | 4/2012 | Van Den Brink et al. | |
| 2012/0114665 A1 | 5/2012 | Martin | |
| 2012/0149876 A1 | 6/2012 | Von Kreudenstein et al. | |
| 2012/0171173 A1 | 7/2012 | Ideno et al. | |
| 2012/0195900 A1 | 8/2012 | Ghayur et al. | |
| 2012/0263722 A1 | 10/2012 | Ghayur et al. | |
| 2012/0269723 A1 | 10/2012 | Brinkmann et al. | |
| 2012/0276046 A1 | 11/2012 | Chapman et al. | |
| 2012/0294796 A1 | 11/2012 | Johnson et al. | |
| 2012/0294857 A1 | 11/2012 | Sentman et al. | |
| 2012/0321626 A1 | 12/2012 | Zhou | |
| 2012/0328619 A1 | 12/2012 | Fey et al. | |
| 2013/0156781 A1 | 6/2013 | Dimitrov et al. | |
| 2013/0177555 A1 | 7/2013 | Wilkinson et al. | |
| 2013/0209514 A1 | 8/2013 | Gilboa et al. | |
| 2013/0216528 A1 | 8/2013 | Cheung et al. | |
| 2013/0216544 A1 | 8/2013 | Bachmann | |
| 2013/0230525 A1 | 9/2013 | Li et al. | |
| 2013/0336977 A1 | 12/2013 | Thompson et al. | |
| 2014/0044739 A1 | 2/2014 | Teng et al. | |
| 2014/0072579 A1 | 3/2014 | De Kruif et al. | |
| 2014/0072581 A1 | 3/2014 | Dixit et al. | |
| 2014/0105889 A1 | 4/2014 | Igawa et al. | |
| 2014/0112926 A1 | 4/2014 | Liu et al. | |
| 2014/0120096 A1 | 5/2014 | Bakker et al. | |
| 2014/0127203 A1 | 5/2014 | Thompson et al. | |
| 2014/0140999 A1 | 5/2014 | De Kruif et al. | |
| 2014/0141022 A1 | 5/2014 | Thompson et al. | |
| 2014/0154250 A1 | 6/2014 | Thompson et al. | |
| 2014/0154252 A1 | 6/2014 | Thompson et al. | |
| 2014/0170168 A1 | 6/2014 | Reiter | |
| 2014/0199294 A1 | 7/2014 | Mimoto et al. | |
| 2014/0234342 A1 | 8/2014 | Narni-Mancinelli et al. | |
| 2014/0242077 A1 | 8/2014 | Choi et al. | |
| 2014/0271617 A1 | 9/2014 | Igawa et al. | |
| 2014/0288275 A1 | 9/2014 | Moore et al. | |
| 2014/0294827 A1 | 10/2014 | Gastwirt et al. | |
| 2014/0302064 A1 | 10/2014 | Moore | |
| 2014/0363426 A1 | 12/2014 | Moore et al. | |
| 2014/0364340 A1 | 12/2014 | Vasquez et al. | |
| 2014/0377269 A1 | 12/2014 | Mabry et al. | |
| 2015/0050269 A1 | 2/2015 | Igawa et al. | |
| 2015/0056206 A1 | 2/2015 | Zhou | |
| 2015/0079088 A1 | 3/2015 | Lowman et al. | |
| 2015/0119555 A1 | 4/2015 | Jung et al. | |
| 2015/0166636 A1 | 6/2015 | Igawa et al. | |
| 2015/0166654 A1 | 6/2015 | Igawa et al. | |
| 2015/0175697 A1 | 6/2015 | Bonvini et al. | |
| 2015/0175700 A1 | 6/2015 | Lum et al. | |
| 2015/0203591 A1 | 7/2015 | Yancopoulos et al. | |
| 2015/0210765 A1 | 7/2015 | Roschke et al. | |
| 2015/0259431 A1 | 9/2015 | Stemmer et al. | |
| 2015/0259434 A1 | 9/2015 | Johnson et al. | |
| 2015/0274838 A1 | 10/2015 | Johnson et al. | |
| 2015/0299319 A1 | 10/2015 | Velardi et al. | |
| 2015/0307617 A1 | 10/2015 | Du et al. | |
| 2015/0307628 A1 | 10/2015 | Kim et al. | |
| 2015/0329637 A1 | 11/2015 | Urech et al. | |

(56) References Cited

U.S. PATENT DOCUMENTS

| | | |
|---|---|---|
| 2015/0353636 A1 | 12/2015 | Parren et al. |
| 2016/0017038 A1 | 1/2016 | Koenig |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Baty et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0272717 A1 | 9/2016 | Lucas et al. |
| 2016/0289341 A1 | 10/2016 | Wu |
| 2016/0311922 A1 | 10/2016 | Ghaderi et al. |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0240645 A1 | 8/2017 | Chen et al. |
| 2017/0291955 A1 | 10/2017 | Li et al. |
| 2017/0362321 A1 | 12/2017 | Campbell et al. |
| 2017/0368169 A1 | 12/2017 | Loew et al. |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Caligiuri et al. |
| 2018/0237541 A1 | 8/2018 | Kim et al. |
| 2018/0273633 A1 | 9/2018 | Jiang et al. |
| 2018/0312592 A1 | 11/2018 | Junutula et al. |
| 2018/0346600 A1 | 12/2018 | Kim et al. |
| 2019/0048079 A1 | 2/2019 | Spies et al. |
| 2019/0225702 A1 | 7/2019 | Baeuerle et al. |
| 2019/0359716 A1 | 11/2019 | Chang et al. |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1 | 7/2020 | Chang et al. |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1 | 9/2020 | Chang et al. |
| 2020/0376034 A1 | 12/2020 | Chang et al. |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1 | 3/2021 | Chang et al. |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1 | 7/2021 | Chang et al. |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0363261 A1 | 11/2021 | Chang et al. |
| 2022/0025037 A1 | 1/2022 | Baruah et al. |
| 2022/0089760 A1 | 3/2022 | Bigelow et al. |
| 2022/0119533 A1 | 4/2022 | Cheung et al. |
| 2022/0119534 A1 | 4/2022 | Baruah et al. |
| 2022/0153848 A1 | 5/2022 | Chang et al. |
| 2022/0195065 A1 | 6/2022 | Chang et al. |
| 2022/0380459 A1 | 12/2022 | Chang et al. |
| 2023/0034186 A1 | 2/2023 | Cuillerot et al. |
| 2023/0203202 A1 | 6/2023 | Bigelow et al. |
| 2023/0227562 A1 | 7/2023 | Chang et al. |
| 2023/0250176 A1 | 8/2023 | Cheung et al. |
| 2023/0257467 A1 | 8/2023 | Cheung et al. |
| 2023/0272041 A1 | 8/2023 | Bigelow et al. |
| 2023/0303702 A1 | 9/2023 | Chang et al. |
| 2023/0357409 A1 | 11/2023 | Chang et al. |
| 2023/0391877 A1 | 12/2023 | Chang et al. |
| 2023/0416402 A1 | 12/2023 | Cuillerot et al. |

FOREIGN PATENT DOCUMENTS

| | | |
|---|---|---|
| CN | 105906722 A | 8/2016 |
| CN | 105814084 B | 9/2019 |
| DE | 102013019352 A1 | 9/2015 |
| EP | 627940 A1 | 12/1994 |
| EP | 845998 A1 | 6/1998 |
| EP | 871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| JP | H11-500915 A | 1/1999 |
| JP | 2011-508604 A | 3/2011 |
| JP | 2011506406 A | 3/2011 |
| JP | 2012-522524 A | 9/2012 |
| JP | 2013506406 A | 1/2013 |
| KR | 10-2013-0103325 A | 9/2013 |
| KR | 10-2013-0135866 A | 12/2013 |
| KR | 10-2014-0067944 A | 6/2014 |
| RU | 2588668 C2 | 7/2016 |
| RU | 2593720 C2 | 8/2016 |
| RU | 2608504 C2 | 1/2017 |
| RU | 2015143457 A | 4/2017 |
| WO | WO-1988008854 A1 | 11/1988 |
| WO | WO-1989006544 A1 | 7/1989 |
| WO | WO-96/27011 A1 | 9/1996 |
| WO | WO-2001071005 A2 | 9/2001 |
| WO | 2004056873 A1 | 7/2004 |
| WO | WO-2004083387 A2 | 9/2004 |
| WO | 2005/003172 A2 | 1/2005 |
| WO | 2005/009465 A1 | 2/2005 |
| WO | 2005/105849 A1 | 11/2005 |
| WO | WO-2006037960 A2 | 4/2006 |
| WO | WO-2007002905 A1 | 1/2007 |
| WO | 2007044756 A2 | 4/2007 |
| WO | WO-2007042573 A2 | 4/2007 |
| WO | WO-2007055926 A1 | 5/2007 |
| WO | WO-2007097812 A2 | 8/2007 |
| WO | 2008/127735 A1 | 10/2008 |
| WO | 2009007124 A1 | 1/2009 |
| WO | WO-2009077483 A1 | 6/2009 |
| WO | WO-2009/089004 A1 | 7/2009 |
| WO | WO-2010017103 A2 | 2/2010 |
| WO | WO-2010080124 A2 | 7/2010 |
| WO | WO-2011014659 A2 | 2/2011 |
| WO | 2011/076922 A1 | 6/2011 |
| WO | WO-2011075636 A2 | 6/2011 |
| WO | 2011109400 A2 | 9/2011 |
| WO | WO-2011/143545 A1 | 11/2011 |
| WO | WO-2012006490 A2 | 1/2012 |
| WO | WO-2012/025530 A1 | 3/2012 |
| WO | WO-2012/032080 A1 | 3/2012 |
| WO | WO-2012034039 A2 | 3/2012 |

(56) References Cited

FOREIGN PATENT DOCUMENTS

| | | |
|---|---|---|
| WO | 2012/045752 A1 | 4/2012 |
| WO | 2012/115241 A1 | 8/2012 |
| WO | WO-2012125850 A1 | 9/2012 |
| WO | 2012/131555 A2 | 10/2012 |
| WO | WO-2012158818 A2 | 11/2012 |
| WO | WO-2012162482 A1 | 11/2012 |
| WO | 2012/163805 A1 | 12/2012 |
| WO | WO-2013013700 A1 | 1/2013 |
| WO | WO-2013036799 A2 | 3/2013 |
| WO | WO-2013092001 A1 | 6/2013 |
| WO | 2013113615 A1 | 8/2013 |
| WO | WO-2013192594 A2 | 12/2013 |
| WO | WO-2014001324 A1 | 1/2014 |
| WO | WO-2014012085 A2 | 1/2014 |
| WO | 2014079000 A1 | 5/2014 |
| WO | 2014110601 A1 | 7/2014 |
| WO | WO-2014124326 A1 | 8/2014 |
| WO | WO-2014131712 A1 | 9/2014 |
| WO | WO-2014144763 A2 | 9/2014 |
| WO | WO-2014145806 A2 | 9/2014 |
| WO | 2014159940 A1 | 10/2014 |
| WO | WO-2014/165818 A2 | 10/2014 |
| WO | WO-2014198748 A1 | 12/2014 |
| WO | WO-2015009856 A2 | 1/2015 |
| WO | WO-2015026894 A2 | 2/2015 |
| WO | 2015036606 A1 | 3/2015 |
| WO | WO-2015036582 A2 | 3/2015 |
| WO | WO-2015063187 A1 | 5/2015 |
| WO | WO-2015070061 A1 | 5/2015 |
| WO | WO-2015089344 A1 | 6/2015 |
| WO | WO-2015095412 A1 | 6/2015 |
| WO | WO-2015095539 A1 | 6/2015 |
| WO | 2015095972 A1 | 7/2015 |
| WO | WO-2015/150447 A1 | 10/2015 |
| WO | WO-2015153765 A1 | 10/2015 |
| WO | WO-2015153912 A1 | 10/2015 |
| WO | WO-2015158636 A1 | 10/2015 |
| WO | WO-2015169781 A1 | 11/2015 |
| WO | WO-2015181282 A1 | 12/2015 |
| WO | WO-2015184203 A1 | 12/2015 |
| WO | WO-2015184207 A1 | 12/2015 |
| WO | WO-2015197582 A1 | 12/2015 |
| WO | WO-2015197593 A1 | 12/2015 |
| WO | WO-2015197598 A2 | 12/2015 |
| WO | 2016001810 A1 | 1/2016 |
| WO | WO-2016011571 A1 | 1/2016 |
| WO | WO-2016023909 A1 | 2/2016 |
| WO | WO-2016025880 A1 | 2/2016 |
| WO | WO-2016028672 A1 | 2/2016 |
| WO | 2016032334 A1 | 3/2016 |
| WO | 2016070959 A1 | 5/2016 |
| WO | 2016090278 A2 | 6/2016 |
| WO | WO-2016097408 A1 | 6/2016 |
| WO | WO-2016100533 A2 | 6/2016 |
| WO | WO-2016109774 A1 | 7/2016 |
| WO | WO-2016115274 A1 | 7/2016 |
| WO | WO-2016122701 A1 | 8/2016 |
| WO | WO-2016134371 A2 | 8/2016 |
| WO | 2016135041 A1 | 9/2016 |
| WO | WO-2016135066 A1 | 9/2016 |
| WO | WO-2016142768 A1 | 9/2016 |
| WO | WO-2016146702 A1 | 9/2016 |
| WO | 2016161390 A1 | 10/2016 |
| WO | 2016166139 A1 | 10/2016 |
| WO | WO-2016164369 A2 | 10/2016 |
| WO | WO-2016164637 A1 | 10/2016 |
| WO | WO-2016166629 A1 | 10/2016 |
| WO | WO-2016168607 A1 | 10/2016 |
| WO | WO-2016184592 A1 | 11/2016 |
| WO | WO-2016187220 A2 | 11/2016 |
| WO | WO-2016/196237 A1 | 12/2016 |
| WO | WO-2016/201389 A2 | 12/2016 |
| WO | WO-2016191305 A1 | 12/2016 |
| WO | WO-2016201300 A1 | 12/2016 |
| WO | WO-2016207273 A2 | 12/2016 |
| WO | WO-2016207278 A1 | 12/2016 |
| WO | 2017011342 A1 | 1/2017 |
| WO | WO-2017005732 A1 | 1/2017 |
| WO | WO-2017008169 A1 | 1/2017 |
| WO | WO-2017021349 A1 | 2/2017 |
| WO | WO-2017040529 A1 | 3/2017 |
| WO | WO-2017048824 A1 | 3/2017 |
| WO | 2017079694 A2 | 5/2017 |
| WO | WO-2017075432 A2 | 5/2017 |
| WO | WO-2017081190 A1 | 5/2017 |
| WO | WO-2017083545 A1 | 5/2017 |
| WO | WO-2017114694 A1 | 7/2017 |
| WO | WO-2017124002 A1 | 7/2017 |
| WO | WO-2017125897 A1 | 7/2017 |
| WO | WO-2017143406 A1 | 8/2017 |
| WO | 2017165464 A1 | 9/2017 |
| WO | WO-2017165683 A1 | 9/2017 |
| WO | 2017180813 A1 | 10/2017 |
| WO | WO-2017177337 A1 | 10/2017 |
| WO | WO-2017211873 A1 | 12/2017 |
| WO | WO-2017218707 A2 | 12/2017 |
| WO | 2018045090 A1 | 3/2018 |
| WO | WO-2018098365 A2 | 5/2018 |
| WO | WO-2018119171 A1 | 6/2018 |
| WO | WO-2018148445 A1 | 8/2018 |
| WO | WO-2018148447 A1 | 8/2018 |
| WO | WO-2018148566 A1 | 8/2018 |
| WO | WO-2018148610 A1 | 8/2018 |
| WO | WO-2018152516 A1 | 8/2018 |
| WO | WO-2018152518 A1 | 8/2018 |
| WO | WO-2018152530 A1 | 8/2018 |
| WO | WO-2018152547 A1 | 8/2018 |
| WO | WO-2018157147 A1 | 8/2018 |
| WO | WO-2018201051 A1 | 11/2018 |
| WO | WO-2018217799 A1 | 11/2018 |
| WO | WO-2018217945 A1 | 11/2018 |
| WO | WO-2018217947 A1 | 11/2018 |
| WO | WO-2019028027 A1 | 2/2019 |
| WO | WO-2019035939 A1 | 2/2019 |
| WO | WO-2019040727 A1 | 2/2019 |
| WO | WO-2019051308 A1 | 3/2019 |
| WO | WO-2019055677 A1 | 3/2019 |
| WO | WO-2019/164929 A1 | 8/2019 |
| WO | WO-2019157332 A1 * | 8/2019 ........... A61K 31/337 |
| WO | WO-2019157366 A1 | 8/2019 |
| WO | WO-2019164930 A1 | 8/2019 |
| WO | WO-2019195408 A1 | 10/2019 |
| WO | WO-2019195409 A1 | 10/2019 |
| WO | WO-2019217332 A1 | 11/2019 |
| WO | WO-2019222449 A1 | 11/2019 |
| WO | WO-2019/231920 A1 | 12/2019 |
| WO | 2020033664 A1 | 2/2020 |
| WO | 2020033702 A1 | 2/2020 |
| WO | WO-2020033587 A1 | 2/2020 |
| WO | WO-2020033630 A1 | 2/2020 |
| WO | 2020086758 A1 | 4/2020 |
| WO | 2020172189 A1 | 8/2020 |
| WO | PCT/US2020/048500 | 8/2020 |
| WO | PCT/US2020/055480 | 10/2020 |
| WO | PCT/US2020/055497 | 10/2020 |
| WO | 2021041878 A1 | 3/2021 |
| WO | 2021076554 A1 | 4/2021 |
| WO | 2021076564 A1 | 4/2021 |
| WO | 2021216916 A1 | 10/2021 |
| WO | 2021/226163 A2 | 11/2021 |
| WO | 2021226193 A1 | 11/2021 |
| WO | 2022031935 A1 | 2/2022 |
| WO | 2022031965 A1 | 2/2022 |
| WO | 2022187539 A1 | 9/2022 |
| WO | 2023056243 A1 | 4/2023 |
| WO | 2023056252 A1 | 4/2023 |
| WO | 2023107954 A1 | 6/2023 |
| WO | 2023107956 A1 | 6/2023 |

(56) References Cited

FOREIGN PATENT DOCUMENTS

| | | |
|---|---|---|
| WO | 2023154796 A2 | 8/2023 |
| WO | 2023168384 A2 | 9/2023 |

OTHER PUBLICATIONS

Tamura et al. Correlation of P-cadherin and beta-catenin expression and phosphorylation with carcinogenesis in rat tongue cancer induced with 4-nitroquinoline 1-oxide. Oral Oncol. Jul. 2003;39(5):506-14. doi: 10.1016/s1368-8375(03)00013-7. (Year: 2003).*

Brinkmann & Kontermann. The making of bispecific antibodies. mAbs. 2017;9:2, 182-212, DOI: 10.1080/19420862.2016.1268307 (Year: 2017).*

Murphy & Weaver. Ch. 4. 2017. Janeway's Immunobiology. 9th Ed. Garland Science. (Year: 2017).*

Affimed, Affimed Enters Into Collaboration With Merck to Evaluate AFM13 in Combination With . . . Retreived < U RL:https ://www.affimed.com/affi med-enters-into-col laboration-with-merck-to-evaluate-afm 13-i n-combination-with-keytruda-pembrolizumab-for-patients-with-hodgkin-lymphoma/>[retrieved on Feb. 1, 2023] Jan. 25, 2016.

Akbar et al. (2021) "A compact vocabulary of paratope-epitope interactions enables predictability of antibody-antigen binding," Cell Reports 34:108856 21 pages.

Altshuler et al. (2010) "Generation of Recombinant Antibodies and Means for Increasing Their Affinity," Biochemistry (Moscow) 75(13):1584-1605.

Berenbaum (1977) "Synergy, additivism and antagonism in immunosuppression," Clin. Exp. Immunol. 28:1-18.

Berenbaum (1989) "What is Synergy?" Pharmacological Reviews 41:93-141.

Bost et al. (1988) "Antibodies Against a Peptide Sequence Within the HIV Envelope Protein Crossreacts with Human Interleukin-2," Immunological Investigations 17(6&7):577-586.

Bowen et al. (2016) "Revisiting the Immunoglobulin Intramolecular Signaling Hypothesis," Trends Immunol. 37(11):721-723.

Branca et al. (2018) "Nature Biotechnology's academic spinouts of 2017," Nature Biotechnology 36(4):297-306.

Bruhns et al. (2009) "Specificity and affinity of human FCg receptors and their polymorphic variants for human IgG subclasses," Blood 113(16):3716-3724.

Busfield et al. (2014) "Targeting of acute myeloid leukemia in vitro and in vivo with an anti-CD123 mAb engineered for optimal ADCC," Leukemia 28(11): 2213-2221.

Dahlberg et al. (2015) "Natural Killer Cell-Based Therapies Targeting Cancer: Possible Strategies to Gain and sustain Anti-Tumor Activity" Frontiers In Immunology 6(Article 605):19 pages.

Davis et al. (1999) "Therapy of B-Cell Lymphoma with Anti-CD20 Antibodies Can Result in the Loss of CD20 Antigen Expression," Clinical Cancer Research 5:611-615.

Dickopf et al. (2020) "Format and geometries matter: Structure-based design defines the functionality of bispecific antibodies," Computational and Structural Biotechnology Journal 18:1221-1227.

El-Amine et al. (2002) "In vivo induction of tolerance by an Ig peptide is not affected by the deletion of FcR or a mutated IgG Fc fragment," International Immunology 14(7):761-766.

Germain et al. (2008) "Redirecting NK cells mediated tumor cell lysis by a new recombinant bifunctional protein," Protein Engineering, Design & Selection 21(11):665-672.

Goel et al. (2004) "Plasticity within the Antigen-Combining Site May Manifest as Molecular Mimicry in the Humoral Immune Response," The Journal of Immunology 173(12):7358-7367.

Hasegawa et al. (2017) "Single amino acid substitution in LC-CDR1 induces Russell body phenotype that attenuates cellular protein synthesis through eIF2a phosphorylation and thereby downregulates IgG secretion despite operational secretory pathway traffic," MABS 9(5):854-873.

Hlavacek et al. 1999 "Steric Effects on Multivalent Ligand-Receptor Binding: Exclusion of Ligand Sites by Bound Cell Surface Receptors," Biophysical Journal 76:3031-3043.

Janeway et al. (1997) Chapter 3, Structure of the Antibody Molecule and Immunoglobulin Genes, Immunology Third Edition, Garland Publishing Inc., 3:1-3:11.

Jonnalagadda et al. (2015) "Chimeric Antigen Receptors With Mutated IgG4 Fc Spacer Avoid Fc Receptor Binding and Improve T Cell Persistence and Antitumor Efficacy," Molecular Therapy 23(4):757-768.

Kanyavuz et al. (2019) "Breaking the law: unconventional strategies for antibody diversification," Nature Reviews Immunology 19(6):355-368.

Kaur et al. (2015) "Applications of In Vitro-In Vivo Correlations in Generic Drug Development: Case Studies," The AAPS Journal 17(4):1035-1039; doi: 10.1208/s12248-015-9765-1.

Kjellev et al. (2007) "Inhibition of NKG2D receptor function by antibody therapy attenuates transfer-induced colitis in SCID mice," Eur. J. Immunol. 37:1397-1406.

Kunik, et al. (2012) "Structural consensus among antibodies defines the antigen binding site," PLoS Comput Biol. 8(2):e1002388.

Lippow et al. (2007) "Computational design of antibody-affinity improvement beyond in vivo maturation," Nature Biotechnology 25(10):1171-1176.

Lo et al. (2021) "Conformational epitope matching and prediction based on protein surface spiral features," BMC Genomics 22(Suppl 2):116 16 pages.

Mandelboim et al. (1999) "Human CD16 as a lysis receptor mediating direct natural killer cell cytotoxicity," PNAS USA 96(10):5640-5644; doi: 10.1073/pnas.96.10.5640.

Marks et al. (2020) "How repertoire data are changing antibody science," J. Biol. Chem. 295(29):9823-9837.

Muller et al. (2015) "Trastuzumab emtansine (T-DM1) renders HER2+ breast cancer highly susceptible to CTLA-4/PD-1 blockade," Sci. Transl. Med. 7(315):1-14.

Piche-Nicholas et al. (2018) "Changes in complementarity-determining regions significantly alter IgG binding to the neonatal Fc receptor (FcRn) and pharmacokinetics," MABS 10(1)81-94.

Rabia et al. (2018) "Understanding and overcoming trade-offs between antibody affinity, specificity, stability and solubility" Biochem Eng J. 137:365-374.

Raulet (2003) "Roles of the NKG2D immunoreceptor and its ligands," Nature: Reviews Immunology 3:781-790; doi: 10.1038/nri1199.

Roell et al. (2017) "An Introduction to Terminology and Methoodology of Chemical Synergy—Perspectives from Across Disciplines," Frontiers in Pharmacology: Cancer Molecular Targets and Therapeutics 8:1-11.

Rosano et al. (2014) "Recombinant protein expression in *Escherichia coli*: advances and challenges" Frontiers in Microbiology 5(172):17 pages.

Sazinsky et al. (2008) "Aglycosylated immunoglobulin G1 variants productively engage activating Fc receptors," Proceedings of the National Academy of Sciences 105(51)20167-20172.

Singer et al. (1998) "Genes and Genomes," Moscow, "Mir" 1:63-64.

Sulea et al. (2018) "Application of Assisted Design of Antibody and Protein Therapeutics (ADAPT) improves efficacy of a Clostridium difficile toxin A single-domain antibody," 8:2260 11 pages.

Tallarida (2000) "Drug Synergism and Dose Effect Analysis," Ed. Chapman & Hall pp. 1-71.

Thakur et al. (2018) "Bispecific antibody based therapeutics: Strengths and challenges," Blood Review 32:339-347.

Vajda et al. (2021) "Progress toward improved understanding of antibody maturation," Current Opinion in Structural Biology 67:226-231.

Ward et al. (1989) "Binding activities of a epertoire of single immunoglobulin variable domains secreted from *Escherichia coli*," Nature 341:544-546.

Wark et al. (2006) "Latest technologies for the enhancement of antibody affinity", Advanced Drug Delivery Reviews 58 (5-6):657-670.

(56) References Cited

OTHER PUBLICATIONS

Wensveen et al. (2018) "NKG2D: A Master Regulator of Immune Cell Responsiveness," Frontiers in Immunology 9 (Article 411):8 pages.
Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php? title=Trifunctional antibody8 oldid=818265015.
Written Opinion for International Application No. PCT/US2018/ 017470 dated Apr. 24, 2018.
Brown, M. et al., "Tolerance of Single, but Not Multiple, Amino Acid Replacements in Antibody VH CDR 2: A Means of Minimizing B Cell Wastage From Somatic Hypermutation?", Journal of Immunology (1996), vol. 156, pp. 3285-3291.
Elliott, J. M. et al., "Antiparallel Conformation of Knob and Hole Aglycosylated Half-Antibody Homodimers is Mediated by a CH2—CH3 Hydrophobic Interaction", J. Mol. Biol. (2014), vol. 426(9), pp. 1947-1957.
Herold, E.M. et al., "Determinants of the Assembly and Function of Antibody Variable Domains", Scientific Reports (2017), vol. 7:12276, 17 pgs.
Long, E. O. et al., "Controlling NK Cell Responses: Integration of Signals for Activation and Inhibition", Annu. Rev Immunol. (2013), vol. 31, 10.1146/annurev-immunol-020711-075005, 36 pgs.
Morvan, M. G. et al., "NK Cells and Cancer: You Can Teach Innate Cells New Tricks", Nature Reviews Cancer (2016), vol. 16(1), pp. 7-19.
Trivedi, A. et al., "Clinical Pharmacology and Translational Aspects of Bispecific Antibodies", Clin. Transl. Sci (2017), vol. 10, pp. 147-162.
Van De Winkel, J. et al., "Human IgG Fc Receptor Heterogeneity: Molecular Aspects and Clinical Implications", Immunology Today (1993), vol. 14(5), pp. 215-221.
Sonderman, P. et al., "The 3.2-[Angstrom] Crystal Structure of the Human IgG1 Fc Fragment-Fc[gamma]RIII Complex", Nature (2000), vol. 406:6793, 12 pgs.
Vidarsson, G. et al., "IgG Subclasses and Allotypes: From Structure to Effector Functions", Frontiers in Immunology (2014), vol. 5:520, 17 pgs.
Zhou, Z. et al., "Characterization of Human Homologue of 4-1BB and its Ligand", Immunology Letters (1995), vol. 45, pp. 67-73.
U.S. Appl. No. 16/483,330, filed Aug. 2, 2019.
U.S. Appl. No. 16/483,572, filed Aug. 5, 2019.
U.S. Appl. No. 16/483,788, filed Aug. 6, 2019.
U.S. Appl. No. 16/486,921, filed Aug. 19, 2019.
U.S. Appl. No. 16/486,569, filed Aug. 16, 2019.
U.S. Appl. No. 16/486,570, filed Aug. 16, 2019.
U.S. Appl. No. 16/488,395, filed Aug. 23, 2019.
U.S. Appl. No. 16/615,203, filed Nov. 20, 2019.
U.S. Appl. No. 16/615,231, filed Nov. 20, 2019.
U.S. Appl. No. 16/638,559, filed Feb. 12, 2020.
U.S. Appl. No. 17/188,978, filed Mar. 1, 2021.
U.S. Appl. No. 16/639,150, filed Feb. 14, 2020.
U.S. Appl. No. 16/644,585, filed Mar. 5, 2020.
U.S. Appl. No. 17/190,155, filed Mar. 2, 2021.
U.S. Appl. No. 16/967,216, filed Aug. 4, 2020.
U.S. Appl. No. 17/045,015, filed Oct. 2, 2020.
U.S. Appl. No. 17/045,016, filed Oct. 2, 2020.
U.S. Appl. No. 17/053,558, filed Nov. 6, 2020.
Bendayan et al. (1995) "Possibilities of False Immunocytochemical Results Generated by the Use of Monoclonal Antibodies: The Example of the Anti-proinsulin Antibody," J. Histochem. Cytochem. 43:881-86.
Bostrom, et al. (2009) "Improving Antibody Binding Affinity and Specificity for Therapeutic Development," Methods and Protocols 525:353-76.
Brinkmann et al. (2017) "The making of bispecific antibodies," MABS 9(2)182-212.

Bryceson et al. (2006) "Synergy among receptors on resting NK cells for the activation of natural cytotoxicity and cytokine secretion," Blood 107(1):159-66.
Casset et al. (2003) "A peptide mimetic of an anti-CD4 monoclonal antibody by rational design," Biochemical and Biophysical Research Communications 307:198-205.
Chen et al. (1995) "Enhancement and destruction of antibody function by somatic mutation: unequal occurrence is controlled by V gene combinatorial associations," The EMBO Journal 14(12):2784-94.
Chen et al. (1999) "Selection and Analysis of an Optimized Anti-VEGF Antibody: Crystal Structure of an Affinity-matured Fab in Complex with Antigen," J. Mol. Biol. 293:865-81.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-84.
Edwards et al. (2003) "The Remarkable Flexibility of the Human Antibody Repertoire; Isolation of Over One Thousand Different Antibodies to a Single Protein, BLyS," J. Mol. Biol. 334:103-18.
Gonzales, et al. (2005) "Minimizing the Immunogenicity of Antibodies for Clinical Application," Tumor Biol. 26(1):31-43.
Henry et al. (2017) "Stability-Diversity Tradeoffs Impose Fundamental Constraints on Selection of Synthetic Human $V_H/V_L$ Single-Domain Antibodies from In Vitro Display Libraries," Frontiers in Immunology, 8:1-15.
Hoseini et al. (2017) "Acute myeloid leukemia targets for bispecific antibodies," Blood Cancer Journal 7(2):e522 (12 pages).
Kijanka et al. (2013) "Rapid optical imaging of human breast tumour xenografts using anti-HER2 VHHs site-directly conjugated to IRDye 800CW for image-guided surgery," Eur J Nucl Med Mol Imaging 40:1718-29.
Kim et al. (2014) "Mutational approaches to improve the biophysical properties of human single-domain antibodies," Biochimica et Biophysica Acta, 1844:1983-2001.
Koerner et al. (2015) "Induction of NK and T Cell Immune Responses Against Leukemia Cells by Bispecific NKG2D-CD16 and -CD3 Fusion Proteins," Blood 126(23):2558, Abstract 606 (2 pages).
Kranz et al. (1981) "Restricted reassociation of heavy and light chains from hapten-specific monoclonal antibodies," Pro. Natl. Acad. Sci. USA 78(9):5807-11.
Krieg et al. (2005) "Functional Analysis of B and T Lymphocyte Attenuator Engagement on CD4+ and CD8+ T Cells," The Journal of Immunology 175(10):6420-27.
Lamminmäki et al. (2001) "Crystal Structure of a Recombinant Anti-estradiol Fab Fragment in Complex with 17β-Estradiol," The Journal of Biological Chemistry 276(39):36687-94.
Lin et al. (2011) "Improved affinity of a chicken single-chain antibody to avian infectious bronchitis virus by site-directed mutagenesis of complementarity-determining region H3," African Journal of Biotechnology 10(79):18294-303.
Lloyd et al. (2009) "Modelling the human immune response: performance of a $10^{11}$ human antibody repertoire against a broad panel of therapeutically relevant antigens," Protein Engineering, Design and Selection 22(3):159-68.
Lund et al. (1996) "Multiple interactions of IgG with its core oligosaccharide can modulate recognition by complement and human Fc gamma receptor I and influence the synthesis of its oligosaccharide chains," J Immunol 157:4963-69.
Maccallum et al. (1996) "Antibody-antigen Interactions: Contact Analysis and Binding Site Topography," J Mol Biol 262:732-45.
Maeda et al. (2015) "New antibody modification technology and its application to antibody drugs," Farumashia 51(5):424-28.
Mariuzza et al. (1987) "The Structural Basis of Antigen-Antibody Recognition," Ann Rev Biophys Chem 16:139:59.
Mccarthy et al. (2001) "Altering the fine specificity of an anti-Legionella single chain antibody by a single amino acid insertion," Journal of Immunological Methods 251:137-49.
Morris "Epitope Mapping of Protein Antigens by Competition ELISA," The Protein Protocols Handbook, Totowa, NJ, Humana Press, (19960101):595-600.

(56) References Cited

OTHER PUBLICATIONS

Padlan et al. (1989) "Structure of an antibody-antigen complex: Crystal structure of the HyHEL-10 Fab-lysozyme complex," *Pro Natl Acad Sci USA* 86:5938-5942.
Paul et al. (1993) "Fundamental Immunology," (textbook) 292-295 (6 pages).
Portolano et al. (1993) "Lack of promiscuity in autoantigen-specific H and L chain combinations as revealed by human H and L chain roulette," *J Immunol* 15(30):880-87.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," *Cancer Research* (4 pages).
Rudikoff et al. (1982) "Single amino acid substitution altering antigen-binding specificity," *Pro Natl Acad Sci USA* 79:1979-83.
Schroeder et al. (2010) "Structure and Function of Immunoglobulins," *J Allergy Clin Immunol* 125:S41-S52 (24 pages).
Shum et al. (2002) "Conservation and Variation in Human and Common Chimpanzee CD94 and NKG2 Genes," *The Journal of Immunology* 168:240-52.
Stein et al. (2012) "Natural Killer (NK)- and T-Cell Engaging Antibody-Derived Therapeutics," *Antibodies* 1:88-123.
Vajdos et al. (2002) "Comprehensive Functional Maps of the Antigen-binding Site of an Anti-ErbB2 Antibody Obtained with Shotgun Scanning Mutagenesis," *J Mol Biol* 320:415-28.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," *Clin Cancer Res*, 22(14):3440-50.
Wang et al. (2018) "IgG Fc engineering to modulate antibody effector functions," *Protein Cell* 9(1):63-73.
Wu et al. (1999) "Humanization of a Murine Monoclonal Antibody by Simultaneous Optimization of Framework and CDR Residues," *J Mol Biol* 294:151-62.
Yan et al. (2014) "Construction of a synthetic phage-displayed Nanobody library with CDR3 regions randomized by trinucleotide cassettes for diagnostic applications," *Journal of Translational Medicine* 12:343 (12 pages).
Zhang et al. (2021) "Bispecific antibody-mediated redirection of NKG2D-CAR natural killer cells facilitates dual targeting and enhances antitumor activity," *Journal for Immuno Therapy of Cancer*; 9:e002980 (24 pages). doi:10.1136/jitc-2021-002980.
Kennedy et al., 2002 "Incidence and nature of CD20-negative relapses following rituximab therapy in aggressive B-cell non-Hodgkin's lymphoma: a retrospective review," *British Journal of Haematology* 119:412-16.
Maeda et al., 1997 "Engineering of Functional Chimeric Protein G-Vargula Luciferase" *Anal Biochem* 249(2):147-52.
Schroeder and Cavacini 2010 "Structure and Function of Immuno-globulins," *J Allergy Clin Immunol* 125:S41-S52.
Notice of Opposition for Colombia Patent Application No. NC2020/0010345 dated Dec. 16, 2020 (13 pages).
Japanese Patent Office; Communication dated Oct. 31, 2017 in counterpart Application No. 2015-543998 (9 pages).
Gunasekaran et al., "Enhancing antibody Fc heterodimer formation through electrostatic steering effects: applications to bispecific molecules and monovalent IgG", JBC Papers in Press, Apr. 16, 2010, pp. 1-20 (20 pages).
Doppalapudi et al., 2010 "Chemical generation of bispecific antibodies," *PNAS* 107(52):22611-16.
Lewis et al., 2014 "Generation of bispecific IgG antibodies by structure-based design of an orthogonal Fab interface," *Nat Biotechnol* 32(2):191-98.
Mimoto et al., 2014 "Crystal structure of a novel asymmetrically engineered Fc variant with improved affinity for FcγRs," *Mol Immunol* 58(1):132-38.
Muda et al., 2011 "Therapeutic assessment of SEED: a new engineered antibody platform designed to generate mono- and bispecific antibodies," *Protein Eng Des Sel* 24(5):447-54.
Wranik et al., 2012 "LUZ-Y, a novel platform for the mammalian cell production of full-length IgG-bispecific antibodies," *J Biol Chem* 287(52):43331-9.
Ahmad et al. (2012) "scFv antibody: principles and clinical application," *Clinical and Developmental Immunology* 2012:1-16.
Averdam et al. (2009) "A Novel System of Polymorphic and Diverse NK Cell Receptors in Primates," *PLoS Genetics* 5(10):e1000688.
Cai et al. (2014) "Autonomous Stimulation of Cancer Cell Plasticity by the Human NKG2D Lymphocyte Receptor Coexpressed with Its Ligands on Cancer Cells," *PLOS One* 9(10):e108942.
Chen et al. (2013) "Fusion protein linkers: property, design and functionality" Advanced drug delivery reviews, 65(10):1357-1369.
Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.
Chu et al. (2014) "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," *Blood* 124(21):2316.
Colman (1994) "Effects of Amino Acid Sequence Changes on Antibody-Antigen Interactions" Research in Immunology 145(1):33-36.
Ding et al. (2018) "Fusion Proteins of NKG2D/NKG2DL in Cancer Immunotherapy," *International Journal of Molecular Sciences* 19(1):177.
Felices et al. (2016) "Generation of BiKEs and TriKEs to Improve NK cell-Mediated Targeting of Tumor Cells," Natural Killer Cells: Methods and Protocols, Methods in Molecular Biology 1441:333-346.
Gantke et al. (2016) "Trispecific Antibodies for Selective CD16A-Directed NK-Cell Engagement in Multiple Myeloma," *Blood* 128(22):4513 (2 pages).
Gantke et al. (2017) "Trispecific antibodies for CD16A-directed NK cell engagement and dual-targeting of tumor cells," Protein Engineering, Design & Selection 38(9):673-684.
Gauthier et al. (2019) "Multifunctional Natural Killer Cell Engagers Targeting NKp46 Trigger Protective Tumor Immunity," *Cell* 177(7):1701-1713.
Germain et al. (2005) "MHC Class I-Related Chain a Conjugated to Antitumor antibodies Can Sensitize Tumor Cells to Specific Lysis by Natural Killer Cells," *Clinical Cancer Research* US 11(20):7516-7522.
Glas et al. (1997) "Analysis of rearranged immunoglobulin heavy chain variable region genes obtained from a bone marrow transplant (BMT) recipient," *Clinical & Experimental Immunology* 107(2):372-380.
Gleason et al. (2012) "Bispecific and Trispecific Killer Cell Engagers Directly Activate Human NK Cells through CD16 Signaling and Induce Cytotoxicity and Cytokine Production," *Molecular Cancer Therapeutics* 11(12):2674-2684.
Gleason et al. (2014) "CD16xCD33 bispecific killer cell engager (BiKE) activates NK cells against primary MDS and MDSC CD33+ targets," *Blood* 123(19):3016-3026.
Gooden et al. (2012) "Infiltrating CTLs are bothered by HLA-E on tumors," OncoImmunology, 1(1):92-93.
Henry et al. (2004) "A Prostate-Specific Membrane Antigen-Targeted Monoclonal Antibody-Chemotherapeutic Conjugate Designed for the Treatment of Prostate Cancer," *Cancer Research* 64:7995-8001.
Hezareh et al. (2001) "Effector Function Activities of a Panel of Mutants of a Broadly Neutralizing Antibody against Human Immunodeficiency Virus Type 1," *Journal of Virology* 75(24):12161-12168.
Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6):1036-1045.
Junttila et al. (2014) "Antitumor Efficacy of a Bispecific Antibody That Targets HER2 and Activates T Cells," *Cancer Research* 74(19):5561-5571.

(56) References Cited

OTHER PUBLICATIONS

Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," *Leukemia* 26:830-834.
Kellner et al. (2013) "Promoting natural killer cell functions by recombinant immunoligands mimicking an induced self phenotype," *Oncoimmunology* 2(6):e24481.
Kellner et al. (2016) "Enhancing natural killer cell-mediated lysis of lymphoma cells by combining therapeutic antibodies with CD20-specific immunoligands engaging NKG2D or NKp30," *OncoImmunology* 5(1):e1058459-1-e1058459-12.
Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.
Kwong et al. (2008) "Generation, affinity maturation, and characterization of a human anti-human NKG2D monoclonal antibody with dual antagonistic and agonistic activity," *Journal of Molecular Biology* 384(5):1143-1156.
Lin et al. (2013) "CD4+ NKG2D+ T cells induce NKG2D down-regulation in natural killer cells in CD86-RAE-1 E transgenic mice," *Immunology* 141(3):401-415.
Liu et al. (2017) "Fc engineering for Developing Therapeutic Bispecific Antibodies and Novel Scaffolds," *Frontiers in Immunology* 8(38):1-15.
Madlener et al. (2010) "A Bispecific Protein Targeting the NKG2D Receptor on Natural Killer Cells: In Vitro and In Vivo activity of ULBP2-CEA," *Blood* 116(21):2095 (3 pages).
Maeda et al. (1997) "Engineering of Functional Chimeric Protein G-Vargula Luciferase" Analytical biochemistry, 249(2):147-152.
Mcwilliams et al. (2016) "Targeting the Tumor Evasion Interaction of NKG2A and Its Ligand HLA-E Increases Natural-Killer Cell Activity in Chronic Lymphocytic Leukemia," Blood 1289-1291.
Morvan et al. (2016)."NK cells and cancer: you can teach innate cells new tricks" *Nat Rev Cancer* 16(1):7-19.
Myers et al. (2021) "Exploring the NK cell platform for cancer immunotherapy," Nature Reviews Clinical Oncology 18(2):85-100.
Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," *British Journal of Cancer* 110(2):469-478.
Nie et al. (2020) "Biology drives the discovery of bispecific antibodies as innovative therapeutics," Antibody Therapeutics 3(1):18-62.
Pakula et al. (1989) "Genetic Analysis of Protein Stability and Function," *Annu. Rev. Genet.* 23:289-310.
Petricevic et al. (2013) "Trastuzumab mediates antibody-dependent cell-mediated cytotoxicity and phagocytosis to the same extent in both adjuvant and metastatic HER2/neu breast cancer patients," *Journal of Translational Medicine* 11(307).
Raab et al. (2014) "Fc-Optimized NKG2D-Fc Constructs Induce NK Cell Antibody-Dependent Cellular Cytotoxicity Against Breast Cancer Cells Independently of HER2/neu Expession Status," *Journal of Immunology* 193(8):4261-72.
Roda-Navarro et al. (2020) "Understanding the Spatial Topology of Artificial Immunological Synapses Assembled in T Cell-Redirecting Strategies: A Major Issue in Cancer Immunotherapy," *Frontiers in Cell and Developmental Biology* 7:1-5.
Romee et al. (2013) "NK cell CD16 surface expression and function is regulated by a disintegrin and metalloprotease-17 (ADAM17)," *Blood* 121(18):3599-608.
Rothe et al. (2013) "The Bispecific Immunoligand ULBP2-aCEA Redirects Natural Killer Cells to Tumor Cells and Reveals Potent Anti-Tumor Activity Against Colon Carcinoma," *Int. J. Cancer* 134(12):2829-2840.
Safdari et al. (2013) "Antibody humanization methods—a review and update" Biotechnology and Genetic Engineering Reviews, 29(2):175-186.
Schuster et al. (2015) "Immunotherapy with the trifunctional anti-CD20 x anti-CD3 antibody FBTA05 (Lymphomun) in paediatric high-risk patients with recurrent CD20-positive B cell malignancies," *British Journal of Haematology* 169(1):90-102.
Shen et al. (2006) "Single variable domain-IgG fusion: a novel recombinant approach to Fc domain-containing bispecific antibodies" Journal of Biological Chemistry, 281(16):10706-10714.
Smits et al. (2016) "Designing multivalent proteins based on natural killer cell receptors and their ligands as immunotherapy for cancer," *Expert Opinion on Biological Therapy* 16(9):1105-1112.
Spear et al. (2013) "NKG2D ligands as therapeutic targets," *Cancer Immunology* 13:8.
Stamova et al. (2011) "Simultaneous engagement of the activatory receptors NKG2D and CD3 for retargeting of effector cells to CD33-positive malignant cells," *Leukemia* 25:1053-1056.
Steigerwald et al. (2009) "Human IgG1 antibodies antagonizing activating receptor NKG2D on natural killer cells," *mAbs* 1(2):115-127.
Steinbacher et al. (2015) "An Fc-optimized NKG2D-immunoglobulin G fusion protein for induction of natural killer cell reactivity against leukemia," *International Journal of Cancer* 136(5):1073-1084.
Strong (2002) "Asymmetric ligand recognition by the activating natural killer cell receptor NKG2D, a symmetric homodimer," *Molecular Immunology* 38(14):1029-1037.
Tay et al. (2016) "TriKEs and BiKEs join CARs on the cancer immunotherapy highway," *Human Vaccines & Immunotherapeutics* 12(11):2790-2796.
Teplyakov et al. (2014) "Antibody modeling assessment II. Structures and models" Proteins: Structure, Function, and Bioinformatics, 82(8):1563-1582.
Torres et al. (2008) "The immunoglobulin constant region contributes to affinity and specificity" Trends in immunology, 29(2):91-97.
Vaks et al. (2018) "Design Principles for Bispecific IgGs, Opportunities and Pitfalls of Artificial Disulfide Bonds," *Antibodies* 7(27):1-28.
Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," *Blood* 107(5):1955-1962.
Vyas et al. (2016) "Mono- and dual-targeting triplebodies activate natural killer cells and have anti-tumor activity in vitro and in vivo against chronic lymphocytic leukemia," Oncoimmunology 5(9):p. e1211220.
Wang et al. (2016) "A bispecific protein rG7S-MICA recruits natural killer cells and enhances NKG2D-mediated immunosurveillance against hepatocellular carcinoma," *Cancer Letters* 372(2):166-178.
Weiss-Steider et al. (2011) "Expression of MICA, MICB and NKG2D in human leukemic myelomonocytic and cervical cancer cells," *Journal of Experimental & Clinical Cancer Research* 30(1):37.
Written Opinion for International Application No. PCT/US2019/045677 dated Nov. 8, 2019.
Xu et al. (2014) "Production of bispecific antibodies in "knobs-into-holes" using a cell-free expression system," mAbs 7(1)231-242.
Xu et al. (2019) "A VEGFR2-MICA bispecific antibody activates tumor-infiltrating lymphocytes and exhibits potent anti-tumor efficacy in mice," *Cancer Immunology Immunotherapy* 68(9):1429-1441.
Yeap et al. (2016) "CD16 is indispensable for antibody dependent cellular cytotoxicity by human monocytes," *Scientific Reports* 6:34310.
Young et al. (1995) "Thermal stabilization of a single-chain Fv antibody fragment by introduction of a disulphide bond," *FEBS Letters* 377(2):135-139.
Atwell et al., "Stable Heterodimers from Remodeling the Domain Interface of a Homodimer using a Phage Display Library", J Mol Biol (1997) 270:26-35.
Baek et al., 2014 "Construction of a Large Synthetic Human Fab Antibody Library on Yeast Cell Surface by Optimized Yeast Mating," J Microbiol Biotechnol 24(3):408-420.

(56) References Cited

OTHER PUBLICATIONS

Boltz (2011) "Bi-specific Aptamers mediating Tumour Cell Lysis", Dissertation, M.Sc. Molekulare Biotechnologie, Technische Universität Darmstadt, Darmstadt, pp. 1-133, XP55860228, Retrieved from the Internet: URL:https://d-nb.inf0/1105386902/34.

Chan et al., "Therapeutic antibodies for autoimmunity and inflammation", Nature Reviews (2010) 10:301-316.

Choi et al., 2013 "A Heterodimeric Fc-Based Bispecific Antibody Simultaneously Targeting VEGFR-2 and Met Exhibits Potent Antitumor Activity," Mol Cancer Ther 12(12):2748-59.

Choi et al., "Engineering of Immunoglobulin Fc Heterodimers Using Yeast Surface-Displayed Combinatorial Fc Library Screening," PloS One. Dec. 16, 2015; 10(12);e0145349; pp. 1-20.

Choi et al., "Crystal structures of immunoglobulin Fc heterodimers reveal the molecular basis for heterodimer formation," Molecular Immunology (2015) 65(2):377-83.

Communication dated May 16, 2012, from the European Patent Office in application No. EP13859121.9 (11 pages).

Communication dated May 23, 2019, from the European Patent Office in application No. EP16855701.5 (17 pages).

Cunningham et al., "Subgroups of Amino Acid Sequences in the Variable Regions of Immunoglobulin Heavy Chains," Proc Natl Acad Sci USA (1969) 64(3):997-1003.

Davis et al., "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Eng Des Sel (2010) 23(4):195-202.

Examination Report dated Nov. 20, 2019 from the Intellectual Property Office of India in Application No. 5014/DELNP/2015 (6 pages).

Feng et al., "Design, Expression and Characterization of a Soluble Single-Chain Functional Human Neonatal Fc Receptor," Protein Expr Purif (2011) 79(1):66-71.

Gunasekaran et al., 2010 "Enhancing Antibody Fc Heterodimer Formation through Electrostatic Steering Effects: Applications to Bispecific Molecules and Monovalent IgG," J Biol Chem 285(25):19637-46.

Ha et al., 2016 "Immunoglobulin Fc Heterodimer Platform Technology: From Design to Applications in Therapeutic Antibodies and Proteins," Front Immuno vol. 7, Article 394 (16 pages).

Holliger et al., "Engineered antibody fragments and the rise of single domains," Nat Biotechnol (2005) 23(9):1126-36.

Kim et al., 2007 "Comparative Analyses of Complex Formation and Binding Sites Between Human Tumor Necrosis Factor-Alpha and Its Three Antagonists Elucidate Their Different Neutralizing Mechanisms," J Mol Biol 374:1374-88.

Klein et al, 2012 "Progress in overcoming the chain association issue in bispecific heterodimeric IgG antibodies," mAbs 4(6);653-663.

Korean Intellectual Property Office, Communication dated Mar. 24, 2015 issued in corresponding Korean application No. 10-2013-0145564.

Korean Intellectual Property Office, Communication issued on Jan. 10, 2017 in application No. PCT/KR2016/011396.

Korean Intellectual Property Office, Communication issued on Mar. 11, 2014 in counterpart application No. PCT/KR2013/010861.

Korean Intellectual Property Office, Notice of Final Rejection for Korean Application No. 10-2015-0142181 dated Jan. 25, 2018.

Korean Intellectual Property Office, Notification of Reason for Refusal for Korean Application No. 10-2015-0142181 dated Jun. 27, 2017.

Korean Intellectual Property Office, Written Opinion for PCT/KR2016/011396 dated Jan. 10, 2017 f PCT/ISA/2371.

Lu et al., "Simultaneous Blockade of Both the Epidermal Growth Factor Receptor and the Insulin-Like Growth Factor Receptor Signaling Pathways in Cancer Cells with a Fully Human Recombinant Bispecific Antibody," J Biol Chem (2004) 279(4):2856-65.

Merchant et al., "An efficient route to human bispecific IgG," Nature Biotechnology 16, 677-681 (1998) doi :10.1038/nbt0798-677.

Miller et al., "Design, Construction, and in Vitro Analyses of Multivalent Antibodies," J Immunol (2003) 170(9):4854-61.

Milstein et al., "Hybrid Hybridomas and Their Use in Immunohistochemistry," Nature (1983) 305:537-540.

Moore et al., "A novel bispecific antibody format enables simultaneous bivalent and monovalent co-engagement of distinct target antigens", mAbs 3:6, 546-557; Nov./Dec. 2011, Landes Bioscience, DOI: 10.4161/mabs.3.6.18123.

Ridgway et al., 1996 "'Knobs-into-Holes' engineering of antibody Ch3 domains for heavy chain heterodimerization," Protein Engineering 9(7):617-21.

Strop et al., "Generating Bispecific Human IgG1 and IgG2 Antibodies from Any Antibody Pair," J Mol Biol (2012) 420:204-19.

Von Kreudenstein et al., "Improving Biophysical Properties of a Bispecific Antibody Scaffold to Aid Developability: Quality by Molecular Design," mAbs (2013) 5(5):646-54.

Von Kreudenstein et al., "Protein Engineering and the Use of Molecular Modeling and Simulation: The Case of Heterodimeric Fc Engineering", Methods (2014) 65(1):77-94.

Xie et al., 2005 "A new format of bispecific antibody: highly efficient heterodimerization, expression and tumor cell lysis," J Immunol Methods 296(1):95-101.

Bogen, J. P. et al., "Design of a Trispecific Checkpoint Inhibitor and Natural Killer Cell Engager Based on a 2+1 Common Light Chain Antibody Architecture", Frontiers in Immunology (2021), vol. 12, 16 pgs.

Briney, B. et al. "Commonality Despite Exceptional Diversity in the Baseline Human Antibody Repertoire", Nature (2019), vol. 566:393, 19 pgs.

Dasgupta, S. et al., "Inhibition of NK Cell Activity through TGF-b1 by Down-Regulation of NKG2D in a Murine Model of Head and Neck Cancer", J Immunol (2005), vol. 175:8, pp. 5541-5550.

Demaria, O. et al. "Natural killer cell engagers in cancer immunotherapy: Next generation of immuno-oncology treatments", Eur. J. Immunol. (2021), vol. 51, pp. 1934-1942.

Feng, P. et al., "NKG2D-Fc Fusion Protein Promotes Antitumor Immunity Through the Depletion of Immunosuppressive Cells", Cancer Immunol. Immunother. (2020), vol. 69:10, pp. 2147-2155.

Giuliani, M. et al. "Activation of NK cells and disruption of PD-L1/PD-1 axis: two different ways for lenalidomide to block myeloma progression", Oncotarget (2017), vol. 8:14, pp. 24031-24044.

Katano, I. et al. "Predominant Development of Mature and Functional Human NK Cells in a Novel Human IL-2-Producing Transgenic NOG Mouse" J. Immunol. (2015), vol. 194:7, pp. 3513-3525.

Khan, T. et al. "Adjustable Locks and Flexible Keys: Plasticity of Epitope-Paratope Interactions in Germline Antibodies", J. Immunol (2014), vol. 192, pp. 5398-5405.

Miller, J. S. et al. "Annual Review of Cancer Biology Natural Killer Cells in Cancer Immunotherapy", Annu. Rev. Cancer Biol. (2019), vol. 8:3, pp. 77-103.

Poosaria, V. G. et al. "Computational de novo Design of Antibodies binding to a Peptide with High Affinity", Biotechnol. Bioeng. (2017), vol. 114:6, pp. 1331-1342.

Spiess, C. et al. "Alternative Molecular Formats and Therapeutic Applications for Bispecific Antibodies", Molecular Immunology (2015), vol. 67, pp. 95-106.

Watanabe, M. et al. "NKG2D Functions as an Activating Receptor on Natural Killer Cells in the Common Marmoset (*Callithrix jacchus*)", International Immunology (2014), vol. 26:11, pp. 597-606.

Whalen, K. A. et al. "Engaging Natural Killer Cells for Cancer Therapy via NKG2D, CD16A and Other Receptors", MABS (2023), vol. 15:1, 15 pgs.

Xie, W., et al. "VEGFR2 Targeted Antibody Fused with MICA Stimultes NKG2D Mediated Immunosurveillance and Exhibits Potent Anti-Tumor Activity Against Breast Cancer," Oncotarget (2015), vol. 7:13, pp. 6455-16471.

Yang, F. et al. "Bispecific Antibodies as a Development Platform for New Concepts and Treatment Strategies" Int. J. Mol. Sci. (2017), vol. 18:48, 21 pgs.

U.S. Appl. No. 16/483,330, filed Aug. 2, 2019, U.S. Pat. No. 11,834,506, Dec. 5, 2023.

(56) References Cited

OTHER PUBLICATIONS

U.S. Appl. No. 18/482,629, filed Oct. 6, 2023.
U.S. Appl. No. 16/484,936, filed Aug. 9, 2019.
U.S. Appl. No. 486,921, filed Aug. 19, 2019.
U.S. Appl. No. 16/486,569, filed Aug. 16, 2019, U.S. Pat. No. 11,884,732, Jan. 30, 2024.
U.S. Appl. No. 18/541,475, filed Dec. 15, 2023.
U.S. Appl. No. 18/304,652, filed Apr. 21, 2023.
U.S. Appl. No. 17/095,238, filed Nov. 11, 2020.
U.S. Appl. No. 18/107,292, filed Feb. 8, 2023.
U.S. Appl. No. 16/615,261, filed Nov. 20, 2019.
U.S. Appl. No. 16/635,079, filed Jan. 29, 2020.
U.S. Appl. No. 18/442,190, filed Feb. 15, 2024.
U.S. Appl. No. 18/108,961, filed Feb. 13, 2023.
U.S. Appl. No. 16/645,613, filed Mar. 9, 2020.
U.S. Appl. No. 16/967,216, filed Aug. 4, 2020, U.S. Pat. No. 11,884,733, Jan. 30, 2024.
U.S. Appl. No. 18/501,413, filed Nov. 3, 2023, U.S. Pat. No. 11,939,384, Mar. 26, 2024.
U.S. Appl. No. 18/501,419, filed Nov. 3, 2023, U.S. Pat. No. 12,129,300, Oct. 9, 2024.
U.S. Appl. No. 18/501,427, filed Nov. 3, 2023.
U.S. Appl. No. 17/058,335, filed Nov. 24, 2020.
U.S. Appl. No. 16/971,098, filed Aug. 19, 2020.
U.S. Appl. No. 16/967,218, filed Aug. 4, 2020.
U.S. Appl. No. 18/149,965, filed Jan. 4, 2023.
U.S. Appl. No. 18/150,040, filed Jan. 4, 2023.
U.S. Appl. No. 17/055,792, filed Nov. 16, 2020.
U.S. Appl. No. 17/265,876, filed Feb. 4, 2021.
U.S. Appl. No. 17/543,628, filed Dec. 6, 2021.
U.S. Appl. No. 17/266,349, filed Feb. 5, 2021.
U.S. Appl. No. 17/265,879, filed Feb. 4, 2021.
U.S. Appl. No. 17/266,966, filed Feb. 8, 2021.
U.S. Appl. No. 17/929,282, filed Sep. 1, 2022.
U.S. Appl. No. 17/287,849, filed Apr. 22, 2021.
U.S. Appl. No. 16/971,104, filed Aug. 19, 2020.
U.S. Appl. No. 17/682,367, filed Feb. 28, 2022.
U.S. Appl. No. 17/769,160, filed Apr. 14, 2022.
U.S. Appl. No. 18/003,308, filed Dec. 23, 2022.
U.S. Appl. No. 17/920,174, filed Oct. 20, 2022.
U.S. Appl. No. 17/308,691, filed May 5, 2021.
U.S. Appl. No. 18/622,766, filed Mar. 29, 2024.
U.S. Appl. No. 17/686,238, filed Mar. 3, 2022.
U.S. Appl. No. 18/166,769, filed Feb. 9, 2023.
U.S. Appl. No. 18/177,847, filed Mar. 3, 2023.
U.S. Appl. No. 18/366,876, filed Aug. 8, 2023.
Epling-Burnette, P. et al., Dysregulated NK Receptor Expression in Patients with Lymphoproliferative Disease of Granular Lymphocytes, Blood (2004), vol. 103:9, pp. 3431-3439.
Novus Biologicals, 2015, "CD-16: Find me on macrophages, neutrophils and NK cells," https://www.novusbio.com/antibody-news/antibodies/cd16-find-me-on-macrophages-neutrophils-and-nk-cells.
Chen, L. et al. "Targeting FLT3 by Chimeric Antigen Receptor T Cells for the Treatment of Acute Myeloid Leukemia", Leukemia (2017), vol. 31:8, pp. 1830-1834.
Eruslanov, E. et al. "Expansion of CCR8+ Inflammatory Myeloid Cells in Cancer Patients with Urothelial and Renal Carcinomas," Clinical Cancer Research (2013), vol. 19:7, pp. 1670-1680.
Nersesian, S. et al., "N K cell infiltration is associated with improved overall survival in solid cancers: A systematic review and meta-analysis," Translational Oncology (2020), vol. 14, 20 pgs.
Plitas, G. et al., "Regulatory T Cells Exhibit Distinct Features in Human Breast Cancer," Immunity (2016), vol. 45:5, pp. 1122-1134.
Raynaud, A., "Anti-NKG2D single domain-based antibodies for the modulation of anti-tumor immune response," Oncoimmunology (2021), vol. 10:1, pp. e1854529-1-e1854529-14.
Stallard, J. et al., "New Approach Could Boost Immunotherapy for Breast Cancer," Memorial Sloan Kettering Cancer Center (2016), 5 pgs.
Weatherill, E. E. et al., "Towards a universal disulphide stabilised single chain Fv format: importance of interchain disulphide bond location and vL-vH orientation," Protein Engineering, Design, and Selection (2012), vol. 25:7, pp. 321-329.
Liu, R. et al., "Fc-Engineering for Modulated Effector Functions—Improving Antibodies for Cancer Treatment", Antibodies (2020), vol. 9:64, 34 pgs.
Davis, Z. B. et al., "Natural Killer Cells Unleashed: Checkpoint Receptor Blockade and BiKE/TriKE Utilization in NK-Mediated Anti-tumor Immunotherapy", Seminars in Immunology (2017), vol. 31, pp. 67-75.
Bryceson, Y. T., et al., "Activation, Coactivation, and Costimulation of Resting Human Natural Killer Cells", Immunological Reviews (2006), vol. 214, pp. 73-91.
Author unknown: Anti-NKG2D [ADI-27749 (A49)] Standard Size Ab03079-3.0, Absolute Antibody (2023), https://Absoluteantibody.com, 1 pg.
Kontermann, R. E. et al. "Bispecific Antibodies", Drug Discovery Today (2015), vol. 20:7, pp. 838-847.
Bartlett, J. B. et al. "Lenalidomide and Pomalidomide Strongly Enhance Tumor Cell Killing In Vitro During Antibody-Dependent Cellular Cytotoxicity (ADCC) Mediated by Trastuzumab, Cetuximab and Rituximab", American Society of Clinical Oncology (2007), vol. 25:18S, 19 pgs.
Hilpert, J. et al. "Comprehensive Analysis of NKG2D Ligand Expression and Release in Leukemia: Implications for NKG2D-Mediated NK Cell Responses", J Immunol (2012), vol. 189:3, pp. 1360-1371.
Rincón, J. "El receptor NKG2D en la Frontera De La Inmunovigilancia Y La Carcinogénesis", Publicación Científica En Ciencias Biomédicas (2014), vol. 2:21, pp. 237-243.
Kim, J. et al. "Evidence That the Hinge Region Plays a Role in Maintaining Serum Levels of the Murine IgG1 Molecule", Molecular Immunology (1995), vol. 32:7, pp. 467-475.
Watzl, C. et al. "Signal Transduction During Activation and Inhibition of Natural Killer Cells", Curr Protoc Immunol. (2010), vol. 90:1, 19 pgs.
Wu, L. et al. "Lenalidomide Enhances Antibody-Dependent Cellular Cytotoxicity of Solid Tumor Cells In Vitro: Influence of Host Immune and Tumor Markers", Cancer Immunology, Immunotherapy, Springer (2011), vol. 60:1, pp. 61-73.
Yang, L. et al. "Enhancing NK Cell-Mediated Cytotoxicity to Cisplatin-Resistant Lung Cancer Cells via MEK/Erk Signaling Inhibition", Nature Scientific Reports (2017), vol. 7:7958, 13 pgs.
Ho, E. et al. "Costimulation of Multiple NK Cell Activation Receptors by NKG2D", Journal of Immunology (2002), vol. 169:7, pp. 3667-3675.
Muyldermans, S. "Nanobodies: Natural Single-Domain Antibodies", Annual Review of Biochemistry (2013), vol. 82:1, pp. 775-797.

* cited by examiner

PROTEINS BINDING NKG2D, CD16 AND A TUMOR-ASSOCIATED ANTIGEN

CROSS-REFERENCE TO RELATED APPLICATIONS

This application claims the benefit of and priority to U.S. Provisional Patent Application No. 62/716,110, filed Aug. 8, 2018, the disclosure of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Aug. 6, 2019, is named DFY-061WO_ST25.txt and is 342,008 bytes in size.

FIELD OF THE INVENTION

The invention relates to multi-specific binding proteins that bind to NKG2D, CD16, and at least one tumor-associated antigen.

BACKGROUND

Cancer continues to be a significant health problem despite the substantial research efforts and scientific advances reported in the literature for treating this disease. Blood and bone marrow cancers are frequently diagnosed cancer types, including multiple myelomas, leukemia, and lymphomas. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, e.g., WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-γ and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals. NKG2D is a type-II transmembrane protein that is expressed by essentially all natural killer cells where NKG2D serves as an activating receptor. NKG2D is also be found on T cells where it acts as a costimulatory receptor. The ability to modulate NK cell function via NKG2D is useful in various therapeutic contexts including malignancy.

SUMMARY

The invention provides multi-specific binding proteins that bind to the NKG2D receptor and CD16 receptor on natural killer cells, and a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. Such proteins can engage more than one kind of NK-activating receptor, and may block the binding of natural ligands to NKG2D. In certain embodiments, the proteins can agonize NK cells in humans. In some embodiments, the proteins can agonize NK cells in humans and in other species such as rodents and cynomolgus monkeys. Various aspects and embodiments of the invention are described in further detail below.

Accordingly, one aspect of the invention provides a protein that incorporates a first antigen-binding site that binds NKG2D; a second antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL; and an antibody Fc domain, a portion thereof sufficient to bind CD16, or a third antigen-binding site that binds CD16.

The antigen-binding sites may each incorporate an antibody heavy chain variable domain and an antibody light chain variable domain (e.g., arranged as in an antibody, or fused together to from an scFv), or one or more of the antigen-binding sites may be a single domain antibody, such as a $V_H H$ antibody like a camelid antibody or a $V_{NAR}$ antibody like those found in cartilaginous fish.

In one aspect, the present invention provides multi-specific binding proteins, which include a first antigen-binding site that binds NKG2D, a second antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, an antibody Fc domain, a portion thereof sufficient to bind CD16, or a third antigen-binding site that binds CD16, and an additional antigen-binding site that binds the same tumor-associated antigen as the second tumor-associated site (e.g., a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL).

The present invention provides a protein in which the first antigen-binding site that binds NKG2D is a single-chain variable fragment (scFv), and the second and/or the additional antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL is an Fab fragment. The present disclosure also provides a protein in which the first antigen-binding site that binds NKG2D is an scFv, and the second and/or the additional antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL is an scFv.

The present invention provides a protein in which the first antigen-binding site that binds NKG2D is an Fab fragment, and the second antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL is an scFv.

The present invention provides a protein in which the first antigen-binding site that binds NKG2D is an scFv, and the second antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL is an Fab fragment.

The antigen-binding sites may each incorporate an antibody heavy chain variable domain and an antibody light chain variable domain (e.g., arranged as in an antibody, or fused together to from an scFv), or one or more of the antigen-binding sites may be a single domain antibody, such as a $V_HH$ antibody like a camelid antibody or a $V_{NAR}$ antibody like those found in cartilaginous fish.

In one aspect, the present invention provides multi-specific binding proteins that bind to the NKG2D receptor and CD16 receptor on natural killer cells, and a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. The first antigen-binding site that binds NKG2D can include a heavy chain variable domain at least 90% identical to an amino acid sequence selected from: SEQ ID NO:1, SEQ ID NO:41, SEQ ID NO:49, SEQ ID NO:57, SEQ ID NO:59, SEQ ID NO:61, SEQ ID NO:69, SEQ ID NO:77, SEQ ID NO:85, and SEQ ID NO:93.

The first antigen-binding site, which binds to NKG2D, in some embodiments can incorporate a heavy chain variable domain related to SEQ ID NO:1, such as by having an amino acid sequence at least 90% (e.g., 90%, 91%, 92%, 93%, 94%, 95%, 96%, 97%, 98%, 99%, or 100%) identical to SEQ ID NO:1, and/or incorporating amino acid sequences identical to the CDR1 (SEQ ID NO:105), CDR2 (SEQ ID NO:106), and CDR3 (SEQ ID NO:107) sequences of SEQ ID NO:1. The heavy chain variable domain related to SEQ ID NO:1 can be coupled with a variety of light chain variable domains to form an NKG2D binding site. For example, the first antigen-binding site that incorporates a heavy chain variable domain related to SEQ ID NO:1 can further incorporate a light chain variable domain selected from any one of the sequences related to SEQ ID NOs:2, 4, 6, 8, 10, 12, 14, 16, 18, 20, 22, 24, 26, 28, 30, 32, 34, 36, 38, and 40. For example, the first antigen-binding site incorporates a heavy chain variable domain with amino acid sequences at least 90% (e.g., 90%, 91%, 92%, 93%, 94%, 95%, 96%, 97%, 98%, 99%, or 100%) identical to SEQ ID NO:1 and a light chain variable domain with amino acid sequences at least 90% (e.g., 90%, 91%, 92%, 93%, 94%, 95%, 96%, 97%, 98%, 99%, or 100%) identical to any one of the sequences selected from SEQ ID NOs:2, 4, 6, 8, 10, 12, 14, 16, 18, 20, 22, 24, 26, 28, 30, 32, 34, 36, 38, and 40.

Alternatively, the first antigen-binding site that binds NKG2D can incorporate a heavy chain variable domain related to SEQ ID NO:41 and a light chain variable domain related to SEQ ID NO:42. For example, the heavy chain variable domain of the first antigen binding site can be at least 90% (e.g., 90%, 91%, 92%, 93%, 94%, 95%, 96%, 97%, 98%, 99%, or 100%) identical to SEQ ID NO:41, and/or incorporate amino acid sequences identical to the CDR1 (SEQ ID NO:43 or 431), CDR2 (SEQ ID NO:44), and CDR3 (SEQ ID NO:45 or 432) sequences of SEQ ID NO:41. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:42, and/or incorporate amino acid sequences identical to the CDR1 (SEQ ID NO:46), CDR2 (SEQ ID NO:47), and CDR3 (SEQ ID NO:48) sequences of SEQ ID NO:42.

In other embodiments, the first antigen-binding site that binds NKG2D can incorporate a heavy chain variable domain related to SEQ ID NO:49 and a light chain variable domain related to SEQ ID NO:50. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:49, and/or incorporate amino acid sequences identical to the CDR1 (SEQ ID NO:51 or 433), CDR2 (SEQ ID NO:52), and CDR3 (SEQ ID NO:53 or 434) sequences of SEQ ID NO:49. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:50, and/or incorporate amino acid sequences identical to the CDR1 (SEQ ID NO:54), CDR2 (SEQ ID NO:55), and CDR3 (SEQ ID NO:56) sequences of SEQ ID NO:50.

Alternatively, the first antigen-binding site that binds NKG2D can incorporate a heavy chain variable domain related to SEQ ID NO:57 and a light chain variable domain related to SEQ ID NO:58, such as by having amino acid sequences at least 90% (e.g., 90%, 91%, 92%, 93%, 94%, 95%, 96%, 97%, 98%, 99%, or 100%) identical to SEQ ID NO:57 and at least 90% (e.g., 90%, 91%, 92%, 93%, 94%, 95%, 96%, 97%, 98%, 99%, or 100%) identical to SEQ ID NO:58, respectively.

In another embodiment, the first antigen-binding site that binds NKG2D can incorporate a heavy chain variable domain related to SEQ ID NO:59 and a light chain variable domain related to SEQ ID NO:60, For example, the heavy chain variable domain of the first antigen binding site can be at least 90% (e.g., 90%, 91%, 92%, 93%, 94%, 95%, 96%, 97%, 98%, 99%, or 100%) identical to SEQ ID NO:59, and/or incorporate amino acid sequences identical to the CDR1 (SEQ ID NO:134), CDR2 (SEQ ID NO:135), and CDR3 (SEQ ID NO:136) sequences of SEQ ID NO:59. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:60, and/or incorporate amino acid sequences identical to the CDR1 (SEQ ID NO:137), CDR2 (SEQ ID NO:138), and CDR3 (SEQ ID NO:139) sequences of SEQ ID NO:60.

The first antigen-binding site, which binds to NKG2D, in some embodiments can incorporate a heavy chain variable domain related to SEQ ID NO:61 and a light chain variable domain related to SEQ ID NO:62. For example, the heavy chain variable domain of the first antigen binding site can be at least 90% (e.g., 90%, 91%, 92%, 93%, 94%, 95%, 96%, 97%, 98%, 99%, or 100%) identical to SEQ ID NO:61, and/or incorporate amino acid sequences identical to the CDR1 (SEQ ID NO:63 or 435), CDR2 (SEQ ID NO:64), and CDR3 (SEQ ID NO:65 or 436) sequences of SEQ ID NO:61. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:62, and/or incorporate amino acid sequences identical to the CDR1 (SEQ ID NO:66), CDR2 (SEQ ID NO:67), and CDR3 (SEQ ID NO:68) sequences of SEQ ID NO:62.

In some embodiments, the first antigen-binding site that binds NKG2D can incorporate a heavy chain variable domain related to SEQ ID NO:69 and a light chain variable domain related to SEQ ID NO:70. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:69, and/or incorporate amino acid sequences identical to the CDR1 (SEQ ID NO:71 or 437), CDR2 (SEQ ID NO:72), and CDR3 (SEQ ID NO:73 or 408) sequences of SEQ ID NO:69. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:70, and/or incorporate amino acid sequences identical to the CDR1 (SEQ ID NO:74), CDR2 (SEQ ID NO:75), and CDR3 (SEQ ID NO:76) sequences of SEQ ID NO:70.

In some embodiments, the first antigen-binding site that binds NKG2D can incorporate a heavy chain variable domain related to SEQ ID NO:77 and a light chain variable domain related to SEQ ID NO:78. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:77, and/or incorporate amino acid sequences identical to the CDR1 (SEQ ID NO:79 or 409), CDR2 (SEQ ID NO:80), and CDR3 (SEQ ID NO:81 or 411) sequences of SEQ ID NO:77. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:78, and/or incorporate amino acid sequences identical to the CDR1 (SEQ ID NO:82), CDR2 (SEQ ID NO:83), and CDR3 (SEQ ID NO:84) sequences of SEQ ID NO:78.

In some embodiments, the first antigen-binding site that binds NKG2D can incorporate a heavy chain variable domain related to SEQ ID NO:85 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:85, and/or incorporate amino acid sequences identical to the CDR1 (SEQ ID NO:87 or 387), CDR2 (SEQ ID NO:88), and CDR3 (SEQ ID NO:89 or 412) sequences of SEQ ID NO:85. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the first antigen-binding site that binds NKG2D can incorporate a heavy chain variable domain related to SEQ ID NO:93 and a light chain variable domain related to SEQ ID NO:94. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:93, and/or incorporate amino acid sequences identical to the CDR1 (SEQ ID NO:95 or 421), CDR2 (SEQ ID NO:96), and CDR3 (SEQ ID NO:97 or 422) sequences of SEQ ID NO:93. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:94, and/or incorporate amino acid sequences identical to the CDR1 (SEQ ID NO:98), CDR2 (SEQ ID NO:99), and CDR3 (SEQ ID NO:100) sequences of SEQ ID NO:94.

In some embodiments, the first antigen-binding site that binds NKG2D can incorporate a heavy chain variable domain related to SEQ ID NO:101 and a light chain variable domain related to SEQ ID NO:102, such as by having amino acid sequences at least 90% (e.g., 90%, 91%, 92%, 93%, 94%, 95%, 96%, 97%, 98%, 99%, or 100%) identical to SEQ ID NO:101 and at least 90% (e.g., 90%, 91%, 92%, 93%, 94%, 95%, 96%, 97%, 98%, 99%, or 100%) identical to SEQ ID NO:102, respectively.

In some embodiments, the first antigen-binding site that binds NKG2D can incorporate a heavy chain variable domain related to SEQ ID NO:103 and a light chain variable domain related to SEQ ID NO:104, such as by having amino acid sequences at least 90% (e.g., 90%, 91%, 92%, 93%, 94%, 95%, 96%, 97%, 98%, 99%, or 100%) identical to SEQ ID NO:103 and at least 90% (e.g., 90%, 91%, 92%, 93%, 94%, 95%, 96%, 97%, 98%, 99%, or 100%) identical to SEQ ID NO:104, respectively.

In some embodiments, the first antigen-binding site can incorporate a heavy chain variable domain related to SEQ ID NO:388 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:388, and/or incorporate amino acid sequences identical to the CDR1 (SEQ ID NO:87 or 387), CDR2 (SEQ ID NO:88), and CDR3 (SEQ ID NO:389 or 390) sequences of SEQ ID NO:388. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the first antigen-binding site can incorporate a heavy chain variable domain related to SEQ ID NO:391 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:391, and/or incorporate amino acid sequences identical to the CDR1 (SEQ ID NO:87 or 387), CDR2 (SEQ ID NO:88), and CDR3 (SEQ ID NO:392 or 393) sequences of SEQ ID NO:391. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the first antigen-binding site can incorporate a heavy chain variable domain related to SEQ ID NO:394 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:394, and/or incorporate amino acid sequences identical to the CDR1 (SEQ ID NO:87 or 387), CDR2 (SEQ ID NO:88), and CDR3 (SEQ ID NO:395 or 396) sequences of SEQ ID NO:394. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the first antigen-binding site can incorporate a heavy chain variable domain related to SEQ ID NO:397 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:397, and/or incorporate amino acid sequences identical to the CDR1 (SEQ ID NO:87 or 387), CDR2 (SEQ ID NO:88), and CDR3 (SEQ ID NO:398 or 399) sequences of SEQ ID NO:397. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the first antigen-binding site can incorporate a heavy chain variable domain related to SEQ ID NO:400 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:400, and/or incorporate amino acid sequences identical to the CDR1 (SEQ ID NO:87 or 387), CDR2 (SEQ ID NO:88), and CDR3 (SEQ ID NO:401 or 402) sequences of SEQ ID NO:400. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the first antigen-binding site can incorporate a heavy chain variable domain related to SEQ ID NO:403 and a light chain variable domain related to SEQ ID NO:86. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:403, and/or incorporate amino acid sequences identical to the CDR1 (SEQ ID NO:87 or 387), CDR2 (SEQ ID NO:88), and CDR3 (SEQ ID NO:404 or 405) sequences of SEQ ID NO:403. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:90), CDR2 (SEQ ID NO:91), and CDR3 (SEQ ID NO:92) sequences of SEQ ID NO:86.

In some embodiments, the second antigen-binding site binding to KIT can incorporate a heavy chain variable domain related to SEQ ID NO:109 and a light chain variable domain related to SEQ ID NO:113. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:109, and/or incorporate amino acid sequences identical to the CDR1 (SEQ ID NO:110), CDR2 (SEQ ID NO:111), and CDR3 (SEQ ID NO:112) sequences of SEQ ID NO:109. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:113, and/or incorporate amino acid sequences identical to the CDR1 (SEQ ID NO:114), CDR2 (SEQ ID NO:115), and CDR3 (SEQ ID NO:116) sequences of SEQ ID NO:113.

Alternatively, the second antigen-binding site binding to KIT can incorporate a heavy chain variable domain related to SEQ ID NO:117 and a light chain variable domain related to SEQ ID NO:121. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:117, and/or incorporate amino acid sequences identical to the CDR1 (SEQ ID NO:118), CDR2 (SEQ ID NO:119), and CDR3 (SEQ ID NO:120) sequences of SEQ ID NO:117. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:121, and/or incorporate amino acid sequences identical to the CDR1 (SEQ ID NO:122), CDR2 (SEQ ID NO:123), and CDR3 (SEQ ID NO:124) sequences of SEQ ID NO:121.

In some embodiments, the second antigen-binding site binding to F3 can incorporate a heavy chain variable domain related to SEQ ID NO:126 and a light chain variable domain related to SEQ ID NO:130. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:126, and/or incorporate amino acid sequences identical to the CDR1 (SEQ ID NO:127), CDR2 (SEQ ID NO:128), and CDR3 (SEQ ID NO:129) sequences of SEQ ID NO:126. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:130, and/or incorporate amino acid sequences identical to the CDR1 (SEQ ID NO:131), CDR2 (SEQ ID NO:132), and CDR3 (SEQ ID NO:133) sequences of SEQ ID NO:130.

In some embodiments, the second antigen-binding site binding to F3 can incorporate a heavy chain variable domain related to SEQ ID NO:140 and a light chain variable domain related to SEQ ID NO:144. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:140, and/or incorporate amino acid sequences identical to the CDR1 (SEQ ID NO:141), CDR2 (SEQ ID NO:142), and CDR3 (SEQ ID NO:143) sequences of SEQ ID NO:140. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:144, and/or incorporate amino acid sequences identical to the CDR1 (SEQ ID NO:145), CDR2 (SEQ ID NO:146), and CDR3 (SEQ ID NO:147) sequences of SEQ ID NO:144.

In some embodiments, the second antigen-binding site binding to IGF1R can incorporate a heavy chain variable domain related to SEQ ID NO:149 and a light chain variable domain related to SEQ ID NO:153. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:149, and/or incorporate amino acid sequences identical to the CDR1 (SEQ ID NO:150), CDR2 (SEQ ID NO:151), and CDR3 (SEQ ID NO:152) sequences of SEQ ID NO:149. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:153, and/or incorporate amino acid sequences identical to the CDR1 (SEQ ID NO:154), CDR2 (SEQ ID NO:155), and CDR3 (SEQ ID NO:156) sequences of SEQ ID NO:153.

In some embodiments, the second antigen-binding site binding to IGF1R can incorporate a heavy chain variable domain related to SEQ ID NO:157 and a light chain variable domain related to SEQ ID NO:161. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:157, and/or incorporate amino acid sequences identical to the CDR1 (SEQ ID NO:158), CDR2 (SEQ ID NO:159), and CDR3 (SEQ ID NO:160) sequences of SEQ ID NO:157. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:161, and/or incorporate amino acid sequences identical to the CDR1 (SEQ ID NO:162), CDR2 (SEQ ID NO:163), and CDR3 (SEQ ID NO:164) sequences of SEQ ID NO:161.

In some embodiments, the second antigen-binding site binding to Lewis Y can incorporate a heavy chain variable domain related to SEQ ID NO:166 and a light chain variable domain related to SEQ ID NO:170. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:166, and/or incorporate amino acid sequences identical to the CDR1 (SEQ ID NO:167), CDR2 (SEQ ID NO:168), and CDR3 (SEQ ID NO:169) sequences of SEQ ID NO:166. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:170, and/or incorporate amino acid sequences identical to the CDR1 (SEQ ID NO:171), CDR2 (SEQ ID NO:172), and CDR3 (SEQ ID NO:173) sequences of SEQ ID NO:170.

In some embodiments, the second antigen-binding site binding to Lewis Y can incorporate a heavy chain variable domain related to SEQ ID NO:174 and a light chain variable domain related to SEQ ID NO:178. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:174, and/or incorporate amino acid sequences identical to the CDR1 (SEQ ID NO:175), CDR2 (SEQ ID NO:176), and CDR3 (SEQ ID NO:177) sequences of SEQ ID NO:174. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:178, and/or incorporate amino acid sequences identical to the CDR1 (SEQ ID NO:179), CDR2 (SEQ ID NO:180), and CDR3 (SEQ ID NO:181) sequences of SEQ ID NO:178.

In some embodiments, the second antigen-binding site binding to MUC13 can incorporate a heavy chain variable domain related to SEQ ID NO:182 and a light chain variable domain related to SEQ ID NO:186. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:182, and/or incorporate amino acid sequences identical to the CDR1 (SEQ ID NO:183), CDR2 (SEQ ID NO:184), and CDR3 (SEQ ID NO:185) sequences of SEQ ID NO:182. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:186, and/or incorporate amino acid sequences identical to the CDR1 (SEQ ID NO:187), CDR2 (SEQ ID NO:188), and CDR3 (SEQ ID NO:189) sequences of SEQ ID NO:186.

In some embodiments, the second antigen-binding site binds to a portion of MUC4 (SEQ ID NO:191).

In some embodiments, the second antigen-binding site binding to MCAM can incorporate a heavy chain variable domain related to SEQ ID NO:192 and a light chain variable domain related to SEQ ID NO:196. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:192, and/or incorporate amino acid sequences identical to the CDR1 (SEQ ID NO:193), CDR2 (SEQ ID NO:194), and CDR3 (SEQ ID NO:195) sequences of SEQ ID NO:192. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:196, and/or incorporate amino acid sequences identical to the CDR1 (SEQ ID NO:197), CDR2 (SEQ ID NO:198), and CDR3 (SEQ ID NO:199) sequences of SEQ ID NO:196.

In some embodiments, the second antigen-binding site binding to MCAM can incorporate a heavy chain variable domain related to SEQ ID NO:200 and a light chain variable domain related to SEQ ID NO:204. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:200, and/or incorporate amino acid sequences identical to the CDR1 (SEQ ID NO:201), CDR2 (SEQ ID NO:202), and CDR3 (SEQ ID NO:203) sequences of SEQ ID NO:200. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:204, and/or incorporate amino acid sequences identical to the CDR1 (SEQ ID NO:205), CDR2 (SEQ ID NO:206), and CDR3 (SEQ ID NO:207) sequences of SEQ ID NO:204.

In some embodiments, the second antigen-binding site binding to LRRC32 can incorporate a heavy chain variable domain related to SEQ ID NO:209 and a light chain variable domain related to SEQ ID NO:213. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:209, and/or incorporate amino acid sequences identical to the CDR1 (SEQ ID NO:210), CDR2 (SEQ ID NO:211), and CDR3 (SEQ ID NO:212) sequences of SEQ ID NO:209. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:213, and/or incorporate amino acid sequences identical to the CDR1 (SEQ ID NO:214), CDR2 (SEQ ID NO:215), and CDR3 (SEQ ID NO:216) sequences of SEQ ID NO:213.

In some embodiments, the second antigen-binding site binding to LRRC32 can incorporate a heavy chain variable domain related to SEQ ID NO:217 and a light chain variable domain related to SEQ ID NO:221. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:217, and/or incorporate amino acid sequences identical to the CDR1 (SEQ ID NO:218), CDR2 (SEQ ID NO:219), and CDR3 (SEQ ID NO:220) sequences of SEQ ID NO:217. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:221, and/or incorporate amino acid sequences identical to the CDR1 (SEQ ID NO:222), CDR2 (SEQ ID NO:223), and CDR3 (SEQ ID NO:224) sequences of SEQ ID NO:221.

In some embodiments, the second antigen-binding site binding to sialyl-Tn can incorporate a heavy chain variable domain related to SEQ ID NO:226 and a light chain variable domain related to SEQ ID NO:230. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:226, and/or incorporate amino acid sequences identical to the CDR1 (SEQ ID NO:227), CDR2 (SEQ ID NO:228), and CDR3 (SEQ ID NO:229) sequences of SEQ ID NO:226. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:230, and/or incorporate amino acid sequences identical to the CDR1 (SEQ ID NO:231), CDR2 (SEQ ID NO:232), and CDR3 (SEQ ID NO:233) sequences of SEQ ID NO:230.

In some embodiments, the second antigen-binding site binding to sialyl-Tn can incorporate a heavy chain variable domain related to SEQ ID NO:234 and a light chain variable domain related to SEQ ID NO:238. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:234, and/or incorporate amino acid sequences identical to the CDR1 (SEQ ID NO:235), CDR2 (SEQ ID NO:236), and CDR3 (SEQ ID NO:237) sequences of SEQ ID NO:234. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:238, and/or incorporate amino acid sequences identical to the CDR1 (SEQ ID NO:239), CDR2 (SEQ ID NO:240), and CDR3 (SEQ ID NO:241) sequences of SEQ ID NO:238.

In some embodiments, the second antigen-binding site binding to gpA33 can incorporate a heavy chain variable domain related to SEQ ID NO:242 and a light chain variable domain related to SEQ ID NO:246. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:242, and/or incorporate amino acid sequences identical to the CDR1 (SEQ ID NO:243), CDR2 (SEQ ID NO:244), and CDR3 (SEQ ID NO:245) sequences of SEQ ID NO:242. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:246 and/or incorporate amino acid sequences identical to the CDR1 (SEQ ID NO:247), CDR2 (SEQ ID NO:248), and CDR3 (SEQ ID NO:249) sequences of SEQ ID NO:246.

In some embodiments, the second antigen-binding site binding to gpA33 can incorporate a heavy chain variable domain related to SEQ ID NO:250 and a light chain variable domain related to SEQ ID NO:254. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:250, and/or incorporate amino acid sequences identical to the CDR1 (SEQ ID NO:251), CDR2 (SEQ ID NO:252), and CDR3 (SEQ ID NO:253) sequences of SEQ ID NO:250. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:254 and/or incorporate amino acid sequences identical to the CDR1 (SEQ ID NO:255), CDR2 (SEQ ID NO:256), and CDR3 (SEQ ID NO:257) sequences of SEQ ID NO:254.

In some embodiments, the second antigen-binding site binding to GD3 can incorporate a heavy chain variable domain related to SEQ ID NO:259 and a light chain variable domain related to SEQ ID NO:263. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:259, and/or incorporate amino acid sequences identical to the CDR1 (SEQ ID NO:260), CDR2 (SEQ ID NO:261), and CDR3 (SEQ ID NO:262) sequences of SEQ ID NO:259. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:263 and/or incorporate amino acid sequences identical to the CDR1 (SEQ ID NO:264), CDR2 (SEQ ID NO:265), and CDR3 (SEQ ID NO:266) sequences of SEQ ID NO:263.

In some embodiments, the second antigen-binding site binding to GD3 can incorporate a heavy chain variable domain related to SEQ ID NO:267 and a light chain variable domain related to SEQ ID NO:271. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:267, and/or incorporate amino acid sequences identical to the CDR1 (SEQ ID NO:268), CDR2 (SEQ ID NO:269), and CDR3 (SEQ ID NO:270) sequences of SEQ ID NO:267. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:271 and/or incorporate amino acid sequences identical to the CDR1 (SEQ ID NO:272), CDR2 (SEQ ID NO:273), and CDR3 (SEQ ID NO:274) sequences of SEQ ID NO:271.

In some embodiments, the second antigen-binding site binding to GM2 can incorporate a heavy chain variable domain related to SEQ ID NO:275 and a light chain variable domain related to SEQ ID NO:279. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:275, and/or incorporate amino acid sequences identical to the CDR1 (SEQ ID NO:276), CDR2 (SEQ ID NO:277), and CDR3 (SEQ ID NO:278) sequences of SEQ ID NO:275. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:279 and/or incorporate amino acid sequences identical to the CDR1 (SEQ ID NO:280), CDR2 (SEQ ID NO:281), and CDR3 (SEQ ID NO:282) sequences of SEQ ID NO:279.

In some embodiments, the second antigen-binding site binding to GM2 can incorporate a heavy chain variable domain related to SEQ ID NO:283 and a light chain variable domain related to SEQ ID NO:287. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:283, and/or incorporate amino acid sequences identical to the CDR1 (SEQ ID NO:284), CDR2 (SEQ ID NO:285), and CDR3 (SEQ ID NO:286) sequences of SEQ ID NO:283. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:287 and/or incorporate amino acid sequences identical to the CDR1 (SEQ ID NO:288), CDR2 (SEQ ID NO:289), and CDR3 (SEQ ID NO:290) sequences of SEQ ID NO:287.

In some embodiments, the second antigen-binding site binding to c-MET can incorporate a heavy chain variable domain related to SEQ ID NO:291 and a light chain variable domain related to SEQ ID NO:295. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:291, and/or incorporate amino acid sequences identical to the CDR1 (SEQ ID NO:292), CDR2 (SEQ ID NO:293 or 406), and CDR3 (SEQ ID NO:294) sequences of SEQ ID NO:291. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:295 and/or incorporate amino acid sequences identical to the CDR1 (SEQ ID NO:296), CDR2 (SEQ ID NO:297 or 407), and CDR3 (SEQ ID NO:298) sequences of SEQ ID NO:295.

In some embodiments, the second antigen-binding site binding to c-MET can incorporate a heavy chain variable domain related to SEQ ID NO:299 and a light chain variable domain related to SEQ ID NO:303. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:299, and/or incorporate amino acid sequences identical to the CDR1 (SEQ ID NO:300), CDR2 (SEQ ID NO:301), and CDR3 (SEQ ID NO:302) sequences of SEQ ID NO:299. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:303 and/or incorporate amino acid sequences identical to the CDR1 (SEQ ID NO:304 or 410), CDR2 (SEQ ID NO:305), and CDR3 (SEQ ID NO:306) sequences of SEQ ID NO:303.

In some embodiments, the second antigen-binding site binding to c-MET can incorporate a heavy chain variable domain related to SEQ ID NO:413 and a light chain variable domain related to SEQ ID NO:417. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:413, and/or incorporate amino acid sequences identical to the CDR1 (SEQ ID NO:414), CDR2 (SEQ ID NO:415), and CDR3 (SEQ ID NO:416) sequences of SEQ ID NO:413. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:417 and/or incorporate amino acid sequences identical to the CDR1 (SEQ ID NO:418), CDR2 (SEQ ID NO:419), and CDR3 (SEQ ID NO:420) sequences of SEQ ID NO:417.

In some embodiments, the second antigen-binding site binding to EPHA3 can incorporate a heavy chain variable domain related to SEQ ID NO:308 and a light chain variable domain related to SEQ ID NO:312. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:308, and/or incorporate amino acid sequences identical to the CDR1 (SEQ ID NO:309), CDR2 (SEQ ID NO:310), and CDR3 (SEQ ID NO:311) sequences of SEQ ID NO:308. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:312 and/or incorporate amino acid sequences identical to the CDR1 (SEQ ID NO:313), CDR2 (SEQ ID NO:314), and CDR3 (SEQ ID NO:315) sequences of SEQ ID NO:312.

In some embodiments, the second antigen-binding site binding to TNFRSF10 can incorporate a heavy chain variable domain related to SEQ ID NO:317 and a light chain variable domain related to SEQ ID NO:321. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:317, and/or incorporate amino acid sequences identical to the CDR1 (SEQ ID NO:318), CDR2 (SEQ ID NO:319), and CDR3 (SEQ ID NO:320) sequences of SEQ ID NO:317. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:321 and/or incorporate amino acid sequences identical to the CDR1 (SEQ ID NO:322), CDR2 (SEQ ID NO:323), and CDR3 (SEQ ID NO:324) sequences of SEQ ID NO:321.

In some embodiments, the second antigen-binding site binding to TNFRSF10 can incorporate a heavy chain variable domain related to SEQ ID NO:325 and a light chain variable domain related to SEQ ID NO:329. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:325, and/or incorporate amino acid sequences identical to the CDR1 (SEQ ID NO:326), CDR2 (SEQ ID NO:327), and CDR3 (SEQ ID NO:328) sequences of SEQ ID NO:325. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:329 and/or incorporate amino acid sequences identical to the CDR1 (SEQ ID NO:330), CDR2 (SEQ ID NO:331), and CDR3 (SEQ ID NO:332) sequences of SEQ ID NO:329.

In some embodiments, the second antigen-binding site binding to TNFSF11 can incorporate a heavy chain variable domain related to SEQ ID NO:334 and a light chain variable domain related to SEQ ID NO:338. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:334, and/or incorporate amino acid sequences identical to the CDR1 (SEQ ID NO:335), CDR2 (SEQ ID NO:336), and CDR3 (SEQ ID NO:337) sequences of SEQ ID NO:334. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:338 and/or incorporate amino acid sequences identical to the CDR1 (SEQ ID NO:339), CDR2 (SEQ ID NO:340), and CDR3 (SEQ ID NO:341) sequences of SEQ ID NO:338.

In some embodiments, the second antigen-binding site binding to TNFSF11 can incorporate a heavy chain variable domain related to SEQ ID NO:342 and a light chain variable domain related to SEQ ID NO:346. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:342, and/or incorporate amino acid sequences identical to the CDR1 (SEQ ID NO:343), CDR2 (SEQ ID NO:344), and CDR3 (SEQ ID NO:345) sequences of SEQ ID NO:342. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:346 and/or incorporate amino acid sequences identical to the CDR1 (SEQ ID NO:347), CDR2 (SEQ ID NO:348), and CDR3 (SEQ ID NO:349) sequences of SEQ ID NO:346.

In some embodiments, the second antigen-binding site binding to CD74 can incorporate a heavy chain variable domain related to SEQ ID NO:351 and a light chain variable domain related to SEQ ID NO:355. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:351, and/or incorporate amino acid sequences identical to the CDR1 (SEQ ID NO:352), CDR2 (SEQ ID NO:353), and CDR3 (SEQ ID NO:354) sequences of SEQ ID NO:351. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:355 and/or incorporate amino acid sequences identical to the CDR1 (SEQ ID NO:356), CDR2 (SEQ ID NO:357), and CDR3 (SEQ ID NO:358) sequences of SEQ ID NO:355.

In some embodiments, the second antigen-binding site binding to CD74 can incorporate a heavy chain variable domain related to SEQ ID NO:359 and a light chain variable domain related to SEQ ID NO:363. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:359, and/or incorporate amino acid sequences identical to the CDR1 (SEQ ID NO:360), CDR2 (SEQ ID NO:361), and CDR3 (SEQ ID NO:362) sequences of SEQ ID NO:359. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:363 and/or incorporate amino acid sequences identical to the CDR1 (SEQ ID NO:364), CDR2 (SEQ ID NO:365), and CDR3 (SEQ ID NO:366) sequences of SEQ ID NO:363.

In some embodiments, the second antigen-binding site binding to PMEL can incorporate a heavy chain variable domain related to SEQ ID NO:369 and a light chain variable domain related to SEQ ID NO:373. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:369, and/or incorporate amino acid sequences identical to the CDR1 (SEQ ID NO:370), CDR2 (SEQ ID NO:371), and CDR3 (SEQ ID NO:372) sequences of SEQ ID NO:369. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:373 and/or incorporate amino acid sequences identical to the CDR1 (SEQ ID NO:374), CDR2 (SEQ ID NO:375), and CDR3 (SEQ ID NO:376) sequences of SEQ ID NO:373.

In some embodiments, the second antigen-binding site binding to PMEL can incorporate a heavy chain variable domain related to SEQ ID NO:377 and a light chain variable domain related to SEQ ID NO:381. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:377, and/or incorporate amino acid sequences identical to the CDR1 (SEQ ID NO:378), CDR2 (SEQ ID NO:379), and CDR3 (SEQ ID NO:380) sequences of SEQ ID NO:377. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:381 and/or incorporate amino acid sequences identical to the CDR1 (SEQ ID NO:382), CDR2 (SEQ ID NO:383), and CDR3 (SEQ ID NO:384) sequences of SEQ ID NO:381.

In some embodiments, the second antigen-binding site incorporates a light chain variable domain having an amino acid sequence identical to the amino acid sequence of the light chain variable domain present in the first antigen-binding site.

In some embodiments, the protein incorporates a portion of an antibody Fc domain (for example, a portion of an antibody Fc domain sufficient to bind CD16), wherein the antibody Fc domain comprises a hinge and a CH2 domain (for example, a hinge and a CH2 domain of a human IgG1 antibody), and/or amino acid sequences at least 90% identical to amino acid sequence 234-332 of a human IgG antibody. Mutations can be introduced into the antibody constant domain to enable heterdimerization with another antibody constant domain. For example, in some embodiments, the antibody Fc domain includes an amino acid sequence at least 90% identical to the antibody Fc domain of human IgG1 and differs at one or more positions selected from the group consisting of Q347, Y349, L351, S354, E356, E357, K360, Q362, S364, T366, L368, K370, N390, K392, T394, D399, S400, D401, F405, Y407, K409, T411, and K439. In some embodiments, the antibody Fc domain can comprise an amino acid sequence at least 90% identical to amino acids 234-332 of a human IgG1 antibody, and differs by one or more substitutions selected from the group consisting of Q347E, Q347R, Y349S, Y349K, Y349T, Y349D, Y349E, Y349C, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, D399R, D399K, D399V, S400K, S400R, D401K, F405A, F405T, Y407A, Y407I, Y407V, K409F, K409W, K409D, T411D, T411E, K439D, and K439E.

Formulations containing any one of the proteins described herein; cells containing one or more nucleic acids expressing the proteins, and methods of enhancing tumor cell death using the proteins are also provided.

Another aspect of the invention provides a method of treating cancer in a patient. The method comprises administering to a patient in need thereof a therapeutically effective amount of the multi-specific binding proteins described herein. Exemplary cancers to be treated using the multi-specific binding proteins include leukemia, for example, acute myeloid leukemia, T-cell leukemia, acute lymphocytic leukemia, chronic lymphocytic leukemia, chronic myeloid leukemia, and hairy cell leukemia.

In one aspect, a protein of the current invention includes a single-chain variable fragment (scFv) that is linked to an antibody constant domain via a hinge sequence. In some embodiments, the hinge comprises amino acids Ala-Ser. In some other embodiments, the hinge comprises amino acids Ala-Ser and Thr-Lys-Gly. The scFv may include a heavy chain variable domain and a light chain variable domain. In some embodiments, the scFv binds NKG2D or a tumor-associated antigen. The hinge sequence provides flexibility of binding to a target antigen, for example, a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL.

In some embodiments of the scFv, the heavy chain variable domain forms a disulfide bridge with the light chain variable domain. For example, a disulfide bridge can be formed between the C44 residue of the heavy chain variable domain and the C100 residue of the light chain variable domain. In some embodiments, the heavy chain variable domain is linked to the light chain variable domain via a flexible linker, such as a peptide linker comprising the amino acid sequence of GGGGSGGGGSGGGGSGGGGS ("(G4S)$_4$") (SEQ ID NO:386). In some embodiments of the scFv, the heavy chain variable domain is positioned at the N terminus of the light chain variable domain. In some embodiments of the scFv, the heavy chain variable domain is positioned at the C terminus of the light chain variable domain.

In some embodiments, the antibody constant domain linked to the scFv or the Fab fragment is able to bind to CD16. In some embodiments, the antibody constant domain comprises a CH2 domain and a CH3 domain of an IgG antibody, for example, a human IgG1 antibody. In some embodiments, the antibody constant domain comprises a hinge and a CH2 domain and/or amino acid sequences at least 90% identical to amino acid sequence 234-332 of a human IgG antibody. In some embodiments, mutations are introduced in the antibody constant domain to enable heterdimerization with another antibody constant domain. For example, if the antibody constant domain is derived from the constant domain of a human IgG1, the antibody constant domain can comprise an amino acid sequence at least 90% identical to amino acids 234-332 of a human IgG1 antibody, and differs at one or more positions selected from the group consisting of Q347, Y349, L351, S354, E356, E357, K360, Q362, S364, T366, L368, K370, N390, K392, T394, D399, S400, D401, F405, Y407, K409, T411, and K439. In some embodiments, the antibody constant domain can comprise an amino acid sequence at least 90% identical to amino acids 234-332 of a human IgG1 antibody, and differs by one or more substitutions selected from the group consisting of Q347E, Q347R, Y349S, Y349K, Y349T, Y349D, Y349E, Y349C, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, D399R, D399K, D399V, S400K, S400R, D401K, F405A, F405T, Y407A, Y407I, Y407V, K409F, K409W, K409D, T411D, T411E, K439D, and K439E.

In some embodiments, a protein of the current invention includes: a first antigen-binding site that binds NKG2D; a second antigen-binding site that binds a tumor-associated antigen selected from the group consisting of KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL; and an antibody Fc domain or a portion thereof sufficient to bind CD16, or a third antigen-binding site that binds CD16. In some embodiments, the protein includes an additional antigen-binding site that binds the same tumor-associated antigen as the second antigen-binding site (e.g., a tumor-associated antigen selected from the group consisting of KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL). In some embodiments, the first antigen-binding site that binds NKG2D is a single-chain variable fragment (scFv), and the second and/or the additional antigen-binding site that binds a tumor-associated antigen is an Fab fragment. In some embodiments, the first antigen-binding site that binds NKG2D is an scFv, and the second and/or the additional antigen-binding site that binds a tumor-associated antigen is an scFv. In some embodiments, the first antigen-binding site that binds NKG2D is an Fab fragment, and the second antigen-binding site that binds a tumor-associated antigen is an scFv.

In some embodiments of a protein described herein, the first antigen-binding site binds to NKG2D in humans.

In some embodiments, the first, the second, and/or the additional antigen-binding site includes a heavy chain variable domain and a light chain variable domain. In some embodiments, within the scFv the heavy chain variable domain is positioned at the N-terminus or the C-terminus of the light chain variable domain. In some embodiments, the scFv is linked to an antibody constant domain or a portion of an antibody constant domain that is sufficient to bind CD16, via a hinge comprising Ala-Ser, where the scFv includes a heavy chain variable domain and a light chain variable domain. In some embodiments, within the scFv the hinge further includes an amino acid sequence Thr-Lys-Gly.

In some embodiments of the protein, the heavy chain variable domain forms a disulfide bridge with the light chain variable domain. In some embodiments, the disulfide bridge is formed between C44 from the heavy chain variable domain and C100 from the light chain variable domain.

In some embodiments, within the scFv the heavy chain variable domain is linked to the light chain variable domain via a flexible linker. In some embodiments, within the scFv the flexible linker comprises (G4S)$_4$.

In another aspect, provided herein is a formulation that includes a protein described herein and a pharmaceutically acceptable carrier.

In yet another aspect, provided herein is a cell that includes one or more nucleic acids expressing a protein described herein.

In a further aspect, the disclosure provides a method of enhancing tumor cell death by exposing a tumor cell and a natural killer cell to an effective amount of a protein described herein, where the tumor cell expresses a tumor-associated antigen selected from the group consisting of KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL.

Also provided herein is a method of treating cancer by administering an effective amount of a protein or a formulation described herein to a patient. For example, the disclosure provides a method of treating cancer by administering an effective amount of a protein or a formulation that includes such a protein to a patient, where the protein includes a first antigen-binding site that binds NKG2D; a second antigen binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL; and an antibody Fc domain (or a portion of an antibody Fc domain) sufficient to bind CD16, or a third antigen-binding site that binds CD16. In some embodiments, the second antigen binding site of the protein binds KIT, and the cancer to be treated is selected from the group consisting of colorectal cancer, acute myeloid leukemia, gastrointestinal stromal tumor, melanoma, small cell lung cancer, non-small cell lung cancer, renal cancer, liver cancer, and testicular cancer. In some embodiments, the second antigen binding site of the protein binds F3, and the cancer to be treated is selected from the group consisting of bladder cancer, breast cancer, cervical cancer, glioblastoma, head and neck cancer, lung cancer, pancreatic cancer, prostate cancer, sarcomas, and colorectal cancer. In some embodiments, the second antigen binding site of the protein binds IGF1R, and the cancer to be treated is selected from the group consisting of breast cancer, cervical cancer, head and neck cancer, lung cancer, melanoma, mesothelioma, ovarian cancer, prostate cancer, sarcoma, thyroid cancer, renal cancer, colorectal cancer, pancreatic cancer, gliobastoma, and liver cancer. In some embodiments, the second antigen binding site of the protein binds Lewis Y, and the cancer to be treated is selected from the group consisting of ovarian cancer, lung cancer, colorectal cancer, gastric cancer, breast cancer, cervical cancer, head and neck cancer, multiple myeloma, and acute myeloid leukemia. In some embodiments, the second antigen binding site of the protein binds MUC13, and the cancer to be treated is selected from the group consisting of ovarian cancer, liver cancer, lung cancer, melanoma, liver cancer, gastric cancer, pancreatic cancer, renal cancer, esophageal cancer, breast cancer, colorectal cancer, cervical cancer, and cholangiocarcinoma. In some embodiments, the second antigen binding site of the protein binds MUC4, and the cancer to be treated is selected from the group consisting of breast cancer, pancreatic cancer, ovarian cancer, lung cancer, acute lymphoblastic leukemia, bladder cancer, cervical cancer, colorectal cancer, head and neck cancer, and prostate cancer. In some embodiments, the second antigen binding site of the protein binds MCAM, and the cancer to be treated is selected from the group consisting of melanoma, breast cancer, small cell lung cancer, sarcoma, colorectal cancer, pancreatic cancer, and renal cancer. In some embodiments, the second antigen binding site of the protein binds LRRC32, and the cancer to be treated is selected from the group consisting of renal cancer, pancreatic cancer, sarcoma, ovarian cancer, lung cancer, gliobastoma, head and neck cancer, prostate cancer, liver cancer, breast cancer, and cervical cancer. In some embodiments, the second antigen binding site of the protein binds sialyl-Tn, and the cancer to be treated is selected from the group consisting of ovarian cancer, pancreatic cancer, bladder cancer, gastric cancer, prostate cancer, colorectal cancer, and breast cancer. In some embodiments, the second antigen binding site of the protein binds gpA33, and the cancer to be treated is selected from the group consisting of colorectal cancer, gastric cancer, and esophageal cancer. In some embodiments, the second antigen binding site of the protein binds GD3, and the cancer to be treated is selected from the group consisting of lung cancer, glioma, breast cancer, melanoma, ovarian cancer, pancreatic cancer, and neuroblastoma. In some embodiments, the second antigen binding site of the protein binds GM2, and the cancer to be treated is selected from the group consisting of gastric cancer, breast cancer, ovarian cancer, uterine cancer, cervical cancer, neuroblastoma, melanoma, lung cancer, mesothelioma, and liver cancer. In some embodiments, the second antigen binding site of the protein binds c-MET, and the cancer to be treated is selected from the group consisting of renal cancer, thyroid cancer, melanoma, lung cancer, melanoma, liver cancer, pancreatic cancer, colorectal cancer, and head and neck cancer. In some embodiments, the second antigen binding site of the protein binds EPHA3, and the cancer to be treated is selected from the group consisting of cervical cancer, head and neck cancer, gastric cancer, multiple myeloma, ovarian cancer, colorectal cancer, melanoma, breast cancer, prostate cancer, pancreatic cancer, lung cancer, and sarcoma. In some embodiments, the second antigen binding site of the protein binds TNFRSF10A, and the cancer to be treated is selected from the group consisting of breast cancer, colorectal cancer, prostate cancer, pancreatic cancer, bladder cancer, and head and neck cancer. In some embodiments, the second antigen binding site of the protein binds TNFSF11, and the cancer to be treated is selected from the group consisting of breast cancer, prostate cancer, and a bone metastatic cancer. In some embodiments, the second antigen binding site of the protein binds CD74, and the cancer to be treated is selected from the group consisting of diffuse large B cell cancer, a B cell malignancy, renal cancer, lung cancer, ovarian cancer, melanoma, sarcoma, head and neck cancer, liver cancer, bladder cancer, glioma, breast cancer, and leukemia. In some embodiments, the second antigen binding site of the protein binds PMEL, and the cancer to be treated is selected from the group consisting of melanoma and a sarcoma.

In another aspect, the current invention provides a protein that contains the scFv linked to an antibody constant region described above or the Fab fragment linked to an antibody constant region described above. In some embodiments, the protein includes a first antigen-binding site, which comprises the scFv linked to an antibody constant domain or the Fab fragment linked to an antibody constant domain; a second antigen-binding site which may take the Fab fragment or the scFv format described here; and a second antibody constant domain linked to the second antigen-binding site. In some embodiments, the protein is multi-specific, wherein the first antigen binding site binds NKG2D, the second antigen binding sites bind a tumor-associated antigen (for example, a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL), and the antibody constant regions bind CD16.

In some embodiments, the protein is multi-specific, wherein the first antigen binding site binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL; the second antigen binding site binds NKG2D; and the antibody constant regions bind CD16. The antibody constant region linked to the scFv or the Fab fragment can heterodimerize with a second antibody constant region. The multi-specific binding proteins in these embodiments bind to the NKG2D receptor and CD16 receptor on natural killer cells, and to a tumor-associated antigen (for example, a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL) on cancer cells. Such proteins can engage more than one kind of NK-activating receptor, and may block the binding of natural ligands to NKG2D. In certain embodiments, the proteins can agonize NK cells in humans. In some embodiments, the proteins can agonize NK cells in humans, and/or in other species such as rodents and/or cynomolgus monkeys.

In another aspect, the current invention provides a multi-specific binding protein, and the protein contains a first antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL; a second antigen-binding site that binds the same tumor-associated antigen as the first antigen-binding site; a third antigen-binding site that binds NKG2D; and an antibody constant region or a portion thereof sufficient to bind CD16, or a fourth antigen-binding site that binds CD16. Any one of the antigen binding sites can either take the form of a nFab fragment or an scFv, such as those described above. The multi-specific protein provided here provides bivalent engagement of tumor-associated antigen, thereby stabilizing the tumor-associated antigen on cancer cell surface, and enhance cytotoxicity towards the cancer cells by NK cells.

In some embodiments, bivalent engagement of tumor-associated antigens by the multi-specific proteins described herein confer stronger binding of the multi-specific proteins to the cancer cells, thereby facilitating stronger cytotoxic response of NK cells towards the cancer cells, especially towards cancer cells expressing a low level of a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL.

The tumor-associated antigen binding site described above can be a site that binds to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL.

Formulations containing any one of the proteins described herein; cells containing one or more nucleic acids expressing the proteins, and methods of enhancing tumor cell death using the proteins are also provided.

Another aspect of the invention provides a method of treating cancer in a patient. The method comprises administering to a patient in need thereof a therapeutically effective amount of the multi-specific proteins described herein. Cancers to be treated may include acute lymphoblastic leukemia, acute myeloid leukemia, acute myelomonocytic leukemia, B cell lymphoma, a B cell malignancy, bladder cancer, a bone metastatic cancer, breast cancer, cervical cancer, cholangiocarcinoma, colorectal cancer, diffuse large B cell lymphoma, esophageal cancer, Ewing's sarcoma, follicular lymphoma, gastric cancer, gastrointestinal cancer, gastrointestinal stromal tumors, glioblastoma, glioma, head and neck cancer, liver cancer, lung cancer, melanoma, mesothelioma, multiple myeloma, myelodysplastic syndrome, neuroblastoma, renal cancer, renal cell carcinoma, neuroblastoma, non-small cell lung cancer, neuroendocrine tumors, ovarian cancer, and pancreatic cancer, prostate cancer, sarcomas, small cell lung cancer, T cell lymphoma, testis cancer, thymic carcinoma, thyroid cancer, urothelial cancer, uterine cancer, cancers infiltrated by myeloid-derived suppressor cells, cancers infiltrated by T regulatory cells, cancers with extracellular matrix deposition, cancers with high levels of reactive stroma, and cancers with neoangiogenesis.

Another aspect of the invention provides a method of treating cancer in a patient. The method comprises administering to a patient in need thereof a therapeutically effective amount of the multi-specific binding proteins described herein. Cancers to be treated using KIT-targeting multi-specific binding proteins include any cancer that expresses KIT, for example, colorectal cancer, acute myeloid leukemia, gastrointestinal stromal tumor, melanoma, small cell lung cancer, non-small cell lung cancer, renal cancer, liver cancer, and testicular cancer. Cancers to be treated using F3-targeting multi-specific binding proteins include any cancer that expresses F3, for example, bladder cancer, breast cancer, cervical cancer, glioblastoma, head and neck cancer, lung cancer, pancreatic cancer, prostate cancer, sarcoma, and colorectal cancer. Cancers to be treated using IGF1R-targeting multi-specific binding proteins include any cancer that expresses IGF1R, for example, breast cancer, cervical cancer, head and neck cancer, lung cancer, melanoma, mesothelioma, ovarian cancer, prostate cancer, sarcoma, thyroid cancer, renal cancer, colorectal cancer, pancreatic cancer, gliobastoma, and liver cancer. Cancers to be treated using Lewis Y-targeting multi-specific binding proteins include any cancer that expresses Lewis Y, for example, ovarian cancer, lung cancer, colorectal cancer, gastric cancer, breast cancer, cervical cancer, head and neck cancer, multiple myeloma, and acute myeloid leukemia. Cancers to be treated using MUC13-targeting multi-specific binding proteins include any cancer that expresses MUC13, for example, ovarian cancer, liver cancer, lung cancer, melanoma, liver cancer, gastric cancer, pancreatic cancer, renal cancer, esophageal cancer, breast cancer, colorectal cancer, cervical cancer, and cholangiocarcinoma. Cancers to be treated using MUC4-targeting multi-specific binding proteins include any cancer that expresses MUC4, for example, breast cancer, pancreatic cancer, ovarian cancer, lung cancer, acute lymphoblastic leukemia, bladder cancer, cervical cancer, colorectal cancer, head and neck cancer, and prostate cancer. Cancers to be treated using MCAM-targeting multi-specific binding proteins include any cancer that expresses MCAM, for example, melanoma, breast cancer, small cell lung cancer, sarcoma, colorectal cancer, pancreatic cancer, and renal cancer. Cancers to be treated using LRRC32-targeting multi-specific binding proteins include any cancer that expresses LRRC32, for example, renal cancer, pancreatic cancer, sarcoma, ovarian cancer, lung cancer, gliobastoma, head and neck cancer, prostate cancer, liver cancer, breast cancer, and cervical cancer. Cancers to be treated using sialyl-Tn-targeting multi-specific binding proteins include any cancer that expresses sialyl-Tn, for example, ovarian cancer, pancreatic cancer, bladder cancer, gastric cancer, prostate cancer, colorectal cancer, and breast cancer. Cancers to be treated using gpA33-targeting multi-specific binding proteins include any cancer that expresses gpA33, for example, colorectal cancer, gastric cancer, and esophageal cancer. Cancers to be treated using GD3-targeting multi-specific binding proteins include any cancer that expresses GD3, for example, lung cancer, glioma, breast cancer, melanoma, ovarian cancer, pancreatic cancer, and neuroblastoma. Cancers to be treated using GM2-targeting multi-specific binding proteins include any cancer that expresses GM2, for example, gastric cancer, breast cancer, ovarian cancer, uterine cancer, cervical cancer, neuroblastoma, melanoma, lung cancer, mesothelioma, and liver cancer. Cancers to be treated using c-MET-targeting multi-specific binding proteins include any cancer that expresses c-MET, for example, renal cancer, thyroid cancer, melanoma, lung cancer, melanoma, liver cancer, pancreatic cancer, colorectal cancer, or head and neck cancer. Cancers to be treated using EPHA3-targeting multi-specific binding proteins include any cancer that expresses EPHA3, for example, cervical cancer, head and neck cancer, gastric cancer, multiple myeloma, ovarian cancer, colorectal cancer, melanoma, breast cancer, prostate cancer, pancreatic cancer, lung cancer, and sarcoma. Cancers to be treated using TNFRSF10A-targeting multi-specific binding proteins include any cancer that expresses TNFRSF10A, for example, breast cancer, colorectal cancer, prostate cancer, pancreatic cancer, bladder cancer, and head and neck cancer. Cancers to be treated using TNFSF11-targeting multi-specific binding proteins include any cancer that expresses TNFSF11, for example, breast cancer, prostate cancer, and a bone metastatic cancer. Cancers to be treated using CD74-targeting multi-specific binding proteins include any cancer that expresses CD74, for example, diffuse large B cell cancer, a B cell malignancy, renal cancer, lung cancer, ovarian cancer, melanoma, sarcoma, head and neck cancer, liver cancer, bladder cancer, glioma, breast cancer, and leukemia. Cancers to be treated using PMEL-targeting multi-specific binding proteins include any cancer that expresses PMEL, for example, melanoma and sarcoma.

BRIEF DESCRIPTION OF THE DRAWINGS

As shown in FIG. 2A, either the NKG2D-binding domain or the tumor-associated antigen-binding domain can take the scFv format (left arm). An antibody that contains a NKG2D-targeting scFv, a tumor-associated antigen-targeting Fab fragment, and a heterodimerized antibody constant region is referred herein as the F3-TriNKET. An antibody that contains a tumor-associated antigen-targeting scFv, a NKG2D-targeting Fab fragment, and a heterodimerized antibody constant region/domain that binds CD16 is referred herein as the F3'-TriNKET (FIG. 2E). As shown in FIG. 2B, both the NKG2D-binding domain and tumor-associated antigen-binding domain can take the scFv format. FIGS. 2C to 2D are illustrations of an antibody with three antigen-binding sites, including two antigen-binding sites that bind a tumor-associated antigen, and the NKG2D-binding site fused to the heterodimerized antibody constant region. These antibody formats are referred herein as F4-TriNKET. FIG. 2C illustrates that the two tumor-associated antigen-binding sites are in the Fab fragment format, and the NKG2D binding site in the scFv format. FIG. 2D illustrates that the tumor-associated antigen-binding sites in the scFv format, and the NKG2D binding site in the scFv format. FIG. 2E represents a trispecific antibody (TriNKET) that contains a tumor-targeting scFv, a NKG2D-targeting Fab fragment, and a heterodimerized antibody constant region/domain ("CD domain") that binds CD16. The antibody format is referred herein as F3'-TriNKET. In certain exemplary multispecific binding proteins, heterodimerization mutations on the antibody constant region include K360E and K409W on one constant domain; and Q347R, D399V and F405T on the opposite constant domain (shown as a triangular lock-and-key shape in the CD domains). The bold bar between the heavy and the light chain variable domains of the Fab fragments represents a disulfide bond.

FIG. 19A demonstrates levels of CD107a; FIG. 19B demonstrates levels of IFN-γ; FIG. 19C demonstrates levels of CD107a and IFN-γ. Graphs indicate the mean (n=2)±SD. Data are representative of five independent experiments using five different healthy donors.

antibodies that exchange Fab fragment arms by swapping a heavy chain and attached light chain (half-molecule) with a heavy-light chain pair from another molecule, resulting in bispecific antibodies. Fab Arm Exchange form (cFae) is a heterodimer containing 2 Fab fragments binding to target 1 and 2, and an Fc stabilized by heterodimerization mutations.

Figure 27:
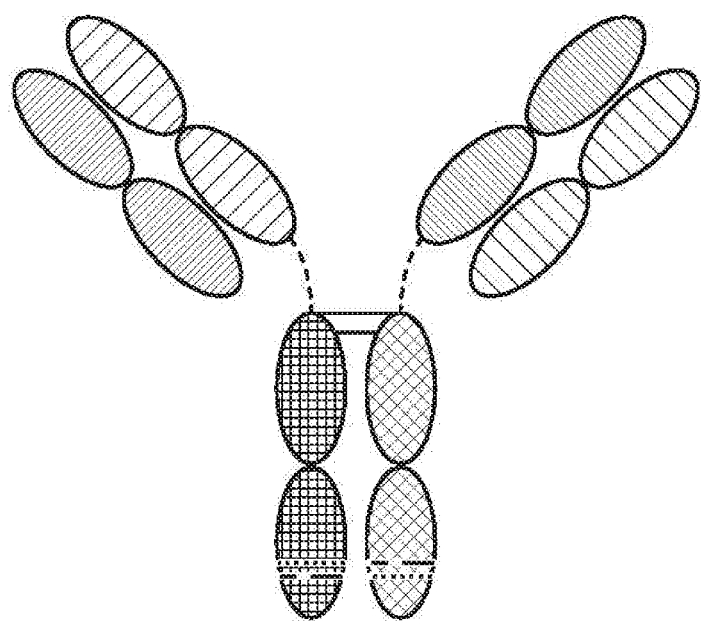

FIG. 27 is a representation of a TriNKET in the SEED Body form, which is a heterodimer containing 2 Fab fragments binding to target 1 and 2, and an Fc stabilized by heterodimerization mutations.

Figure 28:
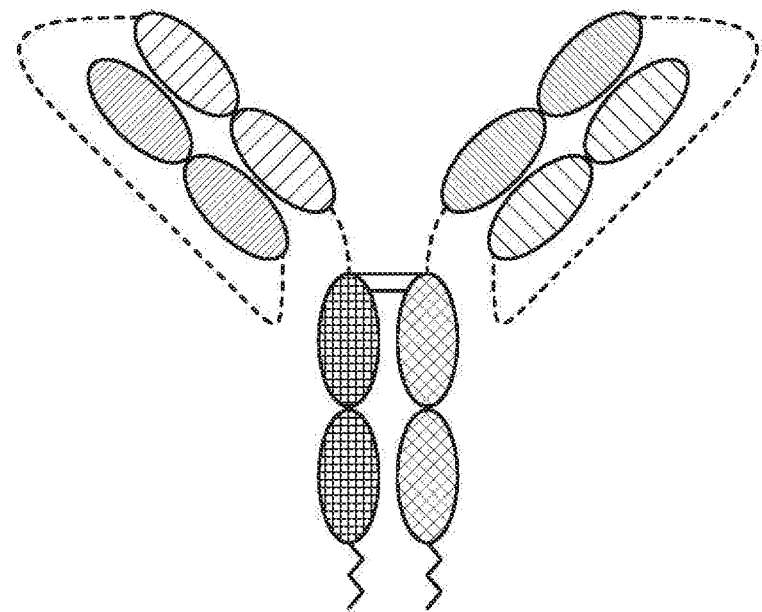

FIG. 28 is a representation of a TriNKET in the LuZ-Y form, in which a leucine zipper is used to induce heterodimerization of two different HCs. The LuZ-Y form is a heterodimer containing two different scFabs binding to target 1 and 2, fused to Fc. Heterodimerization is ensured through leucine zipper motifs fused to C-terminus of Fc.

Figure 29:
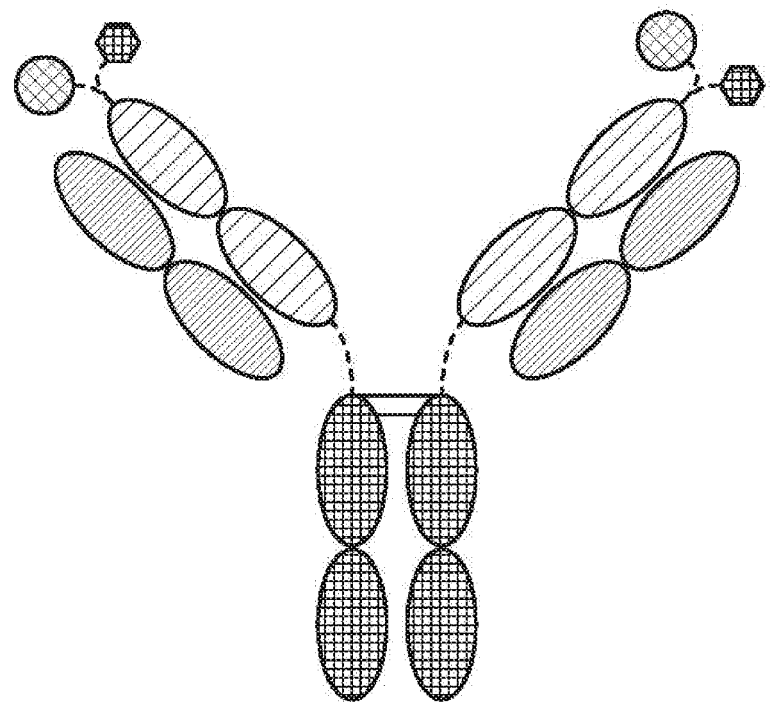

FIG. 29 is a representation of a TriNKET in the Cov-X-Body form.

Figure 30A:
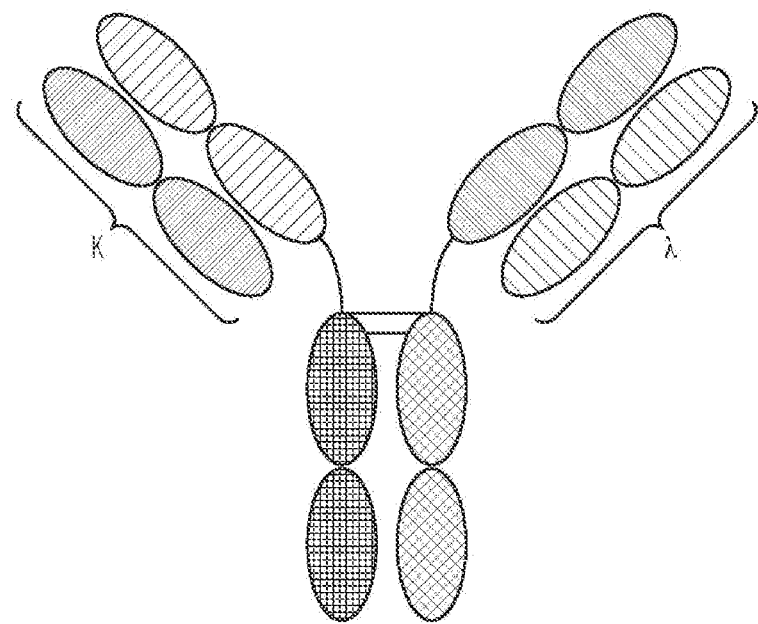
Figure 30B:
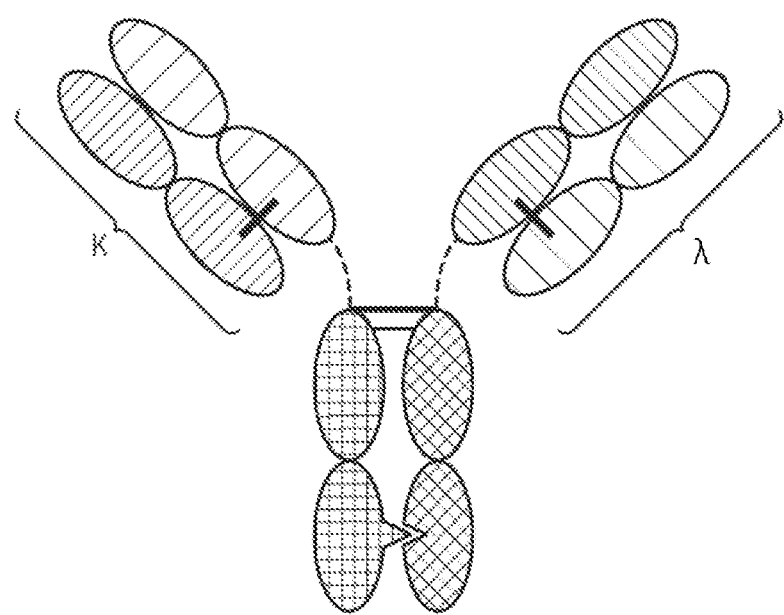

FIGS. 30A to 30B are representations of TriNKETs in the κλ-Body forms, which are heterodimeric constructs with two different Fab fragments fused to Fc stabilized by heterodimerization mutations: one Fab fragment targeting antigen 1 contains kappa LC, and the second Fab fragment targeting antigen 2 contains lambda LC. FIG. 30A is an exemplary representation of one form of a κλ-Body; FIG. 30B is an exemplary representation of another κλ-Body.

Figure 31:
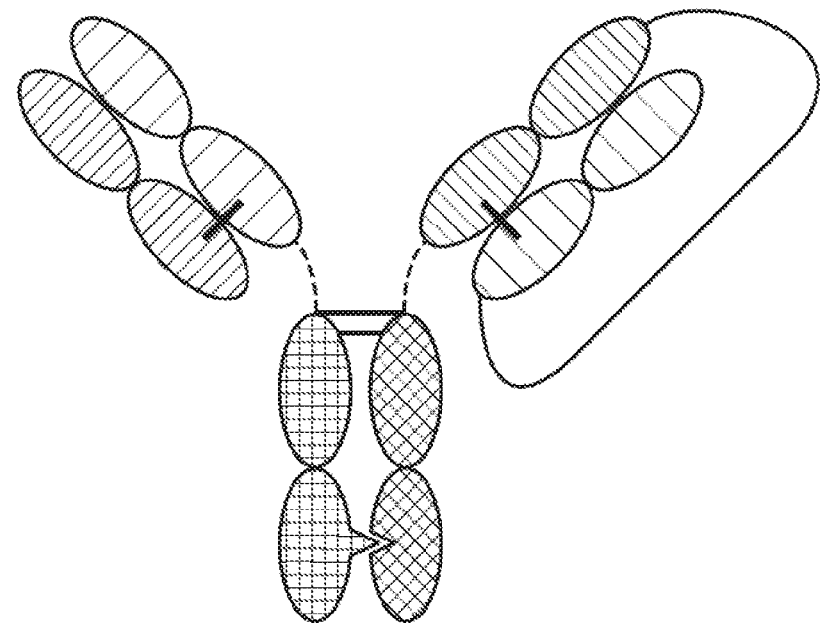

FIG. 31 is an Oasc-Fab heterodimeric construct that includes Fab fragment binding to target 1 and scFab binding to target 2, both of which are fused to the Fc domain. Heterodimerization is ensured by mutations in the Fc domain.

Figure 32:
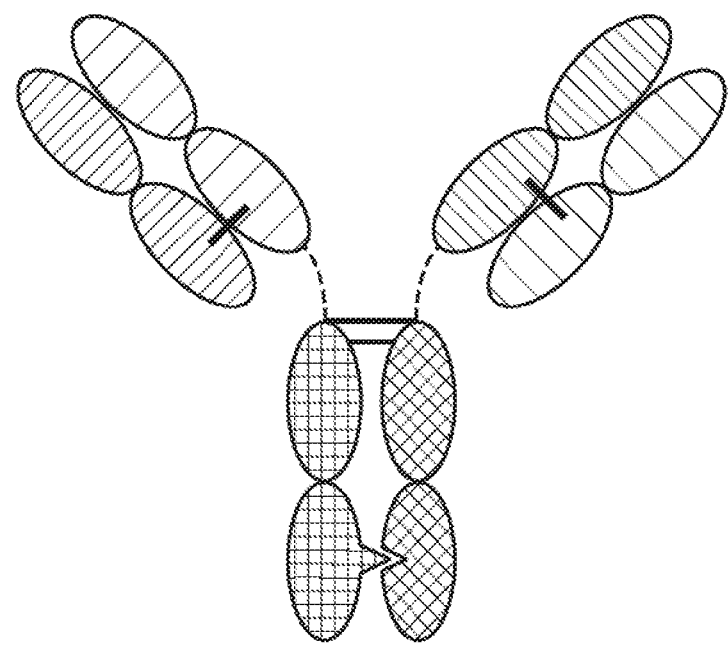

FIG. 32 is a DuetMab, which is a heterodimeric construct containing two different Fab fragments binding to antigens 1 and 2, and an Fc that is stabilized by heterodimerization mutations. Fab fragments 1 and 2 contain differential S—S bridges that ensure correct light chain and heavy chain pairing.

Figure 33:
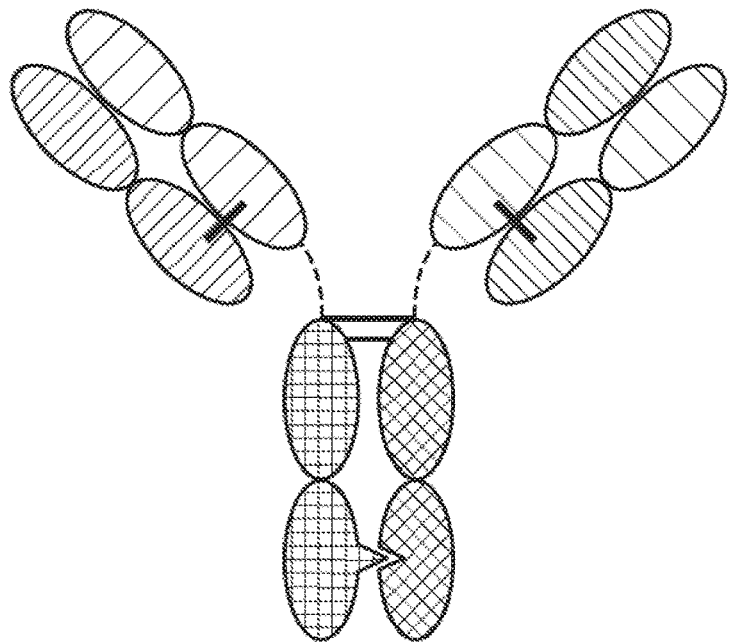

FIG. 33 is a CrossmAb, which is a heterodimeric construct with two different Fab fragments binding to targets 1 and 2, and an Fc stabilized by heterodimerization mutations. CL and CH1 domains, and VH and VL domains are switched, e.g., CH1 is fused in-line with VL, while CL is fused in-line with VH.

Figure 34:
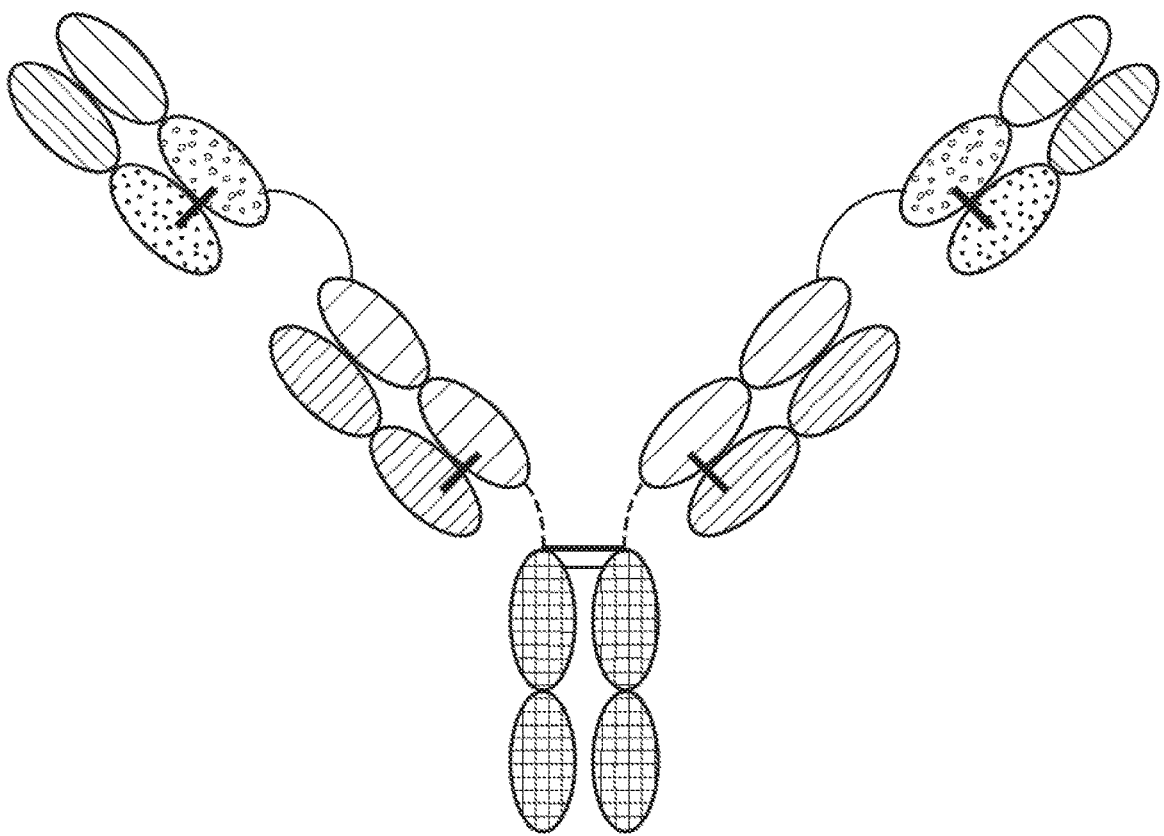

FIG. 34 is a Fit-Ig, which is a homodimeric construct where Fab fragment binding to antigen 2 is fused to the N-terminus of HC of Fab fragment that binds to antigen 1. The construct contains wild-type Fc.

Figure 35:
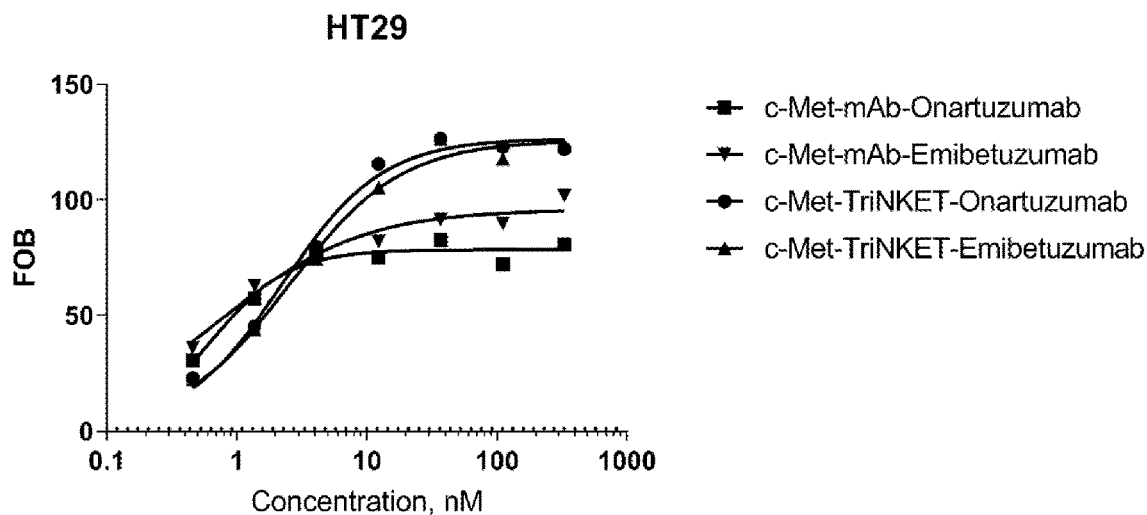

FIG. 35 is a line graph showing binding of anti-c-MET monoclonal antibodies and c-MET-targeting TriNKETs to c-MET positive HT29 colon cancer cells.

Figure 36:
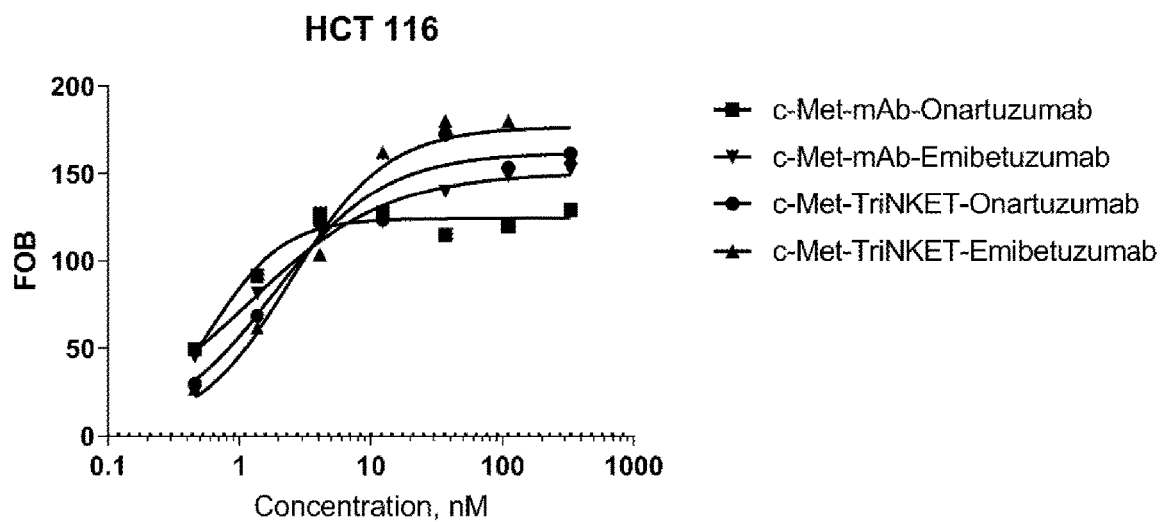

FIG. 36 is a line graph showing binding of anti-c-MET monoclonal antibodies and c-MET-targeting TriNKETs to c-MET positive HCT-116 colon cancer cells.

Figure 37A:
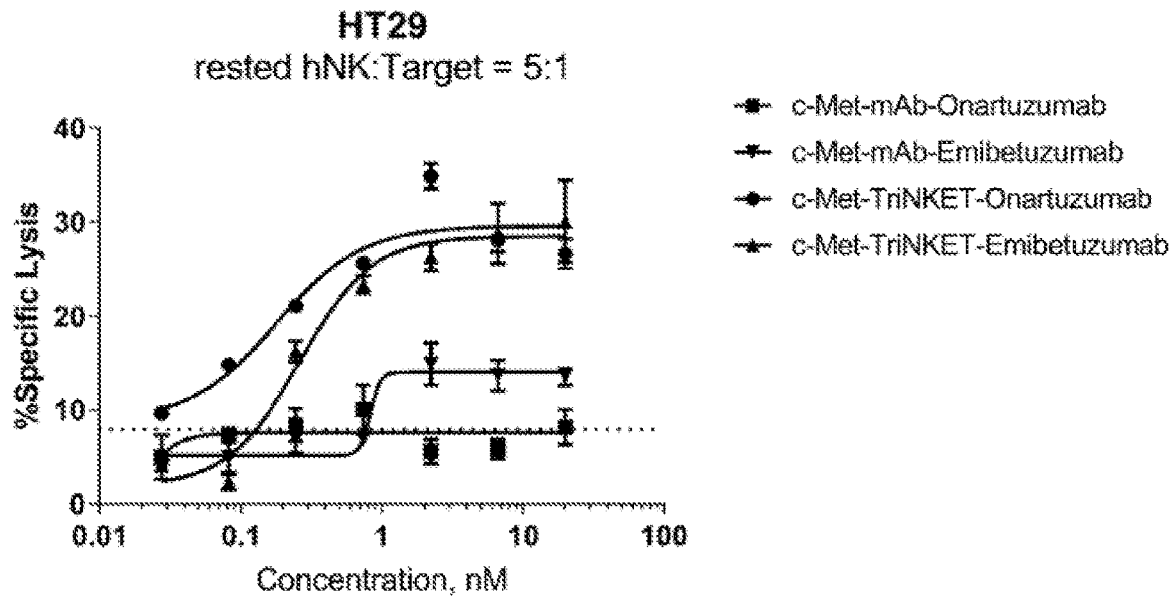
Figure 37B:
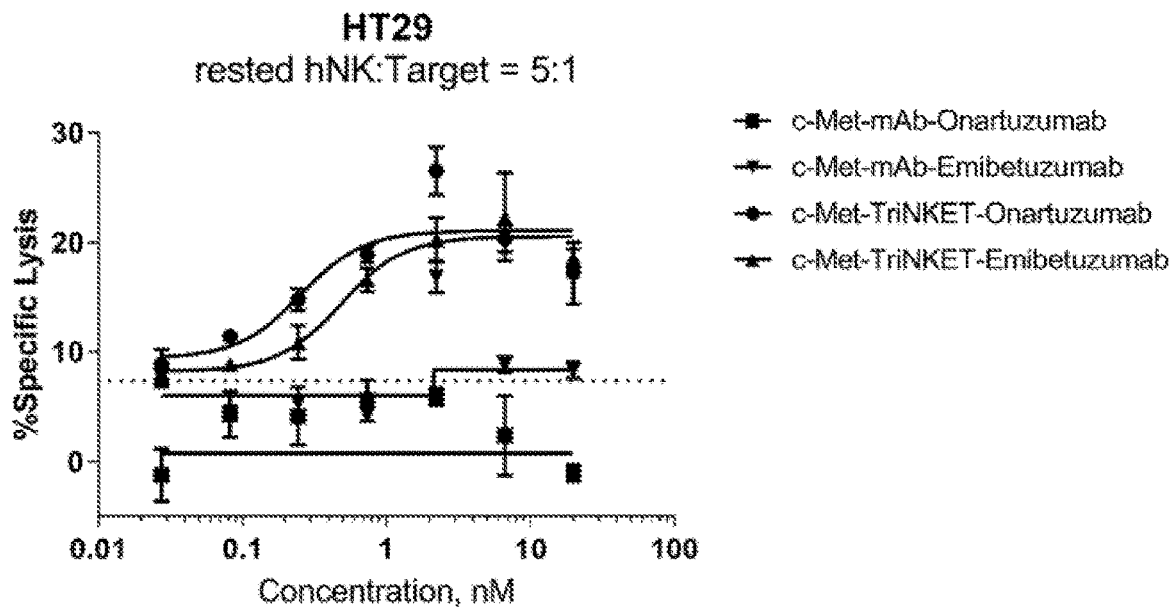
Figure 37C:
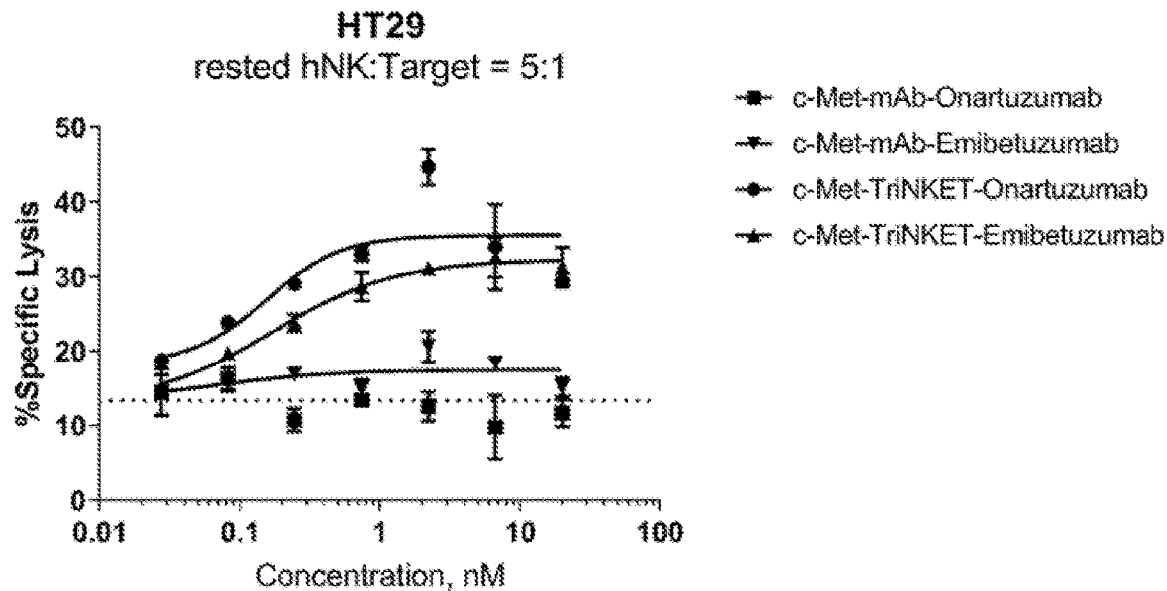

FIGS. 37A to 37C are line graphs showing lysis of c-MET expressing HT29 colon cancer cells by NK cells derived from three different healthy human donors (FIG. 37A are line graphs showing lysis of c-MET expressing HT29 colon cancer cells by NK cells derived from donor 1; FIG. 37B are line graphs showing lysis of c-MET expressing HT29 colon cancer cells by NK cells derived from donor 2; and FIG. 37C are line graphs showing lysis of c-MET expressing HT29 colon cancer cells by NK cells derived from donor 3) in the presence of anti-c-MET mAbs or c-MET-targeting TriNKETs.

Figure 38:
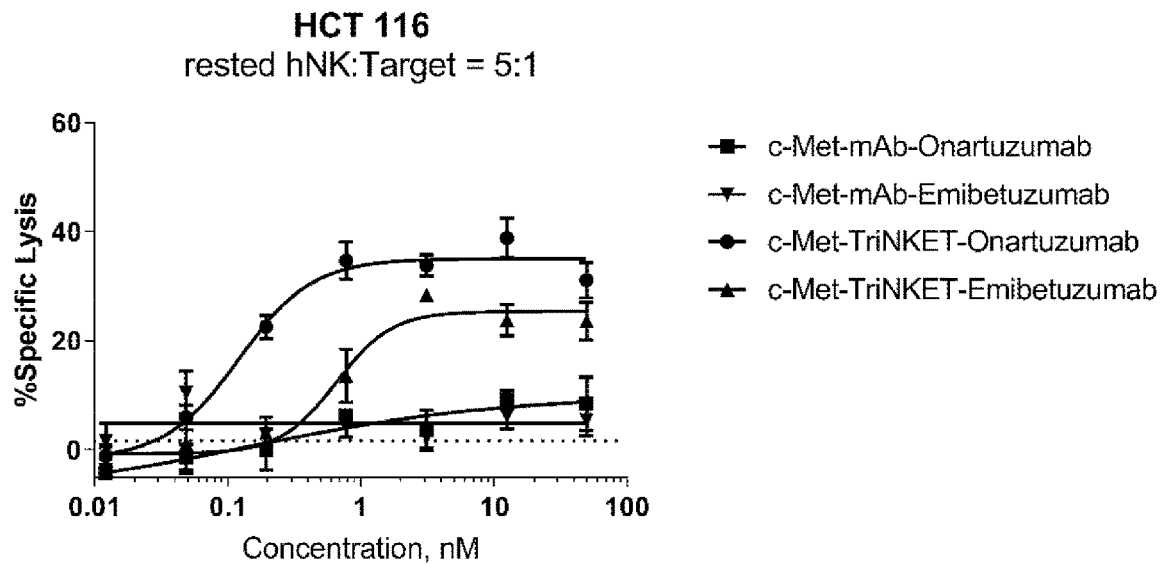

FIG. 38 is a line graph showing lysis of c-MET positive HCT-116 colon cancer cells by NK cells in the presence of anti-c-MET mAbs or c-MET-targeting TriNKETs.

DETAILED DESCRIPTION

The invention provides multi-specific binding proteins that bind the NKG2D receptor and CD16 receptor on natural killer cells, and a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. In some embodiments, the multi-specific proteins further include an additional antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, or another tumor-associated antigen. The invention also provides pharmaceutical compositions comprising such multi-specific binding proteins, and therapeutic methods using such multi-specific proteins and pharmaceutical compositions, for purposes such as treating cancer.

The invention also provides an improvement on a single-chain variable fragment (scFv) that is linked to an antibody constant domain via a hinge sequence. The hinge sequence provides flexibility of the scFv binding to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. This invention also provides multi-specific binding proteins that includes one or more of the scFv, wherein the multi-specific binding proteins bind the NKG2D receptor and CD16 receptor on natural killer cells, and a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. This invention also provides multi-specific binding proteins that contain two tumor-associated antigen binding sites binding to the same tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, and bind the NKG2D receptor and CD16 receptor on natural killer cells. Pharmaceutical compositions comprising such multi-specific binding proteins, and therapeutic methods using such multi-specific proteins and pharmaceutical compositions, for purposes such as treating cancer are also provided.

Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen binding. In human antibodies, the antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

The term "tumor associated antigen" as used herein means any antigen including but not limited to a protein, glycoprotein, ganglioside, carbohydrate, lipid that is associated with cancer. Such antigen can be expressed on malignant cells or in the tumor microenvironment such as on tumor-associated blood vessels, extracellular matrix, mesenchymal stroma, or immune infiltrates.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, "KIT" (also known as PBT, SCFR, C-Kit, CD117, and MASTC) refers to the protein of Uniprot Accession No. P10721 and related isoforms.

As used herein, "F3" (also known as TF; TFA; and CD142) refers to the protein of Uniprot Accession No. P13726 and related isoforms.

As used herein, "IGF1R" (also known as IGFR; CD221; IGFIR; JTK13) refers to the protein of Uniprot Accession No. P08069 and related isoforms.

As used herein, "Lewis Y" (also known as Le(y); Lewis y Tetrasaccharide; Fucalpha1-3 (Fucalpha1-2Galbeta1-4) GclNAc; CHEBI: 59045; and Fucalpha1-2Galbeta1-4(Fucalpha1-3)) refers to the Lewis Y carbohydrate of PubChem CID: 45266908, and related variants.

As used herein, "MUC13" (also known as DRCC1 and MUC-13) refers to the protein of Uniprot Accession No. Q9H3R2 and related isoforms.

As used herein, "MUC4" (also known as ASGP; MUC-4; and HSA276359) refers to the protein of Uniprot Accession No. Q99102 and related isoforms.

As used herein, "MCAM" (also known as CD146; and MUC18) refers to the protein of Uniprot Accession No. P43121 and related isoforms.

As used herein, "LRRC32" (also known as D11S833E and GARP) refers to the protein of Uniprot Accession No. Q14392 and related isoforms.

As used herein, "sialyl-Tn" (also known as Tn Antigen, NeuAc(alpha→6)GalNAc(alpha1→O)Ser, Aandgs, 3-O-(2-Acetamido-6-O—(N-acetylneuraminyl)-2-deoxygalactosyl) serine, 114661-01-7, O—[N-acetyl-alpha-neuraminyl-(2→6)-N-acetyl-alpha-D-galactosaminyl]-L-serine, O-[(5-acetamido-3,5-dideoxy-D-glycero-alpha-D-galactononulopyranosylonic acid)-(2→6)-2-acetamido-2-deoxy-alpha-D-galactopyranosyl]-L-serine, AC1L4ZFL, CHEBI: 53610, and ZINC77313113) refers to the compound of PubChem 195103, and related variants.

As used herein, "gpA33" (also known as A33) refers to the protein of Uniprot Accession No. Q99795 and related isoforms.

As used herein, "GD3" (also known as Ganglioside GD3 (d18:1/16:0) and CHEBI:89636) refers to the ganglioside of PubChem CID: 20057323 and related variants.

As used herein, "GM2" (also known as G(M2) Ganglioside, Ganglioside GM2, GM2 lipid, CHEBI:60327, (2S,3R,4E)-3-hydroxy-2-(octadecanoylamino)octadec-4-en-1-yl 2-acetamido-2-deoxy-beta-D-galactopyranosyl-(1→4)-[5-acetamido-3,5-dideoxy-D-glycero-alpha-D-galacto-non-2-ulopyranonosyl-(2→3)]-beta-D-galactopyranosyl-(1→4)-beta-D-glucopyranoside, beta-D-GalNAc-(1→4)-[alpha-Neu5Ac-(2→3)]-beta-D-Gal-(1→4)-beta-D-Glc-(1<→1)-N-octadecanoylsphingosine, G(M2) GANGLIOSIDE, GM2 ganglioside, monosialoganglioside GM2, Epitope ID:139972, and ganglioside GM2 (18:1/18:0)) refers to the protein of PubChem CID 9898635 and related variants.

As used herein, "c-MET" (also known as HGFR; AUTS9; RCCP2; and c-Met; DFNB97) refers to the protein of Uniprot Accession No. P08581 and related isoforms.

As used herein, "EPHA3" (also known as EK4; ETK; HEK; ETK1; HEK4; and TYRO4) refers to the protein of Uniprot Accession No. P29320 and related isoforms.

As used herein, "TNFRSF10A" (also known as DR4; APO2; CD261; TRAILR1; and TRAILR-1) refers to the protein of Uniprot Accession No. O00220 and related isoforms.

As used herein, "TNFSF11" (also known as ODF; OPGL; sOdf; CD254; OPTB2; RANKL; TNLG6B; TRANCE; and hRANKL2) refers to the protein of Uniprot Accession No. O14788 and related isoforms.

As used herein, "CD74" (also known as Ii; CLIP; DHLAG; HLADG; and Ia-GAMMA) refers to the protein of Uniprot Accession No. P04233 and related isoforms.

As used herein, "PMEL" (also known as melanosome protein; P1; SI; SIL; ME20; P100; SILV; ME20M; gp100; ME20-M; PMEL17; and D12S53E) refers to the protein of Uniprot Accession No. P40967 and related isoforms.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The invention provides multi-specific binding proteins that bind to the NKG2D receptor and CD16 receptor on natural killer cells, and a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. The multi-specific binding proteins are useful in the pharmaceutical compositions and therapeutic methods described herein. Binding of the multi-specific binding proteins to the NKG2D receptor and CD16 receptor on a natural killer cell enhances the activity of the natural killer cell toward destruction of tumor cells expressing a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. Binding of the multi-specific binding proteins to tumor-associated antigen-expressing cells brings the cancer cells into proximity with the natural killer cell, which facilitates direct and indirect destruction of the cancer cells by the natural killer cell. Further description of some exemplary multi-specific binding proteins is provided below.

The first component of the multi-specific binding proteins binds to NKG2D receptor-expressing cells, which can include but are not limited to NK cells, γδ T cells and CD8+ αβ T cells. Upon NKG2D binding, the multi-specific binding proteins may block natural ligands, such as ULBP6 and MICA, from binding to NKG2D and activating NK cells.

The second component of the multi-specific binding proteins binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. Tumor-associated antigen-expressing cells may be found in leukemia, for example, acute myeloid leukemia and T-cell leukemia. Tumor-associated antigen-expressing cells may be found in association with other cancers and tumor types, for example, but not limited to, colorectal cancer, a gastrointestinal stromal tumor, melanoma, lung cancer, small cell lung cancer, non-small cell lung cancer, renal cancer, liver cancer, testicular cancer, bladder cancer, breast cancer, cervical cancer, uterine cancer, glioma, glioblastoma, neuroblastoma, head and neck cancer, lung cancer, pancreatic cancer, prostate cancer, sarcoma, mesothelioma, ovarian cancer, thyroid cancer, gastric cancer, multiple myeloma, esophageal cancer, cholangiocarcinoma, acute lymphoblastic leukemia, a bone metastatic cancer, diffuse large B cell cancer, and a B cell malignancy. KIT-expressing cells may be found in, for example, colorectal cancer, acute myeloid leukemia, gastrointestinal stromal tumor, melanoma, small cell lung cancer, non-small cell lung cancer, renal cancer, liver cancer, and testicular cancer. F3-expressing cells may be found in, for example, bladder cancer, breast cancer, cervical cancer, glioblastoma, head and neck cancer, lung cancer, pancreatic cancer, prostate cancer, sarcoma, and colorectal cancer. IGF1R-expressing cells may be found in, for example, breast cancer, cervical cancer, head and neck cancer, lung cancer, melanoma, mesothelioma, ovarian cancer, prostate cancer, sarcoma, thyroid cancer, renal cancer, colorectal cancer, pancreatic cancer, gliobastoma, and liver cancer. Lewis Y-expressing cells may be found in, for example, ovarian cancer, lung cancer, colorectal cancer, gastric cancer, breast cancer, cervical cancer, head and neck cancer, multiple myeloma, and acute myeloid leukemia. MUC13-expressing cells may be found in, for example, ovarian cancer, liver cancer, lung cancer, melanoma, liver cancer, gastric cancer, pancreatic cancer, renal cancer, esophageal cancer, breast cancer, colorectal cancer, cervical cancer, and cholangiocarcinoma. MUC4-expressing cells may be found in, for example, breast cancer, pancreatic cancer, ovarian cancer, lung cancer, acute lymphoblastic leukemia, bladder cancer, cervical cancer, colorectal cancer, head and neck cancer, and prostate cancer. MCAM-expressing cells may be found in, for example, melanoma, breast cancer, small cell lung cancer, sarcoma, colorectal cancer, pancreatic cancer, and renal cancer. LRRC32-expressing cells may be found in, for example, renal cancer, pancreatic cancer, sarcoma, ovarian cancer, lung cancer, gliobastoma, head and neck cancer, prostate cancer, liver cancer, breast cancer, and cervical cancer. sialyl-Tn-expressing cells may be found in, for example, ovarian cancer, pancreatic cancer, bladder cancer, gastric cancer, prostate cancer, colorectal cancer, and breast cancer. gpA33-expressing cells may be found in, for example, colorectal cancer, gastric cancer, and esophageal cancer. GD3-expressing cells may be found in, for example, lung cancer, glioma, breast cancer, melanoma, ovarian cancer, pancreatic cancer, and neuroblastoma. GM2-expressing cells may be found in, for example, gastric cancer, breast cancer, ovarian cancer, uterine cancer, cervical cancer, neuroblastoma, melanoma, lung cancer, mesothelioma, and liver cancer. c-MET-expressing cells may be found in, for example, renal cancer, thyroid cancer, melanoma, lung cancer, melanoma, liver cancer, pancreatic cancer, colorectal cancer, or head and neck cancer. EPHA3-expressing cells may be found in, for example, cervical cancer, head and neck cancer, gastric cancer, multiple myeloma, ovarian cancer, colorectal cancer, melanoma, breast cancer, prostate cancer, pancreatic cancer, lung cancer, and sarcoma. TNFRSF10A-expressing cells may be found in, for example, breast cancer, colorectal cancer, prostate cancer, pancreatic cancer, bladder cancer, and head and neck cancer. TNFSF11-expressing cells may be found in, for example, breast cancer, prostate cancer, and a bone metastatic cancer. CD74-expressing cells may be found in, for example, diffuse large B cell cancer, a B cell malignancy, renal cancer, lung cancer, ovarian cancer, melanoma, sarcoma, head and neck cancer, liver cancer, bladder cancer, glioma, breast cancer, and leukemia. PMEL-expressing cells may be found in, for example, melanoma and sarcomas.

The third component of the multi-specific binding proteins binds to cells expressing CD16, an Fc receptor on the surface of leukocytes including natural killer cells, macrophages, neutrophils, eosinophils, mast cells, and follicular dendritic cells.

Figure 1:
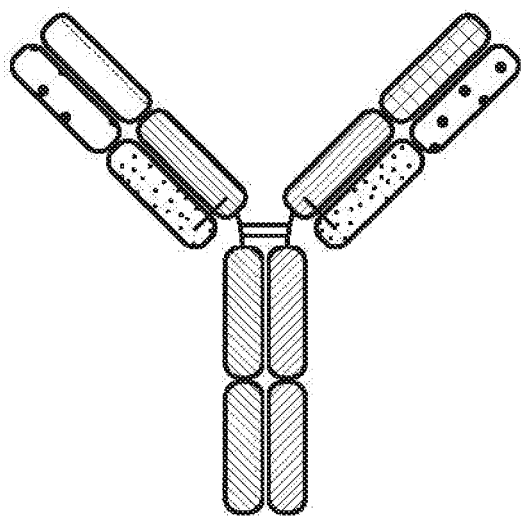
FIG. 1 is a representation of a heterodimeric, multi-specific antibody, e.g., a trispecific binding protein (TriN-KET). Each arm can represent either the NKG2D-binding domain, or the binding domain corresponding to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. In some embodiments, the NKG2D- and the tumor-associated antigen binding domains can share a common light chain.

The multi-specific binding proteins described herein can take various formats. For example, one format is a heterodimeric, multi-specific antibody including a first immunoglobulin heavy chain, a first immunoglobulin light chain, a second immunoglobulin heavy chain and a second immunoglobulin light chain (FIG. 1). The first immunoglobulin heavy chain includes a first Fc (hinge-CH2-CH3) domain, a first heavy chain variable domain and optionally a first CH1 heavy chain domain. The first immunoglobulin light chain includes a first light chain variable domain and optionally a first light chain constant domain. The first immunoglobulin light chain, together with the first immunoglobulin heavy chain, forms an antigen-binding site that binds NKG2D. The second immunoglobulin heavy chain comprises a second Fc (hinge-CH2-CH3) domain, a second heavy chain variable domain and optionally a second CH1 heavy chain domain. The second immunoglobulin light chain includes a second light chain variable domain and optionally a second light chain constant domain. The second immunoglobulin light chain, together with the second immunoglobulin heavy chain, forms an antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. The first Fc domain and second Fc domain together are able to bind to CD16 (FIG. 1). In some embodiments, the first immunoglobulin light chain is identical to the second immunoglobulin light chain.

Figure 2A:
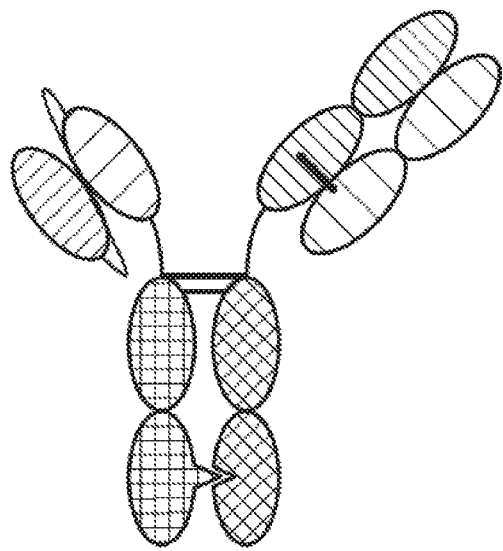
FIGS. 2A to 2E illustrate five exemplary formats of a multi-specific binding protein, e.g., a trispecific binding protein (TriNKET).

Another exemplary format involves a heterodimeric, multi-specific antibody including a first immunoglobulin heavy chain, a second immunoglobulin heavy chain and an immunoglobulin light chain (FIG. 2A). The first immunoglobulin heavy chain includes a first Fc (hinge-CH2-CH3) domain fused via either a linker or an antibody hinge to a single-chain variable fragment (scFv) composed of a heavy chain variable domain and light chain variable domain which pair and bind NKG2D, or bind a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. The second immunoglobulin heavy chain includes a second Fc (hinge-CH2-CH3) domain, a second heavy chain variable domain and a CH1 heavy chain domain. The immunoglobulin light chain includes a light chain variable domain and a light chain constant domain. The second immunoglobulin heavy chain pairs with the immunoglobulin light chain and binds to NKG2D or binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. The first Fc domain and the second Fc domain together are able to bind to CD16 (FIG. 2A).

Figure 2B:
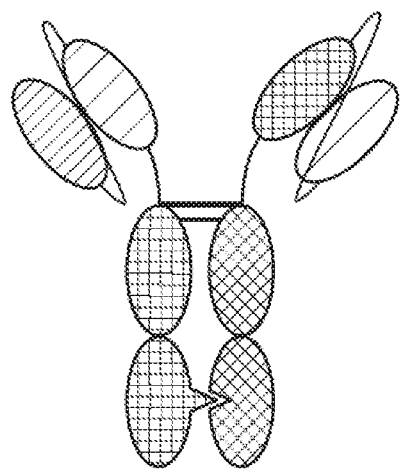

Another exemplary format involves a heterodimeric, multi-specific antibody including a first immunoglobulin heavy chain, and a second immunoglobulin heavy chain (FIG. 2B). The first immunoglobulin heavy chain includes a first Fc (hinge-CH2-CH3) domain fused via either a linker or an antibody hinge to a single-chain variable fragment (scFv) composed of a heavy chain variable domain and light chain variable domain which pair and bind NKG2D, or bind a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. The second immunoglobulin heavy chain includes a second Fc (hinge-CH2-CH3) domain fused via either a linker or an antibody hinge to a single-chain variable fragment (scFv) composed of a heavy chain variable domain and light chain variable domain which pair and bind NKG2D, or bind a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. The first Fc domain and the second Fc domain together are able to bind to CD16 (FIG. 2B).

In some embodiments, the single-chain variable fragment (scFv) described above is linked to the antibody constant domain via a hinge sequence. In some embodiments, the hinge comprises amino acids Ala-Ser. In some other embodiments, the hinge comprises amino acids Ala-Ser and Thr-Lys-Gly. The hinge sequence can provide flexibility of binding to the target antigen, and balance between flexibility and optimal geometry.

In some embodiments, the single-chain variable fragment (scFv) described above includes a heavy chain variable domain and a light chain variable domain. In some embodiments, the heavy chain variable domain forms a disulfide bridge with the light chain variable domain to enhance stability of the scFv. For example, a disulfide bridge can be formed between the C44 residue of the heavy chain variable domain and the C100 residue of the light chain variable domain, the amino acid positions numbered under Kabat. In some embodiments, the heavy chain variable domain is linked to the light chain variable domain via a flexible linker. Any suitable linker can be used, for example, the $(G_4S)_4$ linker. In some embodiments of the scFv, the heavy chain variable domain is positioned at the N-terminus of the light chain variable domain. In some embodiments of the scFv, the heavy chain variable domain is positioned at the C terminus of the light chain variable domain.

The multi-specific binding proteins described herein can further include one or more additional antigen-binding sites. The additional antigen-binding site(s) may be fused to the N-terminus of the constant region CH2 domain or to the C-terminus of the constant region CH3 domain, optionally via a linker sequence. In certain embodiments, the additional antigen-binding site(s) takes the form of a single-chain variable region (scFv) that is optionally disulfide-stabilized, resulting in a tetravalent or trivalent multispecific binding protein. For example, a multi-specific binding protein includes an NKG2D-binding site, a tumor-associated antigen-binding site where the tumor-associated antigen is selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, a third antigen-binding site that binds a tumor-associated antigen, and an antibody constant region or a portion thereof sufficient to bind CD16, or a fourth antigen-binding site that binds CD16. Any one of these antigen binding sites can either take the form of an Fab fragment or an scFv, such as the scFv described above.

Figure 2C:
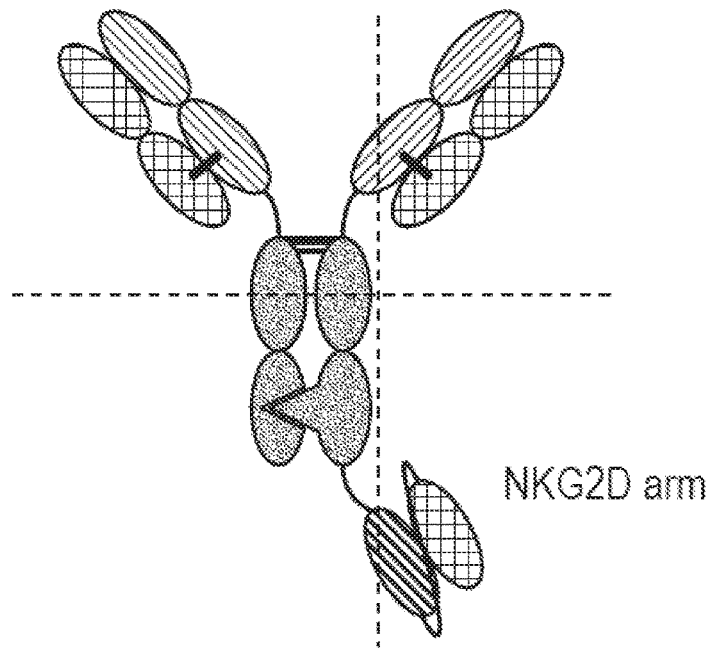
Figure 2D:
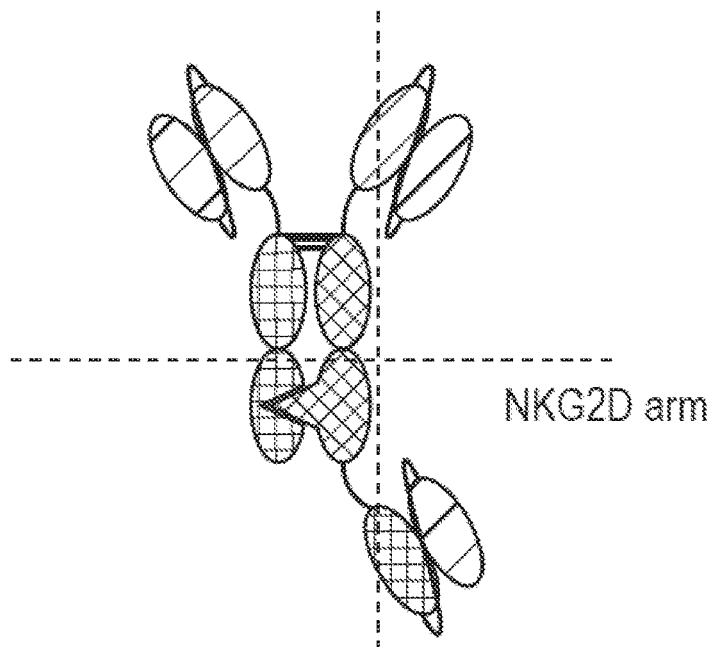
Figure 2E:
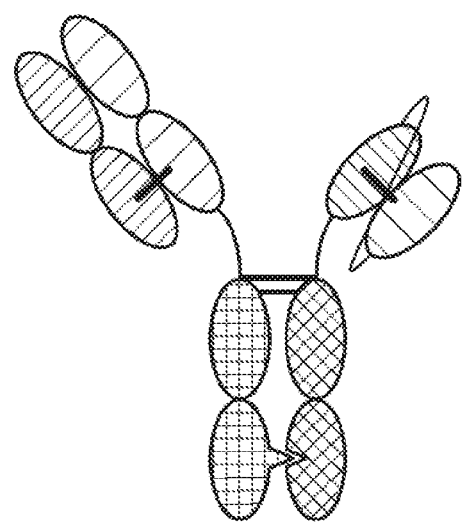

In some embodiments, the third antigen-binding site binds a different tumor-associated antigen from the tumor-associated antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. In some embodiments, the third antigen-binding site binds to the same tumor-associated antigen as the tumor-associated antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. In some embodiments, the third antigen-binding site comprises the same heavy chain and light chain CDR sequences as the tumor-associated antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. In some embodiments, the third antigen-binding site comprises the same heavy chain and light chain variable domain sequences as the tumor-associated antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. In some embodiments, the third antigen-binding site has the same amino acid sequence(s) as the tumor-associated antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. Exemplary formats are shown in FIGS. 2C and 2D. Accordingly, the multi-specific binding proteins can provide bivalent engagement of a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. Bivalent engagement of a tumor-associated antigen by the multi-specific proteins can stabilize the tumor-associated antigen on the cancer cell surface, and enhance cytotoxicity of NK cells towards the cancer cells. Bivalent engagement of a tumor-associated antigen by the multi-specific proteins can confer stronger binding of the multi-specific proteins to the cancer cells, thereby facilitating stronger cytotoxic response of NK cells towards the cancer cells, especially towards cancer cells expressing a low level of a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL.

The multi-specific binding proteins can take additional formats. In some embodiments, the multi-specific binding protein is in the Triomab form, which is a trifunctional, bispecific antibody that maintains an IgG-like shape. This chimera consists of two half antibodies, each with one light and one heavy chain, that originate from two parental antibodies.

In some embodiments, the multi-specific binding protein is the KiHform, which involves the knobs-into-holes (KiHs) technology. The KiH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (e.g., $T366W_{CH3A}$ in EU numbering). To accommodate the "knob," a complementary "hole" surface was created on the other CH3 domain (CH3B) by replacing the closest neighboring residues to the knob with smaller ones (e.g., $T366S/L368A/Y407V_{CH3B}$). The "hole" mutation was optimized by structured-guided phage library screening (Atwell S, Ridgway J B, Wells J A, Carter P., Stable heterodimers from remodeling the domain interface of a homodimer using a phage display library, J. Mol. Biol. (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. *J. Mol. Biol.*

(2014) 426(9):1947-57; Mimoto F, Kadono S, Katada H, Igawa T, Kamikawa T, Hattori K. Crystal structure of a novel asymmetrically engineered Fc variant with improved affinity for FcγRs. Mol. Immunol. (2014) 58(1):132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the multi-specific binding protein is in the dual-variable domain immunoglobulin (DVD-Ig™) form, which combines the target binding domains of two monoclonal antibodies via flexible naturally occurring linkers, and yields a tetravalent IgG-like molecule.

In some embodiments, the multi-specific binding protein is in the Orthogonal Fab interface (Ortho-Fab) form. In the ortho-Fab IgG approach (Lewis S M, Wu X, Pustilnik A, Sereno A, Huang F, Rick H L, et al., Generation of bispecific IgG antibodies by structure-based design of an orthogonal Fab interface. *Nat. Biotechnol*. (2014) 32(2):191-8), structure-based regional design introduces complementary mutations at the LC and $HC_{VH-CH1}$ interface in only one Fab fragment, without any changes being made to the other Fab fragment.

In some embodiments, the multi-specific binding protein is in the 2-in-1 Ig format. In some embodiments, the multi-specific binding protein is in the ES form, which is a heterodimeric construct containing two different Fab fragments binding to targets 1 and target 2 fused to the Fc. Heterodimerization is ensured by electrostatic steering mutations in the Fc.

In some embodiments, the multi-specific binding protein is in the κλ-Body form, which is a heterodimeric construct with two different Fab fragments fused to Fc stabilized by heterodimerization mutations: Fab fragment1 targeting antigen 1 contains kappa LC, while second Fab fragment targeting antigen 2 contains lambda LC. FIG. 30A is an exemplary representation of one form of a κλ-Body; FIG. 30B is an exemplary representation of another κλ-Body.

In some embodiments, the multi-specific binding protein is in Fab Arm Exchange form (antibodies that exchange Fab fragment arms by swapping a heavy chain and attached light chain (half-molecule) with a heavy-light chain pair from another molecule, which results in bispecific antibodies).

In some embodiments, the multi-specific binding protein is in the SEED Body form. The strand-exchange engineered domain (SEED) platform was designed to generate asymmetric and bispecific antibody-like molecules, a capability that expands therapeutic applications of natural antibodies. This protein engineering platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al., *Protein Eng. Des. Sel*. (2011, 24(5):447-54)).

In some embodiments, the multi-specific binding protein is in the LuZ-Y form, in which a leucine zipper is used to induce heterodimerization of two different HCs. (Wranik, B J. et al., *J. Biol. Chem*. (2012), 287:43331-9).

In some embodiments, the multi-specific binding protein is in the Cov-X-Body form. In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., *PNAS* (2010), 107(52); 22611-22616).

In some embodiments, the multi-specific binding protein is in an Oasc-Fab heterodimeric form that includes Fab fragment binding to target 1, and scFab binding to target 2 fused to Fc. Heterodimerization is ensured by mutations in the Fc.

In some embodiments, the multi-specific binding protein is in a DuetMab form, which is a heterodimeric construct containing two different Fab fragments binding to antigens 1 and 2, and Fc stabilized by heterodimerization mutations. Fab fragments 1 and 2 contain differential S—S bridges that ensure correct LC and HC pairing.

In some embodiments, the multi-specific binding protein is in a CrossmAb form, which is a heterodimeric construct with two different Fab fragments binding to targets 1 and 2, fused to Fc stabilized by heterodimerization. CL and CH1 domains and VH and VL domains are switched, e.g., CH1 is fused in-frame with VL, while CL is fused in-frame with VH.

In some embodiments, the multi-specific binding protein is in a Fit-Ig form, which is a homodimeric construct where Fab fragment binding to antigen 2 is fused to the N terminus of HC of Fab fragment that binds to antigen 1. The construct contains wild-type Fc.

Table 1 lists peptide sequences of heavy chain variable domains and light chain variable domains that, in combination, can bind to NKG2D. The NKG2D binding domains can vary in their binding affinity to NKG2D, nevertheless, they all activate human NK cells.

TABLE 1

| Clones | Heavy chain variable region amino acid sequence | Light chain variable region amino acid sequence |
|---|---|---|
| ADI-27705 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS<br>(SEQ ID NO: 1)<br>CDR1 (SEQ ID NO: 105)-GSFSGYYWS<br>CDR2 (SEQ ID NO: 106)-EIDHSGSTNYNPSLKS<br>CDR3 (SEQ ID NO: 107)-ARARGPWSFDP | DIQMTQSPSTLSASVGDRVTITCRASQSISSWLAWYQQKPGKAPKLLIYKASSLESGVPSRFSGSGSGTEFTLTISSLQPDDFATYYCQQYNSYPITFGGGTKVEIK<br>(SEQ ID NO: 2) |

TABLE 1-continued

| Clones | Heavy chain variable region amino acid sequence | Light chain variable region amino acid sequence |
| --- | --- | --- |
| ADI-27724 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 3) | EIVLTQSPGTLSLSPGERATLS CRASQSVSSSYLAWYQQKPG QAPRLLIYGASSRATGIPDRFS GSGSGTDFTLTISRLEPEDFAV YYCQQYGSSPITFGGGTKVEI K (SEQ ID NO: 4) |
| ADI-27740 (A40) | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 5) | DIQMTQSPSTLSASVGDRVTIT CRASQSIGSWLAWYQQKPGK APKLLIYKASSLESGVPSRFSG SGSGTEFTLTISSLQPDDFATY YCQQYHSFYTFGGGTKVEIK (SEQ ID NO: 6) |
| ADI-27741 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 7) | DIQMTQSPSTLSASVGDRVTIT CRASQSIGSWLAWYQQKPGK APKLLIYKASSLESGVPSRFSG SGSGTEFTLTISSLQPDDFATY YCQQSNSYYTFGGGTKVEIK (SEQ ID NO: 8) |
| ADI-27743 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 9) | DIQMTQSPSTLSASVGDRVTIT CRASQSISSWLAWYQQKPGK APKLLIYKASSLESGVPSRFSG SGSGTEFTLTISSLQPDDFATY YCQQYNSYPTFGGGTKVEIK (SEQ ID NO: 10) |
| ADI-28153 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWGFDPWGQGTLVTV SS (SEQ ID NO: 11) | ELQMTQSPSSLSASVGDRVTIT CRTSQSISSYLNWYQQKPGQP PKLLIYWASTRESGVPDRFSGS GSGTDFTLTISSLQPEDSATYY CQQSYDIPYTFGQGTKLEIK (SEQ ID NO: 12) |
| ADI-28226 (C26) | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 13) | DIQMTQSPSTLSASVGDRVTIT CRASQSISSWLAWYQQKPGK APKLLIYKASSLESGVPSRFSG SGSGTEFTLTISSLQPDDFATY YCQQYGSFPITFGGGTKVEIK (SEQ ID NO: 14) |
| ADI-28154 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 15) | DIQMTQSPSTLSASVGDRVTIT CRASQSISSWLAWYQQKPGK APKLLIYKASSLESGVPSRFSG SGSGTDFTLTISSLQPDDFATY YCQQSKEVPWTFGQGTKVEIK (SEQ ID NO: 16) |
| ADI-29399 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 17) | DIQMTQSPSTLSASVGDRVTIT CRASQSISSWLAWYQQKPGK APKLLIYKASSLESGVPSRFSG SGSGTEFTLTISSLQPDDFATY YCQQYNSFPTFGGGTKVEIK (SEQ ID NO: 18) |
| ADI-29401 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 19) | DIQMTQSPSTLSASVGDRVTIT CRASQSIGSWLAWYQQKPGK APKLLIYKASSLESGVPSRFSG SGSGTEFTLTISSLQPDDFATY YCQQYDIYPTFGGGTKVEIK (SEQ ID NO: 20) |
| ADI-29403 | QVQLQQWGAGLLKPSETLSLTCA VYGGSFSGYYWSWIRQPPGKGLE WIGEIDHSGSTNYNPSLKSRVTIS | DIQMTQSPSTLSASVGDRVTIT CRASQSISSWLAWYQQKPGK APKLLIYKASSLESGVPSRFSG |

TABLE 1-continued

| Clones | Heavy chain variable region amino acid sequence | Light chain variable region amino acid sequence |
|---|---|---|
| | VDTSKNQFSLKLSSVTAADTAVY YCARARGPWSFDPWGQGTLVTV SS (SEQ ID NO: 21) | SGSGTEFTLTISSLQPDDFATY YCQQYDSYPTFGGGTKVEIK (SEQ ID NO: 22) |
| ADI-29405 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 23) | DIQMTQSPSTLSASVGDRVTIT CRASQSISSWLAWYQQKPGK APKLLIYKASSLESGVPSRFSG SGSGTEFTLTISSLQPDDFATY YCQQYGSFPTFGGGTKVEIK (SEQ ID NO: 24) |
| ADI-29407 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 25) | DIQMTQSPSTLSASVGDRVTIT CRASQSISSWLAWYQQKPGK APKLLIYKASSLESGVPSRFSG SGSGTEFTLTISSLQPDDFATY YCQQYQSFPTFGGGTKVEIK (SEQ ID NO: 26) |
| ADI-29419 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 27) | DIQMTQSPSTLSASVGDRVTIT CRASQSISSWLAWYQQKPGK APKLLIYKASSLESGVPSRFSG SGSGTEFTLTISSLQPDDFATY YCQQYSSFSTFGGGTKVEIK (SEQ ID NO: 28) |
| ADI-29421 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 29) | DIQMTQSPSTLSASVGDRVTIT CRASQSISSWLAWYQQKPGK APKLLIYKASSLESGVPSRFSG SGSGTEFTLTISSLQPDDFATY YCQQYESYSTFGGGTKVEIK (SEQ ID NO: 30) |
| ADI-29424 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 31) | DIQMTQSPSTLSASVGDRVTIT CRASQSISSWLAWYQQKPGK APKLLIYKASSLESGVPSRFSG SGSGTEFTLTISSLQPDDFATY YCQQYDSFITFGGGTKVEIK (SEQ ID NO: 32) |
| ADI-29425 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 33) | DIQMTQSPSTLSASVGDRVTIT CRASQSISSWLAWYQQKPGK APKLLIYKASSLESGVPSRFSG SGSGTEFTLTISSLQPDDFATY YCQQYQSYPTFGGGTKVEIK (SEQ ID NO: 34) |
| ADI-29426 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 35) | DIQMTQSPSTLSASVGDRVTIT CRASQSIGSWLAWYQQKPGK APKLLIYKASSLESGVPSRFSG SGSGTEFTLTISSLQPDDFATY YCQQHSFPTFGGGTKVEIK (SEQ ID NO: 36) |
| ADI-29429 | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 37) | DIQMTQSPSTLSASVGDRVTIT CRASQSIGSWLAWYQQKPGK APKLLIYKASSLESGVPSRFSG SGSGTEFTLTISSLQPDDFATY YCQQYELYSYTFGGGTKVEIK (SEQ ID NO: 38) |
| ADI-29447 (F47) | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 39) | DIQMTQSPSTLSASVGDRVTIT CRASQSISSWLAWYQQKPGK APKLLIYKASSLESGVPSRFSG SGSGTEFTLTISSLQPDDFATY YCQQYDTFITFGGGTKVEIK (SEQ ID NO: 40) |

TABLE 1-continued

| Clones | Heavy chain variable region amino acid sequence | Light chain variable region amino acid sequence |
|---|---|---|
| ADI-27727 | QVQLVQSGAEVKKPGSSVKVSCK ASGGTFSSYAISWVRQAPGQGLE WMGGIIPIFGTANYAQKFQGRVTI TADESTSTAYMELSSLRSEDTAV YYCARGDSSIRHAYYYYGMDVW GQGTTVTVSS (SEQ ID NO: 41) CDR1 (SEQ ID NO: 43)- GTFSSYAIS (non-Kabat) or SYAIS (SEQ ID NO: 431) CDR2 (SEQ ID NO: 44)- GIIPIFGTANYAQKFQG CDR3 (SEQ ID NO: 45)- ARGDSSIRHAYYYYGMDV (non-Kabat) or GDSSIRHAYYYYGMDV (SEQ ID NO: 432) | DIVMTQSPDSLAVSLGERATIN CKSSQSVLYSSNNKNYLAWY QQKPGQPPKLLIYWASTRESG VPDRFSGSGSGTDFTLTISSLQ AEDVAVYYCQQYYSTPITFGG GTKVEIK (SEQ ID NO: 42) CDR1 (SEQ ID NO: 46)- KSSQSVLYSSNNKNYLA CDR2 (SEQ ID NO: 47)- WASTRES CDR3 (SEQ ID NO: 48)- QQYYSTPIT |
| ADI-29443 (F43) | QLQLQESGPGLVKPSETLSLTCTV SGGSISSSSYYWGWIRQPPGKGLE WIGSIYYSGSTYYNPSLKSRVTISV DTSKNQFSLKLSSVTAADTAVYY CARGSDRFHPYFDYWGQGTLVT VSS (SEQ ID NO: 49) CDR1 (SEQ ID NO: 51)- GSISSSSYYWG (non-Kabat) or SSSYYWG (SEQ ID NO: 433) CDR2 (SEQ ID NO: 52)- SIYYSGSTYYNPSLKS CDR3 (SEQ ID NO: 53)- ARGSDRFHPYFDY (non-Kabat) or GSDRFHPYFDY (SEQ ID NO: 434) | EIVLTQSPATLSLSPGERATLS CRASQSVSRYLAWYQQKPGQ APRLLIYDASNRATGIPARFSG SGSGTDFTLTISSLEPEDFAVY YCQQFDTWPPTFGGGTKVEIK (SEQ ID NO: 50) CDR1 (SEQ ID NO: 54)- RASQSVSRYLA CDR2 (SEQ ID NO: 55)- DASNRAT CDR3 (SEQ ID NO: 56)- QQFDTWPPT |
| ADI-29404 (F04) | QVQLQQWGAGLLKPSETLSLTCA VYGGSFSGYYWSWIRQPPGKGLE WIGEIDHSGSTNYNPSLKSRVTIS VDTSKNQFSLKLSSVTAADTAVY YCARARGPWSFDPWGQGTLVTV SS (SEQ ID NO: 57) | DIQMTQSPSTLSASVGDRVTIT CRASQSISSWLAWYQQKPGK APKLLIYKASSLESGVPSRFSG SGSGTEFTLTISSLQPDDFATY YCEQYDSYPTFGGGTKVEIK (SEQ ID NO: 58) |
| ADI-28200 | QVQLVQSGAEVKKPGSSVKVSCK ASGGTFSSYAISWVRQAPGQGLE WMGGIIPIFGTANYAQKFQGRVTI TADESTSTAYMELSSLRSEDTAV YYCARRGRKASGSFYYYGMDV WGQGTTVTVSS (SEQ ID NO: 59) CDR1 (SEQ ID NO: 134)- GTFSSYAIS CDR2 (SEQ ID NO: 135)- GIIPIFGTANYAQKFQG CDR3 (SEQ ID NO: 136)- ARRGRKASGSFYYYGMDV | DIVMTQSPDSLAVSLGERATIN CESSQSLLNSGNQKNYLTWY QQKPGQPPKPLIYWASTRESG VPDRFSGSGSGTDFTLTISSLQ AEDVAVYYCQNDYSYPYTFG QGTKLEIK (SEQ ID NO: 60) CDR1 (SEQ ID NO: 137)- ESSQSLLNSGNQKNYLT CDR2 (SEQ ID NO: 138)- WASTRES CDR3 (SEQ ID NO: 139)- QNDYSYPYT |
| ADI-29379 (E79) | QVQLVQSGAEVKKPGASVKVSC KASGYTFTSYYMHWVRQAPGQG LEWMGIINPSGGSTSYAQKFQGR VTMTRDTSTSTVYMELSSLRSED TAVYYCARGAPNYGDTTHDYYY MDVWGKGTTVTVSS (SEQ ID NO: 61) CDR1 (SEQ ID NO: 63)- YTFTSYYMH (non-Kabat) or SYYMH (SEQ ID NO: 435) CDR2 (SEQ ID NO: 64)- IINPSGGSTSYAQKFQG CDR3 (SEQ ID NO: 65)- ARGAPNYGDTTHDYYYMDV (non-Kabat) or GAPNYGDTTHDYYYMDV (SEQ ID NO: 436) | EIVMTQSPATLSVSPGERATLS CRASQSVSSNLAWYQQKPGQ APRLLIYGASTRATGIPARFSG SGSGTEFTLTISSLQSEDFAVY YCQQYDDWPFTFGGGTKVEI K (SEQ ID NO: 62) CDR1 (SEQ ID NO: 66)- RASQSVSSNLA CDR2 (SEQ ID NO: 67)- GASTRAT CDR3 (SEQ ID NO: 68)- QQYDDWPFT |

TABLE 1-continued

| Clones | Heavy chain variable region amino acid sequence | Light chain variable region amino acid sequence |
|---|---|---|
| ADI-29463 (F63) | QVQLVQSGAEVKKPGASVKVSC KASGYTFTGYYMHWVRQAPGQG LEWMGWINPNSGGTNYAQKFQG RVTMTRDTSISTAYMELSRLSD DTAVYYCARDTGEYYDTDDHGM DVWGQGTTVTSS (SEQ ID NO: 69) CDR1 (SEQ ID NO: 71)- YTFTGYYMH (non-Kabat) or GYYMH (SEQ ID NO: 437) CDR2 (SEQ ID NO: 72)- WINPNSGGTNYAQKFQG CDR3 (SEQ ID NO: 73)- ARDTGEYYDTDDHGMDV (non-Kabat) or DTGEYYDTDDHGMDV (SEQ ID NO: 408) | EIVLTQSPGTLSLSPGERATLS CRASQSVSSNLAWYQQKPGQ APRLLIYGASTRATGIPARFSG SGSGTEFTLTISSLQSEDFAVY YCQQDDYWPPTFGGGTKVEI K (SEQ ID NO: 70) CDR1 (SEQ ID NO: 74)- RASQSVSSNLA CDR2 (SEQ ID NO: 75)- GASTRAT CDR3 (SEQ ID NO: 76)- QQDDYWPPT |
| ADI-27744 (A44) | EVQLLESGGGLVQPGGSLRLSCA ASGFTFSSYAMSWVRQAPGKGLE WVSAISGSGGSTYYADSVKGRFTI SRDNSKNTLYLQMNSLRAEDTAV YYCAKDGGYYDSGAGDYWGQG TLVTVSS (SEQ ID NO: 77) CDR1 (SEQ ID NO: 79)- FTFSSYAMS (non-Kabat) or SYAMS (SEQ ID NO: 409) CDR2 (SEQ ID NO: 80)- AISGSGGSTYYADSVKG CDR3 (SEQ ID NO: 81)- AKDGGYYDSGAGDY (non-Kabat) or DGGYYDSGAGDY (SEQ ID NO: 411) | DIQMTQSPSSVSASVGDRVTIT CRASQGIDSWLAWYQQKPGK APKLLIYAASSLQSGVPSRFSG SGSGTDFTLTISSLQPEDFATY YCQQGVSYPRTFGGGTKVEIK (SEQ ID NO: 78) CDR1 (SEQ ID NO: 82)- RASQGIDSWLA CDR2 (SEQ ID NO: 83)- AASSLQS CDR3 (SEQ ID NO: 84)- QQGVSYPRT |
| ADI-27749 (A49) | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPMGAAAGWFDPWGQ GTLVTVSS (SEQ ID NO: 85) CDR1 (SEQ ID NO: 87)- FTFSSYSMN (non-Kabat) or SYSMN (SEQ ID NO: 387) CDR2 (SEQ ID NO: 88)- SISSSSSYIYYADSVKG CDR3 (SEQ ID NO: 89)- ARGAPMGAAAGWFDP (non-Kabat) or GAPMGAAAGWFDP (SEQ ID NO: 412) | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 86) CDR1 (SEQ ID NO: 90)- RASQGISSWLA CDR2 (SEQ ID NO: 91)- AASSLQS CDR3 (SEQ ID NO: 92)- QQGVSFPRT |
| ADI-29378 (E78) | QVQLVQSGAEVKKPGASVKVSC KASGYTFTSYYMHWVRQAPGQG LEWMGIINPSGGSTSYAQKFQGR VTMTRDTSTSTVYMELSSLRSED TAVYYCAREGAGFAYGMDYYY MDVWGKGTTVTVSS (SEQ ID NO: 93) CDR1 (SEQ ID NO: 95)- YTFTSYYMH (non-Kabat) or SYYMH (SEQ ID NO: 421) CDR2 (SEQ ID NO: 96)- IINPSGGSTSYAQKFQG CDR3 (SEQ ID NO: 97)- AREGAGFAYGMDYYYMDV (non-Kabat) or EGAGFAYGMDYYYMDV (SEQ ID NO: 422) | EIVLTQSPATLSLSPGERATLS CRASQSVSSYLAWYQQKPGQ APRLLIYDASNRATGIPARFSG SGSGTDFTLTISSLEPEDFAVY YCQQSDNWPFTFGGGTKVEIK (SEQ ID NO: 94) CDR1 (SEQ ID NO: 98)- RASQSVSSYLA CDR2 (SEQ ID NO: 99)- DASNRAT CDR3 (SEQ ID NO: 100)- QQSDNWPFT |
| A49MI | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPIGAAAGWFDPWGQG TLVTVSS (SEQ ID NO: 388) CDR1: FTFSSYSMN (SEQ ID | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 86) CDR1 (SEQ ID NO: 90)- |

TABLE 1-continued

| Clones | Heavy chain variable region amino acid sequence | Light chain variable region amino acid sequence |
|---|---|---|
| | NO: 87) (non-Kabat) or SYSMN (SEQ ID NO: 387) CDR2: SISSSSSYIYYADSVKG (SEQ ID NO: 88) CDR3: (non-Kabat) ARGAPIGAAAGWFDP (SEQ ID NO: 389) or GAPIGAAAGWFDP (SEQ ID NO: 390) | RASQGISSWLA CDR2 (SEQ ID NO: 91)- AASSLQS CDR3 (SEQ ID NO: 92)- QQGVSFPRT |
| | A49MI-HC: EVQLVESGGGLVKPGGSLRLSCAASGFTFSSYSMNWVRQAPGKGL EWVSSISSSSSYIYYADSVKGRFTISRDNAKNSLYLQMNSLRAEDTA VYYCARGAPIGAAAGWFDPWGQGTLVTVSSASTKGPSVFPLAPSSK STSGGTAALGCLVKDYFPEPVTVSWNSGALTSGVHTFPAVLQSSGL YSLSSVVTVPSSSLGTQTYICNVNHKPSNTKVDKKVEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVS LTCLVKGFYPSDIAVEWESNGQPENNYKTTPPVLDSDGSFFLYSRLT VDKSRWQQGNVFSCSVMHEALHNHYTQKSLSLSPG (SEQ ID NO: 423) | |
| | A49MI-LC: DIQMTQSPSSVSASVGDRVTITCRASQGISSWLAWYQQKPGKAPKL LIYAASSLQSGVPSRFSGSGSGTDFTLTISSLQPEDFATYYCQQGVSF PRTFGGGTKVEIKRTVAAPSVFIFPPSDEQLKSGTASVVCLLNNFYPR EAKVQWKVDNALQSGNSQESVTEQDSKDSTYSLSSTLTLSKADYE KHKVYACEVTHQGLSSPVTKSFNRGEC (SEQ ID NO: 424) | |
| A49MQ | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPQGAAAGWFDPWGQ GTLVTVSS (SEQ ID NO: 391) CDR1: FTFSSYSMN (SEQ ID NO: 87) (non-Kabat) or SYSMN (SEQ ID NO: 387) CDR2: SISSSSSYIYYADSVKG (SEQ ID NO: 88) CDR3 (non-Kabat) (SEQ ID NO: 392)-ARGAPQGAAAGWFDP or CDR3 (SEQ ID NO: 393)- GAPQGAAAGWFDP | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 86) CDR1 (SEQ ID NO: 90)- RASQGISSWLA CDR2 (SEQ ID NO: 91)- AASSLQS CDR3 (SEQ ID NO: 92)- QQGVSFPRT |
| A49ML | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPLGAAAGWFDPWGQ GTLVTVSS (SEQ ID NO: 394) CDR1: FTFSSYSMN (SEQ ID NO: 87) (non-Kabat) or SYSMN (SEQ ID NO: 387) CDR2: SISSSSSYIYYADSVKG (SEQ ID NO: 88) CDR3 (non-Kabat) (SEQ ID NO: 395)-ARGAPLGAAAGWFDP or CDR3 (SEQ ID NO: 396)- GAPLGAAAGWFDP | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 86) CDR1 (SEQ ID NO: 90)- RASQGISSWLA CDR2 (SEQ ID NO: 91)- AASSLQS CDR3 (SEQ ID NO: 92)- QQGVSFPRT |
| A49MF | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPFGAAAGWFDPWGQ GTLVTVSS (SEQ ID NO: 397) CDR1: FTFSSYSMN (SEQ ID NO: 87) (non-Kabat) or SYSMN (SEQ ID NO: 387) CDR2: SISSSSSYIYYADSVKG (SEQ ID NO: 88) | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 86) CDR1 (SEQ ID NO: 90)- RASQGISSWLA CDR2 (SEQ ID NO: 91) - AASSLQS CDR3 (SEQ ID NO: 92)- QQGVSFPRT |

TABLE 1-continued

| Clones | Heavy chain variable region amino acid sequence | Light chain variable region amino acid sequence |
| --- | --- | --- |
| | CDR3 (non-Kabat) (SEQ ID NO: 398)-ARGAPFGAAAGWFDP or CDR3 (SEQ ID NO: 399)-GAPFGAAAGWFDP | |
| A49MV | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPVGAAAGWFDPWGQ GTLVTVSS (SEQ ID NO: 400) CDR1: FTFSSYSMN (SEQ ID NO: 87) (non-Kabat) or SYSMN (SEQ ID NO: 387) CDR2: SISSSSSYIYYADSVKG (SEQ ID NO: 88) CDR3 (non-Kabat) (SEQ ID NO: 401)-ARGAPVGAAAGWFDP or CDR3 (SEQ ID NO: 402)-GAPVGAAAGWFDP | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 86) CDR1 (SEQ ID NO: 90)- RASQGISSWLA CDR2 (SEQ ID NO: 91)- AASSLQS CDR3 (SEQ ID NO: 92)- QQGVSFPRT |
| A49-consensus | EVQLVESGGGLVKPGGSLRLSCA ASGFTFSSYSMNWVRQAPGKGLE WVSSISSSSSYIYYADSVKGRFTIS RDNAKNSLYLQMNSLRAEDTAV YYCARGAPXGAAAGWFDPWGQ GTLVTVSS, wherein X is M, L, I, V, Q, or F (SEQ ID NO: 403) CDR1: FTFSSYSMN (SEQ ID NO: 87) (non-Kabat) or SYSMN (SEQ ID NO: 387) CDR2: SISSSSSYIYYADSVKG (SEQ ID NO: 88) CDR3 (non-Kabat) (SEQ ID NO: 404)-ARGAPXGAAAGWFDP or CDR3 (SEQ ID NO: 405)- GAPXGAAAGWFDP, wherein X is M, L, I, V, Q, or F | DIQMTQSPSSVSASVGDRVTIT CRASQGISSWLAWYQQKPGK APKLLIYAASSLQSGVPSRFSG SGSGTDFTLTISSLQPEDFATY YCQQGVSFPRTFGGGTKVEIK (SEQ ID NO: 86) CDR1 (SEQ ID NO: 90)- RASQGISSWLA CDR2 (SEQ ID NO: 91)- AASSLQS CDR3 (SEQ ID NO: 92)- QQGVSFPRT |

Alternatively, a heavy chain variable domain represented by SEQ ID NO:101 can be paired with a light chain variable domain represented by SEQ ID NO:102 to form an antigen-binding site that can bind to NKG2D, as illustrated in U.S. Pat. No. 9,273,136.

SEQ ID NO: 101
QVQLVESGGGLVKPGGSLRLSCAASGFTFSSYGMEIWVRQAPGKGLEWVA

FIRYDGSNKYYADSVKGRFTISRDNSKNTLYLQMNSLRAEDTAVYYCAKD

RGLGDGTYFDYWQGTTVTVSS

SEQ ID NO: 102
QSALTQPASVSGSPGQSITISCSGSSSNIGNNAVNWYQQLPGKAPKLLIY

YDDLLPSGVSDRFSGSKSGTSAFLAISGLQSEDEADYYCAAWDDSLNGPV

FGGGTKLTVL

Alternatively, a heavy chain variable domain represented by SEQ ID NO:103 can be paired with a light chain variable domain represented by SEQ ID NO:104 to form an antigen-binding site that can bind to NKG2D, as illustrated in U.S. Pat. No. 7,879,985.

SEQ ID NO: 103
QVHLQESGPGLVKPSETLSLTCTVSDDSISSYYWSWIRQPPGKGLEWIGH

ISYSGSANYNPSLKSRVTISVDTSKNQFSLKLSSVTAADTAVYYCANWDD

AFNIWGQGTMVTVSS

SEQ ID NO: 104
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

QGTKVEIK

In one aspect, the present disclosure provides multi-specific binding proteins that bind to the NKG2D receptor and CD16 receptor on natural killer cells, and the antigen KIT. Table 2 lists some exemplary sequences of heavy chain variable domains and light chain variable domains that, in combination, can bind to KIT.

TABLE 2

| Clones | Heavy chain variable domain amino acid sequence | Light chain variable domain amino acid sequence |
|---|---|---|
| anti-KIT (AMG191) (U.S. Publication No. 2013/0288303 A1) | QVQLQQPGAELVKPGASVKMS CKASGYTFTSYNMHWVKQTP GQGLEWIGVIYSGNGDTSYNQ KFKGKATLTADKSSSTAYMQI NSLTSEDSAVYYCARERDTRF GNWGQGTLVTVSA (SEQ ID NO: 109) CDR1 (SEQ ID NO: 110) - SYNMH CDR2 (SEQ ID NO: 111) - VIYSGNGDTSYNQKFKG CDR3 (SEQ ID NO: 112) - RDTRFGN | NIVLTQSPASLAVSLGLRA TISCRASESVDIYGNSFMH WYQQKPGQPPKLLIYLAS NLESGVPARFSGSGSRTDF TLTIDPVEADDAATYYCQ QNNEDPYTFGGGTKLEIK R (SEQ ID NO: 113) CDR1(SEQ ID NO: 114) - RASESVDIYGNSFMH CDR2 (SEQ ID NO: 115) - LASNLES CDR3 (SEQ ID NO: 116) - QQNNEDPYT |
| anti-KIT (CDX-0158) (U.S. Publication No. 2017/0158778) | QVQLKQSGAELVRPGASVKLS CKASGYTFTDYYINWVKQRPG QGLEWIARIYPGSGNTYYNEKF KGKATLTAEKSSSTAYMQLSS LTSEDSAVYFCARGVYYFDYW GQ GTTLTVSS (SEQ ID NO: 117) CDR1 (SEQ ID NO: 118) - DYYIN CDR2 (SEQ ID NO: 119) - RIYPGSGNTYYNEKFKG CDR3 (SEQ ID NO: 120) - GWYYFDY | DIVMTQSQKFMSTSVGDR VSVTCKASQNVRTNVAW YQQKPGQSPKALIYSASY RYSGVPDRFTGSGSGTDFT LTISNVQSEDLADYFCQQ YNSYPRTFGGGTKLEIKR (SEQ ID NO: 121) CDR1 (SEQ ID NO: 122) - KASQNVRTNVA CDR2 (SEQ ID NO: 123) - SASYRYS CDR3 (SEQ ID NO: 124) - QQYNSYPRT |

Alternatively, novel antigen-binding sites that can bind to KIT can be identified by screening for binding to the amino acid sequence defined by SEQ ID NO:125 or a mature extracellular fragment thereof.

SEQ ID NO: 125
MRGARGAWDFLCVLLLLLRVQTGSSQPSVSPGEPSPPSIHPGKSDLIVRV

GDEIRLLCTDPGFVKWTFEILDETNENKQNEWITEKAEATNTGKYTCTNK

HGLSNSIYVFVRDPAKLFLVDRSLYGKEDNDTLVRCPLTDPEVTNYSLKG

CQGKPLPKDLRFIPDPKAGIMIKSVKRAYHRLCLHCSVDQEGKSVLSEKF

ILKVRPAFKAVPVVSVSKASYLLREGEEFTVTCTIKDVSSSVYSTWKREN

SQTKLQEKYNSWHHGDFNYERQATLTISSARVNDSGVFMCYANNTFGSAN

VTTTLEVVDKGFINIFPMINTTVFVNDGENVDLIVEYEAFPKPEHQQWIY

MNRTFTDKWEDYPKSENESNIRYVSELHLTRLKGTEGGTYTFLVSNSDVN

AAIAFNVYVNTKPEILTYDRLVNGMLQCVAAGFPEPTIDWYFCPGTEQRC

SASVLPVDVQTLNSSGPPFGKLVVQSSIDSSAFKHNGTVECKAYNDVGKT

SAYFNFAFKGNNKEQIHPHTLFTPLLIGFVIVAGMMCIIVMILTYKYLQK

PMYEVQWKVVEEINGNNYVYIDPTQLPYDHKWEFPRNRLSFGKTLGAGAF

GKVVEATAYGLIKSDAAMTVAVKMLKPSAHLTEREALMSELKVLSYLGNH

MNIVNLLGACTIGGPTLVITEYCCYGDLLNFLRRKRDSFICSKQEDHAEA

ALYKNLLHSKESSCSDSTNEYMDMKPGVSYVVPTKADKRRSVRIGSYIER

DVTPAIMEDDELALDLEDLLSFSYQVAKGMAFLASKNCIHRDLAARNILL

THGRITKICDFGLARDIKNDSNYVVKGNARLPVKWMAPESIFNCVYTFES

DVWSYGIFLWELFSLGSSPYPGMPVDSKFYKMIKEGFRMLSPEHAPAEMY

DIMKTCWDADPLKRPTFKQIVQLIEKQISESTNHIYSNLANCSPNRQKPV

VDHSVRINSVGSTASSSQPLLVHDDV

In another aspect, the present disclosure provides multi-specific binding proteins that bind to the NKG2D receptor and CD16 receptor on natural killer cells, and the antigen F3. Table 3 lists some exemplary sequences of heavy chain variable domains and light chain variable domains that, in combination, can bind to F3.

TABLE 3

| Clones | Heavy chain variable domain amino acid sequence | Light chain variable domain amino acid sequence |
|---|---|---|
| anti-F3 (tisotumab vedotin) | EVQLLESGGGLVQPGGSLRLSC AASGFTFSNYAMSWVRQAPGK GLEWVSSISGSGDYTYYTDSVK GRFTISRDNSKNTLYLQMNSLR AEDTAVYYCARSPWGYYLDSW GQGTLVTVSSA (SEQ ID NO: 126) CDR1 (SEQ ID NO: 127)- GFTFSNY CDR2 (SEQ ID NO: 128)- SGSGDY CDR3 (SEQ ID NO: 129)- SPWGYYLDS | DIQMTQSPPSLSASAGDRV TITCRASQGISSRLAWYQQ KPEKAPKSLIYAASSLQSG VPSRFSGSGSGTDFTLTISS LQPEDFATYYCQQYNSYP YTFGQGTKLEIKR (SEQ ID NO: 130) CDR1 (SEQ ID NO: 131)- QGISSRLA CDR2 (SEQ ID NO: 132)- AASSLQS CDR3 (SEQ ID NO: 133)- QQYNSYPYT |
| anti-F3 (TNX-832) | EIQLQQSGPELVKPGASVQVSCK TSGYSFTDYNVYWVRQSHGKSL EWIGYIDPYNGITIYDQNFKGKA TLTVDKSSTTAFMHLNSLTSDDS AVYFCARDVTTALDFWGQGTT LTVSS (SEQ ID NO: 140) CDR1 (SEQ ID NO: 141)- GYSFTDY CDR2 (SEQ ID NO: 142)- DPYNGI CDR3 (SEQ ID NO: 143)- DVTTALDF | DIQMTQSPASQSASLGESV TITCLASQTIDTWLAWYQQ KPGKSPQLLIYAATNLADG VPSRFSGSGSGTKFSFKISS LQAEDFVNYYCQQVYSSP FTFGAGTKLELK (SEQ ID NO: 144) CDR1 (SEQ ID NO: 145)- QTIDTWLA CDR2 (SEQ ID NO: 146)- AATNLAD CDR3 (SEQ ID NO: 147)- QQVYSSPFT |

Alternatively, novel antigen-binding sites that can bind to F3 can be identified by screening for binding to the amino acid sequence defined by SEQ ID NO:148 or a mature extracellular fragment thereof.

SEQ ID NO: 148
METPAWPRVPRPETAVARTLLLGWVFAQVAGASGTTNTVAAYNLTWKSTN
FKTILEWEPKPVNQVYTVQISTKSGDWKSKCFYTTDTECDLTDEIVKDVK
QTYLARVFSYPAGNVESTGSAGEPLYENSPEFTPYLETNLGQPTIQSFEQ
VGTKVNVTVEDERTLVRRNNTFLSLRDVFGKDLIYTLYYWKSSSSGKKTA

-continued

KTNTNEFLIDVDKGENYCFSVQAVIPSRTVNRKSTDSPVECMGQEKGEFR
EIFYIIGAVVFVVIILVIILAISLHKCRKAGVGQSWKENSPLNVS

In another aspect, the present disclosure provides multi-specific binding proteins that bind to the NKG2D receptor and CD16 receptor on natural killer cells, and the antigen IGF1R. Table 4 lists some exemplary sequences of heavy chain variable domains and light chain variable domains that, in combination, can bind to IGF1R.

TABLE 4

| Clones | Heavy chain variable domain amino acid sequence | Light chain variable domain amino acid sequence |
|---|---|---|
| anti-IGF1R (cixutumumab) | EVQLVQSGAEVKKPGSSVKVSC KASGGTFSSYAISWVRQAPGQG LEWMGGIIPIFGTANYAQKFQGR VTITADKSTSTAYMELSSLRSED TAVYYCARAPLRFLEWSTQDHY YYYYMDVWGKGTTVTVSSA (SEQ ID NO: 149) CDR1 (SEQ ID NO: 150)- GGTFSSY CDR2 (SEQ ID NO: 151)- IPIFGT CDR3 (SEQ ID NO: 152)- APLRFLEWSTQDHYYYYMDV | SSELTQDPAVSVALGQT VRITCQGDSLRSYYATW YQQKPGQAPILVIYGEN KRPSGIPDRFSGSSSGNT ASLTITGAQAEDEADYY CKSRDGSGQHLVFGGGT KLTVLG (SEQ ID NO: 153) CDR1 (SEQ ID NO: 154)- SLRSYYAT CDR2 (SEQ ID NO: 155)- GENKRPS CDR3 (SEQ ID NO: 156)- KSRDGSGQHLV |
| anti-IGF1R (ganitumab) | QVQLQESGPGLVKPSGTLSLTCA VSGGSISSSNWWSWVRQPPGKG LEWIGEIYHSGSTNYNPSLKSRV TISVDKSKNQFSLKLSSVTAADT AVYYCARWTGRTDAFDIWGQG TMVTVSSA (SEQ ID NO: 157) | DVVMTQSPLSLPVTPGE PASISCRSSQSLLHSNGY NYLDWYLQKPGQSPQL LIYLGSNRASGVPDRFSG SGSGTDFTLKISRVEAED VGVYYCMQGTHWPLTF GQGTKVEIKR |

TABLE 4-continued

| Clones | Heavy chain variable domain amino acid sequence | Light chain variable domain amino acid sequence |
|---|---|---|
| | CDR1 (SEQ ID NO: 158)- GGSISSSN<br>CDR2 (SEQ ID NO: 159)- YHSGS<br>CDR3 (SEQ ID NO: 160)- WTGRTDAFDI | (SEQ ID NO: 161)<br>CDR1 (SEQ ID NO: 162)- QSLLHSNGYNYLD<br>CDR2 (SEQ ID NO: 163)- LGSNRAS<br>CDR3 (SEQ ID NO: 164)- MQGTHWPLT |

Alternatively, novel antigen-binding sites that can bind to IGF1R can be identified by screening for binding to the amino acid sequence defined by SEQ ID NO:165 or a mature extracellular fragment thereof.

SEQ ID NO: 165
MKSGSGGGSPTSLWGLLFLSAALSLWPTSGEICGPGIDIRNDYQQLKRLEN

CTVIEGYLHILLISKAEDYRSYRFPKLTVITEYLLLFRVAGLESLGDLFPN

LTVIRGWKLFYNYALVIFEMTNLKDIGLYNLRNITRGAIRIEKNADLCYLS

TVDWSLILDAVSNNYIVGNKPPKECGDLCPGTMEEKPMCEKTTINNEYNYR

CWTTNRCQKMCPSTCGKRACTENNECCHPECLGSCSAPDNDTACVACRHYY

YAGVCVPACPPNTYRFEGWRCVDRDFCANILSAESSDSEGFVIHDGECMQE

CPSGFIRNGSQSMYCIPCEGPCPKVCEEEKKTKTIDSVTSAQMLQGCTIFK

GNLLINIRRGNNIASELENFMGLIEVVTGYVKIRHSHALVSLSFLKNLRLI

LGEEQLEGNYSFYVLDNQNLQQLWDWDHRNLTIKAGKMYFAFNPKLCVSEI

YRMEEVTGTKGRQSKGDINTRNNGERASCESDVLHFTSTTTSKNRIIITWH

DRYRPPDYRLISFTVYYKEAPFKNVTEYDGQDACGSNSWNMVDVDLPPNKD

VEPGILLHGLKPWTQYAVYVKAVTLTMVENDHIRGAKSEILYIRTNASVPS

IPLDVLSASNSSSQLIVKWNPPSLPNGNLSYYIVRWQRQPQDGYLYRHNYC

SKDKIPIRKYADGTIDIEEVTENPKTEVCGGEKGPCCACPKTEAEKQAEKE

EAEYRKVFENFLHNSIFVPRPERKRRDVMQVANTTMSSRSRNTTAADTYNI

TDPEELETEYPFFESRVDNKERTVISNLRPFTLYRIDIHSCNHEAEKLGCS

ASNFVFARTMPAEGADDIPGPVTWEPRPENSIFLKWPEPENPNGLILMYEI

KYGSQVEDQRECVSRQEYRKYGGAKLNRLNPGNYTARIQATSLSGNGSWTD

PVFFYVQAKTGYENFIHLIIALPVAVLLIVGGLVIMLYVFHRKRNNSRLGN

GVLYASVNPEYFSAADVYVPDEWEVAREKITMSRELGQGSF GMVYEGVAK

GVVKDEPETRVAIKTVNEAASMRERIEFLNEASVMKEFNCHHVVRLLGVVS

QGQPTLVIMELMTRGDLKSYLRSLRPEMENNPVLAPPSLSKMIQMAGEIAD

GMAYLNANKFVHRDLAARNCMVAEDFTVKIGDFGMTRDIYETDYYRKGGKG

LLPVRWMSPESLKDGVFTTYSDVWSFGVVLWEIATLAEQPYQGLSNEQVLR

FVMEGGLLDKPDNCPDMLFELMRMCWQYNPKMRPSFLEIISSIKEEMEPGF

REVSFYYSEENKLPEPEELDLEPENMESVPLDPSASSSSLPLPDRHSGHKA

ENGPGPGVLVLRASFDERQPYAHMNGGRKNERALPLPQSSTC

In another aspect, the present disclosure provides multi-specific binding proteins that bind to the NKG2D receptor and CD16 receptor on natural killer cells, and the antigen Lewis Y. Table 5 lists some exemplary sequences of heavy chain variable domains and light chain variable domains that, in combination, can bind to Lewis Y.

TABLE 5

| Clones | Heavy chain variable domain amino acid sequence | Light chain variable domain amino acid sequence |
|---|---|---|
| anti-Lewis Y (MB 311) | EVQLLESGGGLVQPGGSLRLSCA ASGFTFSDYYMYWVRQAPEKRL EWVAYISNGGGSSHYVDSVKGR FTISRDNAKNTLYLQMNSLRAED TALYHCARGMDYGAWFAYWG QGTLVTVSS<br>(SEQ ID NO: 166)<br>CDR1 (SEQ ID NO: 167) - GFTFSDY<br>CDR2 (SEQ ID NO: 168) - SNGGGS<br>CDR3 (SEQ ID NO: 169) - GMDYGAWFAY | DIVMTQSPLSLPVTPGEP ASISCRSSQSIVHSNGNT YLEWYLQKPGQSPQLLI SKVSNRFSGVPDRFSGS GSGTDFTLKISRVEAEDV GVYYCFQGSHVPFTFGQ GTKLEIK<br>(SEQ ID NO: 170)<br>CDR1(SEQ ID NO: 171) - QSIVHSNGNTYLE<br>CDR2 (SEQ ID NO: 172) - KVSNRFS<br>CDR3 (SEQ ID NO: 173) - FQGSHVPFT |
| anti-Lewis Y (Rebmab 100) (U.S. Pat. | EVQLVESGGGVVQPGRSLRLSCS SSGFTFSDYMYWVRQAPGKGL EWVAYMSNVGAITDYPDTVKG | DIQMTQSPSSLSASVGDR VTITCRSSQRIVHSNGNT YLEWYQQTPGKAPKLLI |

TABLE 5-continued

| Clones | Heavy chain variable domain amino acid sequence | Light chain variable domain amino acid sequence |
|---|---|---|
| No. 6,518,415) | RFTISRDNSKNTLFLQMDSLRPE DTGVYFCARGTRDGSWFAYWG QGTPVTVSS (SEQ ID NO: 174) CDR1 (SEQ ID NO: 175) - DYYMY CDR2 (SEQ ID NO: 176) - YMSNVGAITDYPDTVKG CDR3 (SEQ ID NO: 177) - GTRDGSWFAY | YKVSNRFSGVPSRFSGS GSGTDYTFTISSLQPEDI ATYYCFQGSHVPFTFGQ GTKLQIT (SEQ ID NO: 178) CDR1 (SEQ ID NO: 179) - RSSQRIVHSNGNTYLE CDR2 (SEQ ID NO: 180) - KVSNRFS CDR3 (SEQ ID NO: 181) - FQGSHVPFT |

Alternatively, novel antigen-binding sites that can bind to Lewis Y can be identified by screening for binding to Lewis Y antigen or a mature extracellular fragment thereof.

In another aspect, the present disclosure provides multi-specific binding proteins that bind to the NKG2D receptor and CD16 receptor on natural killer cells, and the antigen MUC13. Table 6 lists some exemplary sequences of heavy chain variable domains and light chain variable domains that, in combination, can bind to MUC13.

TABLE 6

| Clones | Heavy chain variable domain amino acid sequence | Light chain variable domain amino acid sequence |
|---|---|---|
| anti-MUC13 (International Publication No. WO 2016/168607) | QVQLQQSGAELVRPGSSVKISCK ASGYAFSTYWMNWVKQRPGQG LEWIGQIYPGDGDTYYNGNFKG KATLTADKSSSTAYMQLSSLTSE DSAVYFCAVFWDGYWGQGTTL TVSS (SEQ ID NO: 182) CDR1 (SEQ ID NO: 183) - TYWMN CDR2 (SEQ ID NO: 184) - QIYPGDGDTYYNGNFKG CDR3 (SEQ ID NO: 185) - FWDGY | QIVLTQSPTIMSASPGEK VTMTCSASSSVTYIHWY QQKSGTSPKRWIYDTSK LASGVPARFGGSGSGTS YSLTINSMETEDAATYY CQQWSSNPFTFGSGTKL EIKRAD (SEQ ID NO: 186) CDR1(SEQ ID NO: 187) - SASSSVTYIH CDR2 (SEQ ID NO: 188) - DTSKLAS CDR3 (SEQ ID NO: 189) - QQWSSNPFT |

Alternatively, novel antigen-binding sites that can bind to MUC13 can be identified by screening for binding to the amino acid sequence defined by SEQ ID NO:190 or a mature extracellular fragment thereof.

(SEQ ID NO: 190)
MKAIIHLTLLALLSVNTATNQGNSADAVTTTETATSGPTVAAADTTETNFP

ETASTTANTPSFPTATSPAPPIISTHSSSTIPTPAPPIISTHSSSTIPIPT

AADSESTTNVNSLATSDIITASSPNDGLITMVPSETQSNNEMSPTTEDNQS

SGPPTGTALLETSTLNSTGPSNPCQDDPCADNSLCVKLHNTSFCLCLEGYY

YNSSTCKKGKVFPGKISVTVSETFDPEEKHSMAYQDLHSEITSLFKDVFGT

SVYGQTVILTVSTSLSPRSEMRADDKFVNVTIVTILAETTSDNEKTVTEKI

NKAIRSSSSNFLNYDLTLRCDYYGCNQTADDCLNGLACDCKSDLQRPNPQS

PFCVASSLKCPDACNAQHKQCLIKKSGGAPECACVPGYQEDANGNCQKCAF

-continued
GYSGLDCKDKFQLILTIVGTIAGIVILSMIIALIVTARSNNKTKHIEEENL

IDEDFQNLKLRSTGFTNLGAEGSVFPKVRITASRDSQMQNPYSRHSSMPRP

DY

In another aspect, the present disclosure provides multi-specific binding proteins that bind to the NKG2D receptor and CD16 receptor on natural killer cells, and the antigen MUC4. Novel antigen-binding sites that can bind to MUC4 can be identified by screening for binding to the amino acid sequence defined by SEQ ID NO:191 or a mature extracellular fragment thereof.

(SEQ ID NO: 191)
MKGARWRRVPWVSLSCLCLCLLPHVVPGTTEDTLITGSKTAAPVTSTGSTT

ATLEGQSTAASSRTSNQDISASSQNHQTKSTETTSKAQTDTLTQMMTSTLF

SSPSVHNVMETVTQETAPPDEMTTSFPSSVTNTLMMTSKTITMTTSTDSTL

GNTEETSTAGTESSTPVTSAVSITAGQEGQSRTTSWRTSIQDTSASSQNHW

TRSTQTTRESQTSTLTHRTTSTPSFSPSVHNVTGTVSQKTSPSGETATSSL

CSVTNTSMMTSEKITVTTSTGSTLGNPGETSSVPVTGSLMPVTSAALVTVD

PEGQSPATFSRTSTQDTTAFSKNHQTQSVETTRVSQINTLNTLTPVTTSTV

LSSPSGFNPSGTVSQETFPSGETTISSPSSVSNTFLVTSKVFRMPISRDST

-continued
```
LGNTEETSLSVSGTISAITSKVSTIWWSDTLSTALPSSLPPKISTAFHTQ
QSEGAETTGRPHERSSFSPGVSQEIFTLHETTTWPSSFSSKGHTTWSQTEL
PSTSTGAATRLVTGNPSTRAAGTIPRVPSKVSAIGEPGEPTTYSSHSTTLP
KTTGAGAQTQWTQETGTTGEALLSSPSYSVIQMIKTATSPSSSPMLDRHTS
QQITTAPSTNHSTIHSTSTSPQESPAVSQRGHTRAPQTTQESQTTRSVSPM
TDTKTVTTPGSSFTASGHSPSEIVPQDAPTISAATTFAPAPTGNGHTTQAP
TTALQAAPSSHDATLGPSGGTSLSKTGALTLANSVVSTPGGPEGQWTSASA
STSPDTAAAMTHTHQAESTEASGQTQTSEPASSGSRTTSAGTATPSSSGAS
GTTPSGSEGISTSGETTRFSSNPSRDSHTTQSTTELLSASASHGAIPVSTG
MASSIVPGTFHPTLSEASTAGRPTGQSSPTSPSASPQETAAISRMAQTQRT
GTSRGSDTISLASQATDTFSTVPPTPPSITSSGLTSPQTQTHTLSPSGSGK
TFTTALISNATPLPVTSTSSASTGHATPLAVSSATSASTVSSDSPLKMETS
GMTTPSLKTDGGRRTATSPPPTTSQTIISTIPSTAMHTRSTAAPIPILPER
GVSLFPYGAGAGDLEFVRRTVDFTSPLFKPATGFPLGSSLRDSLYFTDNGQ
IIFPESDYQIFSYPNPLPTGFTGRDPVALVAPFWDDADFSTGRGTTFYQEY
ETFYGEHSLLVQQAESWIRKMTNNGGYKARWALKVTWVNAHAYPAQWTLGS
NTYQAILSTDGSRSYALFLYQSGGMQWDVAQRSGNPVLMGFSSGDGYFENS
PLMSQPVWERYRPDRFLNSNSGLQGLQFYRLHREERPNYRLECLQWLKSQP
RWPSWGWNQVSCPCSWQQGRRDLRFQPVSIGRWGLGSRQLCSFTSWRGGVC
CSYGPWGEFREGWHVQRPWQLAQELEPQSWCCRWNDKPYLCALYQQRRPHV
GCATYRPPQPAWMFGDPHITTLDGVSYTFNGLGDFLLVGAQDGNSSFLLQG
RTAQTGSAQATNFIAFAAQYRSSSLGPVTVQWLLEPHDAIRVLLDNQTVTF
QPDHEDGGGQETFNATGVLLSRNGSEVSASFDGWATVSVIALSNILHASAS
LPPEYQNRTEGLLGVWNNNPEDDFRMPNGSTIPPGSPEEMLFHFGMTWQIN
GTGLLGKRNDQLPSNFTPVFYSQLQKNSSWAEHLISNCDGDSSCIYDTLAL
RNASIGLHTREVSKNYEQANATLNQYPPSINGGRVIEAYKGQTTLIQYTSN
AEDANFTLRDSCTDLELFENGTLLWTPKSLEPFTLEILARSAKIGLASALQ
PRTVVCHCNAESQCLYNQTSRVGNSSLEVAGCKCDGGTFGRYCEGSEDACE
EPCFPSVHCVPGKGCEACPPNLTGDGRHCAALGSSFLCQNQSCPVNYCYNQ
GHCYISQTLGCQPMCTCPPAFTDSRCFLAGNNFSPTVNLELPLRVIQLLLS
EEENASMAEVNASVAYRLGTLDMRAFLRNSQVERIDSAAPASGSPIQHWMV
ISEFQYRPRGPVIDFLNNQLLAAVVEAFLYHVPRRSEEPRNDVVFQPISGE
DVRDVTALNVSTLKAYFRCDGYKGYDLVYSPQSGFTCVSPCSRGYCDHGGQ
CQHLPSGPRCSCVSFSIYTAWGEHCEHLSMKLDAFFGIFFGALGGLLLLGV
GTFVVLRFWGCSGARFSYFLNSAEALP
```

In another aspect, the present disclosure provides multi-specific binding proteins that bind to the NKG2D receptor and CD16 receptor on natural killer cells, and the antigen MCAM. Table 7 lists some exemplary sequences of heavy chain variable domains and light chain variable domains that, in combination, can bind to MCAM.

TABLE 7

| Clones | Heavy chain variable domain amino acid sequence | Light chain variable domain amino acid sequence |
| --- | --- | --- |
| anti-MCAM (imaprelimab) | QVTLKESGPVLVKPTETLTLTCTV SGFSLTSNAVSWVRQPPGKALEW IAAISSGGTTYYNSAFKSRLTISRD TSKSQVVLTMTNMDPVDTATYY CARRYGYGWYFDFWGQGTLVTV SSA (SEQ ID NO: 192) CDR1 (SEQ ID NO: 193) - GFSLTSN CDR2 (SEQ ID NO: 194) - SSGGT CDR3 (SEQ ID NO: 195) - TYYCARRYG | DIQMTQSPSSLSASVGDR VTINCKASQNIYNSLAW YQQKPGKAPKVLIFNAN SLQTGIPSRFSGSGSGTD FTLTISSLQPEDFATYYC QQFYSGYTFGQGTKLEI KR (SEQ ID NO: 196) CDR1(SEQ ID NO:197) - KASQNIYNSLA CDR2 (SEQ ID NO: 198) - NANSLQT CDR3 (SEQ ID NO: 199) - QQFYSGYT |
| anti-MCAM (ABX-MA1) | QVQLQESGPGLVKPSETLSLTCTV SGGSISSYYWSWIRQPPGKGLEWI GYIYYTWTSNYNPSLKSRVTISVD TSKNQFSLRLSSVTAADTAVYYC ARDQGQWLLPDAFDIWGQGTMV TVSS (SEQ ID NO: 200) CDR1 (SEQ ID NO: 201) - GGSISSY CDR2 (SEQ ID NO: 202) - YYTWT CDR3 (SEQ ID NO: 203) - DQGQWLLPDAFDI | DIVMTQSPLSLPVTPGEP ASISCRSSQSLLRSNGYN YLDWYLQKPGQSPHLLI YLGSNRASGVPDRFSGS GSGTDFTLKISRVEAEDV GVYYCMQAQQSPITFGQ GTRLEIK (SEQ ID NO: 204) CDR1 (SEQ ID NO: 205) - RSSQSLLRSNGYNYLD CDR2 (SEQ ID NO: 206) - LGSNRAS CDR3 (SEQ ID NO: 207) - MQAQQSPIT |

Alternatively, novel antigen-binding sites that can bind to MCAM can be identified by screening for binding to the amino acid sequence defined by SEQ ID NO:208 or a mature extracellular fragment thereof.

```
                                         SEQ ID NO: 208
MGLPRLVCAFLLAACCCCPRVAGVPGEAEQPAPELVEVEVGSTALLKCGLS

QSQGNLSHVDWFSVHKEKRTLIFRVRQGQGQSEPGEYEQRLSLQDRGATLA

LTQVTPQDERIFLCQGKRPRSQEYRIQLRVYKAPEEPNIQVNPLGIPVNSK

EPEEVATCVGRNGYPIPQVIWYKNGRPLKEEKNRVHIQSSQTVESSGLYTL

QSILKAQLVKEDKDAQFYCELNYRLPSGNHMKESREVTVPVFYPTEKVWLE

VEPVGMLKEGDRVEIRCLADGNPPPHFSISKQNPSTREAEEETTNDNGVLV

LEPARKEHSGRYECQGLDLDTMISLLSEPQELLVNYVSDVRVSPAAPERQE

GSSLTLTCEAESSQDLEFQWLREETGQVLERGPVLQLHDLKREAGGGYRCV

ASVPSIPGLNRTQLVNVAIFGPPWMAFKERKVWVKENMVLNLSCEASGHPR

PTISWNVNGTASEQDQDPQRVLSTLNVLVTPELLETGVECTASNDLGKNTS

ILFLELVNLTTLTPDSNTTTGLSTSTASPHTRANSTSTERKLPEPESRGVV

IVAVIVCILVLAVLGAVLYFLYKKGKLPCRRSGKQEITLPPSRKSELVVEV

KSDKLPEEMGLLQGSSGDKRAPGDQGEKYIDLRH
```

In another aspect, the present disclosure provides multi-specific binding proteins that bind to the NKG2D receptor and CD16 receptor on natural killer cells, and the antigen LRRC32. Table 8 lists some exemplary sequences of heavy chain variable domains and light chain variable domains that, in combination, can bind to LRRC32.

Alternatively, novel antigen-binding sites that can bind to LRRC32 can be identified by screening for binding to the amino acid sequence defined by SEQ ID NO:225 or a mature extracellular fragment thereof.

```
                                        (SEQ ID NO: 225)
MRPQILLLLALLTLGLAAQHQDKVPCKMVDKKVSCQVLGLLQVPSVLPPDT

ETLDLSGNQLRSILASPLGFYTALRHLDLSTNEISFLQPGAFQALTHLEHL

SLAHNRLAMATALSAGGLGPLPRVTSLDLSGNSLYSGLLERLLGEAPSLHT

LSLAENSLTRLTRHTFRDMPALEQLDLHSNVLMDIEDGAFEGLPRLTHLNL

SRNSLTCISDFSLQQLRVLDLSCNSIEAFQTASQPQAEFQLTWLDLRENKL

LHFPDLAALPRLIYLNLSNNLIRLPTGPPQDSKGIHAPSEGWSALPLSAPS

GNASGRPLSQLLNLDLSYNEIELIPDSFLEHLTSLCFLNLSRNCLRTFEAR

RLGSLPCLMLLDLSHNALETLELGARALGSLRTLLLQGNALRDLPPYTFAN

LASLQRLNLQGNRVSPCGGPDEPGPSGCVAFSGITSLRSLSLVDNEIELLR

AGAFLHTPLTELDLSSNPGLEVATGALGGLEASLEVLALQGNGLMVLQVDL

PCFICLKRLNLAENRLSHLPAWTQAVSLEVLDLRNNSFSLLPGSAMGGLET

SLRRLYLQGNPLSCCGNGWLAAQLHQGRVDVDATQDLICRFSSQEEVSLSH

VRPEDCEKGGLKNINLIIILTFILVSAILLTTLAACCCVRRQKFNQQYKA
```

In another aspect, the present disclosure provides multi-specific binding proteins that bind to the NKG2D receptor and CD16 receptor on natural killer cells, and the antigen sialyl-Tn. Table 9 lists some exemplary sequences of heavy chain variable domains and light chain variable domains that, in combination, can bind to sialyl-Tn.

TABLE 8

| Clones | Heavy chain variable domain amino acid sequence | Light chain variable domain amino acid sequence |
|---|---|---|
| anti-LRRC32 (U.S. Publication No. 2016/0272717) | MAVLALLFCLVTFPSCILSQVQL KESGPGLVAPSQSLSITCTVSGF SLTGYGINWVRQPPGKGLEWL GMIWSDGSTDYNSVLTSRLRIS KDNSNSQVFLKMNSLQVDDTA RYYCARDRNYYDYDGAMDYW GQGTSVTVSS (SEQ ID NO: 209) CDR1 (SEQ ID NO: 210) - GFSLTGYGIN CDR2 (SEQ ID NO: 211) - MIWSDGSTDYNSVLTS CDR3 (SEQ ID NO: 212) - DRNYYDYDGAMDY | MKFPSQLLLFLLFRITGII CDIQVTQSSSYLSVSLGD RVTITCKASDHIKNWLA WYQQKPGIAPRLLVSGA TSLEAGVPSRFSGSGSGK NFTLSITSLQTEDVATYY CQQYWSTPWTFGGGTT LEIR (SEQ ID NO: 213) CDR1(SEQ ID NO: 214) - KASDHIKNWLA CDR2 (SEQ ID NO: 215) - GATSLEA CDR3 (SEQ ID NO: 216) - QQYWSTPWT |
| anti-LRRC32 (H198D-H3L4) (International Publication No. WO 2017/051888) | VQLVESGGGLVKPSQTLSLTCT VSGFSLTSFHVSWVRQPPGKGL EWIATISSGGGTYYNPSLKSRVT ISRDTSKNQVSLKLSSVTAADTA VYYCARISGWGHYYVMDVWG QGTLVTVSS (SEQ ID NO: 217) CDR1 (SEQ ID NO: 218) - GFSLTSF CDR2 (SEQ ID NO: 219) - SSGGG CDR3 (SEQ ID NO: 220) - ISGWGHYYVMDV | DIQMTQSPSSLSASVGDR VTITCQASEDIYSGLAW YQQKPGKSPKLLIYGAG SLQDGVPSRFSGSGSGT HYTLTISSLQPEDFATYF CQQGLKFPLTFGQGTKV EIKRT (SEQ ID NO: 221) CDR1 (SEQ ID NO: 222) - QASEDIYSGLA CDR2 (SEQ ID NO: 223) - GAGSLQD CDR3 (SEQ ID NO: 224) - QQGLKFPLT |

TABLE 9

| Clones | Heavy chain variable domain amino acid sequence | Light chain variable domain amino acid sequence |
|---|---|---|
| anti-sialyl-Tn (Bluebird) (International Publication No. WO 2017/040529) | QVQLVQSGAEVKKPGASVKVS CKASGYTFTDHAIHWVRQAPG QRLEWMGYFSPGNDDFKY SQKFQGRVTITADKSASTAYME LSSLRSEDTAVYYCARSWIMQY WGQGTLVTVSS (SEQ ID NO: 226) CDR1 (SEQ ID NO: 227) - GYTFTDHAIH CDR2 (SEQ ID NO: 228) - YFSPGNDDFKYSQKFQG CDR3 (SEQ ID NO: 229) - SWIMQY | DIVMTQSPDSLAVSLGE RATINCKSSQSVLYSSNN KNYLAWYQQKPGQPPK LLIYWASTRESGVPDRFS GSGSGTDFTLTISSLQAE DVAVYYCQQYYSYPLTF GQGTKVEIK (SEQ ID NO: 230) CDR1(SEQ ID NO: 231) - KSSQSVLYSSNNKNYLA CDR2 (SEQ ID NO: 232) - WASTRES CDR3 (SEQ ID NO: 233) - QQYYSYPLT |
| anti-sialyl-Tn (Siamab Tx) (U.S. Publication No. 2016/0311922) | QVQLKESGPGLVAPSQSLSITCT VSGFSLTSYGWSWWRQPPGKG LEWLGVIWGDGSTNYHSALISR LSISKDNSKSQVFLKLNSLQTDD TATYYCAKGGYFDYWGQGTTL TVSS (SEQ ID NO: 234) CDR1 (SEQ ID NO: 235) - GFSLTSYG CDR2 (SEQ ID NO: 236) - IWGDGST CDR3 (SEQ ID NO: 237) - AKGGYFDY | QIVLTQSPAVMSASPGE KVAITCSASSSVSYMHW FQQKPGTSPKLWIYSTSN LASGVPARFSGSGSGTS YSLTISRMEAEDAATYY CQQRSSYPWTFGGG TKLEIK (SEQ ID NO: 238) CDR1 (SEQ ID NO: 239) - SSVSY CDR2 (SEQ ID NO: 240) - STS CDR3 (SEQ ID NO: 241) - QQRSSYPWT |

Alternatively, novel antigen-binding sites that can bind to sialyl-Tn can be identified by screening for binding to sialyl-Tn antigen or a mature extracellular fragment thereof.

In another aspect, the present disclosure provides multispecific binding proteins that bind to the NKG2D receptor and CD16 receptor on natural killer cells, and the antigen gpA33. Table 10 lists some exemplary sequences of heavy chain variable domains and light chain variable domains that, in combination, can bind to gpA33.

TABLE 10

| Clones | Heavy chain variable domain amino acid sequence | Light chain variable domain amino acid sequence |
|---|---|---|
| anti-gpA33 (KYOWA) (U.S. Publication No. 2009/0299039) | MDLMCKKMKHLWFFLLLVAAP RWVLSQLQVQESGPGLVKPSET LSLICTVSGGSIRTSGYYWGWF RQPPGKGLEWIGTSHNSGSTYY NPSLKSRVTISVDTSKNQFSLKL NSVTAADTAVYYCARQGYDFK VNIDVWGQGTTVTVSSAS (SEQ ID NO: 242) CDR1 (SEQ ID NO: 243) - GGSIRTSGY CDR2 (SEQ ID NO: 244) - HNSGS CDR3 (SEQ ID NO: 245) - QGYDFKVNIDV | MEAPAQLLFLLLLWLPD TTGEIVLTQSPATLSLSP GERATLSCRASQSVSSY LAWYQQKPGQAPRLLIY DASNRATGIPARFSGSGS GTDFTLTISSLEPEDFAV YYCQQRSNWPLTFGGG TKVEIKR (SEQ ID NO: 246) CDR1(SEQ ID NO: 247) - RASQSVSSYLA CDR2 (SEQ ID NO: 248) - DASNRAT CDR3 (SEQ ID NO: 249) - QQRSNWPLT |
| anti-gpA33 (DART-2 w/Fc Version 1) (International Publication No. WO 2015/026894) | QVQLVQSGAEVKKPGASVKVS CKASGYTFTGSWMNWVRQAPG QGLEWIGRIYPGDGETNYNGKF KDRVIADKSSAYMELSSLRSED TAVYYCARIYGNVYFDVWGQG TTVTVSS (SEQ ID NO: 250) CDR1 (SEQ ID NO: 251) - GSWMN CDR2 (SEQ ID NO: 252) - RIYPGD CDR3 (SEQ ID NO: 253) - IYGNVYFDV | DIQLTQSPSFLSASVGDR VICSARSSISFMYWYQQ KPGKAPKLLIYDTSNLAS GVPSRFSGSGSGTEFTLIS SLEAEDAATYYCQQWSS YPLTFGQGTKLEIK (SEQ ID NO: 254) CDR1 (SEQ ID NO: 255) - SARSSISFMY CDR2 (SEQ ID NO: 256) - GETNYNGKFKDDTSNLAS CDR3 (SEQ ID NO: 257) - QQWSSYPLT |

Alternatively, novel antigen-binding sites that can bind to gpA33 can be identified by screening for binding to the amino acid sequence defined by SEQ ID NO:258 or a mature extracellular fragment thereof.

SEQ ID NO: 258
MVGKMWPVLWTLCAVRVTVDAISVETPQDVLRASQGKSVTLPCTYHTSTSS
REGLIQWDKLLLTHTERVVIWPFSNKNYIHGELYKNRVSISNNAEQSDASI
TIDQLTMADNGTYECSVSLMSDLEGNTKSRVRLLVLVPPSKPECGIEGETI
IGNNIQLTCQSKEGSPTPQYSWKRYNILNQEQPLAQPASGQPVSLKNISTD
TSGYYICTSSNEEGTQFCNITVAVRSPSMNVALYVGIAVGVVAALIIIGII
IYCCCCRGKDDNTEDKEDARPNREAYEEPPEQLRELSREREEEDDYRQEEQ
RSTGRESPDHLDQ

In another aspect, the present disclosure provides multi-specific binding proteins that bind to the NKG2D receptor and CD16 receptor on natural killer cells, and the antigen GD3. Table 11 lists some exemplary sequences of heavy chain variable domains and light chain variable domains that, in combination, can bind to GD3.

TABLE 11

| Clones | Heavy chain variable domain amino acid sequence | Light chain variable domain amino acid sequence |
| --- | --- | --- |
| anti-GD3 (KM871) (U.S. Publication No. 2009/0226399) | EVQLVESGGDFVQPGGSLRVSC AASGFAFSHYAMSWVRQAPGK GLEWVAYISSGGSGTYYSDSVK GRFTISRDNSKNTLYLQMRSLR AEDSAVYFCTRVKLGTYYFDS WGQGTLLTVSS (SEQ ID NO: 259) CDR1 (SEQ ID NO: 260) - HYAMS CDR2 (SEQ ID NO: 261) - YISSGGSGTYYSDSVKG CDR3 (SEQ ID NO: 262) - VKLGTYYFDS | DIQMTQSPSSLSASVGDR VTITCSASQDISNYLNW YQQKPDKAPKLLIFYSS NLHSGVPSRFSGGGSGT DYTLTISSLQPEDIATYF CHQYSKLPWTFGQGTK VEIKR (SEQ ID NO: 263) CDR1(SEQ ID NO: 264) - SASQDISNYLN CDR2 (SEQ ID NO: 265) - YSSNLHS CDR3 (SEQ ID NO: 266) - HQYSKLPWT |
| anti-GD3 (LD47) (U.S. Publication No. 2012/0276046) | DVQLVESGGGLVQPGGSRKLSC AASGFTFSNFGMEIWVRQAPEK GLEWVAYISSGGSSINYADTVK GRFTISRDNPKNTLFLQMTSLRS EDTAIYYCTRGGTGTRSLYYFD YWGQGATLIVSS (SEQ ID NO: 267) CDR1 (SEQ ID NO: 268) - NFGMH CDR2 (SEQ ID NO: 269) - YISSGGSSINYADTV CDR3 (SEQ ID NO: 270) - GGTGTRSLYYFDY | DIQMTQSPSSLSASVGDR VTITCRASQDIGNFLNW YQQKPGKAPKLLIYYTS RLQSGVPSRFSGSGSGTD YTLTISSLQPEDFATYYC QQGKTLPYTFGGGTKVE IK (SEQ ID NO: 271) CDR1 (SEQ ID NO: 272) - RASQDIGNFLN CDR2 (SEQ ID NO: 273) - YTSRLQS CDR3 (SEQ ID NO: 274) - QQGKTLPYT |

Alternatively, novel antigen-binding sites that can bind to GD3 can be identified by screening for binding to GD3 ganglioside or a mature extracellular fragment thereof.

In another aspect, the present disclosure provides multi-specific binding proteins that bind to the NKG2D receptor and CD16 receptor on natural killer cells, and the antigen GM2. Table 12 lists some exemplary sequences of heavy chain variable domains and light chain variable domains that, in combination, can bind to GM2.

TABLE 12

| Clones | Heavy chain variable domain amino acid sequence | Light chain variable domain amino acid sequence |
| --- | --- | --- |
| anti-GM2 (BIW-8962) (U.S. Publication No. 2011/0236374) | EVQLQQSGPELVKPGASVKISC KASGYTFTDYNMDWVKQSHG KSLEWIGYIYPNNGGTGYNQKF KSKATLTVDKSSSTAYMELHSL TSEDSAVYYCATYGHYYGYMF AYWGQGTLVTVSA (SEQ ID NO: 275) CDR1 (SEQ ID NO: 276) - DYNMD CDR2 (SEQ ID NO: 277) - YIYPNNGGTGYNQKFK CDR3 (SEQ ID NO: 278) - YGHYYGYMFAY | QIVLTQSPAIMSASPGEK VTITCSASSSVSYMHWF QQKPGTSPKLWIYSTSN LASGVPARFSGSGSGTS YSLTISRMEAEDAATYY CQQRSSYPYTFGGGTKL EIKR (SEQ ID NO: 279) CDR1(SEQ ID NO: 280) - SASSSVSYMH CDR2 (SEQ ID NO: 281) - STSNLAS CDR3 (SEQ ID NO: 282) - QQRSSYPYT |
| anti-GM2 (International Publication No. WO 2004/083387) | QVQLQQSGAELVKPGASVRLSC KTSGYTFTTHYVSWVKQKPGQ GLEWIGWIFGGSARTNYNQKFQ GKATLTVDTSSSTAYMDLRSLT SDDSAVYFCVRQVGWDDALDF WGQGTQVTVSS (SEQ ID NO: 283) CDR1 (SEQ ID NO: 284) - QVGWDDALDF CDR2 (SEQ ID NO: 285) - WIFGGSARTNYNQKFQG CDR3 (SEQ ID NO: 286) - THYVS | DIVMTQSPSSLAVSAGD TVTINCRSSQSLFSGNYN YLAWYQQKTGQTPKLLI SYASTRHTGVPDRFVGS GSGTDFILTIYNFQTEDL GDYYCQQHYSSPRTFGP GTKLKIK (SEQ ID NO: 287) CDR1 (SEQ ID NO: 288) - QQHYSSPRT CDR2 (SEQ ID NO: 289) - YASTRHT CDR3 (SEQ ID NO: 290) - RSSQSLFSGNYNYLA |

Alternatively, novel antigen-binding sites that can bind to GM2 can be identified by screening for binding to GM2 ganglioside or a mature extracellular fragment thereof.

In another aspect, the present disclosure provides multi-specific binding proteins that bind to the NKG2D receptor and CD16 receptor on natural killer cells, and the antigen c-MET. Table 13 lists some exemplary sequences of heavy chain variable domains and light chain variable domains that, in combination, can bind to c-MET.

TABLE 13

| Clones | Heavy chain variable domain amino acid sequence | Light chain variable domain amino acid sequence |
| --- | --- | --- |
| anti-c-MET (onartuzumab) | EVQLVESGGGLVQPGGSLRLSC AASGYTFTSYWLHWVRQAPGK GLEWVGMIDPSNSDTRFNPNFK DRFTISADTSKNTAYLQMNSLR AEDTAVYYCATYRSYVTPLDY WGQGTLVTVSSA (SEQ ID NO: 291) CDR1 (SEQ ID NO: 292) - GYTFTSY CDR2 (SEQ ID NO: 293) - DPSNSDTRFNP or Chothia | DIQMTQSPSSLSASVGDR VTITCKSSQSLLYTSSQK NYLAWYQQKPGKAPKL LIYWASTRESGVPSRFSG SGSGTDFTLTISSLQPEDF ATYYCQQYYAYPWTFG QGTKVEIKR (SEQ ID NO: 295) CDR1(SEQ ID NO: 296) - QSLLYTSSQKNYLA or Chothia |

TABLE 13-continued

| Clones | Heavy chain variable domain amino acid sequence | Light chain variable domain amino acid sequence |
|---|---|---|
| | DPSNSD (SEQ ID NO: 406) CDR3 (SEQ ID NO: 294) - YRSYVTPLDY | KSSQSLLYTSSQKNYLA (SEQ ID NO: 407) CDR2 (SEQ ID NO: 297) - WASTRES CDR3 (SEQ ID NO: 298) - QQYYAYPWT |

Onartuzumab-HC
EVQLVESGGGLVQPGGSLRLSCAASGYTFTSYWLHWVRQAPGKGLEWVGMI
DPSNSDTRFNPNFKDRFTISADTSKNTAYLQMNSLRAEDTAVYYCATYRSYV
TPLDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVS
LTCLVKGFYPSDIAVEWESNGQPENNYKTTPPVLDSDGSFLLYSKLTVDKSRW
QQGNVFSCSVMHEALHNHYTQKSLSLSPG (SEQ ID NO: 425)

Onartuzumab-LC
DIQMTQSPSSLSASVGDRVTITCKSSQSLLYTSSQKNYLAWYQQKPGKAPKLL
IYWASTRESGVPSRFSGSGSGTDFTLTISSLQPEDFATYYCQQYYAYPWTFGQ
GTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVT
KSFNRGEC (SEQ ID NO: 426)

| anti-c-MET (emibetuzumab) | QVQLVQSGAEVKKPGASVKVS CKASGYTFTDYYMHWVRQAPG QGLEWMGRVNPNRRGTTYNQK FEGRVTMTTDTSTSTAYMELRS LRSDDTAVYYCARANWLDYW GQGTTVTVSSA (SEQ ID NO: 299) CDR1 (SEQ ID NO: 300) - GYTFTDY CDR2 (SEQ ID NO: 301) - NPNRRG CDR3 (SEQ ID NO: 302) - ANWLDY | DIQMTQSPSSLSASVGDR VTITCSVSSSVSSIYLHW YQQKPGKAPKLLIYSTS NLASGVPSRFSGSGSGT DFTLTISSLQPEDFATYY CQVYSGYPLTFGGGTKV EIKR (SEQ ID NO: 303) CDR1 (SEQ ID NO: 304) - SSVSSIYLH or Chothia SVSSSVSSIYLH (SEQ ID NO: 410) CDR2 (SEQ ID NO: 305) - STSNLAS CDR3 (SEQ ID NO: 306) - QVYSGYPLT | c-MET-Emibetuzumab-HC (G.A)
QVQLVQSGAEVKKPGASVKVSCKASGYTFTDYYMEIWVRQAPGQGLEWMG
RVNPNRRGTTYNQKFEGRVTMTTDTSTSTAYMELRSLRSDDTAVYYCARAN
WLDYWGQGTTVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVS
LTCLVKGFYPSDIAVEWESNGQPENNYKTTPPVLDSDGSFLLYSKLTVDKSRW
QQGNVFSCSVMHEALHNHYTQKSLSLSPG (SEQ ID NO: 427)

c-MET-Emibetuzumab-LC
DIQMTQSPSSLSASVGDRVTITCSVSSSVSSIYLHWYQQKPGKAPKWYSTSNL
ASGVPSRFSGSGSGTDFTLTISSLQPEDFATYYCQVYSGYPLTFGGGTKVEIKR
TVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGE
C (SEQ ID NO: 428)

| ABT-700 (Abbvie) | QVQLVQSGAEVKKPGASVKVS CKASGYIFTAYTMHWVRQAPG QGLEWMGWIKPNNGLANYAQ KFQGRVTMTRDTSISTAYMELS RLRSDDTAVYYCARSEITTEFD YWGQGTLVTVSS (SEQ ID NO: 413) CDR1 (SEQ ID NO: 414) - GYIFTAY CDR2 (SEQ ID NO: 415) - KPNNGL CDR3 (SEQ ID NO: 416) - SEITTEFDY | DIVMTQSPDSLAVSLGE RATINCKSSESVDSYANS FLHWYQQKPGQPPKLLI YRASTRESGVPDRFSGS GSGTDFTLTISSLQAEDV AVYYCQQSKEDPLTFGG GTKVEIK (SEQ ID NO: 417) CDR1 (SEQ ID NO: 418) - KSSESVDSYANSFLH CDR2 (SEQ ID NO: 419) - RASTRES CDR3 (SEQ ID NO: 420) - QQSKEDPLT |

TABLE 13-continued

| Clones | Heavy chain variable domain amino acid sequence | Light chain variable domain amino acid sequence |
|---|---|---| c-MET-ABT_700_HC (GA)
QVQLVQSGAEVKKPGASVKVSCKASGYIFTAYTMHWVRQAPGQGLEWMGW
IKPNNGLANYAQKFQGRVTMTRDTSISTAYMELSRLRSDDTAVYYCARSEITT
EFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSL
TCLVKGFYPSDIAVEWESNGQPENNYKTTPPVLDSDGSFLLYSKLTVDKSRW
QQGNVFSCSVMHEALHNHYTQKSLSLSPG (SEQ ID NO: 429)

c-MET-ABT_700_LC
DIVMTQSPDSLAVSLGERATINCKSSESVDSYANSFLHWYQQKPGQPPKLLIY
RASTRESGVPDRFSGSGSGTDFTLTISSLQAEDVAVYYCQQSKEDPLTFGGGT
KVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKS
FNRGEC (SEQ ID NO: 430)

Alternatively, novel antigen-binding sites that can bind to c-MET can be identified by screening for binding to the amino acid sequence defined by SEQ ID NO:307 or a mature extracellular fragment thereof.

(SEQ ID NO: 307)
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFISGGSTITGVGKNLNSVSVPRMVINVHEAGRNFTVACQHRSNSEIIC

CTTPSLQQLNLQLPLKTKAFFMLDGILSKYFDLIYVHNPVFKPFEKPVMI

SMGNENVLEIKGNDIDPEAVKGEVLKVGNKSCENIHLHSEAVLCTVPNDL

LKLNSELNIEWKQAISSTVLGKVIVQPDQNFTGLIAGVVSISTALLLLLG

FFLWLKKRKQIKDLGSELVRYDARVHTPHLDRLVSARSVSPTTEMVSNES

VDYRATFPEDQFPNSSQNGSCRQVQYPLTDMSPILTSGDSDISSPLLQNT

VHIDLSALNPELVQAVQHVVIGPSSLIVHFNEVIGRGHFGCVYHGTLLDN

DGKKIHCAVKSLNRITDIGEVSQFLTEGIIMKDFSHPNVLSLLGICLRSE

GSPLVVLPYMKHGDLRNFIRNETHNPTVKDLIGFGLQVAKGMKYLASKKF

VHRDLAARNCMLDEKFTVKVADFGLARDMYDKEYYSVHNKTGAKLPVKWM

ALESLQTQKFTTKSDVWSFGVLLWELMTRGAPPYPDVNTFDITVYLLQGR

RLLQPEYCPDPLYEVMLKCWHPKAEMRPSFSELVSRISAIFSTFIGEHYV

HVNATYVNVKCVAPYPSLLSSEDNADDEVDTRPASFWETS

In another aspect, the present disclosure provides multi-specific binding proteins that bind to the NKG2D receptor and CD16 receptor on natural killer cells, and the antigen EPHA3. Table 14 lists some exemplary sequences of heavy chain variable domains and light chain variable domains that, in combination, can bind to EPHA3.

TABLE 14

| Clones | Heavy chain variable domain amino acid sequence | Light chain variable domain amino acid sequence |
|---|---|---|
| anti-EPHA3 (ifabotuzumab) | QVQLVQSGAEVKKPGA SVKVSCKASGYTFTGY WMNWVRQAPGQGLEWM GDIYPGSGNTNYDEKF QGRVTMTRDTSISTAY MELSRLRSDDTAVYYC ARGGYYEDFDSWGQGT TVTVSSA (SEQ ID NO: 308) CDR1 (SEQ ID NO: 309)- GYTFTGY CDR2 (SEQ ID NO: 310)- YPGSGN CDR3 (SEQ ID NO: 311)- GGYYEDFDS | DIQMTQSPSFLSASVG DRVTITCRASQGIISY LAWYQQKPEKAPKRLI YAASSLQSGVPSRFSG SGSGTEFTLTISSLQP EDFATYYCQYANYPY TFGQGTKLEIKR (SEQ ID NO: 312) CDR1 (SEQ ID NO: 313)- QGIISYLA CDR2 (SEQ ID NO: 314)- AASSLQS CDR3 (SEQ ID NO: 315)- GQYANYPYT |

Alternatively, novel antigen-binding sites that can bind to EPHA3 can be identified by screening for binding to the amino acid sequence defined by SEQ ID NO:316 or a mature extracellular fragment thereof.

(SEQ ID NO: 316)
MDCQLSILLLLSCSVLDSFGELIPQPSNEVNLLDSKTIQGELGWISYPSH

GWEEISGVDEHYTPIRTYQVCNVMDHSQNNWLRTNWVPRNSAQKIYVELK

FTLRDCNSIPLVLGTCKETFNLYYMESDDDHGVKFREHQFTKIDTIAADE

SFTQMDLGDRILKLNTEIREVGPVNKKGFYLAFQDVGACVALVSVRVYFK

KCPFTVKNLAMFPDTVPMDSQSLVEVRGSCVNNSKEEDPPRMYCSTEGEW

LVPIGKCSCNAGYEERGFMCQACRPGFYKALDGNMKCAKCPPHSSTQEDG

SMNCRCENNYFRADKDPPSMACTRPPSSPRNVISNINETSVILDWSWPLD

TGGRKDVTFNIICKKCGWNIKQCEPCSPNVRFLPRQFGLTNTTVTVTDLL

AHTNYTFEIDAVNGVSELSSPPRQFAAVSITTNQAAPSPVLTIKKDRTSR

NSISLSWQEPEHPNGIILDYEVKYYEKQEQETSYTILRARGTNVTISSLK

PDTIYVFQIRARTAAGYGTNSRKFEFETSPDSFSISGESSQVVMIAISAA

VAIILLTVVIYVLIGRFCGYKSKHGADEKRLHFGNGHLKLPGLRTYVDPH

TYEDPTQAVHEFAKELDATNISIDKVVGAGEFGEVCSGRLKLPSKKEISV

AIKTLKVGYTEKQRRDFLGEASIMGQFDHPNIIRLEGVVTKSKPVMIVTE

YMENGSLDSFLRKHDAQFTVIQLVGMLRGIASGMKYLSDMGYVHRDLAAR

NILINSNLVCKVSDFGLSRVLEDDPEAAYTTRGGKIPIRWTSPEAIAYRK

FTSASDVWSYGIVLWEVMSYGERPYWEMSNQDVIKAVDEGYRLPPPMDCP

AALYQLMLDCWQKDRNNRPKFEQIVSILDKLIRNPGSLKIITSAAARPSN

LLLDQSNVDITTFRTTGDWLNGVWTAHCKEIFTGVEYSSCDTIAKISTDD

MKKVGVTVVGPQKKIISSIKALETQSKNGPVPV

In another aspect, the present disclosure provides multi-specific binding proteins that bind to the NKG2D receptor and CD16 receptor on natural killer cells, and the antigen TNFRSF10. Table 15 lists some exemplary sequences of heavy chain variable domains and light chain variable domains that, in combination, can bind to TNFRSF10.

TABLE 15

| Clones | Heavy chain variable domain amino acid sequence | Light chain variable domain amino acid sequence |
|---|---|---|
| anti-TNFRSF10 (T1014G03) (U.S. Publication No. 2009/0226429) | EVQLVQSGAEVKMPGA SVKLSCRVSGDTFTAY FIHWVRQAPGQGLEWM GWFNPISGTAGSAEKF RGRVAMTRDTSISTAY MELNRLTFDDTAVYYC ARQHRGNTFDPWGQGT LVTVSS (SEQ ID NO: 317) CDR1 (SEQ ID NO: 318)- DTFTAYFIH CDR2 (SEQ ID NO: 319)- | SALTQPASVSGSPGQS ITISCTGTSSDIGAYK YVSWYQQHPGKAPKLV IYEVSNRPSGVSSRFS GSKSGQTASLTISGLQ ADDEADYYCNSYQGYN TWVFGGGTKVTLG (SEQ ID NO: 321) CDR1 (SEQ ID NO: 322)- TGTSSDIGAYKYVS CDR2 (SEQ ID NO: 323)- EVSNRPS |

TABLE 15-continued

| Clones | Heavy chain variable domain amino acid sequence | Light chain variable domain amino acid sequence |
|---|---|---|
| | WFNPISGTAGSAEKFR G CDR3 (SEQ ID NO: 320)- QHRGNTFDP | CDR3 (SEQ ID NO: 324)- SYQGYNTWV |
| anti-TNFRSF10 (m921) (U.S. Publication No. 2013/0156781) | QVQLQQSGPGLVKPSQ TLSLTCAISGDSVSSN SAAWNWIRQSPSRGLE WLGRTYYRSKWYNDYA VSVKGRITINPDTSKN QFSLQLNSVTPEDTAV YYCARDLGVAAADSYY YYGMDVWGQGTTVTVS S (SEQ ID NO: 325) CDR1 (SEQ ID NO: 326)- GDSVSSNSAA CDR2 (SEQ ID NO: 327)- TYYRSKWYN CDR3 (SEQ ID NO: 328)- ARDLGVAAADSYYYYG MDVW | QPVLTQPPSASATPGQ RVTISCSGSSSNIGSN TLDWFQQLPGTAPKLL IFDTNRRPSGVPDRFS GSKSGTSASLAISGLQ AEDEAVYFCATWDNSL NGAVFGGGTKLSVP (SEQ ID NO: 329) CDR1 (SEQ ID NO: 330)- SSNIGSNT CDR2 (SEQ ID NO: 331)- DTN CDR3 (SEQ ID NO: 332)- ATWDNSLNGAVF |

Alternatively, novel antigen-binding sites that can bind to TNFRSF10 can be identified by screening for binding to the amino acid sequence defined by SEQ ID NO:333 or a mature extracellular fragment thereof.

SEQ ID NO: 333
MAPPPARVHLGAFLAVTPNPGSAASGTEAAAATPSKVWGSSAGRIEPR

GGGRGALPTSMGQHGPSARARAGRAPGPRPAREASPRLRVHKTFKFVV

VGVLLQVVPSSAATIKLHDQSIGTQQWEHSPLGELCPPGSHRSEHPGA

CNRCTEGVGYTNASNNLFACLPCTACKSDEEERSPCTTTRNTACQCKP

GTFRNDNSAEMCRKCSRGCPRGMVKVKDCTPWSDIECVHKESGNGHNI

WVILVVTLVVPLLLVAVLIVCCCIGSGCGGDPKCMDRVCFWRLGLLRG

PGAEDNAHNEILSNADSLSTFVSEQQMESQEPADLTGVTVQSPGEAQC

LLGPAEAEGSQRRRLLVPANGADPTETLMLFFDKFANIVPFDSWDQLM

RQLDLTKNEIDVVRAGTAGPGDALYAMLMKWVNKTGRNASIHTLLDAL

ERMEERHAREKIQDLLVDSGKFIYLEDGTGSAVSLE

In another aspect, the present disclosure provides multi-specific binding proteins that bind to the NKG2D receptor and CD16 receptor on natural killer cells, and the antigen TNFSF11. Table 16 lists some exemplary sequences of heavy chain variable domains and light chain variable domains that, in combination, can bind to TNFSF11.

TABLE 16

| Clones | Heavy chain variable domain amino acid sequence | Light chain variable domain amino acid sequence |
|---|---|---|
| anti-TNFSF11 (denosumab) | EVQLLESGGGLVQPGG SLRLSCAASGFTFSSY AMSWVRQAPGKGLEWV | EIVLTQSPGTLSLSPG ERATLSCRASQSVRGR YLAWYQQKPGQAPRLL |

TABLE 16-continued

| Clones | Heavy chain variable domain amino acid sequence | Light chain variable domain amino acid sequence |
|---|---|---|
| | SGITGSGGSTYYADSV KGRFTISRDNSKNTLY LQMNSLRAEDTAVYYC AKDPGTTVIMSWFDPW GQGTLVTVSS (SEQ ID NO: 334) CDR1 (SEQ ID NO: 335)- GFTFSSY CDR2 (SEQ ID NO: 336)- TGSGGS CDR3 (SEQ ID NO: 337)- DPGTTVIMSWFDP | IYGASSRATGIPDRFS GSGSGTDFTLTISRLE PEDFAVFYCQQYGSSP RTFGQGTKVEIK (SEQ ID NO: 338) CDR1 (SEQ ID NO: 339)- QSVRGRYLA CDR2 (SEQ ID NO: 340)- GASSRAT CDR3 (SEQ ID NO: 341)- QQYGSSPRT |
| anti-TNFSF11 (H4H010P) (U.S. Publication No. 2012/0114665) | QVQLVESGGGVVQPGR SLRLSCAASGFTFSGY GMHWVRQAPGKGLDWV TVISYDGSNKHYADSV KGRFTISRDNSKNTLY LQMSSLGPEDTAVYYC AKSLSGTYWGYGMDVW GQGTTVTVS (SEQ ID NO: 342) CDR1 (SEQ ID NO: 343)- GFTFSGYG CDR2 (SEQ ID NO: 344)- ISYDGSNK CDR3 (SEQ ID NO: 345)- CAKSLSGTYWGYGMDV | DIQMTQSPSTLSASVG DRVTITCRASQNISSW LAWYQQKPGKAPKLLI YKASSLESGVPSRFSG SGSGTEFTLTVSSLQP DDFATYYCQQYNRYSW TFGQGTKVEIK (SEQ ID NO: 346) CDR1 (SEQ ID NO: 347)- QNISSW CDR2 (SEQ ID NO: 348)- KAS CDR3 (SEQ ID NO: 349)- QQYNRYSWT |

Alternatively, novel antigen-binding sites that can bind to TNFSF11 can be identified by screening for binding to the amino acid sequence defined by SEQ ID NO:350 or a mature extracellular fragment thereof.

SEQ ID NO: 350
MRRASRDYTKYLRGSEEMGGGPGAPHEGPLHAPPPPAPHQPPAASRSM

FVALLGLGLGQVVCSVALFFYFRAQMDPNRISEDGTHCIYRILRLHEN

ADFQDTTLESQDTKLIPDSCRRIKQAFQGAVQKELQHIVGSQHIRAEK

AMVDGSWLDLAKRSKLEAQPFAHLTINATDIPSGSHKVSLSSWYHDRG

WAKISNMTFSNGKLIVNQDGFYYLYANICFRHHETSGDLATEYLQLMV

YVTKTSIKIPSSHTLMKGGSTKYWSGNSEFHFYSINVGGFFKLRSGEE

ISIEVSNPSLLDPDQDATYFGAFKVRDID

In another aspect, the present disclosure provides multispecific binding proteins that bind to the NKG2D receptor and CD16 receptor on natural killer cells, and the antigen CD74. Table 17 lists some exemplary sequences of heavy chain variable domains and light chain variable domains that, in combination, can bind to CD74.

TABLE 17

| Clones | Heavy chain variable domain amino acid sequence | Light chain variable domain amino acid sequence |
|---|---|---|
| anti-CD74 (milatuzumab) | QVQLQQSGSELKKPGA SVKVSCKASGYTFTNY GVNWIKQAPGQGLQWM GWINPNTGEPTFDDDF KGRFAFSLDTSVSTAY LQISSLKADDTAVYFC SRSRGKNEAWFAYWGQ GTLVTVSSA (SEQ ID NO: 351) CDR1 (SEQ ID NO: 352)- GYTFTNY CDR2 (SEQ ID NO: 353)- NPNTGEPTFDD CDR3 (SEQ ID NO: 354)- SRGKNEAWFAY | DIQLTQSPLSLPVTLG QPASISCRSSQSLVHR NGNTYLHWFQQRPGQS PRLLIYTVSNRFSGVP DRFSGSGSGTDFTLKI SRVEAEDVGVYFCSQS SHVPPTFGAGTRLEIK R (SEQ ID NO: 355) CDR1 (SEQ ID NO: 356)- QSLVHRNGNTYLH CDR2 (SEQ ID NO: 357)- TVSNRFS CDR3 (SEQ ID NO: 358)- SQSSHVPPT |
| anti-CD74 (1B11) (U.S. Publication No. 2014/0170168) | EVQLVQSGAEVKKPGA SVRVSCKASGYTFTSY GISWVRQAPGQGLEWM GWISAYNGNTNYAQKL QGRVTMTTDTSTSTAY MELRSLRSDDTAVYYC ARDIRAYGSGSYSRYY YYGMDVWGQGTTVTVS S (SEQ ID NO: 359) CDR1 (SEQ ID NO: 360)- GYTFTSYGIS CDR2 (SEQ ID NO: 361)- WISAYNGNTNYAQKLQ CDR3 (SEQ ID NO: 362)- DIRAYGSGSYSRYYYY GMDV | LEIVLTQSPATLSVSP GERATLSCRASQNIGS ILAWYQHKPGQAPRLL IYGASTRATGIPARFS GSGSGTEFTLTISSLQ SDDFAVYYCQQYLYWP FTFGGGTKVEIK (SEQ ID NO: 363) CDR1 (SEQ ID NO: 364)- RASQNIGSILA CDR2 (SEQ ID NO: 365)- GASTRAT CDR3 (SEQ ID NO: 366)- QQYLYWPFT |

Alternatively, novel antigen-binding sites that can bind to CD74 can be identified by screening for binding to the amino acid sequence defined by SEQ ID NO:367 or SEQ ID NO: 368 or a mature extracellular fragment thereof.

SEQ ID NO: 367
MHRRRSRSCREDQKPVMDDQRDLISNNEQLPMLGRRPGAPESKCSRGALY

TGFSILVTLLLAGQATTAYFLYQQQGRLDKLTVTSQNLQLENLRMKLPKP

PKPVSKMRMATPLLMQALPMGALPQGPMQNATKYGNMTEDHVMHLLQNAD

PLKVYPPLKGSFPENLRHLKNTMETIDWKVFESWMHHWLLFEMSRHSLEQ

KPTDAPPKVLTKCQEEVSHIPAVHPGSFRPKCDENGNYLPLQCYGSIGYC

WCVFPNGTEVPNTRSRGHHNCSESLELEDPSSGLGVTKQDLGPVPM

SEQ ID NO: 368
MHRRRSRSCREDQKPVMDDQRDLISNNEQLPMLGRRPGAPESKCSRGALY

TGFSILVTLLLAGQATTAYFLYQQQGRLDKLTVTSQNLQLENLRMKLPKP

PKPVSKMRMATPLLMQALPMGALPQGPMQNATKYGNMTEDHVMHLLQSHW

NWRTRLLGWV

In another aspect, the present disclosure provides multispecific binding proteins that bind to the NKG2D receptor and CD16 receptor on natural killer cells, and the antigen PMEL. Table 18 lists some exemplary sequences of heavy chain variable domains and light chain variable domains that, in combination, can bind to PMEL

TABLE 18

| Clones | Heavy chain variable domain amino acid sequence | Light chain variable domain amino acid sequence |
|---|---|---|
| anti-PMEL (17A9) (U.S. Publication No. 2017/0240645) | EVQLQQSGPELVKPGA SMKISCKSSGYSFTRY TMNWVKQSHGKNLEWI GVINPYNGGTVYNQKF KGKATLTVDKSSSTAY MELLSLTSEDSAVYYC ARTDYDGYAMDYWGQG TSVTVSSAKT (SEQ ID NO: 369) CDR1 (SEQ ID NO: 370)- GYSFTRYTMN CDR2 (SEQ ID NO: 371)- VINPYNGGTVYNQKFK G CDR3 (SEQ ID NO: 372)- TDYDGYAMDY | DVQITQSPSYLAASPG ETITINCRATKSISKY LAWYQEPGKTNNLLI YSGSTLQSGIPSRFSG SGSGTDFTLTISSLEP EDFAMYYCQQHNEYPY TFGSGTKLEIK (SEQ ID NO: 373) CDR1 (SEQ ID NO: 374)- RATKSISKYLA CDR2 (SEQ ID NO: 375)- SGSTLQS CDR3 (SEQ ID NO: 376)- QQHNEYPYT |
| anti-PMEL (8G3) (U.S. Publication No. 2017/0240645) | EVQLQQSGPELVKPGA SMRISCKASGYSFTGY TMNWVKQSHGKNLEWI GVYNPYNGGTVYNQKF KGKATLTVDKSSSTTY MELLSLTSEDSAVYYC ARTDSGGYAMDCWGQG TSVTVSSAKT (SEQ ID NO: 377) CDR1 (SEQ ID NO: 378)- GYSFTGYTMN CDR2 (SEQ ID NO: 379)- VYNPYNGGTVYNQKFK G CDR3 (SEQ ID NO: 380)- TDSGGYAMDC | DVQITQSPSYLDASPG ETITINCRASKTISKY LAWYQEKPGKTNKLLI YSGSTLQSGIPSRFSG SGSGTDFTLTISSLEP EDFAMYYCQQHNEYPY TFGSGTKLEIK (SEQ ID NO: 381) CDR1 (SEQ ID NO: 382)- RASKTISKYLA CDR2 (SEQ ID NO: 383)- SGSTLQS CDR3 (SEQ ID NO: 384)- QQHNEYPYT |

Alternatively, novel antigen-binding sites that can bind to PMEL can be identified by screening for binding to the amino acid sequence defined by SEQ ID NO:385 or a mature extracellular fragment thereof.

SEQ ID NO: 385
MDLVLKRCLLHLAVIGALLAVGATKVPRNQDWLGVSRQLRTKAWNRQLY

PEWTEAQRLDCWRGGQVSLKVSNDGPTLIGANASFSIALNFPGSQKVLP

DGQVIWVNNTIINGSQVWGGQPVYPQETDDACIFPDGGPCPSGSWSQKR

SFVYVWKTWGQYWQVLGGPVSGLSIGTGRAMLGTHTMEVTVYHRRGSRS

YVPLAHSSSAFTITDQVPFSVSVSQLRALDGGNKHFLRNQPLTFALQLH

DPSGYLAEADLSYTWDFGDSSGTLISRALVVTHTYLEPGPVTAQVVLQA

AIPLTSCGSSPVPGTTDGHRPTAEAPNTTAGQVPTTEVVGTTPGQAPTA

EPSGTTSVQVPTTEVISTAPVQMPTAESTGMTPEKVPVSEVMGTTLAEM

STPEATGMTPAEVSIVVLSGTTAAQVTTTEWVETTARELPIPEPEGPDA

SSIMSTESITGSLGPLLDGTATLRLVKRQVPLDCVLYRYGSFSVTLDIV

QGIESAEILQAVPSGEGDAFELTVSCQGGLPKEACMEISSPGCQPPAQR

-continued
LCQPVLPSPACQLVLHQILKGGSGTYCLNVSLADTNSLAVVSTQLIMPG

QEAGLGQVPLIVGILLVLMAVVLASLIYRRRLMKQDFSVPQLPHSSSHW

LRLPRIFCSCPIGENSPLLSGQQV

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as a human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, K409R, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Alternatively, amino acid substitutions could be selected from the following sets of substitutions shown in Table 19.

TABLE 19

|  | First Polypeptide | Second Polypeptide |
| --- | --- | --- |
| Set 1 | S364E/F405A | Y349/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 20.

TABLE 20

|  | First Polypeptide | Second Polypeptide |
| --- | --- | --- |
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 21.

TABLE 21

|  | First Polypeptide | Second Polypeptide |
| --- | --- | --- |
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 22.

TABLE 22

| First Polypeptide | Second Polypeptide |
| --- | --- |
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitutions could be selected from the following set of substitutions in Table 23, where the position(s) indicated in the First Polypeptide column is replaced by any known negatively-charged amino acid, and the position(s) indicated in the Second Polypeptide Column is replaced by any known positively-charged amino acid.

TABLE 23

| First Polypeptide | Second Polypeptide |
| --- | --- |
| K392, K370, K409, or K439 | D399, E356, or E357 |

Alternatively, at least one amino acid substitutions could be selected from the following set of in Table 24, where the position(s) indicated in the First Polypeptide column is replaced by any known positively-charged amino acid, and the position(s) indicated in the Second Polypeptide Column is replaced by any known negatively-charged amino acid.

TABLE 24

| First Polypeptide | Second Polypeptide |
| --- | --- |
| D399, E356, or E357 | K409, K439, K370, or K392 |

Alternatively, amino acid substitutions could be selected from the following set in Table 25.

TABLE 25

| First Polypeptide | Second Polypeptide |
| --- | --- |
| T350V, L351Y, F405A, and Y407V | T350V, T366L, K392L, and T394W |

Alternatively, or in addition, the structural stability of a hetero-multimeric protein may be increased by introducing S354C on either of the first or second polypeptide chain, and Y349C on the opposing polypeptide chain, which forms an artificial disulfide bridge within the interface of the two polypeptides.

In some embodiments, the amino acid sequence of one polypeptide chain of the antibody constant region differs from the amino acid sequence of an IgG1 constant region at position T366, and wherein the amino acid sequence of the other polypeptide chain of the antibody constant region differs from the amino acid sequence of an IgG1 constant region at one or more positions selected from the group consisting of T366, L368 and Y407.

In some embodiments, the amino acid sequence of one polypeptide chain of the antibody constant region differs from the amino acid sequence of an IgG1 constant region at one or more positions selected from the group consisting of T366, L368 and Y407, and wherein the amino acid sequence of the other polypeptide chain of the antibody constant region differs from the amino acid sequence of an IgG1 constant region at position T366.

In some embodiments, the amino acid sequence of one polypeptide chain of the antibody constant region differs from the amino acid sequence of an IgG1 constant region at one or more positions selected from the group consisting of E357, K360, Q362, 5364, L368, K370, T394, D401, F405, and T411 and wherein the amino acid sequence of the other polypeptide chain of the antibody constant region differs from the amino acid sequence of an IgG1 constant region at one or more positions selected from the group consisting of Y349, E357, 5364, L368, K370, T394, D401, F405 and T411.

In some embodiments, the amino acid sequence of one polypeptide chain of the antibody constant region differs from the amino acid sequence of an IgG1 constant region at one or more positions selected from the group consisting of Y349, E357, S364, L368, K370, T394, D401, F405 and T411 and wherein the amino acid sequence of the other polypeptide chain of the antibody constant region differs from the amino acid sequence of an IgG1 constant region at one or more positions selected from the group consisting of E357, K360, Q362, S364, L368, K370, T394, D401, F405, and T411.

In some embodiments, the amino acid sequence of one polypeptide chain of the antibody constant region differs from the amino acid sequence of an IgG1 constant region at one or more positions selected from the group consisting of L351, D399, 5400 and Y407 and wherein the amino acid sequence of the other polypeptide chain of the antibody constant region differs from the amino acid sequence of an IgG1 constant region at one or more positions selected from the group consisting of T366, N390, K392, K409 and T411.

In some embodiments, the amino acid sequence of one polypeptide chain of the antibody constant region differs from the amino acid sequence of an IgG1 constant region at one or more positions selected from the group consisting of T366, N390, K392, K409 and T411 and wherein the amino acid sequence of the other polypeptide chain of the antibody constant region differs from the amino acid sequence of an IgG1 constant region at one or more positions selected from the group consisting of L351, D399, 5400 and Y407.

In some embodiments, the amino acid sequence of one polypeptide chain of the antibody constant region differs from the amino acid sequence of an IgG1 constant region at one or more positions selected from the group consisting of Q347, Y349, K360, and K409, and wherein the amino acid sequence of the other polypeptide chain of the antibody constant region differs from the amino acid sequence of an IgG1 constant region at one or more positions selected from the group consisting of Q347, E357, D399 and F405.

In some embodiments, the amino acid sequence of one polypeptide chain of the antibody constant region differs from the amino acid sequence of an IgG1 constant region at one or more positions selected from the group consisting of Q347, E357, D399 and F405, and wherein the amino acid sequence of the other polypeptide chain of the antibody constant region differs from the amino acid sequence of an IgG1 constant region at one or more positions selected from the group consisting of Y349, K360, Q347 and K409.

In some embodiments, the amino acid sequence of one polypeptide chain of the antibody constant region differs from the amino acid sequence of an IgG1 constant region at one or more positions selected from the group consisting of K370, K392, K409 and K439, and wherein the amino acid sequence of the other polypeptide chain of the antibody constant region differs from the amino acid sequence of an IgG1 constant region at one or more positions selected from the group consisting of D356, E357 and D399.

In some embodiments, the amino acid sequence of one polypeptide chain of the antibody constant region differs from the amino acid sequence of an IgG1 constant region at one or more positions selected from the group consisting of D356, E357 and D399, and wherein the amino acid sequence of the other polypeptide chain of the antibody constant region differs from the amino acid sequence of an IgG1 constant region at one or more positions selected from the group consisting of K370, K392, K409 and K439.

In some embodiments, the amino acid sequence of one polypeptide chain of the antibody constant region differs from the amino acid sequence of an IgG1 constant region at one or more positions selected from the group consisting of L351, E356, T366 and D399, and wherein the amino acid sequence of the other polypeptide chain of the antibody constant region differs from the amino acid sequence of an IgG1 constant region at one or more positions selected from the group consisting of Y349, L351, L368, K392 and K409.

In some embodiments, the amino acid sequence of one polypeptide chain of the antibody constant region differs from the amino acid sequence of an IgG1 constant region at one or more positions selected from the group consisting of Y349, L351, L368, K392 and K409, and wherein the amino acid sequence of the other polypeptide chain of the antibody constant region differs from the amino acid sequence of an IgG1 constant region at one or more positions selected from the group consisting of L351, E356, T366 and D399.

In some embodiments, the amino acid sequence of one polypeptide chain of the antibody constant region differs from the amino acid sequence of an IgG1 constant region by an S354C substitution and wherein the amino acid sequence of the other polypeptide chain of the antibody constant region differs from the amino acid sequence of an IgG1 constant region by a Y349C substitution.

In some embodiments, the amino acid sequence of one polypeptide chain of the antibody constant region differs from the amino acid sequence of an IgG1 constant region by a Y349C substitution and wherein the amino acid sequence of the other polypeptide chain of the antibody constant region differs from the amino acid sequence of an IgG1 constant region by an S354C substitution.

In some embodiments, the amino acid sequence of one polypeptide chain of the antibody constant region differs from the amino acid sequence of an IgG1 constant region by K360E and K409W substitutions and wherein the amino acid sequence of the other polypeptide chain of the antibody constant region differs from the amino acid sequence of an IgG1 constant region by Q347R, D399V and F405T substitutions.

In some embodiments, the amino acid sequence of one polypeptide chain of the antibody constant region differs from the amino acid sequence of an IgG1 constant region by Q347R, D399V and F405T substitutions and wherein the amino acid sequence of the other polypeptide chain of the antibody constant region differs from the amino acid sequence of an IgG1 constant region by K360E and K409W substitutions.

In some embodiments, the amino acid sequence of one polypeptide chain of the antibody constant region differs from the amino acid sequence of an IgG1 constant region by a T366W substitutions and wherein the amino acid sequence of the other polypeptide chain of the antibody constant region differs from the amino acid sequence of an IgG1 constant region by T366S, T368A, and Y407V substitutions.

In some embodiments, the amino acid sequence of one polypeptide chain of the antibody constant region differs from the amino acid sequence of an IgG1 constant region by T366S, T368A, and Y407V substitutions and wherein the amino acid sequence of the other polypeptide chain of the antibody constant region differs from the amino acid sequence of an IgG1 constant region by a T366W substitution.

In some embodiments, the amino acid sequence of one polypeptide chain of the antibody constant region differs from the amino acid sequence of an IgG1 constant region by T350V, L351Y, F405A, and Y407V substitutions and wherein the amino acid sequence of the other polypeptide chain of the antibody constant region differs from the amino acid sequence of an IgG1 constant region by T350V, T366L, K392L, and T394W substitutions.

In some embodiments, the amino acid sequence of one polypeptide chain of the antibody constant region differs from the amino acid sequence of an IgG1 constant region by T350V, T366L, K392L, and T394W substitutions and wherein the amino acid sequence of the other polypeptide chain of the antibody constant region differs from the amino acid sequence of an IgG1 constant region by T350V, L351Y, F405A, and Y407V substitutions.

Exemplary Multi-Specific Binding Proteins

A TriNKET of the present disclosure is A49MI-Duobody-TriNKET-Onartuzumab. A49MI-Duobody-TriNKET-Onartuzumab comprises four polypeptide chains: (a) Onartuzumab-HC: the heavy chain portion of anti-c-MET antibody onartuzumab (SEQ ID NO:425); (b) Onartuzumab-LC: the light chain portion of anti-c-MET antibody onartuzumab (SEQ ID NO:426); (c) A49MI-HC: the heavy chain portion of anti-NKG2D antibody A49MI (SEQ ID NO:423); and (d) A49MI-LC: the light chain portion of anti-NKG2D antibody A49MI (SEQ ID NO:424). The Fc domain of SEQ ID NO:425 comprises a mutation F405L, and the Fc domain of SEQ ID NO:423 comprises a mutation K409R, thereby facilitating Fc heterodimerization. The sequences of A49MI-Duobody-TriNKET-Onartuzumab are provided below. The CDRs under Chothia numbering of these sequences are underlined.

Onartuzumab-HC
(SEQ ID NO: 425)
EVQLVESGGGLVQPGGSLRLSCAAS<u>GYTFTSY</u>WLHWVRQAPGKGLEWV GMID<u>PSNSDTRFNPNFKDR</u>FTISADTSKNTAYLQMNSLRAEDTAVYYC <u>ATYRSYVTPLDY</u>WGQGTLVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWE

SNGQPENNYKTTPPVLDSDGSFLLYSKLTVDKSRWQQGNVFSCSVMHE

ALHNHYTQKSLSLSPG

A49MI-HC
(SEQ ID NO: 423)
EVQLVESGGGLVKPGGSLRLSCAAS<u>GFTFSSY</u>SMNWVRQAPGKGLEWV

SSI<u>SSSSSYI</u>YYADSVKGRFTISRDNAKNSLYLQMNSLRAEDTAVYYC

ARG<u>APIGAAAGWFDP</u>WGQGTLVTVSSASTKGPSVFPLAPSSKSTSGGT

AALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAV

EWESNGQPENNYKTTPPVLDSDGSFFLYSRLTVDKSRWQQGNVFSCSV

MHEALHNHYTQKSLSLSPG

A49MI-LC
(SEQ ID NO: 424)
DIQMTQSPSSVSASVGDRVTITC<u>RASQGISSWLA</u>WYQQKPGKAPKLLI

YAA<u>SSLQS</u>GVPSRFSGSGSGTDFTLTISSLQPEDFATYYC<u>QQGVSFPR</u>

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

Onartuzumab-LC
(SEQ ID NO: 426)
DIQMTQSPSSLSASVGDRVTITC<u>KSSQSLLYTSSQKNYLA</u>WYQQKPGK APKLLIY<u>WASTRES</u>GVPSRFSGSGSGTDFTLTISSLQPEDFATYYC<u>QQ</u>

<u>YYAYPWT</u>FGQGTKVEIKRTVAAPSVFIFPPSDEQLKSGTASVVCLLNN

FYPREAKVQWKVDNALQSGNSQESVTEQDSKDSTYSLSSTLTLSKADY

EKHKVYACEVTHQGLSSPVTKSFNRGEC

Another TriNKET of the present disclosure is A49MI-Duobody-TriNKET-Emibetuzumab. A49MI-Duobody-TriNKET-Emibetuzumab comprises four polypeptide chains: (a) Emibetuzumab-HC: the heavy chain portion of anti-c-MET antibody emibetuzumab (SEQ ID NO:427); (b) Emibetuzumab-LC: the light chain portion of anti-c-MET antibody emibetuzumab (SEQ ID NO:428); (c) A49MI-HC: the heavy chain portion of anti-NKG2D antibody A49MI (SEQ ID NO:423); and (d) A49MI-LC: the light chain portion of anti-NKG2D antibody A49MI (SEQ ID NO:424). The Fc domain of SEQ ID NO:427 comprises a mutation F405L, and the Fc domain of SEQ ID NO:423 comprises a mutation K409R, thereby facilitating Fc heterodimerization. The sequences of A49MI-Duobody-TriNKET-Emibetuzumab are provided below. The CDRs under Chothia numbering of these sequences are underlined.

Emibetuzumab-HC
(SEQ ID NO: 427)
QVQLVQSGAEVKKPGASVKVSCKAS<u>GYTFTDY</u>YMHWVRQAPGQGLEWM GRV<u>NPNRRGT</u>TYNQKFEGRVTMTTDTSTSTAYMELRSLRSDDTAVYYC AR<u>ANWLDY</u>WGQGTTVTVSSASTKGPSVFPLAPSSKSTSGGTAALGCLV

KDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFL

-continued

FPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQ

PENNYKTTPPVLDSDGSFLLYSKLTVDKSRWQQGNVFSCSVMHEALHN

HYTQKSLSLSPG

A49MI-HC
(SEQ ID NO: 423)
EVQLVESGGGLVKPGGSLRLSCAAS<u>GFTFSSY</u>SMNWVRQAPGKGLEWV

SS<u>ISSSSSY</u>IYYADSVKGRFTISRDNAKNSLYLQ<u>MN</u>SLRAEDTAVYYC

AR<u>GAPIGAAAGWFDPW</u>GQGTLVTVSSASTKGPSVFPLAPSSKSTSGGT

AALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAV

EWESNGQPENNYKTTPPVLDSDGSFFLYSRLTVDKSRWQQGNVFSCSV

MHEALHNHYTQKSLSLSPG

A49MI-LC
(SEQ ID NO: 424)
DIQMTQSPSSVSASVGDRVTITC<u>RASQGISSWLA</u>WYQQKPGKAPKLLI

Y<u>AASSLQS</u>GVPSRFSGSGSGTDFTLTISSLQPEDFATYYC<u>QQGVSFPR</u>

<u>T</u>FGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

Emibetuzumab-LC
(SEQ ID NO: 428)
DIQMTQSPSSLSASVGDRVTITC<u>SVSSSVSSIYLH</u>WYQQKPGKAPKLL IY<u>STSNLAS</u>GVPSRFSGSGSGTDFTLTISSLQPEDFATYYC<u>QVYSGYP</u>

<u>LT</u>FGGGTKVEIKRTVAAPSVFIFPPSDEQLKSGTASVVCLLNNFYPRE

AKVQWKVDNALQSGNSQESVTEQDSKDSTYSLSSTLTLSKADYEKHKV

YACEVTHQGLSSPVTKSFNRGEC

Another TriNKET of the present disclosure is A49MI-Duobody-TriNKET-ABT-700. A49MI-Duobody-TriNKET-ABT-700 comprises four polypeptide chains: (a) ABT-700-HC: the heavy chain portion of anti-c-MET antibody ABT-700 (SEQ ID NO:429); (b) ABT-700-LC: the light chain portion of anti-c-MET antibody ABT-700 (SEQ ID NO:430); (c) A49MI-HC: the heavy chain portion of anti-NKG2D antibody A49MI (SEQ ID NO:423); and (d) A49MI-LC: the light chain portion of anti-NKG2D antibody A49MI (SEQ ID NO:424). The Fc domain of SEQ ID NO:429 comprises a mutation F405L, and the Fc domain of SEQ ID NO:423 comprises a mutation K409R, thereby facilitating Fc heterodimerization. The sequences of A49MI-Duobody-TriNKET-ABT-700 are provided below. The CDRs under Chothia numbering of these sequences are underlined.

ABT-700-HC
(SEQ ID NO: 429)
QVQLVQSGAEVKKPGASVKVSCKASG<u>YIFTAY</u>TMHWVRQAPGQGLEWM

GW<u>IKPNNGLANY</u>AQKFQGRVTMTRDTSISTAYMELSRLRSDDTAVYYC

AR<u>SEITTEFDYW</u>GQGTLVTVSSASTKGPSVFPLAPSSKSTSGGTAALG

CLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPS

VFLEPPKPKDTLMISRTPEVTCVVVDVSHEDPEVKFNWYVDGVEVHNA

KTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWES

NGQPENNYKTTPPVLDSDGSFLLYSKLTVDKSRWQQGNVFSCSVMHEA

LHNHYTQKSLSLSPG

A49MI-HC
(SEQ ID NO: 423)
EVQLVESGGGLVKPGGSLRLSCAAS<u>GFTFSSY</u>SMNWVRQAPGKGLEWV

SS<u>ISSSSSY</u>IYYADSVKGRFTISRDNAKNSLYLQ<u>MN</u>SLRAEDTAVYYC

AR<u>GAPIGAAAGWFDPW</u>GQGTLVTVSSASTKGPSVFPLAPSSKSTSGGT

AALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELL

GGPSVFLEPPKPKDTLMISRTPEVTCVVVDVSHEDPEVKFNWYVDGVE

VHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAV

EWESNGQPENNYKTTPPVLDSDGSFFLYSRLTVDKSRWQQGNVFSCSV

MHEALHNHYTQKSLSLSPG

A49MI-LC
(SEQ ID NO: 424)
DIQMTQSPSSVSASVGDRVTITC<u>RASQGISSWLA</u>WYQQKPGKAPKLLI

Y<u>AASSLQS</u>GVPSRFSGSGSGTDFTLTISSLQPEDFATYYC<u>QQGVSFPR</u>

<u>T</u>FGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

ABT-700-LC
(SEQ ID NO: 430)
DIVMTQSPDSLAVSLGERATINC<u>KSSESVDSYANSFLHW</u>YQQKPGQPP

KLLIY<u>RASTRES</u>GVPDRFSGSGSGTDFTLTISSLQAEDVAVYYC<u>QQSK</u>

<u>EDPLT</u>FGGGTKVEIKRTVAAPSVFIFPPSDEQLKSGTASVVCLLNNEY

PREAKVQWKVDNALQSGNSQESVTEQDSKDSTYSLSSTLTLSKADYEK

HKVYACEVTHQGLSSPVTKSFNRGEC

The multi-specific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; and the first, second, and third expression vectors can be stably transfected together into host cells to produce the multimeric proteins.

To achieve the highest yield of the multi-specific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multispecific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of the Multi-Specific Proteins

The multi-specific proteins described herein include an NKG2D-binding site, a tumor-associated antigen-binding site that binds a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, and an antibody Fc domain or a portion thereof sufficient to bind CD16, or an antigen-binding site that binds CD16. In some embodiments, the multi-specific proteins contains an additional antigen-binding site that binds to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, as exemplified in the F4-TriNKET format.

In some embodiments, the multi-specific proteins display similar thermal stability to the corresponding monoclonal antibody, i.e., a monoclonal antibody containing the same tumor-associated antigen-binding site as the one incorporated in the multi-specific proteins (e.g., an antigen-binding site that binds to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL).

In some embodiments, the multi-specific proteins bind to cells expressing NKG2D and/or CD16, such as NK cells, and tumor cells expressing the tumor-associated antigen simultaneously. Binding of the multi-specific proteins to NK cells can enhance the activity of the NK cells toward destruction of the tumor cells.

In some embodiments, the multi-specific proteins bind to the tumor-associated antigen with a similar affinity to the corresponding the tumor-associated antigen monoclonal antibody (i.e., a monoclonal antibody containing the same tumor-associated antigen-binding site as the one incorporated in the multi-specific proteins, for example, a monoclonal antibody containing the same KIT-binding site as the one incorporated in the multi-specific proteins). In some embodiments, the multi-specific proteins are more effective in killing the tumor cells expressing the tumor-associated antigen than the corresponding tumor-associated antigen monoclonal antibodies.

In certain embodiments, the multi-specific proteins described herein, which include a binding site for a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, activate primary human NK cells when co-culturing with cells expressing the tumor-associated antigen. NK cell activation is marked by the increase in CD107a degranulation and IFN-γ cytokine production. Furthermore, compared to a corresponding tumor-associated antigen monoclonal antibody, the multi-specific proteins can show superior activation of human NK cells in the presence of cells expressing the tumor-associated antigen.

In some embodiments, the multi-specific proteins described herein, which include a binding site for a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, enhance the activity of rested and IL-2-activated human NK cells when co-culturing with cells expressing the selected tumor-associated antigen.

In some embodiments, compared to the corresponding monoclonal antibody that binds to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, the multi-specific proteins offer an advantage in targeting tumor cells that express medium and low levels of the tumor-associated antigen.

In some embodiments, the bivalent F4 format of the TriNKETs (i.e., TriNKETs include an additional antigen-binding site that binds to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL) improve the avidity with which the TriNKETs binds to a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL, which in effect stabilize expression and maintenance of high levels of the selected tumor-associated antigen (e.g., KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, or PMEL) on the tumor cell surface. In some embodiments, the F4-TriNKETs mediate more potent killing of tumor cells expressing the selected tumor-associated antigen (e.g., KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, or PMEL) than the corresponding F3-TriNKETs or F3'-TriNKETs.

III. Therapeutic Applications

The invention provides methods for treating cancer using a multi-specific binding protein described herein and/or a pharmaceutical composition described herein. The methods may be used to treat a variety of cancers expressing a tumor-associated antigen selected from KIT, F3, IGF1R, Lewis Y, MUC13, MUC4, MCAM, LRRC32, sialyl-Tn, gpA33, GD3, GM2, c-MET, EPHA3, TNFRSF10A, TNFSF11, CD74, and PMEL. Exemplary cancers to be treated by the KIT-targeting multi-specific binding proteins may be colorectal cancer, acute myeloid leukemia, gastrointestinal stromal tumor, melanoma, small cell lung cancer, non-small cell lung cancer, renal cancer, liver cancer, and testicular cancer. Exemplary cancers to be treated by the F3-targeting multi-specific binding proteins may be bladder cancer, breast cancer, cervical cancer, glioblastoma, head and neck cancer, lung cancer, pancreatic cancer, prostate cancer, sarcomas, and colorectal cancer. Exemplary cancers to be treated by the IGF1R-targeting multi-specific binding proteins may be breast cancer, cervical cancer, head and neck cancer, lung cancer, melanoma, mesothelioma, ovarian cancer, prostate cancer, sarcoma, thyroid cancer, renal cancer, colorectal cancer, pancreatic cancer, gliobastoma, and liver cancer. Exemplary cancers to be treated by the Lewis Y-targeting multi-specific binding proteins may be ovarian cancer, lung cancer, colorectal cancer, gastric cancer, breast cancer, cervical cancer, head and neck cancer, multiple myeloma, and acute myeloid leukemia. Exemplary cancers to be treated by the MUC13-targeting multi-specific binding proteins may be ovarian cancer, liver cancer, lung cancer, melanoma, liver cancer, gastric cancer, pancreatic cancer, renal cancer, esophageal cancer, breast cancer, colorectal cancer, cervical cancer, and cholangiocarcinoma. Exemplary cancers to be treated by the MUC4-targeting multi-specific binding proteins may be breast cancer, pancreatic cancer, ovarian cancer, lung cancer, acute lymphoblastic leukemia, bladder cancer, cervical cancer, colorectal cancer, head and neck cancer, and prostate cancer. Exemplary cancers to be treated by the MCAM-targeting multi-specific binding proteins may be melanoma, breast cancer, small cell lung cancer, sarcoma, colorectal cancer, pancreatic cancer, and renal cancer. Exemplary cancers to be treated by the LRRC32-targeting multi-specific binding proteins may be renal cancer, pancreatic cancer, sarcoma, ovarian cancer, lung cancer, gliobastoma, head and neck cancer, prostate cancer, liver cancer, breast cancer, and cervical cancer. Exemplary cancers to be treated by the sialyl-Tn-targeting multi-specific binding proteins may be ovarian cancer, pancreatic cancer, bladder cancer, gastric cancer, prostate cancer, colorectal cancer, and breast cancer. Exemplary cancers to be treated by the gpA33-targeting multi-specific binding proteins may be colorectal cancer, gastric cancer, and esophageal cancer. Exemplary cancers to be treated by the GD3-targeting multi-specific binding proteins may be lung cancer, glioma, breast cancer, melanoma, ovarian cancer, pancreatic cancer, and neuroblastoma. Exemplary cancers to be treated by the GM2-targeting multi-specific binding proteins may be gastric cancer, breast cancer, ovarian cancer, uterine cancer, cervical cancer, neuroblastoma, melanoma, lung cancer, mesothelioma, and liver cancer. Exemplary cancers to be treated by the c-MET-targeting multi-specific binding proteins may be renal cancer, thyroid cancer, melanoma, lung cancer, melanoma, liver cancer, pancreatic cancer, colorectal cancer, and head and neck cancer. Exemplary cancers to be treated by the EPHA3-targeting multi-specific binding proteins may be cervical cancer, head and neck cancer, gastric cancer, multiple myeloma, ovarian cancer, colorectal cancer, melanoma, breast cancer, prostate cancer, pancreatic cancer, lung cancer, and sarcoma. Exemplary cancers to be treated by the TNFRSF10A-targeting multi-specific binding proteins may be breast cancer, colorectal cancer, prostate cancer, pancreatic cancer, bladder cancer, and head and neck cancer. Exemplary cancers to be treated by the TNFSF11-targeting multi-specific binding proteins may be breast cancer, prostate cancer, and a bone metastatic cancer. Exemplary cancers to be treated by the CD74-targeting multi-specific binding proteins may be diffuse large B cell cancer, a B cell malignancy, renal cancer, lung cancer, ovarian cancer, melanoma, sarcoma, head and neck cancer, liver cancer, bladder cancer, glioma, breast cancer, and leukemia. Exemplary cancers to be treated by the PMEL-targeting multi-specific binding proteins may be melanoma and sarcomas.

In some other embodiments, the cancer is breast, ovarian, esophageal, bladder or gastric cancer, salivary duct carcinoma, salivary duct carcinomas, adenocarcinoma of the lung or aggressive forms of uterine cancer, such as uterine serous endometrial carcinoma. In some other embodiments, the cancer is brain cancer, breast cancer, cervical cancer, colon cancer, colorectal cancer, endometrial cancer, esophageal cancer, leukemia, lung cancer, liver cancer, melanoma, ovarian cancer, pancreatic cancer, rectal cancer, renal cancer, stomach cancer, testicular cancer, or uterine cancer. In yet other embodiments, the cancer is a squamous cell carcinoma, adenocarcinoma, small cell carcinoma, melanoma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well-differentiated carcinoma, or Wilms tumor.

In some other embodiments, the cancer to be treated is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non- Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

In some embodiments, a protein that includes an antigen-binding site that binds KIT can be used to treat colorectal cancer, acute myeloid leukemia, gastrointestinal stromal tumor, melanoma, small cell lung cancer, non-small cell lung cancer, renal cancer, liver cancer, or testicular cancer.

In some embodiments, a protein that includes an antigen-binding site that binds F3 can be used to treat bladder cancer, breast cancer, cervical cancer, glioblastoma, head and neck cancer, lung cancer, pancreatic cancer, prostate cancer, sarcoma, or colorectal cancer.

In some embodiments, a protein that includes an antigen-binding site that binds IGF1R can be used to treat breast cancer, cervical cancer, head and neck cancer, lung cancer, melanoma, mesothelioma, ovarian cancer, prostate cancer, sarcoma, thyroid cancer, renal cancer, colorectal cancer, pancreatic cancer, gliobastoma, or liver cancer.

In some embodiments, a protein that includes an antigen-binding site that binds Lewis Y can be used to treat ovarian cancer, lung cancer, colorectal cancer, gastric cancer, breast cancer, cervical cancer, head and neck cancer, multiple myeloma, or acute myeloid leukemia.

In some embodiments, a protein that includes an antigen-binding site that binds MUC13 can be used to treat ovarian cancer, liver cancer, lung cancer, melanoma, liver cancer, gastric cancer, pancreatic cancer, renal cancer, esophageal cancer, breast cancer, colorectal cancer, cervical cancer, or cholangiocarcinoma.

In some embodiments, a protein that includes an antigen-binding site that binds MUC4 can be used to treat breast cancer, pancreatic cancer, ovarian cancer, lung cancer, acute lymphoblastic leukemia, bladder cancer, cervical cancer, colorectal cancer, head and neck cancer, or prostate cancer.

In some embodiments, a protein that includes an antigen-binding site that binds MCAM can be used to treat melanoma, breast cancer, small cell lung cancer, sarcoma, colorectal cancer, pancreatic cancer, or renal cancer.

In some embodiments, a protein that includes an antigen-binding site that binds LRRC32 can be used to treat. In some embodiments, a protein that includes an antigen-binding site that binds can be used to treat renal cancer, pancreatic cancer, sarcoma, ovarian cancer, lung cancer, gliobastoma, head and neck cancer, prostate cancer, liver cancer, breast cancer, or cervical cancer.

In some embodiments, a protein that includes an antigen-binding site that binds sialyl-Tn can be used to treat ovarian cancer, pancreatic cancer, bladder cancer, gastric cancer, prostate cancer, colorectal cancer, or breast cancer.

In some embodiments, a protein that includes an antigen-binding site that binds gpA33 can be used to treat colorectal cancer, gastric cancer, or esophageal cancer.

In some embodiments, a protein that includes an antigen-binding site that binds GD3 can be used to treat lung cancer, glioma, breast cancer, melanoma, ovarian cancer, pancreatic cancer, or neuroblastoma.

In some embodiments, a protein that includes an antigen-binding site that binds GM2 can be used to treat gastric cancer, breast cancer, ovarian cancer, uterine cancer, cervical cancer, neuroblastoma, melanoma, lung cancer, mesothelioma, or liver cancer.

In some embodiments, a protein that includes an antigen-binding site that binds c-MET can be used to treat renal cancer, thyroid cancer, melanoma, lung cancer, melanoma, liver cancer, pancreatic cancer, colorectal cancer, or head and neck cancer.

In some embodiments, a protein that includes an antigen-binding site that binds EPHA3 can be used to treat cervical cancer, head and neck cancer, gastric cancer, multiple myeloma, ovarian cancer, colorectal cancer, melanoma, breast cancer, prostate cancer, pancreatic cancer, lung cancer, or sarcoma.

In some embodiments, a protein that includes an antigen-binding site that binds TNFRSF10A can be used to treat breast cancer, colorectal cancer, prostate cancer, pancreatic cancer, bladder cancer, head and neck cancer.

In some embodiments, a protein that includes an antigen-binding site that binds TNFSF11 can be used to treat breast cancer, prostate cancer, or a bone metastatic cancer.

In some embodiments, a protein that includes an antigen-binding site that binds CD74 can be used to treat diffuse large B cell cancer, a B cell malignancy, renal cancer, lung cancer, ovarian cancer, melanoma, sarcoma, head and neck cancer, liver cancer, bladder cancer, glioma, breast cancer, or leukemia.

In some embodiments, a protein that includes an antigen-binding site that binds PMEL can be used to treat melanoma or a sarcoma.

IV. Combination Therapy

Another aspect of the invention provides for combination therapy. A multi-specific binding protein described herein can be used in combination with additional therapeutic agents to treat cancer.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, ellaptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma (IFN-γ), colony stimulating factor-1, colony stimulating factor-2, denileukin diftitox, interleukin-2, luteinizing hormone releasing factor and variations of the aforementioned agents that may exhibit differential binding to its cognate receptor, or increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze-dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

The protein could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g., sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/mL of citric acid (e.g., 1.305 mg/mL), about 0.3 mg/mL of sodium citrate (e.g., 0.305 mg/mL), about 1.5 mg/mL of disodium phosphate dihydrate (e.g., 1.53 mg/mL), about 0.9 mg/mL of sodium dihydrogen phosphate dihydrate (e.g., 0.86), and about 6.2 mg/mL of sodium chloride (e.g., 6.165 mg/mL). In certain embodiments, the buffer system includes 1-1.5 mg/mL of citric acid, 0.25 to 0.5 mg/mL of sodium citrate, 1.25 to 1.75 mg/mL of disodium phosphate dihydrate, 0.7 to 1.1 mg/mL of sodium dihydrogen phosphate dihydrate, and 6.0 to 6.4 mg/mL of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/mL. In certain embodiments, the concentration of mannitol may be about 7.5 to 15 mg/mL. In certain embodiments, the concentration of mannitol may be about 10-14 mg/mL. In certain embodiments, the concentration of mannitol may be about 12 mg/mL. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th ed., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 dalton mass decrease of the parent peptide. The subsequent hydrolysis results in an 18 dalton mass increase. Isolation of the succinimide intermediate is difficult due to instability under aqueous conditions. As such, deamidation is typically detectable as 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The protein of the present disclosure could exist in a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 ng/kg of body weight, about 0.01 µg to about 50 µg/kg of body weight, about 0.01 µg to about 10 ng/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 ng/kg of body weight, about 0.1 µg to about 10 ng/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 ng/kg of body weight, about 1 µg to about 50 ng/kg of body weight, about 1 µg to about 10 ng/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 ng/kg of body weight, about 10 µg to about 50 ng/kg of body weight, about 50 µg to about 100 mg/kg of body weight, about 50 µg to about 50 mg/kg of body weight, about 50 µg to about 10 mg/kg of body weight, about 50 µg to about 1 mg/kg of body weight, about 50 µg to about 100 ng/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—NKG2D Binding Domains Bind to NKG2D

NKG2D-Binding Domains Bind to Purified Recombinant NKG2D

The nucleic acid sequences of human, mouse or cynomolgus NKG2D ectodomains were fused with nucleic acid sequences encoding human IgG1 Fc domains and introduced into mammalian cells to be expressed. After purification, NKG2D-Fc fusion proteins were adsorbed to wells of microplates. After blocking the wells with bovine serum albumin to prevent non-specific binding, NKG2D-binding domains were titrated and added to the wells pre-adsorbed with NKG2D-Fc fusion proteins. Primary antibody binding was detected using a secondary antibody which was conjugated to horseradish peroxidase and specifically recognizes a human kappa light chain to avoid Fc cross-reactivity. 3,3', 5,5'-Tetramethylbenzidine (TMB), a substrate for horseradish peroxidase, was added to the wells to visualize the binding signal, whose absorbance was measured at 450 nM and corrected at 540 nM. An NKG2D-binding domain clone, an isotype control or a positive control (comprising heavy chain and light chain variable domains selected from SEQ ID NOs:101-104, or anti-mouse NKG2D clones MI-6 and CX-5 available at eBioscience) was added to each well.

Figure 3:
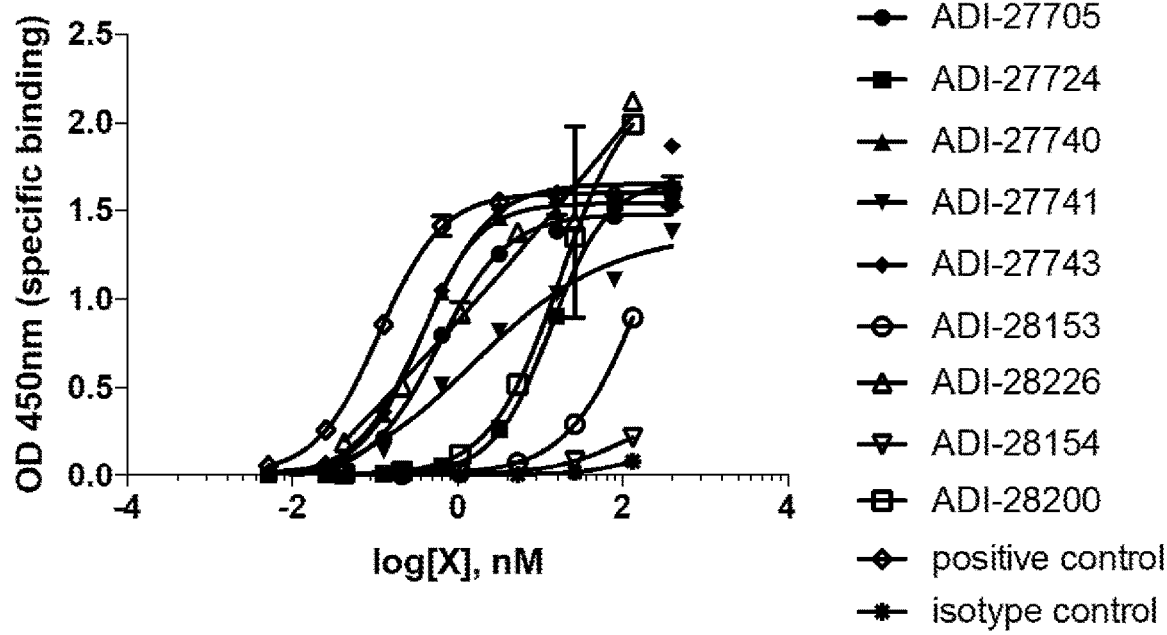
FIG. 3 are line graphs demonstrating the binding affinity of NKG2D-binding domains (listed as clones) to human recombinant NKG2D in an ELISA assay.
Figure 4:
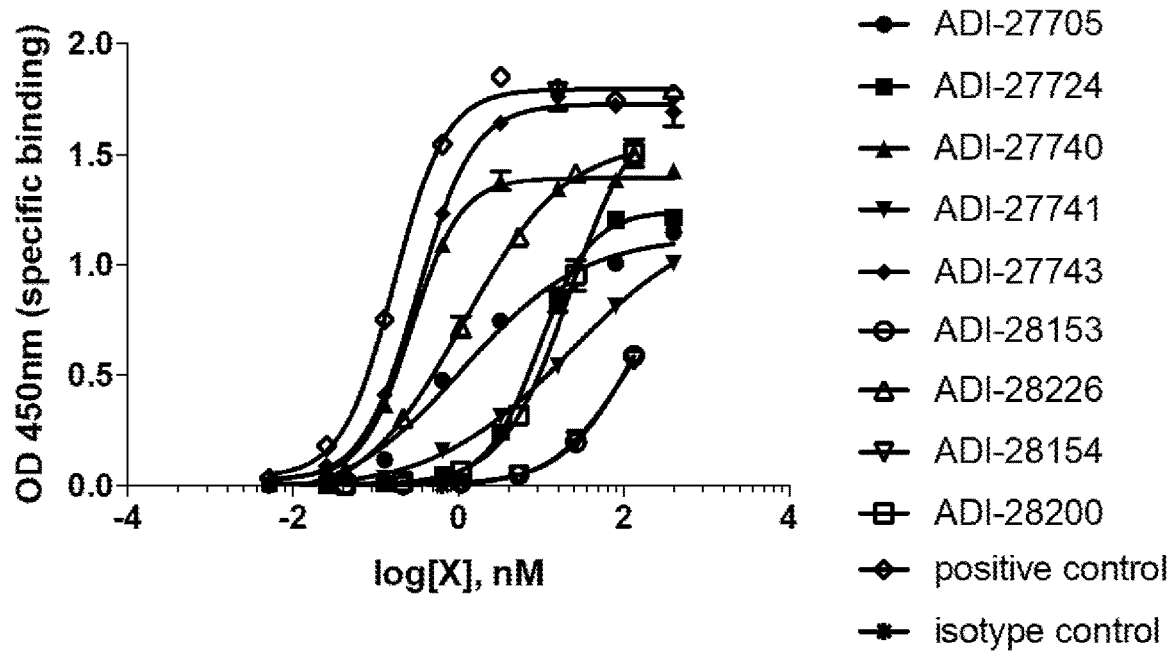
FIG. 4 are line graphs demonstrating the binding affinity of NKG2D-binding domains (listed as clones) to cynomolgus recombinant NKG2D in an ELISA assay.
Figure 5:
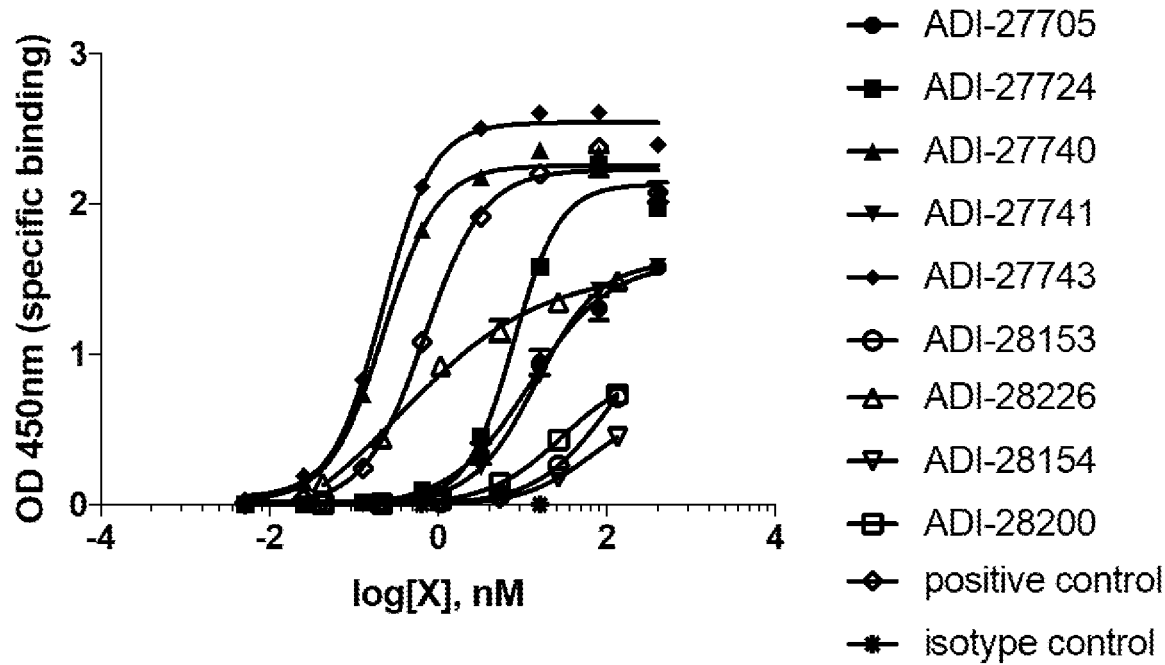
FIG. 5 are line graphs demonstrating the binding affinity of NKG2D-binding domains (listed as clones) to mouse recombinant NKG2D in an ELISA assay.

The isotype control showed minimal binding to recombinant NKG2D-Fc proteins, while the positive control bound strongest to the recombinant antigens. NKG2D-binding domains produced by all clones demonstrated binding across human, mouse, and cynomolgus recombinant NKG2D-Fc proteins, although with varying affinities from clone to clone. Generally, each anti-NKG2D clone bound to human (FIG. 3) and cynomolgus (FIG. 4) recombinant NKG2D-Fc with similar affinity, but with lower affinity to mouse (FIG. 5) recombinant NKG2D-Fc.

NKG2D-Binding Domains Bind to Cells Expressing NKG2D

EL4 mouse lymphoma cell lines were engineered to express human or mouse NKG2D-CD3 zeta signaling domain chimeric antigen receptors. An NKG2D-binding clone, an isotype control or a positive control was used at a 100 nM concentration to stain extracellular NKG2D expressed on the EL4 cells. The antibody binding was detected using fluorophore-conjugated anti-human IgG secondary antibodies. Cells were analyzed by flow cytometry, and fold-over-background (FOB) was calculated using the mean fluorescence intensity (MFI) of NKG2D-expressing cells compared to parental EL4 cells.

Figure 6:
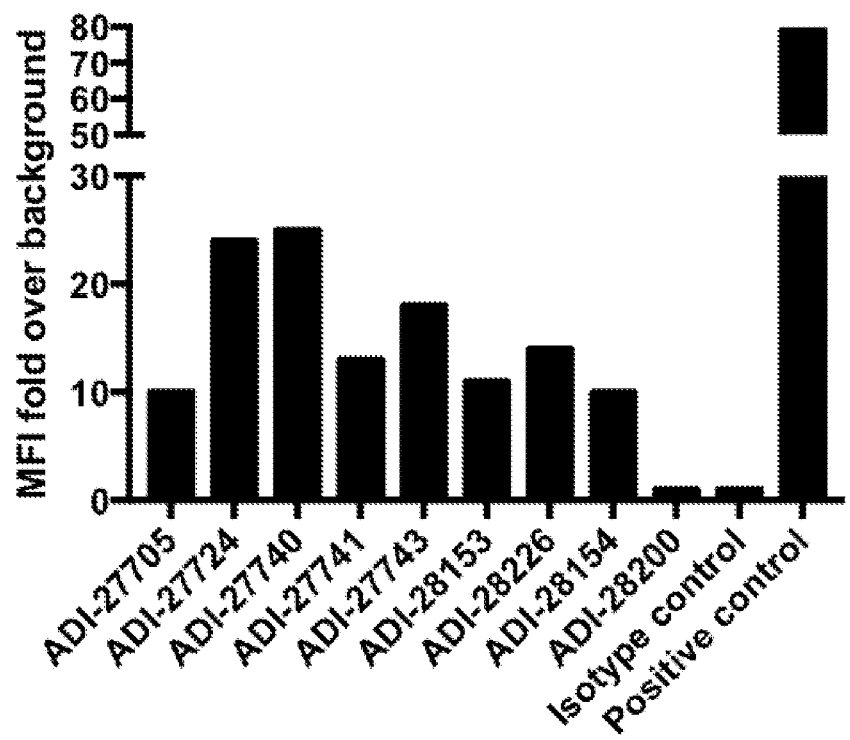
FIG. 6 are bar graphs demonstrating the binding of NKG2D-binding domains (listed as clones) to EL4 cells expressing human NKG2D by flow cytometry showing mean fluorescence intensity (MFI) fold over background (FOB).
Figure 7:
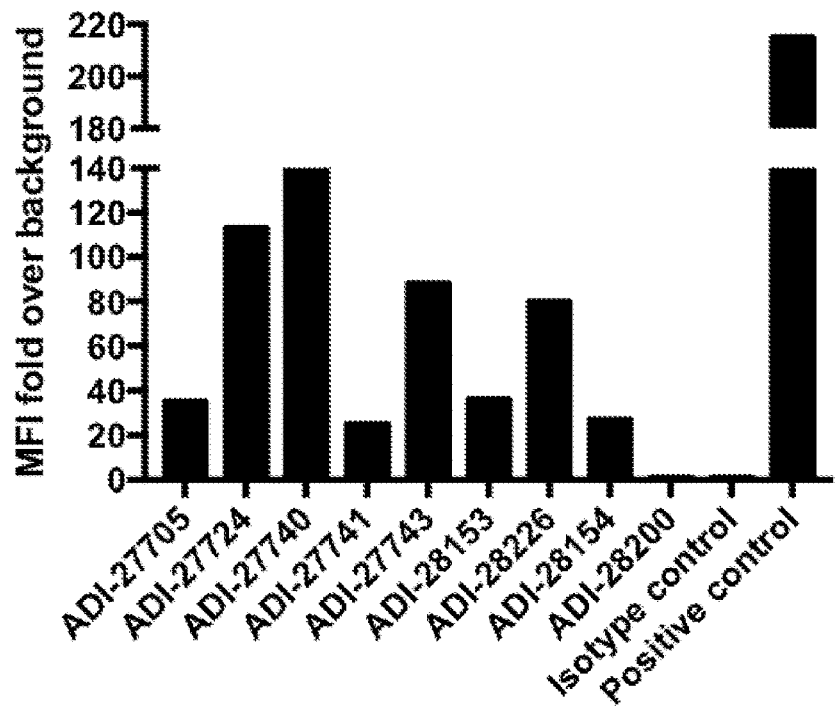
FIG. 7 are bar graphs demonstrating the binding of NKG2D-binding domains (listed as clones) to EL4 cells expressing mouse NKG2D by flow cytometry showing mean fluorescence intensity (MFI) fold over background (FOB).

NKG2D-binding domains produced by all clones bound to EL4 cells expressing human and mouse NKG2D. Positive control antibodies (comprising heavy chain and light chain variable domains selected from SEQ ID NOs:101-104, or anti-mouse NKG2D clones MI-6 and CX-5 available at eBioscience) gave the best FOB binding signal. The NKG2D-binding affinity for each clone was similar between cells expressing human NKG2D (FIG. 6) and mouse (FIG. 7) NKG2D.

Example 2—NKG2D-Binding Domains Block Natural Ligand Binding to NKG2D

Competition with ULBP-6

Figure 8:
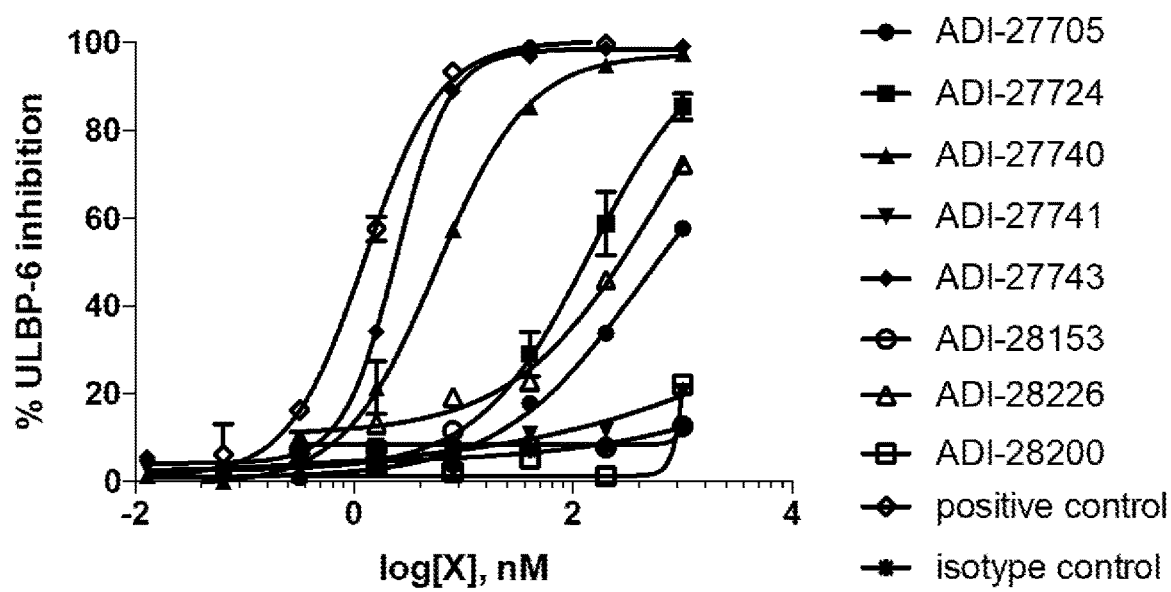
FIG. 8 are line graphs demonstrating specific binding affinity of NKG2D-binding domains (listed as clones) to recombinant human NKG2D-Fc by competing with natural ligand ULBP-6.

Recombinant human NKG2D-Fc proteins were adsorbed to wells of a microplate, and the wells were blocked with bovine serum albumin to reduce non-specific binding. A saturating concentration of ULBP-6-His-biotin was added to the wells, followed by addition of the NKG2D-binding domain clones. After a 2-hour incubation, wells were washed and ULBP-6-His-biotin that remained bound to the NKG2D-Fc coated wells was detected by streptavidin-conjugated to horseradish peroxidase and TMB substrate. Absorbance was measured at 450 nM and corrected at 540 nM. After subtracting background, specific binding of NKG2D-binding domains to the NKG2D-Fc proteins was calculated from the percentage of ULBP-6-His-biotin that was blocked from binding to the NKG2D-Fc proteins in wells. The positive control antibody (comprising heavy chain and light chain variable domains selected from SEQ ID NOs:101-104) and various NKG2D-binding domains blocked ULBP-6 binding to NKG2D, while isotype control showed little competition with ULBP-6 (FIG. 8).

ULBP-6 sequence is represented by SEQ ID NO:108.

```
                                         (SEQ ID NO: 108)
MAAAAIPALLLCLPLLFLLFGWSRARRDDPHSLCYDITVIPKFRPGPR

WCAVQGQVDEKTFLHYDCGNKTVTPVSPLGKKLNVTMAWKAQNPVLRE

VVDILTEQLLDIQLENYTPKEPLTLQARMSCEQKAEGHSSGSWQFSID

GQTFLLFDSEKRMWTTVHPGARKMKEKWENDKDVAMSFHYISMGDCIG

WLEDFLMGMDSTLEPSAGAPLAMSSGTTQLRATATTLILCCLLIILPC

FILPGI
```

Competition with MICA

Figure 9:
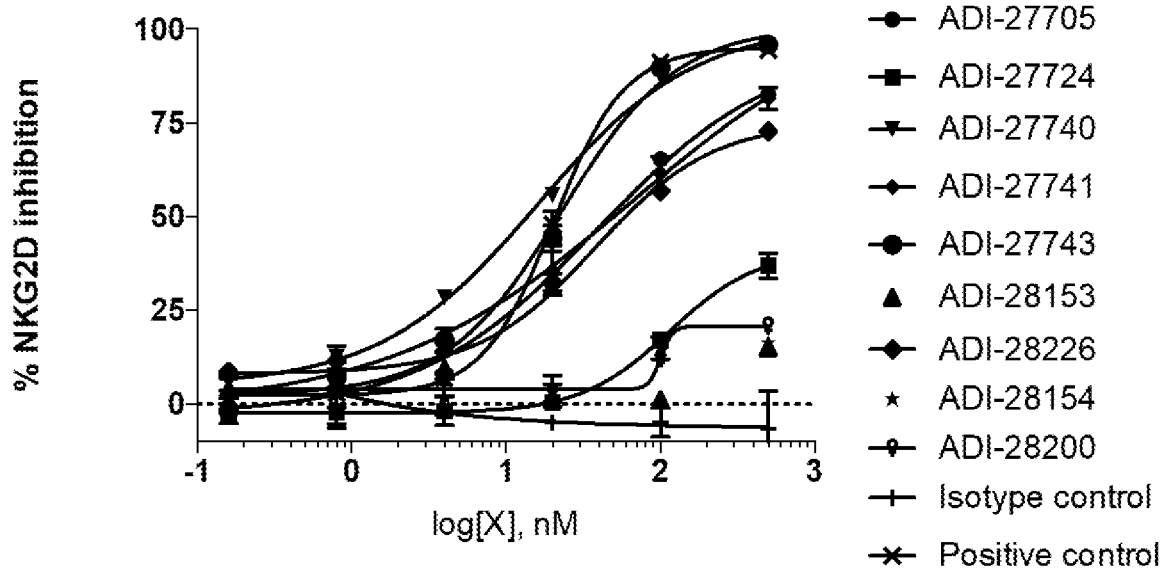
FIG. 9 are line graphs demonstrating specific binding affinity of NKG2D-binding domains (listed as clones) to recombinant human NKG2D-Fc by competing with natural ligand MICA.

Recombinant human MICA-Fc proteins were adsorbed to wells of a microplate, and the wells were blocked with bovine serum albumin to reduce non-specific binding. NKG2D-Fc-biotin was added to wells followed by NKG2D-binding domains. After incubation and washing, NKG2D-Fc-biotin that remained bound to MICA-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the MICA-Fc coated wells. The positive control antibody (comprising heavy chain and light chain variable domains selected from SEQ ID NOs:101-104) and various NKG2D-binding domains blocked MICA binding to NKG2D, while isotype control showed little competition with MICA (FIG. 9).

Competition with Rae-1 Delta

Figure 10:
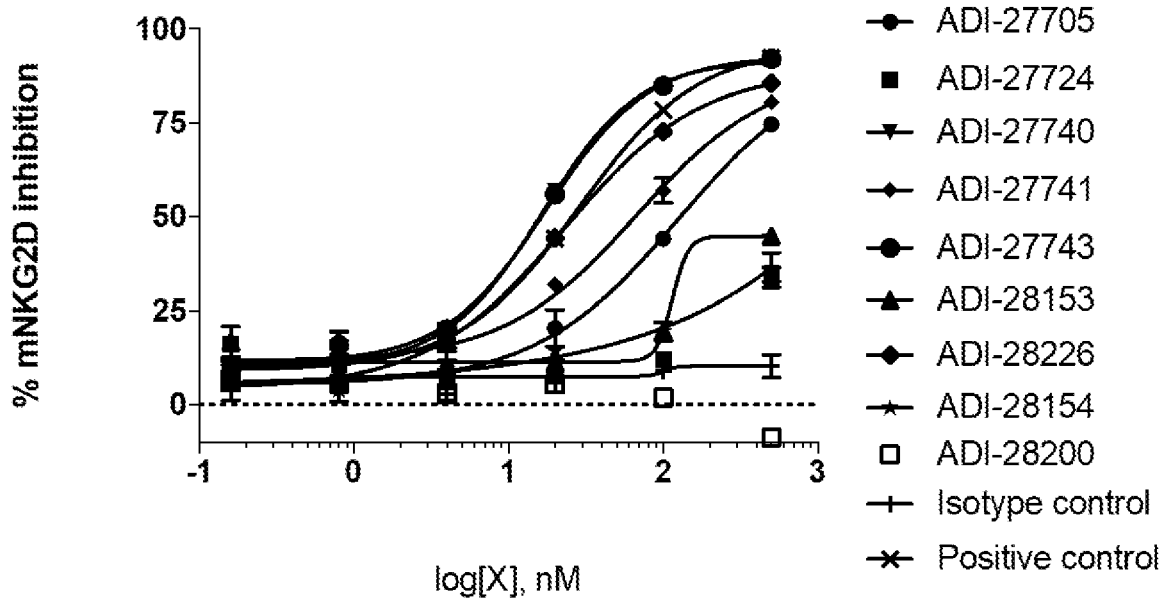
FIG. 10 are line graphs demonstrating specific binding affinity of NKG2D-binding domains (listed as clones) to recombinant mouse NKG2D-Fc by competing with natural ligand Rae-1 delta.

Recombinant mouse Rae-1delta-Fc (purchased from R&D Systems) was adsorbed to wells of a microplate, and the wells were blocked with bovine serum albumin to reduce non-specific binding. Mouse NKG2D-Fc-biotin was added to the wells followed by NKG2D-binding domains. After incubation and washing, NKG2D-Fc-biotin that remained bound to Rae-1delta-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the Rae-1delta-Fc coated wells. The positive control (comprising heavy chain and light chain variable domains selected from SEQ ID NOs:101-104, or anti-mouse NKG2D clones MI-6 and CX-5 available at eBioscience) and various NKG2D-binding domain clones blocked Rae-1delta binding to mouse NKG2D, while the isotype control antibody showed little competition with Rae-1delta (FIG. 10).

Example 3—NKG2D-Binding Domain Clones Activate NKG2D

Nucleic acid sequences of human and mouse NKG2D were fused to nucleic acid sequences encoding a CD3 zeta signaling domain to obtain chimeric antigen receptor (CAR) constructs. The NKG2D-CAR constructs were then cloned into a retrovirus vector using Gibson assembly and transfected into expi293 cells for retrovirus production. EL4 cells were infected with viruses containing NKG2D-CAR together with 8 μg/mL polybrene. 24 hours after infection, the expression levels of NKG2D-CAR in the EL4 cells were analyzed by flow cytometry, and clones which express high levels of the NKG2D-CAR on the cell surface were selected.

Figure 11:
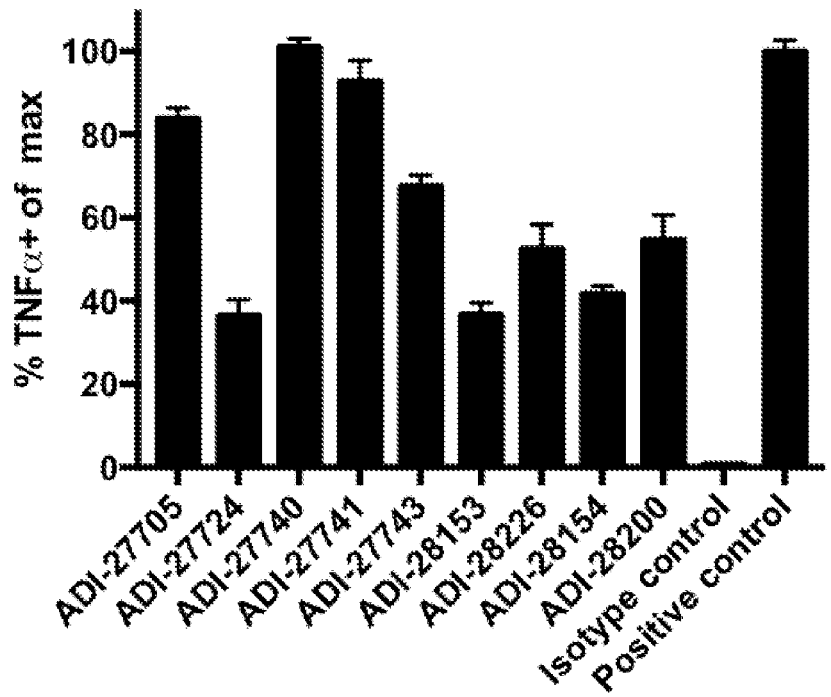
FIG. 11 are bar graphs showing activation of human NKG2D by NKG2D-binding domains (listed as clones) by quantifying the percentage of TNF-α positive cells, which express human NKG2D-CD3 zeta fusion proteins.
Figure 12:
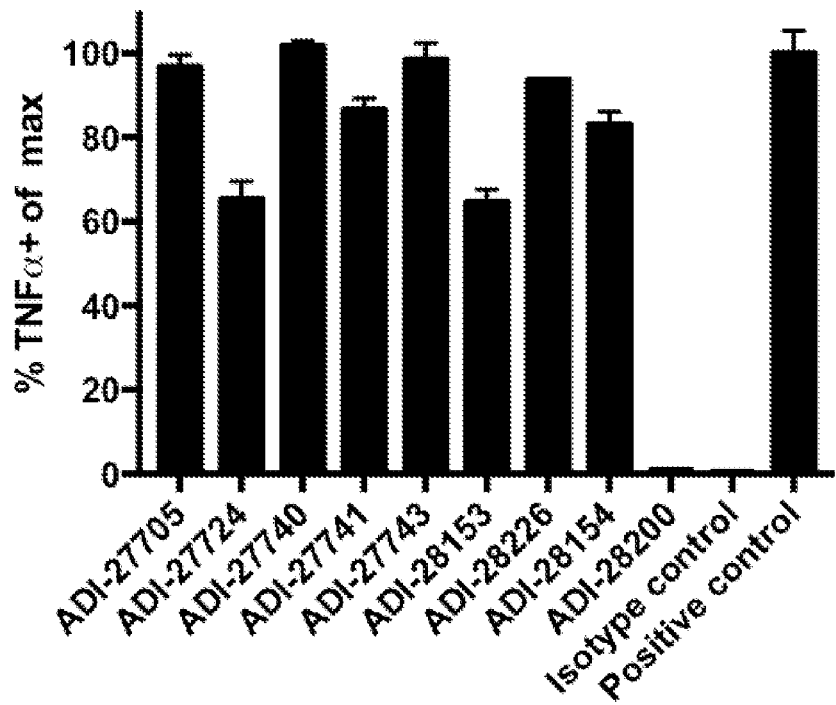
FIG. 12 are bar graphs showing activation of mouse NKG2D by NKG2D-binding domains (listed as clones) by quantifying the percentage of TNF-α positive cells, which express mouse NKG2D-CD3 zeta fusion proteins.

To determine whether NKG2D-binding domains activate NKG2D, they were adsorbed to wells of a microplate, and NKG2D-CAR EL4 cells were cultured on the antibody fragment-coated wells for 4 hours in the presence of brefeldin-A and monensin. Intracellular TNF-α production, an indicator for NKG2D activation, was assayed by flow cytometry. The percentage of TNF-α positive cells was normalized to the cells treated with the positive control. All NKG2D-binding domains activated both human NKG2D (FIG. 11) and mouse NKG2D (FIG. 12).

Example 4—NKG2D-Binding Domains Activate NK Cells

Primary Human NK Cells

Figure 13:
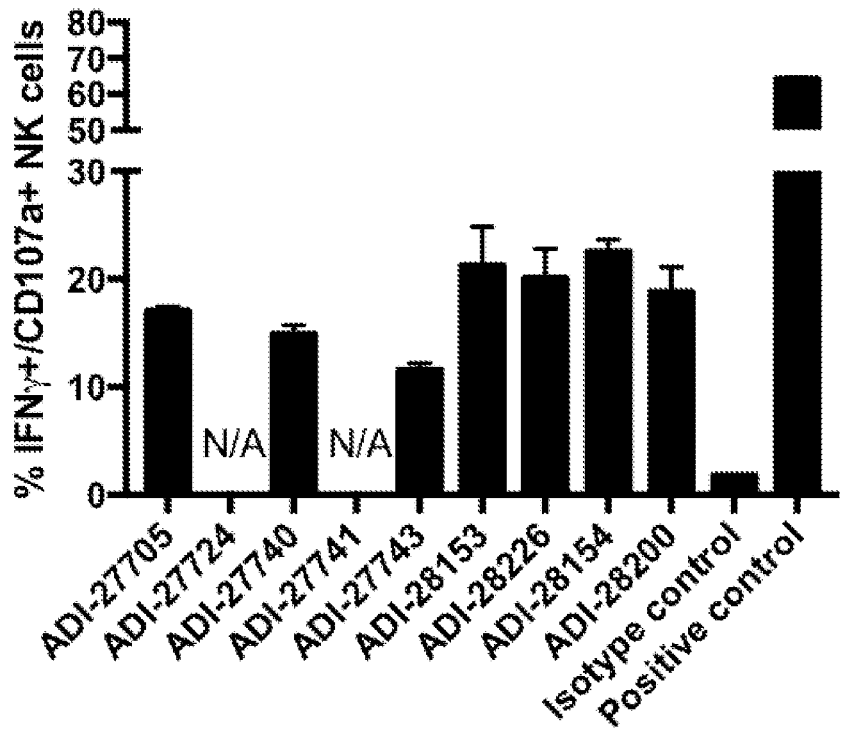
FIG. 13 are bar graphs showing activation of human NK cells by NKG2D-binding domains (listed as clones).
Figure 14:
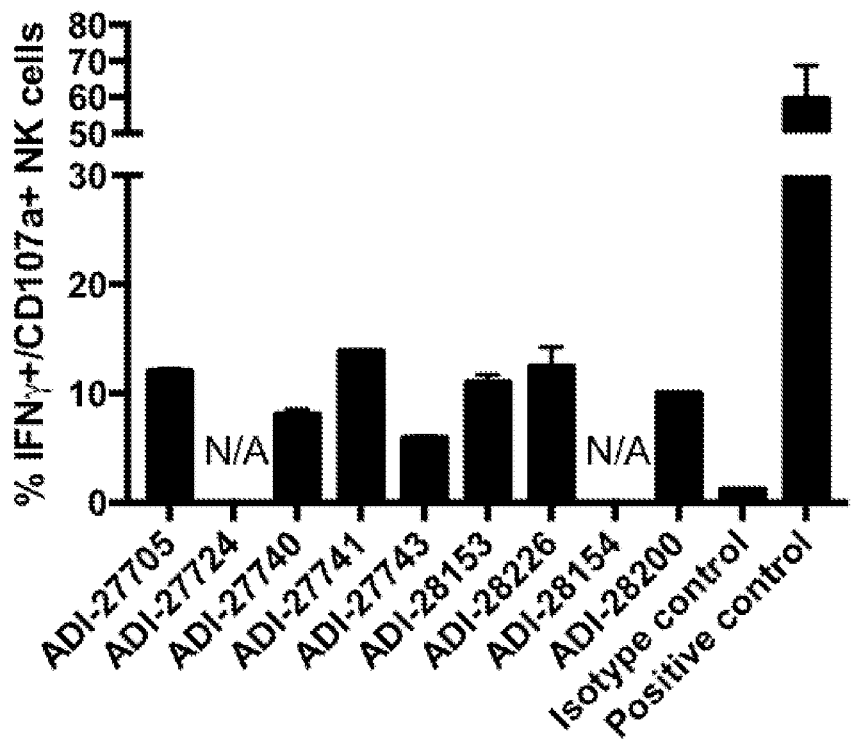
FIG. 14 are bar graphs showing activation of human NK cells by NKG2D-binding domains (listed as clones).

Peripheral blood mononuclear cells (PBMCs) were isolated from human peripheral blood buffy coats using density gradient centrifugation. NK cells (CD3" CD56$^+$) were isolated using negative selection with magnetic beads from PBMCs, and the purity of the isolated NK cells was typically >95%. Isolated NK cells were then cultured in media containing 100 ng/mL IL-2 for 24-48 hours before they were transferred to the wells of a microplate to which the NKG2D-binding domains were adsorbed, and cultured in the media containing fluorophore-conjugated anti-CD107a antibody, brefeldin-A, and monensin. Following culture, NK cells were assayed by flow cytometry using fluorophore-conjugated antibodies against CD3, CD56 and IFN-γ. CD107a and IFN-γ staining were analyzed in CD3$^-$ CD56$^+$ cells to assess NK cell activation. The increase in CD107a/IFN-γ double-positive cells is indicative of better NK cell activation through engagement of two activating receptors rather than one receptor. NKG2D-binding domains and the positive control (e.g., heavy chain variable domain represent by SEQ ID NO:101 or SEQ ID NO:103, and light chain variable domain represented by SEQ ID NO:102 or SEQ ID NO:104) showed a higher percentage of NK cells becoming CD107a$^+$ and IFN-γ$^+$ than the isotype control (FIG. 13 & FIG. 14 represent data from two independent experiments, each using a different donor's PBMC for NK cell preparation).

Primary Mouse NK Cells

Figure 15:
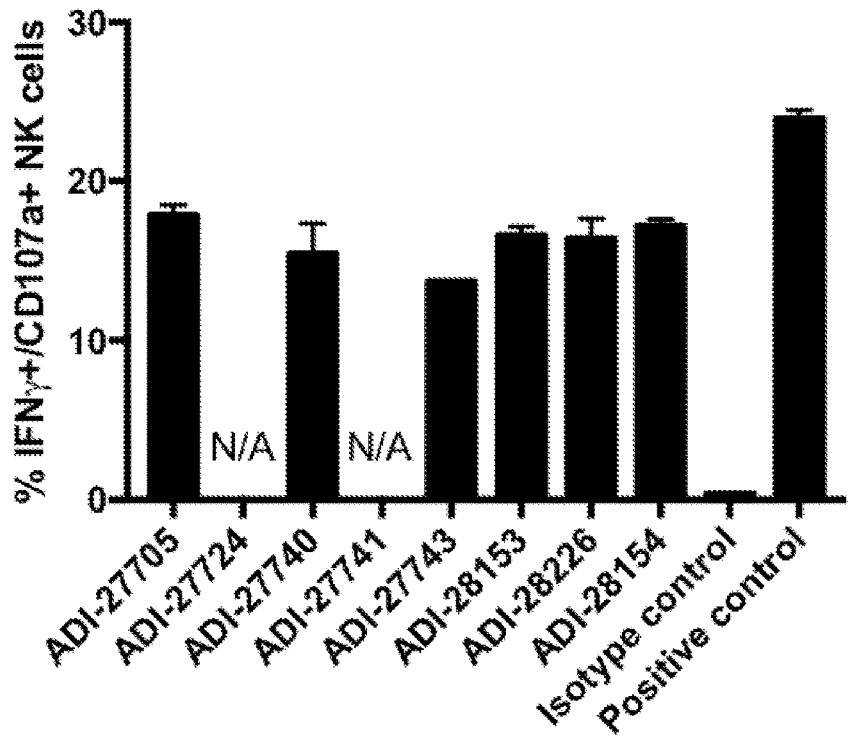
FIG. 15 are bar graphs showing activation of mouse NK cells by NKG2D-binding domains (listed as clones).
Figure 16:
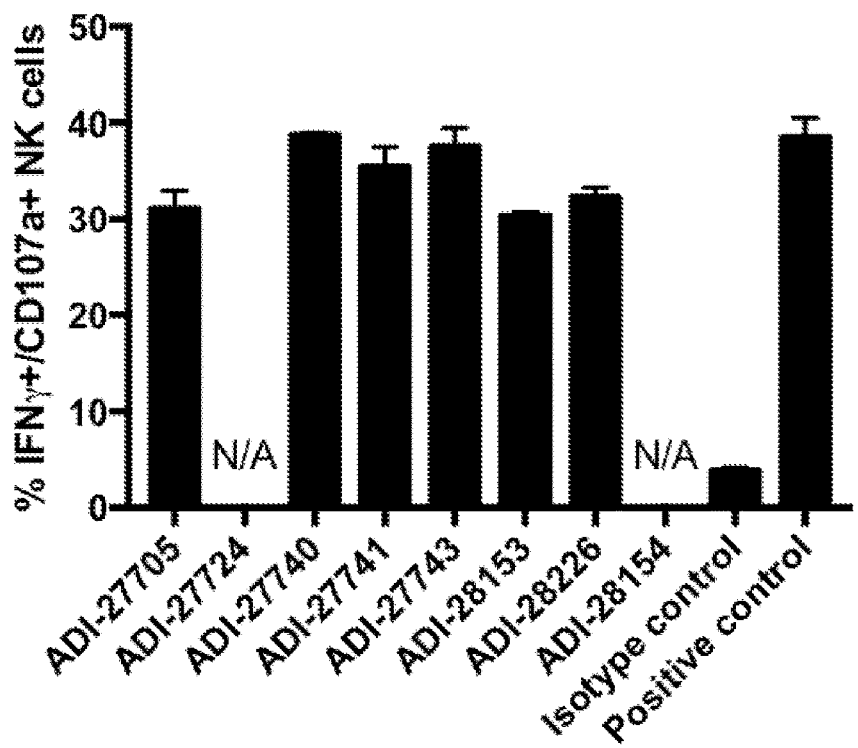
FIG. 16 are bar graphs showing activation of mouse NK cells by NKG2D-binding domains (listed as clones).

Spleens were obtained from C57Bl/6 mice and crushed through a 70 μm cell strainer to obtain single cell suspension. Cells were pelleted and resuspended in ACK lysis buffer (purchased from Thermo Fisher Scientific #A1049201; 155 mM ammonium chloride, 10 mM potassium bicarbonate, 0.01 mM EDTA) to remove red blood cells. The remaining cells were cultured with 100 ng/mL hIL-2 for 72 hours before being harvested and prepared for NK cell isolation. NK cells (CD3$^-$NK1.1$^+$) were then isolated from spleen cells using a negative depletion technique with magnetic beads with typically >90% purity. Purified NK cells were cultured in media containing 100 ng/mL mIL-15 for 48 hours before they were transferred to the wells of a microplate to which the NKG2D-binding domains were adsorbed, and cultured in the media containing fluorophore-conjugated anti-CD107a antibody, brefeldin-A, and monensin. Following culture in NKG2D-binding domain-coated wells, NK cells were assayed by flow cytometry using fluorophore-conjugated antibodies against CD3, NK1.1 and IFN-γ. CD107a and IFN-γ staining were analyzed in CD3$^-$NK1.1$^+$ cells to assess NK cell activation. The increase in CD107a/IFN-γ double-positive cells is indicative of better NK cell activation through engagement of two activating receptors rather than one receptor. NKG2D-binding domains and the positive control (selected from anti-mouse NKG2D clones MI-6 and CX-5 available at eBioscience) showed a higher percentage of NK cells becoming CD107a$^+$ and IFN-γ$^+$ than the isotype control (FIG. 15 & FIG. 16 represent data from two independent experiments, each using a different mouse for NK cell preparation).

Example 5—NKG2D-Binding Domains Enable Cytotoxicity of Target Tumor Cells

Human and mouse primary NK cell activation assays demonstrated increased cytotoxicity markers on NK cells after incubation with NKG2D-binding domains. To address whether this translates into increased tumor cell lysis, a cell-based assay was utilized where each NKG2D-binding domain was developed into a monospecific antibody. The Fc region was used as one targeting arm, while the Fab fragment region (NKG2D-binding domain) acted as another targeting arm to activate NK cells. THP-1 cells, which are of human origin and express high levels of Fc receptors, were used as a tumor target and a Perkin Elmer DELFIA Cytotoxicity Kit was used. THP-1 cells were labeled with BATDA reagent, and resuspended at $10^5$/mL in culture media. Labeled THP-1 cells were then combined with NKG2D antibodies and isolated mouse NK cells in wells of a microtiter plate at 37° C. for 3 hours. After incubation, 20 μL of the culture supernatant were removed, mixed with 200 of Europium solution and incubated with shaking for 15 minutes in the dark. Fluorescence was measured over time by a PheraStar plate reader equipped with a time-resolved fluorescence module (Excitation 337 nm, Emission 620 nm) and specific lysis was calculated according to the kit instructions.

Figure 17:
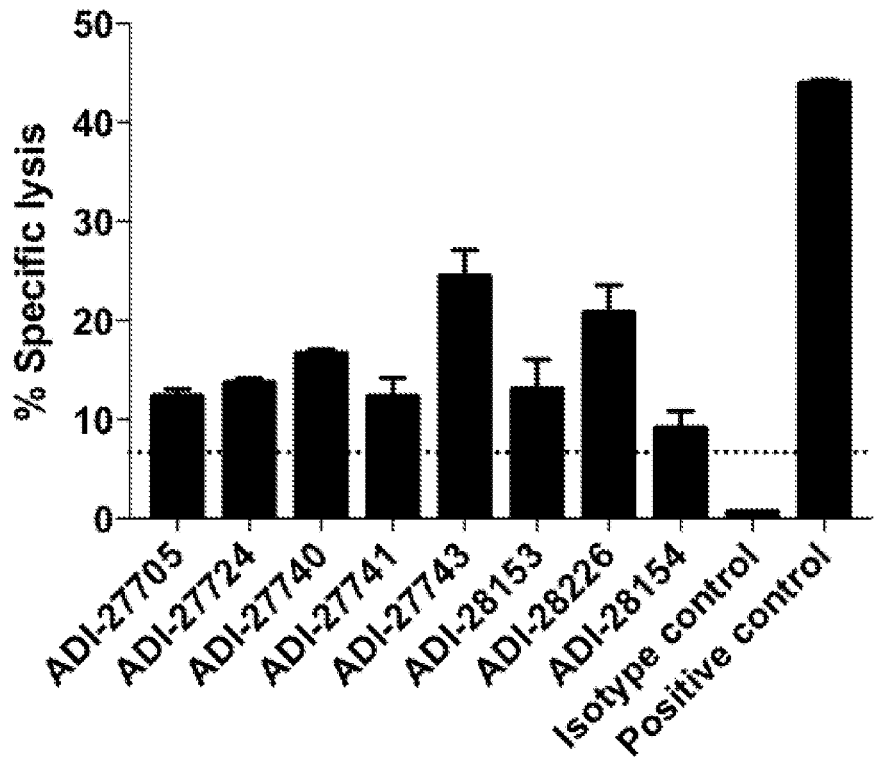
FIG. 17 are bar graphs showing the cytotoxic effect of NKG2D-binding domains (listed as clones) on tumor cells.

The positive control, ULBP-6—a natural ligand for NKG2D, showed increased specific lysis of THP-1 target cells by mouse NK cells. NKG2D antibodies also increased specific lysis of THP-1 target cells, while isotype control antibody showed reduced specific lysis. The dotted line indicates specific lysis of THP-1 cells by mouse NK cells without antibody added (FIG. 17).

Example 6—NKG2D Antibodies Show High Thermostability

Figure 18:
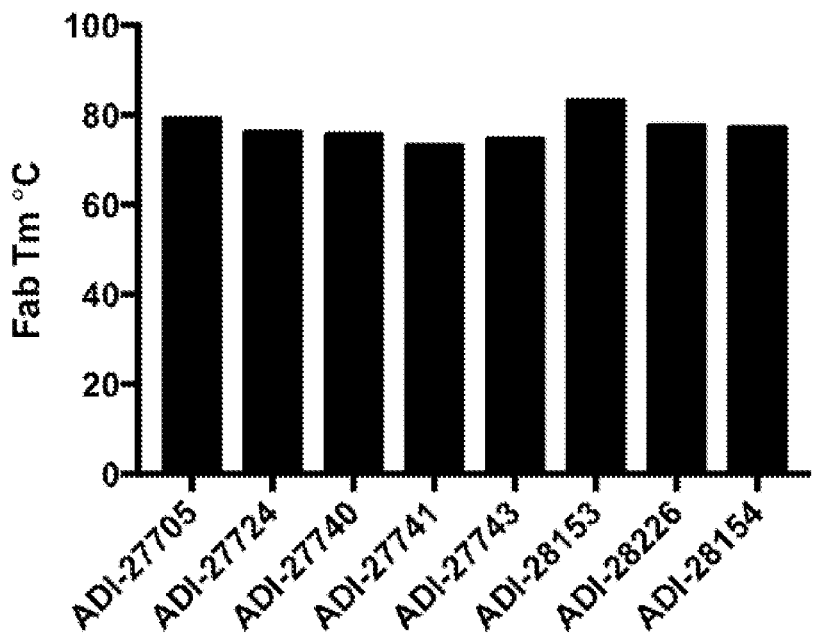
FIG. 18 are bar graphs showing the melting temperature of NKG2D-binding domains (listed as clones) measured by differential scanning fluorimetry.

Melting temperatures of NKG2D-binding domains were assayed using differential scanning fluorimetry. The extrapolated apparent melting temperatures are high relative to typical IgG1 antibodies (FIG. 18).

Example 7—Synergistic Activation of Human NK Cells by Cross-Linking NKG2D and CD16

Primary Human NK Cell Activation Assay

Peripheral blood mononuclear cells (PBMCs) were isolated from peripheral human blood buffy coats using density gradient centrifugation. NK cells were purified from PBMCs using negative magnetic beads (StemCell #17955). NK cells were >90% $CD3^-$ $CD56^+$ as determined by flow cytometry. Cells were then expanded 48 hours in media containing 100 ng/mL hIL-2 (Peprotech #200-02) before use in activation assays. Antibodies were coated onto a 96-well flat-bottom plate at a concentration of 2 µg/mL (anti-CD16, Biolegend #302013) and 5 µg/mL (anti-NKG2D, R&D #MAB139) in 100 µL sterile PBS overnight at 4° C. followed by washing the wells thoroughly to remove excess antibody. For the assessment of degranulation IL-2-activated NK cells were resuspended at $5 \times 10^5$ cells/mL in culture media supplemented with 100 ng/mL human IL-2 (hIL2) and 1 µg/mL APC-conjugated anti-CD107a mAb (Biolegend #328619). $1 \times 10^5$ cells/well were then added onto antibody coated plates. The protein transport inhibitors Brefeldin A (BFA, Biolegend #420601) and Monensin (Biolegend #420701) were added at a final dilution of 1:1000 and 1:270, respectively. Plated cells were incubated for 4 hours at 37° C. in 5% $CO_2$. For intracellular staining of IFN-γ, NK cells were labeled with anti-CD3 (Biolegend #300452) and anti-CD56 mAb (Biolegend #318328), and subsequently fixed, permeabilized and labeled with anti-IFN-γ mAb (Biolegend #506507). NK cells were analyzed for expression of CD107a and IFN-γ by flow cytometry after gating on live $CD56^+CD3^-$ cells.

Figure 19A:
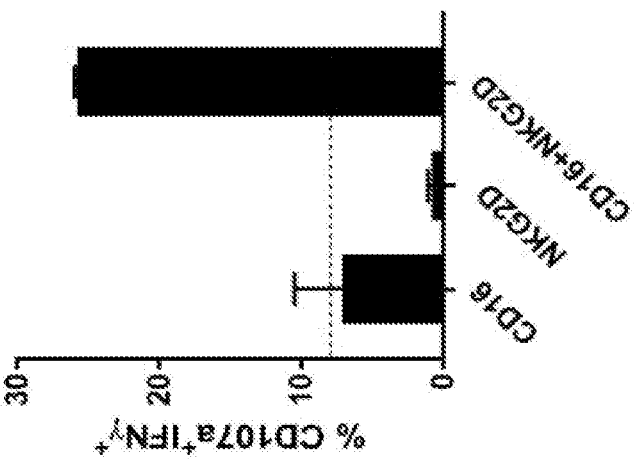
FIGS. 19A to 19C are bar graphs of synergistic activation of NK cells using CD16 and NKG2D-binding.
Figure 19B:
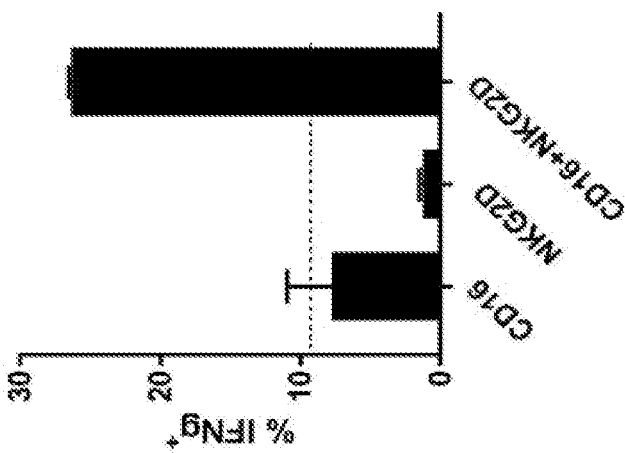
Figure 19C:
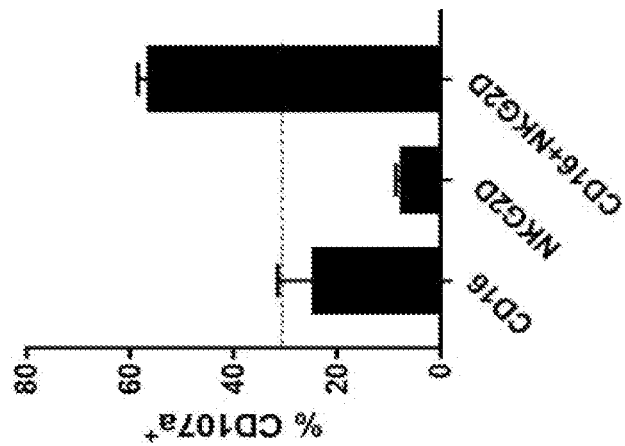
Figure 20:
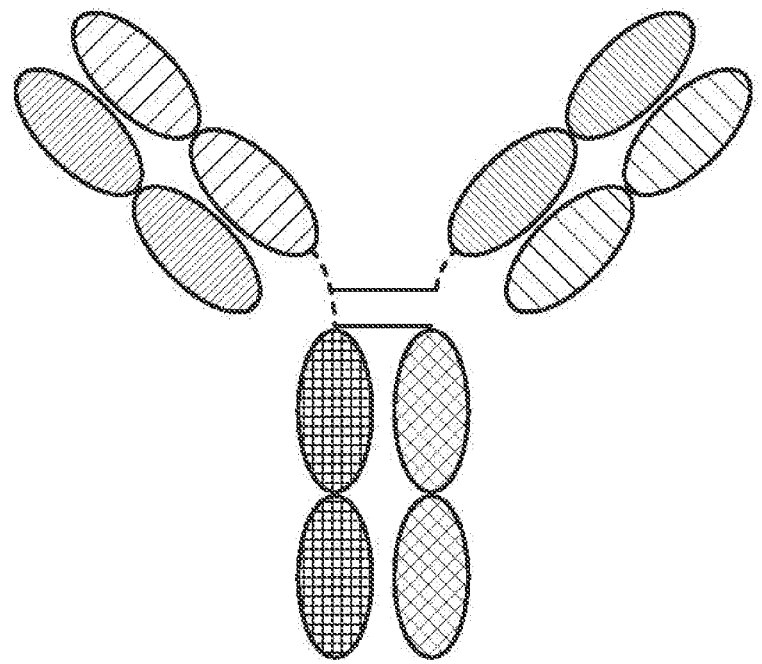
FIG. 20 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form may be a heterodimeric construct containing ½ of rat antibody and ½ of mouse antibody.
Figure 21:
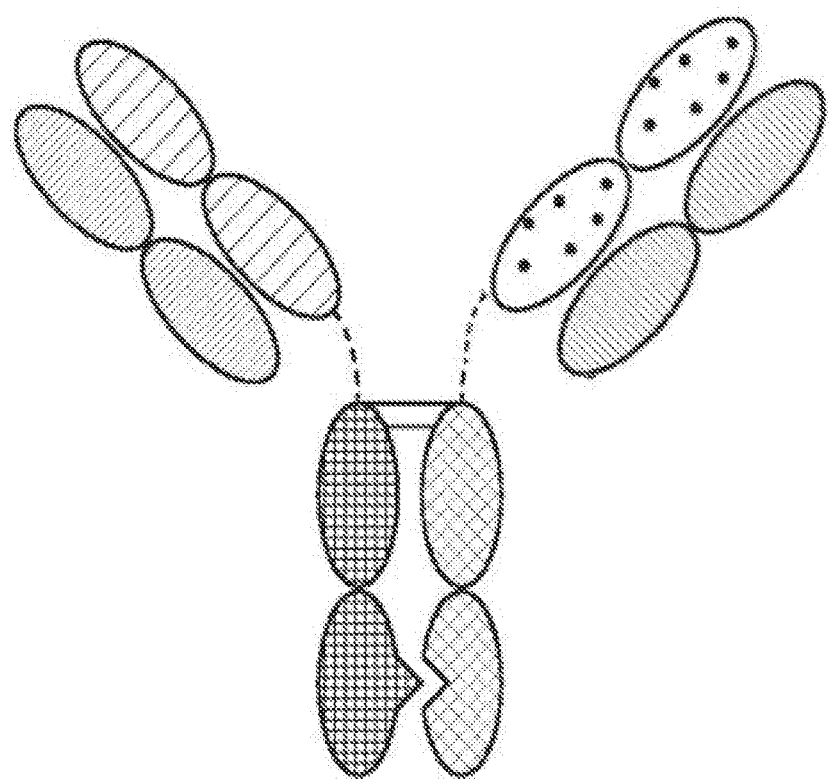
FIG. 21 is a representation of a TriNKET in the KiH Common Light Chain form, which involves the knobs-into-holes (KIHs) technology. KiH is a heterodimer containing 2 Fab fragments binding to target 1 and 2, and an Fc stabilized by heterodimerization mutations. TriNKET in the KiH format may be a heterodimeric construct with 2 Fab fragments binding to target 1 and target 2, containing two different heavy chains and a common light chain that pairs with both heavy chains.
Figure 22:
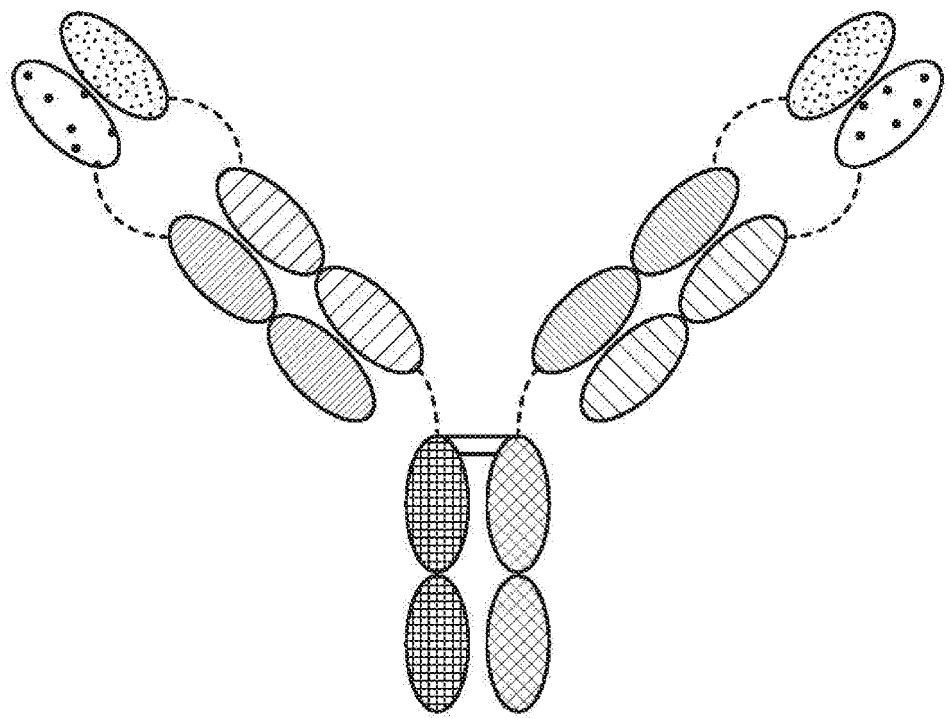
FIG. 22 is a representation of a TriNKET in the dual-variable domain immunoglobulin (DVD-Ig™) form, which combines the target-binding domains of two monoclonal antibodies via flexible naturally occurring linkers, and yields a tetravalent IgG-like molecule. DVD-Ig™ is a homodimeric construct where variable domain targeting antigen 2 is fused to the N-terminus of a variable domain of Fab fragment targeting antigen 1. DVD-Ig™ form contains normal Fc.
Figure 23:
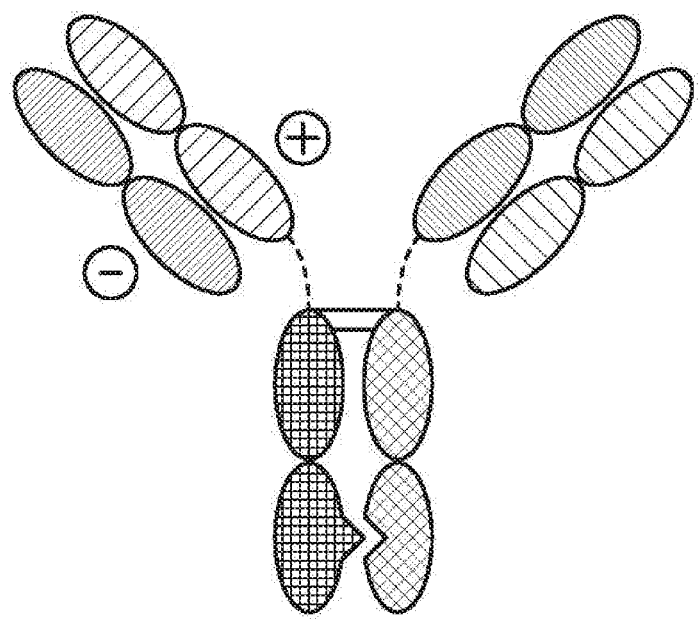
FIG. 23 is a representation of a TriNKET in the Orthogonal Fab fragment interface (Ortho-Fab) form, which is a heterodimeric construct that contains 2 Fab fragments binding to target 1 and target 2 fused to Fc. Light chain (LC)-heavy chain (HC) pairing is ensured by orthogonal interface. Heterodimerization is ensured by mutations in the Fc.
Figure 24:
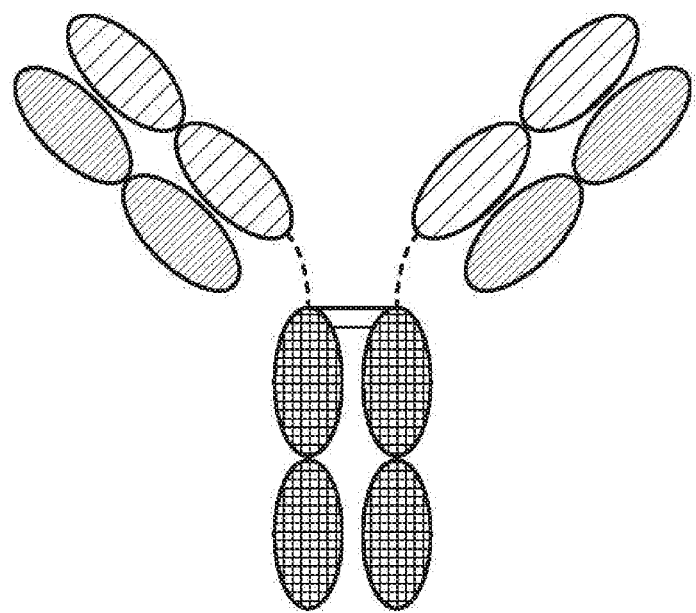
FIG. 24 is a representation of a TriNKET in the 2-in-1 Ig format.
Figure 25:
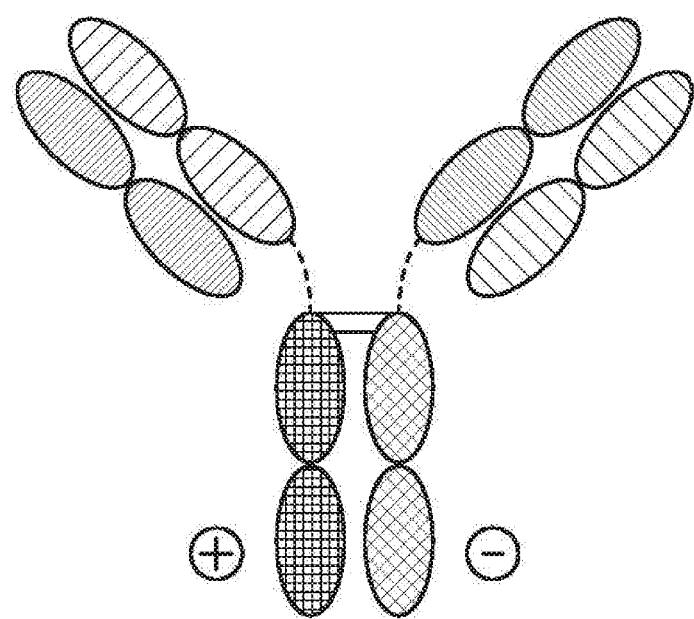
FIG. 25 is a representation of a TriNKET in the ES form, which is a heterodimeric construct containing two different Fab fragments binding to target 1 and target 2 fused to the Fc. Heterodimerization is ensured by electrostatic steering mutations in the Fc.
Figure 26:
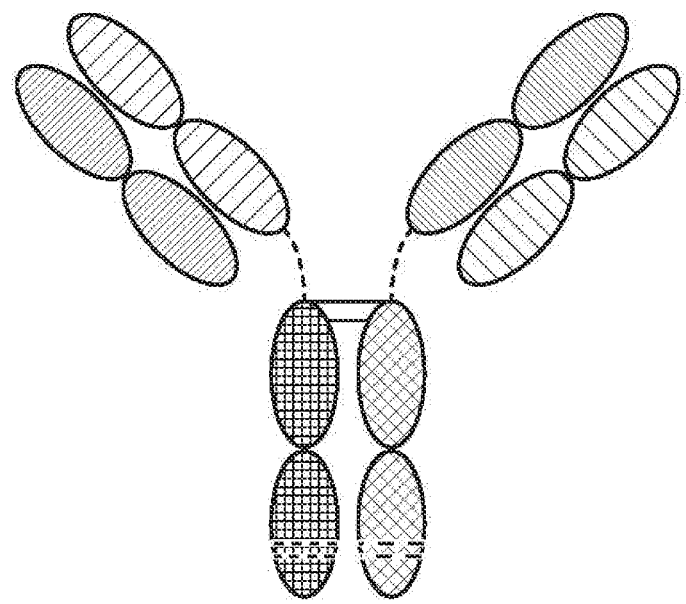
FIG. 26 is a representation of a TriNKET in the Fab Arm Exchange form.

To investigate the relative potency of receptor combination, crosslinking of NKG2D or CD16, and co-crosslinking of both receptors by plate-bound stimulation was performed. As shown in FIG. 19 (FIGS. 19A-19C), combined stimulation of CD16 and NKG2D resulted in highly elevated levels of CD107a (degranulation) (FIG. 19A) and/or IFN-γ production (FIG. 19B). Dotted lines represent an additive effect of individual stimulations of each receptor.

CD107a levels and intracellular IFN-γ production of IL-2-activated NK cells were analyzed after 4 hours of plate-bound stimulation with anti-CD16, anti-NKG2D or a combination of both monoclonal antibodies. Graphs indicate the mean (n=2)±SD. FIG. 19A demonstrates levels of CD107a; FIG. 19B demonstrates levels of IFN-γ; FIG. 19C demonstrates levels of CD107a and IFN-γ. Data shown in FIGS. 19A-19C are representative of five independent experiments using five different healthy donors.

Example 8—c-MET TriNKETs Bind to c-MET on Tumor Cells

HT29 and HCT-116 human colon cancer cell lines were used to assess TriNKET binding to cell surface c-MET. A49MI-Duobody-TriNKETs were diluted and incubated with either HT29 and HCT-116 cells. Binding patterns of TriNKETs and parental monoclonal antibodies were detected using a fluorophore conjugated anti-human IgG secondary antibody. Cells were analyzed by flow cytometry and fold MFI over secondary-antibody only controls was reported. FIG. 35 and FIG. 36 show dose-dependent binding of anti-c-MET monoclonal antibodies and corresponding TriNKETs incorporating the same anti-c-MET binding Fabs to colon cancer cell lines HT29 and HCT-116, respectively. The TriNKETs bound to each cell line with a higher maximum level of binding but a slightly increased half-maximal binding concentration (i.e., slightly reduced affinity) compared to the corresponding monoclonal antibodies, though these differences were more pronounced with HT29.

Example 9—Short-Term NK Cytotoxicity Mediated by TriNKET

The ability of c-MET-targeting TriNKETs to elicit cytotoxicity of primary NK cells against c-MET positive cancer cells was assessed using the DELFIA cytotoxicity assay. Briefly, PBMCs were isolated from human peripheral blood buffy coats using density gradient centrifugation. The isolated PBMCs were washed, and NK cells were isolated using a negative selection technique with magnetic beads. The purity of the isolated NK cells was typically >90% $CD3^-CD56^+$. The isolated NK cells were rested without cytokine overnight.

On the following day, c-MET positive human cancer cell lines HT29 and HCT-116 were harvested from culture. The cancer cells were washed with HBS, and were resuspended in growth media at $10^6$ cells/mL for labeling with BATDA reagent (Perkin Elmer AD0116) following the manufacturer instructions. After labeling, the cancer cells were washed three times with HBS, and were resuspended at $0.5-1.0 \times 10^5$ cells/mL in culture media. 100 µl of BATDA labeled cells were added to each well of a 96-well plate.

The tested TriNKET or mAb was diluted in culture media, and 50 µl of diluted TriNKET or mAb were added to each well. Rested NK cells were harvested from culture, washed, and resuspended at $10^5-2.0 \times 10^6$ cells/mL in culture media to attain a desired E:T ratio of 5:1. 50 µl of NK cells were added to each well of the plate to make a total of 200 µl culture volume in each well. The plate was incubated at 37 C with 5% $CO_2$ for 2-3 hours.

After the culturing, the plate was removed from the incubator, and the cells were pelleted by centrifugation at 200×g for 5 minutes. 20 µl of culture supernatant were transferred to a clean microplate provided from the manufacturer. Supernatant from the labeled cells incubated alone was used to measure spontaneous release of TDA. Supernatant from labeled cells incubated with 1% Triton-X was used to measure maximum lysis of the target cells. Supernatant from the labeled cells prior to the 2-3 hours of incubation was used to measure the background and for quality control purposes.

200 µl of room temperature europium solution were added to each well containing culture supernatant. The plate was protected from light and incubated on a plate shaker at 250 rpm for 15 minutes. Fluorescence was measured using a Victor 3 or SpectraMax i3X instrument.

The fluorescent levels represented lysis of the target cells. The values of % specific lysis were calculated as: % specific lysis=((Experimental release−Spontaneous release)/(Maximum release−Spontaneous release))×100%.

FIGS. 37A to 37C and 38 show human NK cell lysis of c-MET positive target cell lines in the presence of anti-c-MET TriNKETs or monoclonal antibodies within 2 hours. In FIGS. 37A to 37C (FIG. 37A are line graphs showing lysis of c-MET expressing HT29 colon cancer cells by NK cells derived from donor 1; FIG. 37B are line graphs showing lysis of c-MET expressing HT29 colon cancer cells by NK cells derived from donor 2; and FIG. 37C are line graphs showing lysis of c-MET expressing HT29 colon cancer cells by NK cells derived from donor 3), HT29 cells were used as target cells with NK effector cells derived from three different healthy human donors. FIG. 38 shows lysis of HCT-116 target cells mediated by NK cells from a single donor.

Against both cell lines and across multiple donors, the c-MET-TriNKETs had subnanomolar $EC_{50}$ values. Compared to the low to absent activity of the corresponding monoclonal antibodies, the TriNKETs provided greater maximum specific lysis and potency.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A trispecific binding protein comprising an Fc region that binds CD16 and two antigen binding sites, wherein the two antigen binding sites consist of a first antigen binding site that binds NKG2D and a second antigen binding site that binds cMET, wherein the protein comprises three polypeptides, and wherein
 a) the first polypeptide comprises, from N-terminus to C-terminus,
  i) a heavy chain variable domain of a Fab fragment that binds NKG2D,
  ii) a CH1 domain,
  iii) a first CH2 domain and
  iv) a first CH3 domain;
 b) the second polypeptide comprises, from N-terminus to C-terminus,
  i) a light chain variable domain of the Fab fragment that binds NKG2D and
  ii) a CL domain;
 c) the third polypeptide comprises, from N-terminus to C-terminus,
  i) an scFv that binds cMET,
  ii) a second CH2 domain and
  iii) a second CH3 domain,
   (1) wherein the heavy chain variable domain of the Fab fragment that binds NKG2D comprises CDR1, CDR2, and CDR3 of amino acid sequence SEQ ID NO: 387, SEQ ID NO: 88, and SEQ ID NO: 390, respectively; and the light chain variable domain of the Fab fragment that binds NKG2D comprises CDR1, CDR2, and CDR3 of amino acid sequence SEQ ID NO: 90, SEQ ID NO: 91, and SEQ ID NO: 92, respectively; and (2) wherein a heavy chain variable domain of the scFv that binds cMET comprises CDR1, CDR2, and CDR3 of amino acid sequence SEQ ID NO: 414, SEQ ID NO: 415, and SEQ ID NO: 416, respectively; and a light chain variable domain of the scFv that binds cMET comprises CDR1, CDR2, and CDR3 of amino acid sequence SEQ ID NO: 418, SEQ ID NO: 419, and SEQ ID NO: 420, respectively; and (3) wherein the Fc region comprises the first CH2 domain, first CH3 domain, second CH2 domain and second CH3 domain.

2. The protein according to claim 1, wherein the first antigen-binding site that binds NKG2D comprises a heavy chain variable domain comprising the amino acid sequence of SEQ ID NO: 388 and a light chain variable domain comprising the amino acid sequence of SEQ ID NO: 86.

3. The protein according to claim 2, wherein the second antigen-binding site that binds cMET comprises an scFv heavy chain variable domain comprising the amino acid sequence of SEQ ID NO: 413 and an scFv light chain variable domain comprising the amino acid sequence of SEQ ID NO: 417.

4. The protein according to claim 3, wherein the scFv heavy chain variable domain forms a disulfide bridge with the scFv light chain variable domain.

5. The protein according to claim 2, wherein the second antigen-binding site that binds cMET comprises an scFv heavy chain variable domain comprising the amino acid sequence SEQ ID NO: 413 with a G44C mutation using the Kabat numbering system and an scFv light chain variable domain comprising the amino acid sequence of SEQ ID NO: 417 with a G100C mutation using the Kabat numbering system, wherein the scFv heavy chain variable domain forms a disulfide bridge with the scFv light chain variable domain between the cysteine at position 44 from the scFv heavy chain variable domain and the cysteine at position 100 from the scFv light chain variable domain.

6. The protein according to claim 5, wherein the scFv heavy chain variable domain is linked to the scFv light chain variable domain via a flexible linker.

7. The protein according to claim 6, wherein the flexible linker comprises (G4S)4.

8. The protein according to claim 7, wherein the scFv heavy chain variable domain is positioned at the C-terminus of the scFv light chain variable domain within the scFv.

9. The protein according to claim 3, wherein the Fc region comprises an amino acid sequence of the Fc region of human IgG1, wherein one chain of the Fc region comprises S354C, Q347R, D399V, and F405T mutations, and the other chain of the Fc region comprises Y349C, K360E, and K409W mutations, according to the EU index as in Kabat.

10. The protein according to claim 8, wherein the Fc region comprises an amino acid sequence of the Fc region of human IgG1, wherein one chain of the Fc region comprises S354C, Q347R, D399V, and F405T mutations, and the other chain of the Fc region comprises Y349C, K360E, and K409W mutations, according to the EU index as in Kabat.

11. A trispecific binding protein comprising an Fc region that binds CD16 and two antigen binding sites, wherein the two antigen binding sites consist of a first antigen binding site that binds NKG2D and a second antigen binding site that binds cMET, wherein the protein comprises three polypeptides, and wherein a) the first polypeptide comprises, from N-terminus to C-terminus,
  i) a heavy chain variable domain of a Fab fragment that binds NKG2D,
  ii) an IgG1 CH1 domain,
  iii) a first IgG1 CH2 domain and
  iv) a first IgG1 CH3 domain;

b) the second polypeptide comprises, from N-terminus to C-terminus,
  i) a light chain variable domain of the Fab fragment that binds NKG2D and
  ii) a CL domain;

c) the third polypeptide comprises, from N-terminus to C-terminus,
  i) an scFv that binds cMET,
  ii) a second IgG1 CH2 domain and
  iii) a second IgG1 CH3 domain,
    (1) wherein the heavy chain variable domain of the Fab fragment that binds NKG2D comprises amino acid sequence SEQ ID NO: 388 and the light chain variable domain of the Fab fragment that binds NKG2D comprises the amino acid sequence SEQ ID NO: 86;
    (2) wherein a heavy chain variable domain of the scFv that binds cMET comprises the amino acid sequence of SEQ ID NO: 413 with a G44C mutation using the Kabat numbering system; and a light chain variable domain of the scFv that binds cMET comprises the amino acid sequence SEQ ID NO: 417 with a G100C mutation using the Kabat numbering system, wherein the heavy chain variable domain of the scFv that binds cMET is linked to the light chain variable domain of the scFv that binds cMET via a (G4S) 4 linker, wherein the scFv heavy chain variable domain is positioned at the C-terminus of the scFv light chain variable domain within the scFv, and wherein the scFv heavy chain variable domain forms a disulfide bridge with the scFv light chain variable domain between the cysteine at position 44 from the scFv heavy chain variable domain and the cysteine at position 100 from the scFv light chain variable domain; and
    (3) wherein the Fc region comprises two amino acid chains, wherein the first amino acid chain comprises the first IgG1 CH2 domain and the first IgG1 CH3 domain, and the second amino acid chain comprises the second IgG1 CH2 domain and the second IgG1 CH3 domain, wherein one chain of the Fc region comprises S354C, Q347R, D399V, and F405T mutations, and the other chain of the Fc region comprises Y349C, K360E, and K409W mutations, according to the EU index as in Kabat.

* * * * *

SEQUENCE LISTING

```
<160> NUMBER OF SEQ ID NOS: 437

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
```

```
                        85                  90                  95
Thr Phe Gly Gly Gly Thr Lys Val Glu Ile Lys
            100                 105

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
```

-continued

```
        polypeptide

<400> SEQUENCE: 5

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Tyr Thr
                85                  90                  95

Phe Gly Gly Gly Thr Lys Val Glu Ile Lys
            100                 105

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45
```

```
Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110
```

```
<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

```
Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gly Ser Phe Pro Ile
                 85                  90                  95

Thr Phe Gly Gly Gly Thr Lys Val Glu Ile Lys
                100                 105
```

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asp His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
                100                 105                 110

Val Thr Val Ser Ser
        115
```

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Ser Lys Glu Val Pro Trp
                 85                  90                  95

Thr Phe Gly Gln Gly Thr Lys Val Glu Ile Lys
                100                 105
```

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 17

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 19

Gln Val Gln Leu Gln Gln Trp Gly Ala Gly Leu Leu Lys Pro Ser Glu

```
                1               5                  10                 15
            Thr Leu Ser Leu Thr Cys Ala Val Tyr Gly Gly Ser Phe Ser Gly Tyr
                        20                  25                 30

Tyr Trp Ser Trp Ile Arg Gln Pro Pro Gly Lys Gly Leu Glu Trp Ile
                        35                  40                 45

Gly Glu Ile Asp His Ser Gly Ser Thr Asn Tyr Asn Pro Ser Leu Lys
                        50                  55                 60

Ser Arg Val Thr Ile Ser Val Asp Thr Ser Lys Asn Gln Phe Ser Leu
            65                  70                  75                 80

Lys Leu Ser Ser Val Thr Ala Ala Asp Thr Ala Val Tyr Tyr Cys Ala
                        85                  90                 95

Arg Ala Arg Gly Pro Trp Ser Phe Asp Pro Trp Gly Gln Gly Thr Leu
                        100                 105                110

Val Thr Val Ser Ser
                        115
```

<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Asp Ile Gln Met Thr Gln Ser Pro Ser Thr Leu Ser Ala Ser Val Gly
1               5                  10                 15

Asp Arg Val Thr Ile Thr Cys Arg Ala Ser Gln Ser Ile Gly Ser Trp
            20                  25                 30

Leu Ala Trp Tyr Gln Gln Lys Pro Gly Lys Ala Pro Lys Leu Leu Ile
            35                  40                 45

Tyr Lys Ala Ser Ser Leu Glu Ser Gly Val Pro Ser Arg Phe Ser Gly
            50                  55                 60

Ser Gly Ser Gly Thr Glu Phe Thr Leu Thr Ile Ser Ser Leu Gln Pro
65                  70                  75                 80

Asp Asp Phe Ala Thr Tyr Tyr Cys Gln Gln Tyr Asp Ile Tyr Pro Thr
            85                  90                 95

Phe Gly Gly Gly Thr Lys Val Glu Ile Lys
            100                 105
```

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Val Gln Leu Gln Gln Trp Gly Ala Gly Leu Leu Lys Pro Ser Glu
1               5                  10                 15

Thr Leu Ser Leu Thr Cys Ala Val Tyr Gly Gly Ser Phe Ser Gly Tyr
            20                  25                 30

Tyr Trp Ser Trp Ile Arg Gln Pro Pro Gly Lys Gly Leu Glu Trp Ile
            35                  40                 45

Gly Glu Ile Asp His Ser Gly Ser Thr Asn Tyr Asn Pro Ser Leu Lys
            50                  55                 60

Ser Arg Val Thr Ile Ser Val Asp Thr Ser Lys Asn Gln Phe Ser Leu
```

```
                65                  70                  75                  80
Lys Leu Ser Ser Val Thr Ala Ala Asp Thr Ala Val Tyr Tyr Cys Ala
                    85                  90                  95

Arg Ala Arg Gly Pro Trp Ser Phe Asp Pro Trp Gly Gln Gly Thr Leu
                100                 105                 110

Val Thr Val Ser Ser
            115

<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser
            115
```

```
<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Thr Leu Ser Ala Ser Val Gly
1               5                   10                  15
```

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95

Phe Gly Gly Gly Thr Lys Val Glu Ile Lys
            100                 105

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

```
Asp Asp Phe Ala Thr Tyr Tyr Cys Gln Gln Tyr Ser Ser Phe Ser Thr
                85                  90                  95

Phe Gly Gly Gly Thr Lys Val Glu Ile Lys
            100                 105

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105

<210> SEQ ID NO 31
<211> LENGTH: 117
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                85                  90                  95

Phe Gly Gly Gly Thr Lys Val Glu Ile Lys
            100                 105

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30
```

```
Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                   70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser
            115

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                   70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
                100                 105

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                   70                  75                  80

Lys Leu Ser Ser Val Thr Ala Ala Asp Thr Ala Val Tyr Tyr Cys Ala
                85                  90                  95
```

Arg Ala Arg Gly Pro Trp Ser Phe Asp Pro Trp Gly Gln Gly Thr Leu
            100                 105                 110

Val Thr Val Ser Ser
        115

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
            100                 105

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 38
<211> LENGTH: 107
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
```

```
                 35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Phe Ile Thr
                 85                  90                  95

Phe Gly Gly Gly Thr Lys Val Glu Ile Lys
                100                 105

<210> SEQ ID NO 41
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
                 35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Ser Ser Ile Arg His Ala Tyr Tyr Tyr Gly Met
                100                 105                 110

Asp Val Trp Gly Gln Gly Thr Thr Val Thr Val Ser Ser
            115                 120                 125

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Ile Thr Phe Gly Gly Gly Thr Lys Val Glu Ile
```

Lys

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Thr Phe Ser Ser Tyr Ala Ile Ser
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ile Ile Pro Ile Phe Gly Thr Ala Asn Tyr Ala Gln Lys Phe Gln
1               5                   10                  15

Gly

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Arg Gly Asp Ser Ser Ile Arg His Ala Tyr Tyr Tyr Tyr Gly Met
1               5                   10                  15

Asp Val

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Ser Ser Gln Ser Val Leu Tyr Ser Ser Asn Asn Lys Asn Tyr Leu
1               5                   10                  15

Ala

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Ala Ser Thr Arg Glu Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Tyr Tyr Ser Thr Pro Ile Thr
1               5

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ser Ile Ser Ser Ser Ser Tyr Tyr Trp Gly
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Ile Tyr Tyr Ser Gly Ser Thr Tyr Tyr Asn Pro Ser Leu Lys Ser
1               5                   10                  15

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Gly Ser Asp Arg Phe His Pro Tyr Phe Asp Tyr
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Ser Val Ser Arg Tyr Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ala Ser Asn Arg Ala Thr
1               5

<210> SEQ ID NO 56
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 56

Gln Gln Phe Asp Thr Trp Pro Pro Thr
1               5

<210> SEQ ID NO 57
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Glu Gln Tyr Asp Ser Tyr Pro Thr
                85                  90                  95

Phe Gly Gly Gly Thr Lys Val Glu Ile Lys
            100                 105

<210> SEQ ID NO 59
<211> LENGTH: 126
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Phe Tyr Tyr Tyr Tyr Gly
            100                 105                 110

Met Asp Val Trp Gly Gln Gly Thr Thr Val Thr Val Ser Ser
        115                 120                 125

<210> SEQ ID NO 60
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 61
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
            100                 105                 110

Met Asp Val Trp Gly Lys Gly Thr Thr Val Thr Val Ser Ser
        115                 120                 125

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Thr Phe Thr Ser Tyr Tyr Met His
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Ile Asn Pro Ser Gly Gly Ser Thr Ser Tyr Ala Gln Lys Phe Gln
```

-continued

```
                1               5                  10                  15

Gly

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Arg Gly Ala Pro Asn Tyr Gly Asp Thr Thr His Asp Tyr Tyr Tyr
1               5                  10                  15

Met Asp Val

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ala Ser Gln Ser Val Ser Ser Asn Leu Ala
1               5                  10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ala Ser Thr Arg Ala Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Tyr Asp Asp Trp Pro Phe Thr
1               5

<210> SEQ ID NO 69
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Tyr
                20                  25                  30
```

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Thr Gly Glu Tyr Tyr Asp Thr Asp Asp His Gly Met Asp
                100                 105                 110

Val Trp Gly Gln Gly Thr Thr Val Thr Val Ser Ser
            115                 120

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
                100                 105

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Thr Phe Thr Gly Tyr Tyr Met His
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Ile Asn Pro Asn Ser Gly Gly Thr Asn Tyr Ala Gln Lys Phe Gln
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Asp Thr Gly Glu Tyr Tyr Asp Thr Asp Asp His Gly Met Asp
1               5                   10                  15

Val

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ala Ser Gln Ser Val Ser Ser Asn Leu Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ala Ser Thr Arg Ala Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Asp Asp Tyr Trp Pro Pro Thr
1               5

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser
            115                 120

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Val Ser Tyr Pro Arg
                 85                  90                  95

Thr Phe Gly Gly Gly Thr Lys Val Glu Ile Lys
            100                 105

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Thr Phe Ser Ser Tyr Ala Met Ser
 1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ile Ser Gly Ser Gly Gly Ser Thr Tyr Tyr Ala Asp Ser Val Lys
 1               5                  10                  15

Gly

<210> SEQ ID NO 81
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Lys Asp Gly Gly Tyr Tyr Asp Ser Gly Ala Gly Asp Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ala Ser Gln Gly Ile Asp Ser Trp Leu Ala
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ala Ser Ser Leu Gln Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gln Gly Val Ser Tyr Pro Arg Thr
1               5

<210> SEQ ID NO 85
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser
        115                 120

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Phe Thr Phe Ser Ser Tyr Ser Met Asn
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ile Ser Ser Ser Ser Ser Tyr Ile Tyr Tyr Ala Asp Ser Val Lys
1               5                   10                  15

Gly

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 89

Ala Arg Gly Ala Pro Met Gly Ala Ala Ala Gly Trp Phe Asp Pro
1               5                   10                  15

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Ala Ser Gln Gly Ile Ser Ser Trp Leu Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Ala Ser Ser Leu Gln Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Gly Val Ser Phe Pro Arg Thr
1               5

<210> SEQ ID NO 93
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Ala Tyr Gly Met Asp Tyr Tyr Tyr Met

```
            100                 105                 110
Asp Val Trp Gly Lys Gly Thr Thr Val Thr Val Ser Ser
        115                 120                 125

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Tyr Thr Phe Thr Ser Tyr Tyr Met His
1               5

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ile Ile Asn Pro Ser Gly Gly Ser Thr Ser Tyr Ala Gln Lys Phe Gln
1               5                   10                  15

Gly

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Glu Gly Ala Gly Phe Ala Tyr Gly Met Asp Tyr Tyr Tyr Met
```

-continued

```
1               5                   10                  15

Asp Val

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Ser Gln Ser Val Ser Ser Tyr Leu Ala
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Ala Ser Asn Arg Ala Thr
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln Ser Asp Asn Trp Pro Phe Thr
1               5

<210> SEQ ID NO 101
<211> LENGTH: 121
<212> TYPE: PRT
<213> ORGANISM: Homo sapiens

<400> SEQUENCE: 101

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120
```

```
<210> SEQ ID NO 102
<211> LENGTH: 110
<212> TYPE: PRT
<213> ORGANISM: Homo sapiens

<400> SEQUENCE: 102

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 103
<211> LENGTH: 115
<212> TYPE: PRT
<213> ORGANISM: Homo sapiens

<400> SEQUENCE: 103

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115

<210> SEQ ID NO 104
<211> LENGTH: 108
<212> TYPE: PRT
<213> ORGANISM: Homo sapiens

<400> SEQUENCE: 104

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ser Phe Ser Gly Tyr Tyr Trp Ser
1               5

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Glu Ile Asp His Ser Gly Ser Thr Asn Tyr Asn Pro Ser Leu Lys Ser
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Arg Ala Arg Gly Pro Trp Ser Phe Asp Pro
1               5                   10

<210> SEQ ID NO 108
<211> LENGTH: 246
<212> TYPE: PRT
<213> ORGANISM: Homo sapiens

<400> SEQUENCE: 108

Met Ala Ala Ala Ala Ile Pro Ala Leu Leu Cys Leu Pro Leu Leu
1               5                   10                  15

Phe Leu Leu Phe Gly Trp Ser Arg Ala Arg Arg Asp Asp Pro His Ser
                20                  25                  30

Leu Cys Tyr Asp Ile Thr Val Ile Pro Lys Phe Arg Pro Gly Pro Arg
            35                  40                  45

Trp Cys Ala Val Gln Gly Gln Val Asp Glu Lys Thr Phe Leu His Tyr
        50                  55                  60

Asp Cys Gly Asn Lys Thr Val Thr Pro Val Ser Pro Leu Gly Lys Lys
65                  70                  75                  80

Leu Asn Val Thr Met Ala Trp Lys Ala Gln Asn Pro Val Leu Arg Glu
                85                  90                  95

Val Val Asp Ile Leu Thr Glu Gln Leu Leu Asp Ile Gln Leu Glu Asn

```
                100             105             110
Tyr Thr Pro Lys Glu Pro Leu Thr Leu Gln Ala Arg Met Ser Cys Glu
            115             120             125

Gln Lys Ala Glu Gly His Ser Ser Gly Ser Trp Gln Phe Ser Ile Asp
            130             135             140

Gly Gln Thr Phe Leu Leu Phe Asp Ser Glu Lys Arg Met Trp Thr Thr
145             150             155             160

Val His Pro Gly Ala Arg Lys Met Lys Glu Lys Trp Glu Asn Asp Lys
                165             170             175

Asp Val Ala Met Ser Phe His Tyr Ile Ser Met Gly Asp Cys Ile Gly
                180             185             190

Trp Leu Glu Asp Phe Leu Met Gly Met Asp Ser Thr Leu Glu Pro Ser
            195             200             205

Ala Gly Ala Pro Leu Ala Met Ser Ser Gly Thr Thr Gln Leu Arg Ala
            210             215             220

Thr Ala Thr Thr Leu Ile Leu Cys Cys Leu Leu Ile Ile Leu Pro Cys
225             230             235             240

Phe Ile Leu Pro Gly Ile
                245

<210> SEQ ID NO 109
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
            35                  40                  45

Gly Val Ile Tyr Ser Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Ile Asn Ser Leu Thr Ser Glu Asp Ser Ala Val Tyr Tyr Cys
                85                  90                  95

Ala Arg Glu Arg Asp Thr Arg Phe Gly Asn Trp Gly Gln Gly Thr Leu
            100                 105                 110

Val Thr Val Ser Ala
        115

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Tyr Asn Met His
1               5
```

```
<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Val Ile Tyr Ser Gly Asn Gly Asp Thr Ser Tyr Asn Gln Lys Phe Lys
1               5                   10                  15

Gly

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Asp Thr Arg Phe Gly Asn
1               5

<210> SEQ ID NO 113
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asn Ile Val Leu Thr Gln Ser Pro Ala Ser Leu Ala Val Ser Leu Gly
1               5                   10                  15

Leu Arg Ala Thr Ile Ser Cys Arg Ala Ser Glu Ser Val Asp Ile Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Glu Ser Val Asp Ile Tyr Gly Asn Ser Phe Met His
1               5                   10                  15

<210> SEQ ID NO 115
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 115

Leu Ala Ser Asn Leu Glu Ser
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Asn Asn Glu Asp Pro Tyr Thr
1               5

<210> SEQ ID NO 117
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Tyr Tyr Phe Asp Tyr Trp Gly Gln Gly Thr Thr Leu
            100                 105                 110

Thr Val Ser Ser
        115

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Tyr Tyr Ile Asn
1               5

<210> SEQ ID NO 119
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 119

Arg Ile Tyr Pro Gly Ser Gly Asn Thr Tyr Tyr Asn Glu Lys Phe Lys
1               5                   10                  15

Gly

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Trp Tyr Tyr Phe Asp Tyr
1               5

<210> SEQ ID NO 121
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Arg Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Arg
                85                  90                  95

Thr Phe Gly Gly Gly Thr Lys Leu Glu Ile Lys Arg
            100                 105

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Lys Ala Ser Gln Asn Val Arg Thr Asn Val Ala
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 123

Ser Ala Ser Tyr Arg Tyr Ser
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Gln Tyr Asn Ser Tyr Pro Arg Thr
1               5

<210> SEQ ID NO 125
<211> LENGTH: 976
<212> TYPE: PRT
<213> ORGANISM: Homo sapiens

<400> SEQUENCE: 125

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe 275                 280                 285
Met Cys Tyr Ala Asn Asn Thr Phe Gly Ser Ala Asn Val Thr Thr Thr
290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
                340                 345                 350
Arg Thr Phe Thr Asp Lys Trp Glu Asp Tyr Pro Lys Ser Glu Asn Glu
                355                 360                 365
Ser Asn Ile Arg Tyr Val Ser Glu Leu His Leu Thr Arg Leu Lys Gly
370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
                420                 425                 430
Phe Pro Glu Pro Thr Ile Asp Trp Tyr Phe Cys Pro Gly Thr Glu Gln
                435                 440                 445
Arg Cys Ser Ala Ser Val Leu Pro Val Asp Val Gln Thr Leu Asn Ser
450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
                500                 505                 510
Lys Glu Gln Ile His Pro His Thr Leu Phe Thr Pro Leu Leu Ile Gly
                515                 520                 525
Phe Val Ile Val Ala Gly Met Met Cys Ile Ile Val Met Ile Leu Thr
                530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
                580                 585                 590
Lys Thr Leu Gly Ala Gly Ala Phe Gly Lys Val Val Glu Ala Thr Ala
                595                 600                 605
Tyr Gly Leu Ile Lys Ser Asp Ala Ala Met Thr Val Ala Val Lys Met
                610                 615                 620
Leu Lys Pro Ser Ala His Leu Thr Glu Arg Glu Ala Leu Met Ser Glu
625                 630                 635                 640
Leu Lys Val Leu Ser Tyr Leu Gly Asn His Met Asn Ile Val Asn Leu
                645                 650                 655
Leu Gly Ala Cys Thr Ile Gly Gly Pro Thr Leu Val Ile Thr Glu Tyr
                660                 665                 670
Cys Cys Tyr Gly Asp Leu Leu Asn Phe Leu Arg Arg Lys Arg Asp Ser
                675                 680                 685
Phe Ile Cys Ser Lys Gln Glu Asp His Ala Glu Ala Leu Tyr Lys
                690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Pro Thr Lys Ala
            725                 730                 735

Asp Lys Arg Arg Ser Val Arg Ile Gly Ser Tyr Ile Glu Arg Asp Val
            740                 745                 750

Thr Pro Ala Ile Met Glu Asp Glu Leu Ala Leu Asp Leu Glu Asp
            755                 760                 765

Leu Leu Ser Phe Ser Tyr Gln Val Ala Lys Gly Met Ala Phe Leu Ala
            770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 126
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

-continued

```
                85                  90                  95

Ala Arg Ser Pro Trp Gly Tyr Tyr Leu Asp Ser Trp Gly Gln Gly Thr
            100                 105                 110

Leu Val Thr Val Ser Ser Ala
        115

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Phe Thr Phe Ser Asn Tyr
1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Gly Ser Gly Asp Tyr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Pro Trp Gly Tyr Tyr Leu Asp Ser
1               5

<210> SEQ ID NO 130
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Gln Met Thr Gln Ser Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95
```

```
Thr Phe Gly Gln Gly Thr Lys Leu Glu Ile Lys Arg
            100                 105
```

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Gln Gly Ile Ser Ser Arg Leu Ala
1               5
```

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Ala Ala Ser Ser Leu Gln Ser
1               5
```

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

```
Gln Gln Tyr Asn Ser Tyr Pro Tyr Thr
1               5
```

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Gly Thr Phe Ser Ser Tyr Ala Ile Ser
1               5
```

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

```
Gly Ile Ile Pro Ile Phe Gly Thr Ala Asn Tyr Ala Gln Lys Phe Gln
1               5                   10                  15

Gly
```

<210> SEQ ID NO 136
<211> LENGTH: 19
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 136

Ala Arg Arg Gly Arg Lys Ala Ser Gly Ser Phe Tyr Tyr Tyr Gly
1               5                   10                  15

Met Asp Val

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Ser Ser Gln Ser Leu Leu Asn Ser Gly Asn Gln Lys Asn Tyr Leu
1               5                   10                  15

Thr

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Trp Ala Ser Thr Arg Glu Ser
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Asn Asp Tyr Ser Tyr Pro Tyr Thr
1               5

<210> SEQ ID NO 140
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Ile Gln Leu Gln Gln Ser Gly Pro Glu Leu Val Lys Pro Gly Ala
1               5                   10                  15

Ser Val Gln Val Ser Cys Lys Thr Ser Gly Tyr Ser Phe Thr Asp Tyr
            20                  25                  30

Asn Val Tyr Trp Val Arg Gln Ser His Gly Lys Ser Leu Glu Trp Ile
        35                  40                  45

Gly Tyr Ile Asp Pro Tyr Asn Gly Ile Thr Ile Tyr Asp Gln Asn Phe
    50                  55                  60
```

```
Lys Gly Lys Ala Thr Leu Thr Val Asp Lys Ser Ser Thr Thr Ala Phe
 65                  70                  75                  80

Met His Leu Asn Ser Leu Thr Ser Asp Asp Ser Ala Val Tyr Phe Cys
                 85                  90                  95

Ala Arg Asp Val Thr Thr Ala Leu Asp Phe Trp Gly Gln Gly Thr Thr
            100                 105                 110

Leu Thr Val Ser Ser
        115

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Tyr Ser Phe Thr Asp Tyr
1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Pro Tyr Asn Gly Ile
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Val Thr Thr Ala Leu Asp Phe
1               5

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Asp Thr Trp
            20                  25                  30

Leu Ala Trp Tyr Gln Gln Lys Pro Gly Lys Ser Pro Gln Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80
```

Glu Asp Phe Val Asn Tyr Tyr Cys Gln Gln Val Tyr Ser Ser Pro Phe
                85                  90                  95

Thr Phe Gly Ala Gly Thr Lys Leu Glu Leu Lys
            100                 105

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Thr Ile Asp Thr Trp Leu Ala
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Ala Thr Asn Leu Ala Asp
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Gln Val Tyr Ser Ser Pro Phe Thr
1               5

<210> SEQ ID NO 148
<211> LENGTH: 295
<212> TYPE: PRT
<213> ORGANISM: Homo sapiens

<400> SEQUENCE: 148

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
        50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn

```
            115                 120                 125
Ser Pro Glu Phe Thr Pro Tyr Leu Glu Thr Asn Leu Gly Gln Pro Thr
130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
                195                 200                 205

Ile Asp Val Asp Lys Gly Glu Asn Tyr Cys Phe Ser Val Gln Ala Val
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
                275                 280                 285

Asn Ser Pro Leu Asn Val Ser
290                 295

<210> SEQ ID NO 149
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
            115                 120                 125

Ser Ser Ala
    130

<210> SEQ ID NO 150
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 150

Gly Gly Thr Phe Ser Ser Tyr
1               5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Pro Ile Phe Gly Thr
1               5

<210> SEQ ID NO 152
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Pro Leu Arg Phe Leu Glu Trp Ser Thr Gln Asp His Tyr Tyr Tyr
1               5                   10                  15

Tyr Tyr Met Asp Val
            20

<210> SEQ ID NO 153
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Thr Trp Tyr Gln Gln Lys Pro Gly Gln Ala Pro Ile Leu Val Ile Tyr
            35                  40                  45

Gly Glu Asn Lys Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly
            100                 105

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 154

Ser Leu Arg Ser Tyr Tyr Ala Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Glu Asn Lys Arg Pro Ser
1               5

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Lys Ser Arg Asp Gly Ser Gly Gln His Leu Val
1               5                   10

<210> SEQ ID NO 157
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Thr Gly Arg Thr Asp Ala Phe Asp Ile Trp Gly Gln Gly
            100                 105                 110

Thr Met Val Thr Val Ser Ser Ala
        115                 120

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

```
Gly Gly Ser Ile Ser Ser Ser Asn
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Tyr His Ser Gly Ser
1               5

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Thr Gly Arg Thr Asp Ala Phe Asp Ile
1               5                   10

<210> SEQ ID NO 161
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Ser Leu Leu His Ser Asn Gly Tyr Asn Tyr Leu Asp
1               5                   10
```

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Leu Gly Ser Asn Arg Ala Ser
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Met Gln Gly Thr His Trp Pro Leu Thr
1               5

<210> SEQ ID NO 165
<211> LENGTH: 1367
<212> TYPE: PRT
<213> ORGANISM: Homo sapiens

<400> SEQUENCE: 165

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

-continued

```
Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
        260                 265                 270

Gly Trp Arg Cys Val Asp Arg Asp Phe Cys Ala Asn Ile Leu Ser Ala
    275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
        420                 425                 430

Asp Trp Asp His Arg Asn Leu Thr Ile Lys Ala Gly Lys Met Tyr Phe
    435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
        500                 505                 510

Arg Pro Pro Asp Tyr Arg Asp Leu Ile Ser Phe Thr Val Tyr Tyr Lys
    515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
        580                 585                 590

His Ile Arg Gly Ala Lys Ser Glu Ile Leu Tyr Ile Arg Thr Asn Ala
    595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
```

-continued

```
                645                 650                 655
Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
                755                 760                 765

Glu Glu Leu Glu Thr Glu Tyr Pro Phe Phe Glu Ser Arg Val Asp Asn
                770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                    805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
        930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
            995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065
```

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 166
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Glu Lys Arg Leu Glu Trp Val

```
                35                  40                  45
Ala Tyr Ile Ser Asn Gly Gly Ser His Tyr Val Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Leu Tyr His Cys
                85                  90                  95

Ala Arg Gly Met Asp Tyr Gly Ala Trp Phe Ala Tyr Trp Gly Gln Gly
            100                 105                 110

Thr Leu Val Thr Val Ser Ser
            115

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Phe Thr Phe Ser Asp Tyr
1               5

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Asn Gly Gly Gly Ser
1               5

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Met Asp Tyr Gly Ala Trp Phe Ala Tyr
1               5                   10

<210> SEQ ID NO 170
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45
```

```
Pro Gln Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110
```

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

```
Gln Ser Ile Val His Ser Asn Gly Asn Thr Tyr Leu Glu
1               5                   10
```

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

```
Lys Val Ser Asn Arg Phe Ser
1               5
```

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Phe Gln Gly Ser His Val Pro Phe Thr
1               5
```

<210> SEQ ID NO 174
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

```
Glu Val Gln Leu Val Glu Ser Gly Gly Gly Val Val Gln Pro Gly Arg
1               5                   10                  15

Ser Leu Arg Leu Ser Cys Ser Ser Gly Phe Thr Phe Ser Asp Tyr
                20                  25                  30

Tyr Met Tyr Trp Val Arg Gln Ala Pro Gly Lys Gly Leu Glu Trp Val
            35                  40                  45

Ala Tyr Met Ser Asn Val Gly Ala Ile Thr Asp Tyr Pro Asp Thr Val
        50                  55                  60

Lys Gly Arg Phe Thr Ile Ser Arg Asp Asn Ser Lys Asn Thr Leu Phe
65                  70                  75                  80
```

Leu Gln Met Asp Ser Leu Arg Pro Glu Asp Thr Gly Val Tyr Phe Cys
                85                  90                  95

Ala Arg Gly Thr Arg Asp Gly Ser Trp Phe Ala Tyr Trp Gly Gln Gly
            100                 105                 110

Thr Pro Val Thr Val Ser Ser
        115

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Tyr Tyr Met Tyr
1               5

<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Tyr Met Ser Asn Val Gly Ala Ile Thr Asp Tyr Pro Asp Thr Val Lys
1               5                   10                  15

Gly

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Thr Arg Asp Gly Ser Trp Phe Ala Tyr
1               5                   10

<210> SEQ ID NO 178
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Val His Ser
            20                  25                  30

Asn Gly Asn Thr Tyr Leu Glu Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Tyr Thr Phe Thr Ile
65                  70                  75                  80

```
Ser Ser Leu Gln Pro Glu Asp Ile Ala Thr Tyr Tyr Cys Phe Gln Gly
            85                  90                  95

Ser His Val Pro Phe Thr Phe Gly Gln Gly Thr Lys Leu Gln Ile Thr
            100                 105                 110
```

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Arg Ser Ser Gln Arg Ile Val His Ser Asn Gly Asn Thr Tyr Leu Glu
1               5                   10                  15
```

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Lys Val Ser Asn Arg Phe Ser
1               5
```

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Phe Gln Gly Ser His Val Pro Phe Thr
1               5
```

<210> SEQ ID NO 182
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Thr Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Tyr Tyr Asn Gly Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Val Phe Trp Asp Gly Tyr Trp Gly Gln Gly Thr Thr Leu Thr Val
```

100                 105                 110
Ser Ser

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Thr Tyr Trp Met Asn
1               5

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Ile Tyr Pro Gly Asp Gly Asp Thr Tyr Tyr Asn Gly Asn Phe Lys
1               5                   10                  15

Gly

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Phe Trp Asp Gly Tyr
1               5

<210> SEQ ID NO 186
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Ile Val Leu Thr Gln Ser Pro Thr Ile Met Ser Ala Ser Pro Gly
1               5                   10                  15

Glu Lys Val Thr Met Thr Cys Ser Ala Ser Ser Val Thr Tyr Ile
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Gly Gly Ser
    50                  55                  60

Gly Ser Gly Thr Ser Tyr Ser Leu Thr Ile Asn Ser Met Glu Thr Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys Arg Ala Asp
                100                 105

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Ser Ala Ser Ser Ser Val Thr Tyr Ile His
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Asp Thr Ser Lys Leu Ala Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Gln Gln Trp Ser Ser Asn Pro Phe Thr
1               5

<210> SEQ ID NO 190
<211> LENGTH: 512
<212> TYPE: PRT
<213> ORGANISM: Homo sapiens

<400> SEQUENCE: 190

Met Lys Ala Ile Ile His Leu Thr Leu Leu Ala Leu Leu Ser Val Asn
1               5                   10                  15

Thr Ala Thr Asn Gln Gly Asn Ser Ala Asp Ala Val Thr Thr Thr Glu
                20                  25                  30

Thr Ala Thr Ser Gly Pro Thr Val Ala Ala Ala Asp Thr Thr Glu Thr
            35                  40                  45

Asn Phe Pro Glu Thr Ala Ser Thr Thr Ala Asn Thr Pro Ser Phe Pro
        50                  55                  60

Thr Ala Thr Ser Pro Ala Pro Pro Ile Ile Ser Thr His Ser Ser Ser
65                  70                  75                  80

Thr Ile Pro Thr Pro Ala Pro Pro Ile Ile Ser Thr His Ser Ser Ser
                85                  90                  95

Thr Ile Pro Ile Pro Thr Ala Ala Asp Ser Glu Ser Thr Thr Asn Val
                100                 105                 110

Asn Ser Leu Ala Thr Ser Asp Ile Ile Thr Ala Ser Pro Asn Asp
            115                 120                 125

Gly Leu Ile Thr Met Val Pro Ser Glu Thr Gln Ser Asn Asn Glu Met
        130                 135                 140

Ser Pro Thr Thr Glu Asp Asn Gln Ser Ser Gly Pro Pro Thr Gly Thr

```
                145                 150                 155                 160
Ala Leu Leu Glu Thr Ser Thr Leu Asn Ser Thr Gly Pro Ser Asn Pro
            165                 170                 175

Cys Gln Asp Asp Pro Cys Ala Asp Asn Ser Leu Cys Val Lys Leu His
            180                 185                 190

Asn Thr Ser Phe Cys Leu Cys Leu Glu Gly Tyr Tyr Tyr Asn Ser Ser
            195                 200                 205

Thr Cys Lys Lys Gly Lys Val Phe Pro Gly Lys Ile Ser Val Thr Val
            210                 215                 220

Ser Glu Thr Phe Asp Pro Glu Glu Lys His Ser Met Ala Tyr Gln Asp
225                 230                 235                 240

Leu His Ser Glu Ile Thr Ser Leu Phe Lys Asp Val Phe Gly Thr Ser
                245                 250                 255

Val Tyr Gly Gln Thr Val Ile Leu Thr Val Ser Thr Ser Leu Ser Pro
                260                 265                 270

Arg Ser Glu Met Arg Ala Asp Asp Lys Phe Val Asn Val Thr Ile Val
                275                 280                 285

Thr Ile Leu Ala Glu Thr Thr Ser Asp Asn Glu Lys Thr Val Thr Glu
290                 295                 300

Lys Ile Asn Lys Ala Ile Arg Ser Ser Ser Asn Phe Leu Asn Tyr
305                 310                 315                 320

Asp Leu Thr Leu Arg Cys Asp Tyr Tyr Gly Cys Asn Gln Thr Ala Asp
                325                 330                 335

Asp Cys Leu Asn Gly Leu Ala Cys Asp Cys Lys Ser Asp Leu Gln Arg
                340                 345                 350

Pro Asn Pro Gln Ser Pro Phe Cys Val Ala Ser Ser Leu Lys Cys Pro
                355                 360                 365

Asp Ala Cys Asn Ala Gln His Lys Gln Cys Leu Ile Lys Lys Ser Gly
                370                 375                 380

Gly Ala Pro Glu Cys Ala Cys Val Pro Gly Tyr Gln Glu Asp Ala Asn
385                 390                 395                 400

Gly Asn Cys Gln Lys Cys Ala Phe Gly Tyr Ser Gly Leu Asp Cys Lys
                405                 410                 415

Asp Lys Phe Gln Leu Ile Leu Thr Ile Val Gly Thr Ile Ala Gly Ile
                420                 425                 430

Val Ile Leu Ser Met Ile Ile Ala Leu Ile Val Thr Ala Arg Ser Asn
                435                 440                 445

Asn Lys Thr Lys His Ile Glu Glu Asn Leu Ile Asp Glu Asp Phe
                450                 455                 460

Gln Asn Leu Lys Leu Arg Ser Thr Gly Phe Thr Asn Leu Gly Ala Glu
465                 470                 475                 480

Gly Ser Val Phe Pro Lys Val Arg Ile Thr Ala Ser Arg Asp Ser Gln
                485                 490                 495

Met Gln Asn Pro Tyr Ser Arg His Ser Ser Met Pro Arg Pro Asp Tyr
                500                 505                 510

<210> SEQ ID NO 191
<211> LENGTH: 2169
<212> TYPE: PRT
<213> ORGANISM: Homo sapiens

<400> SEQUENCE: 191

Met Lys Gly Ala Arg Trp Arg Arg Val Pro Trp Val Ser Leu Ser Cys
1               5                   10                  15
```

```
Leu Cys Leu Cys Leu Leu Pro His Val Val Pro Gly Thr Glu Asp
            20                  25                  30
Thr Leu Ile Thr Gly Ser Lys Thr Ala Ala Pro Val Thr Ser Thr Gly
            35                  40                  45
Ser Thr Thr Ala Thr Leu Glu Gly Gln Ser Thr Ala Ala Ser Ser Arg
    50                  55                  60
Thr Ser Asn Gln Asp Ile Ser Ala Ser Ser Gln Asn His Gln Thr Lys
65                  70                  75                  80
Ser Thr Glu Thr Thr Ser Lys Ala Gln Thr Asp Thr Leu Thr Gln Met
                85                  90                  95
Met Thr Ser Thr Leu Phe Ser Ser Pro Ser Val His Asn Val Met Glu
                100                 105                 110
Thr Val Thr Gln Glu Thr Ala Pro Pro Asp Glu Met Thr Thr Ser Phe
        115                 120                 125
Pro Ser Ser Val Thr Asn Thr Leu Met Met Thr Ser Lys Thr Ile Thr
        130                 135                 140
Met Thr Thr Ser Thr Asp Ser Thr Leu Gly Asn Thr Glu Glu Thr Ser
145                 150                 155                 160
Thr Ala Gly Thr Glu Ser Ser Thr Pro Val Thr Ser Ala Val Ser Ile
                165                 170                 175
Thr Ala Gly Gln Glu Gly Gln Ser Arg Thr Thr Ser Trp Arg Thr Ser
                180                 185                 190
Ile Gln Asp Thr Ser Ala Ser Ser Gln Asn His Trp Thr Arg Ser Thr
                195                 200                 205
Gln Thr Thr Arg Glu Ser Gln Thr Ser Thr Leu Thr His Arg Thr Thr
        210                 215                 220
Ser Thr Pro Ser Phe Ser Pro Ser Val His Asn Val Thr Gly Thr Val
225                 230                 235                 240
Ser Gln Lys Thr Ser Pro Ser Gly Glu Thr Ala Thr Ser Ser Leu Cys
                245                 250                 255
Ser Val Thr Asn Thr Ser Met Met Thr Ser Glu Lys Ile Thr Val Thr
                260                 265                 270
Thr Ser Thr Gly Ser Thr Leu Gly Asn Pro Gly Glu Thr Ser Ser Val
        275                 280                 285
Pro Val Thr Gly Ser Leu Met Pro Val Thr Ser Ala Ala Leu Val Thr
        290                 295                 300
Val Asp Pro Glu Gly Gln Ser Pro Ala Thr Phe Ser Arg Thr Ser Thr
305                 310                 315                 320
Gln Asp Thr Thr Ala Phe Ser Lys Asn His Gln Thr Gln Ser Val Glu
                325                 330                 335
Thr Thr Arg Val Ser Gln Ile Asn Thr Leu Asn Thr Leu Thr Pro Val
        340                 345                 350
Thr Thr Ser Thr Val Leu Ser Ser Pro Ser Gly Phe Asn Pro Ser Gly
        355                 360                 365
Thr Val Ser Gln Glu Thr Phe Pro Ser Gly Thr Thr Ile Ser Ser
        370                 375                 380
Pro Ser Ser Val Ser Asn Thr Phe Leu Val Thr Ser Lys Val Phe Arg
385                 390                 395                 400
Met Pro Ile Ser Arg Asp Ser Thr Leu Gly Asn Thr Glu Glu Thr Ser
                405                 410                 415
Leu Ser Val Ser Gly Thr Ile Ser Ala Ile Thr Ser Lys Val Ser Thr
                420                 425                 430
Ile Trp Trp Ser Asp Thr Leu Ser Thr Ala Leu Ser Pro Ser Ser Leu
```

-continued

```
                435                 440                 445
Pro Pro Lys Ile Ser Thr Ala Phe His Thr Gln Gln Ser Glu Gly Ala
450                 455                 460

Glu Thr Thr Gly Arg Pro His Glu Arg Ser Ser Phe Ser Pro Gly Val
465                 470                 475                 480

Ser Gln Glu Ile Phe Thr Leu His Glu Thr Thr Thr Trp Pro Ser Ser
                485                 490                 495

Phe Ser Ser Lys Gly His Thr Thr Trp Ser Gln Thr Glu Leu Pro Ser
            500                 505                 510

Thr Ser Thr Gly Ala Ala Thr Arg Leu Val Thr Gly Asn Pro Ser Thr
            515                 520                 525

Arg Ala Ala Gly Thr Ile Pro Arg Val Pro Ser Lys Val Ser Ala Ile
            530                 535                 540

Gly Glu Pro Gly Glu Pro Thr Thr Tyr Ser Ser His Ser Thr Thr Leu
545                 550                 555                 560

Pro Lys Thr Thr Gly Ala Gly Ala Gln Thr Gln Trp Thr Gln Glu Thr
                565                 570                 575

Gly Thr Thr Gly Glu Ala Leu Leu Ser Ser Pro Ser Tyr Ser Val Ile
            580                 585                 590

Gln Met Ile Lys Thr Ala Thr Ser Pro Ser Ser Pro Met Leu Asp
            595                 600                 605

Arg His Thr Ser Gln Gln Ile Thr Thr Ala Pro Ser Thr Asn His Ser
            610                 615                 620

Thr Ile His Ser Thr Ser Thr Ser Pro Gln Glu Ser Pro Ala Val Ser
625                 630                 635                 640

Gln Arg Gly His Thr Arg Ala Pro Gln Thr Thr Gln Glu Ser Gln Thr
                645                 650                 655

Thr Arg Ser Val Ser Pro Met Thr Asp Thr Lys Thr Val Thr Thr Pro
            660                 665                 670

Gly Ser Ser Phe Thr Ala Ser Gly His Ser Pro Ser Glu Ile Val Pro
            675                 680                 685

Gln Asp Ala Pro Thr Ile Ser Ala Ala Thr Thr Phe Ala Pro Ala Pro
690                 695                 700

Thr Gly Asn Gly His Thr Thr Gln Ala Pro Thr Thr Ala Leu Gln Ala
705                 710                 715                 720

Ala Pro Ser Ser His Asp Ala Thr Leu Gly Pro Ser Gly Gly Thr Ser
                725                 730                 735

Leu Ser Lys Thr Gly Ala Leu Thr Leu Ala Asn Ser Val Val Ser Thr
            740                 745                 750

Pro Gly Gly Pro Glu Gly Gln Trp Thr Ser Ala Ser Ala Ser Thr Ser
            755                 760                 765

Pro Asp Thr Ala Ala Ala Met Thr His Thr His Gln Ala Glu Ser Thr
770                 775                 780

Glu Ala Ser Gly Gln Thr Gln Thr Ser Glu Pro Ala Ser Ser Gly Ser
785                 790                 795                 800

Arg Thr Thr Ser Ala Gly Thr Ala Thr Pro Ser Ser Ser Gly Ala Ser
                805                 810                 815

Gly Thr Thr Pro Ser Gly Ser Glu Gly Ile Ser Thr Ser Gly Glu Thr
            820                 825                 830

Thr Arg Phe Ser Ser Asn Pro Ser Arg Asp Ser His Thr Thr Gln Ser
            835                 840                 845

Thr Thr Glu Leu Leu Ser Ala Ser Ala Ser His Gly Ala Ile Pro Val
850                 855                 860
```

```
Ser Thr Gly Met Ala Ser Ser Ile Val Pro Gly Thr Phe His Pro Thr
865                 870                 875                 880

Leu Ser Glu Ala Ser Thr Ala Gly Arg Pro Thr Gly Gln Ser Ser Pro
            885                 890                 895

Thr Ser Pro Ser Ala Ser Pro Gln Glu Thr Ala Ala Ile Ser Arg Met
        900                 905                 910

Ala Gln Thr Gln Arg Thr Gly Thr Ser Arg Gly Ser Asp Thr Ile Ser
            915                 920                 925

Leu Ala Ser Gln Ala Thr Asp Thr Phe Ser Val Pro Pro Thr Pro
930                 935                 940

Pro Ser Ile Thr Ser Ser Gly Leu Thr Ser Pro Gln Thr Gln Thr His
945                 950                 955                 960

Thr Leu Ser Pro Ser Gly Ser Gly Lys Thr Phe Thr Thr Ala Leu Ile
                965                 970                 975

Ser Asn Ala Thr Pro Leu Pro Val Thr Ser Thr Ser Ser Ala Ser Thr
            980                 985                 990

Gly His Ala Thr Pro Leu Ala Val Ser Ser Ala Thr Ser Ala Ser Thr
            995                 1000                1005

Val Ser Ser Asp Ser Pro Leu Lys Met Glu Thr Ser Gly Met Thr
1010                1015                1020

Thr Pro Ser Leu Lys Thr Asp Gly Gly Arg Arg Thr Ala Thr Ser
1025                1030                1035

Pro Pro Pro Thr Thr Ser Gln Thr Ile Ile Ser Thr Ile Pro Ser
1040                1045                1050

Thr Ala Met His Thr Arg Ser Thr Ala Ala Pro Ile Pro Ile Leu
1055                1060                1065

Pro Glu Arg Gly Val Ser Leu Phe Pro Tyr Gly Ala Gly Ala Gly
1070                1075                1080

Asp Leu Glu Phe Val Arg Arg Thr Val Asp Phe Thr Ser Pro Leu
1085                1090                1095

Phe Lys Pro Ala Thr Gly Phe Pro Leu Gly Ser Ser Leu Arg Asp
1100                1105                1110

Ser Leu Tyr Phe Thr Asp Asn Gly Gln Ile Ile Phe Pro Glu Ser
1115                1120                1125

Asp Tyr Gln Ile Phe Ser Tyr Pro Asn Pro Leu Pro Thr Gly Phe
1130                1135                1140

Thr Gly Arg Asp Pro Val Ala Leu Val Ala Pro Phe Trp Asp Asp
1145                1150                1155

Ala Asp Phe Ser Thr Gly Arg Gly Thr Thr Phe Tyr Gln Glu Tyr
1160                1165                1170

Glu Thr Phe Tyr Gly Glu His Ser Leu Leu Val Gln Gln Ala Glu
1175                1180                1185

Ser Trp Ile Arg Lys Met Thr Asn Asn Gly Gly Tyr Lys Ala Arg
1190                1195                1200

Trp Ala Leu Lys Val Thr Trp Val Asn Ala His Ala Tyr Pro Ala
1205                1210                1215

Gln Trp Thr Leu Gly Ser Asn Thr Tyr Gln Ala Ile Leu Ser Thr
1220                1225                1230

Asp Gly Ser Arg Ser Tyr Ala Leu Phe Leu Tyr Gln Ser Gly Gly
1235                1240                1245

Met Gln Trp Asp Val Ala Gln Arg Ser Gly Asn Pro Val Leu Met
1250                1255                1260
```

```
Gly Phe Ser Ser Gly Asp Gly Tyr Phe Glu Asn Ser Pro Leu Met
1265                 1270                1275

Ser Gln Pro Val Trp Glu Arg Tyr Arg Pro Asp Arg Phe Leu Asn
1280                 1285                1290

Ser Asn Ser Gly Leu Gln Gly Leu Gln Phe Tyr Arg Leu His Arg
1295                 1300                1305

Glu Glu Arg Pro Asn Tyr Arg Leu Glu Cys Leu Gln Trp Leu Lys
1310                 1315                1320

Ser Gln Pro Arg Trp Pro Ser Trp Gly Trp Asn Gln Val Ser Cys
1325                 1330                1335

Pro Cys Ser Trp Gln Gln Gly Arg Arg Asp Leu Arg Phe Gln Pro
1340                 1345                1350

Val Ser Ile Gly Arg Trp Gly Leu Gly Ser Arg Gln Leu Cys Ser
1355                 1360                1365

Phe Thr Ser Trp Arg Gly Gly Val Cys Cys Ser Tyr Gly Pro Trp
1370                 1375                1380

Gly Glu Phe Arg Glu Gly Trp His Val Gln Arg Pro Trp Gln Leu
1385                 1390                1395

Ala Gln Glu Leu Glu Pro Gln Ser Trp Cys Cys Arg Trp Asn Asp
1400                 1405                1410

Lys Pro Tyr Leu Cys Ala Leu Tyr Gln Gln Arg Arg Pro His Val
1415                 1420                1425

Gly Cys Ala Thr Tyr Arg Pro Pro Gln Pro Ala Trp Met Phe Gly
1430                 1435                1440

Asp Pro His Ile Thr Thr Leu Asp Gly Val Ser Tyr Thr Phe Asn
1445                 1450                1455

Gly Leu Gly Asp Phe Leu Leu Val Gly Ala Gln Asp Gly Asn Ser
1460                 1465                1470

Ser Phe Leu Leu Gln Gly Arg Thr Ala Gln Thr Gly Ser Ala Gln
1475                 1480                1485

Ala Thr Asn Phe Ile Ala Phe Ala Ala Gln Tyr Arg Ser Ser Ser
1490                 1495                1500

Leu Gly Pro Val Thr Val Gln Trp Leu Leu Glu Pro His Asp Ala
1505                 1510                1515

Ile Arg Val Leu Leu Asp Asn Gln Thr Val Thr Phe Gln Pro Asp
1520                 1525                1530

His Glu Asp Gly Gly Gly Gln Glu Thr Phe Asn Ala Thr Gly Val
1535                 1540                1545

Leu Leu Ser Arg Asn Gly Ser Glu Val Ser Ala Ser Phe Asp Gly
1550                 1555                1560

Trp Ala Thr Val Ser Val Ile Ala Leu Ser Asn Ile Leu His Ala
1565                 1570                1575

Ser Ala Ser Leu Pro Pro Glu Tyr Gln Asn Arg Thr Glu Gly Leu
1580                 1585                1590

Leu Gly Val Trp Asn Asn Asn Pro Glu Asp Asp Phe Arg Met Pro
1595                 1600                1605

Asn Gly Ser Thr Ile Pro Pro Gly Ser Pro Glu Glu Met Leu Phe
1610                 1615                1620

His Phe Gly Met Thr Trp Gln Ile Asn Gly Thr Gly Leu Leu Gly
1625                 1630                1635

Lys Arg Asn Asp Gln Leu Pro Ser Asn Phe Thr Pro Val Phe Tyr
1640                 1645                1650

Ser Gln Leu Gln Lys Asn Ser Ser Trp Ala Glu His Leu Ile Ser
```

```
            1655                1660                1665
Asn Cys Asp Gly Asp Ser Ser Cys Ile Tyr Asp Thr Leu Ala Leu
    1670                1675                1680

Arg Asn Ala Ser Ile Gly Leu His Thr Arg Glu Val Ser Lys Asn
    1685                1690                1695

Tyr Glu Gln Ala Asn Ala Thr Leu Asn Gln Tyr Pro Pro Ser Ile
    1700                1705                1710

Asn Gly Gly Arg Val Ile Glu Ala Tyr Lys Gly Gln Thr Thr Leu
    1715                1720                1725

Ile Gln Tyr Thr Ser Asn Ala Glu Asp Ala Asn Phe Thr Leu Arg
    1730                1735                1740

Asp Ser Cys Thr Asp Leu Glu Leu Phe Glu Asn Gly Thr Leu Leu
    1745                1750                1755

Trp Thr Pro Lys Ser Leu Glu Pro Phe Thr Leu Glu Ile Leu Ala
    1760                1765                1770

Arg Ser Ala Lys Ile Gly Leu Ala Ser Ala Leu Gln Pro Arg Thr
    1775                1780                1785

Val Val Cys His Cys Asn Ala Glu Ser Gln Cys Leu Tyr Asn Gln
    1790                1795                1800

Thr Ser Arg Val Gly Asn Ser Ser Leu Glu Val Ala Gly Cys Lys
    1805                1810                1815

Cys Asp Gly Gly Thr Phe Gly Arg Tyr Cys Glu Gly Ser Glu Asp
    1820                1825                1830

Ala Cys Glu Glu Pro Cys Phe Pro Ser Val His Cys Val Pro Gly
    1835                1840                1845

Lys Gly Cys Glu Ala Cys Pro Pro Asn Leu Thr Gly Asp Gly Arg
    1850                1855                1860

His Cys Ala Ala Leu Gly Ser Ser Phe Leu Cys Gln Asn Gln Ser
    1865                1870                1875

Cys Pro Val Asn Tyr Cys Tyr Asn Gln Gly His Cys Tyr Ile Ser
    1880                1885                1890

Gln Thr Leu Gly Cys Gln Pro Met Cys Thr Cys Pro Pro Ala Phe
    1895                1900                1905

Thr Asp Ser Arg Cys Phe Leu Ala Gly Asn Asn Phe Ser Pro Thr
    1910                1915                1920

Val Asn Leu Glu Leu Pro Leu Arg Val Ile Gln Leu Leu Leu Ser
    1925                1930                1935

Glu Glu Glu Asn Ala Ser Met Ala Glu Val Asn Ala Ser Val Ala
    1940                1945                1950

Tyr Arg Leu Gly Thr Leu Asp Met Arg Ala Phe Leu Arg Asn Ser
    1955                1960                1965

Gln Val Glu Arg Ile Asp Ser Ala Ala Pro Ala Ser Gly Ser Pro
    1970                1975                1980

Ile Gln His Trp Met Val Ile Ser Glu Phe Gln Tyr Arg Pro Arg
    1985                1990                1995

Gly Pro Val Ile Asp Phe Leu Asn Asn Gln Leu Leu Ala Ala Val
    2000                2005                2010

Val Glu Ala Phe Leu Tyr His Val Pro Arg Arg Ser Glu Glu Pro
    2015                2020                2025

Arg Asn Asp Val Val Phe Gln Pro Ile Ser Gly Glu Asp Val Arg
    2030                2035                2040

Asp Val Thr Ala Leu Asn Val Ser Thr Leu Lys Ala Tyr Phe Arg
    2045                2050                2055
```

```
Cys Asp Gly Tyr Lys Gly Tyr Asp Leu Val Tyr Ser Pro Gln Ser
    2060                2065                2070

Gly Phe Thr Cys Val Ser Pro Cys Ser Arg Gly Tyr Cys Asp His
    2075                2080                2085

Gly Gly Gln Cys Gln His Leu Pro Ser Gly Pro Arg Cys Ser Cys
    2090                2095                2100

Val Ser Phe Ser Ile Tyr Thr Ala Trp Gly Glu His Cys Glu His
    2105                2110                2115

Leu Ser Met Lys Leu Asp Ala Phe Phe Gly Ile Phe Phe Gly Ala
    2120                2125                2130

Leu Gly Gly Leu Leu Leu Gly Val Gly Thr Phe Val Val Leu
    2135                2140                2145

Arg Phe Trp Gly Cys Ser Gly Ala Arg Phe Ser Tyr Phe Leu Asn
    2150                2155                2160

Ser Ala Glu Ala Leu Pro
    2165

<210> SEQ ID NO 192
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
            20                  25                  30

Ala Val Ser Trp Val Arg Gln Pro Pro Gly Lys Ala Leu Glu Trp Ile
        35                  40                  45

Ala Ala Ile Ser Ser Gly Gly Thr Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser Ala
        115

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Phe Ser Leu Thr Ser Asn
1               5

<210> SEQ ID NO 194
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 194

Ser Ser Gly Gly Thr
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Tyr Tyr Cys Ala Arg Arg Tyr Gly
1               5

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asn Ile Tyr Asn Ser
            20                  25                  30

Leu Ala Trp Tyr Gln Gln Lys Pro Gly Lys Ala Pro Lys Val Leu Ile
        35                  40                  45

Phe Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Gly Tyr Thr
                85                  90                  95

Phe Gly Gln Gly Thr Lys Leu Glu Ile Lys Arg
            100                 105

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Lys Ala Ser Gln Asn Ile Tyr Asn Ser Leu Ala
1               5                   10

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198
```

Asn Ala Asn Ser Leu Gln Thr
1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Gln Phe Tyr Ser Gly Tyr Thr
1               5

<210> SEQ ID NO 200
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Thr Trp Thr Ser Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Gln Gly Gln Trp Leu Leu Pro Asp Ala Phe Asp Ile Trp Gly
            100                 105                 110

Gln Gly Thr Met Val Thr Val Ser Ser
        115                 120

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gly Ser Ile Ser Ser Tyr
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Tyr Tyr Thr Trp Thr

```
1               5

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asp Gln Gly Gln Trp Leu Leu Pro Asp Ala Phe Asp Ile
1               5                   10

<210> SEQ ID NO 204
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gln Gln Ser Pro Ile Thr Phe Gly Gln Gly Thr Arg Leu Glu Ile Lys
            100                 105                 110

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Ser Ser Gln Ser Leu Leu Arg Ser Asn Gly Tyr Asn Tyr Leu Asp
1               5                   10                  15

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Leu Gly Ser Asn Arg Ala Ser
1               5

<210> SEQ ID NO 207
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Met Gln Ala Gln Gln Ser Pro Ile Thr
1               5

<210> SEQ ID NO 208
<211> LENGTH: 646
<212> TYPE: PRT
<213> ORGANISM: Homo sapiens

<400> SEQUENCE: 208

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320
```

Gln Gly Leu Asp Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Gly Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Ser Glu Leu
        595                 600                 605

Val Val Glu Val Lys Ser Asp Lys Leu Pro Glu Glu Met Gly Leu Leu
    610                 615                 620

Gln Gly Ser Ser Gly Asp Lys Arg Ala Pro Gly Asp Gln Gly Glu Lys
625                 630                 635                 640

Tyr Ile Asp Leu Arg His
                645

<210> SEQ ID NO 209
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Ala Val Leu Ala Leu Leu Phe Cys Leu Val Thr Phe Pro Ser Cys
1               5                   10                  15

Ile Leu Ser Gln Val Gln Leu Lys Glu Ser Gly Pro Gly Leu Val Ala
            20                  25                  30

```
Pro Ser Gln Ser Leu Ser Ile Thr Cys Thr Val Ser Gly Phe Ser Leu
        35                  40                  45

Thr Gly Tyr Gly Ile Asn Trp Val Arg Gln Pro Pro Gly Lys Gly Leu
    50                  55                  60

Glu Trp Leu Gly Met Ile Trp Ser Asp Gly Ser Thr Asp Tyr Asn Ser
65                  70                  75                  80

Val Leu Thr Ser Arg Leu Arg Ile Ser Lys Asp Asn Ser Asn Ser Gln
                85                  90                  95

Val Phe Leu Lys Met Asn Ser Leu Gln Val Asp Asp Thr Ala Arg Tyr
            100                 105                 110

Tyr Cys Ala Arg Asp Arg Asn Tyr Tyr Asp Tyr Asp Gly Ala Met Asp
        115                 120                 125

Tyr Trp Gly Gln Gly Thr Ser Val Thr Val Ser Ser
    130                 135                 140

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Phe Ser Leu Thr Gly Tyr Gly Ile Asn
1               5                   10

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Met Ile Trp Ser Asp Gly Ser Thr Asp Tyr Asn Ser Val Leu Thr Ser
1               5                   10                  15

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Arg Asn Tyr Tyr Asp Tyr Asp Gly Ala Met Asp Tyr
1               5                   10

<210> SEQ ID NO 213
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Met Lys Phe Pro Ser Gln Leu Leu Leu Phe Leu Leu Phe Arg Ile Thr
1               5                   10                  15

Gly Ile Ile Cys Asp Ile Gln Val Thr Gln Ser Ser Ser Tyr Leu Ser
```

-continued

```
                    20                  25                  30
Val Ser Leu Gly Asp Arg Val Thr Ile Thr Cys Lys Ala Ser Asp His
                35                  40                  45

Ile Lys Asn Trp Leu Ala Trp Tyr Gln Gln Lys Pro Gly Ile Ala Pro
            50                  55                  60

Arg Leu Leu Val Ser Gly Ala Thr Ser Leu Glu Ala Gly Val Pro Ser
65                  70                  75                  80

Arg Phe Ser Gly Ser Gly Ser Gly Lys Asn Phe Thr Leu Ser Ile Thr
                85                  90                  95

Ser Leu Gln Thr Glu Asp Val Ala Thr Tyr Tyr Cys Gln Gln Tyr Trp
            100                 105                 110

Ser Thr Pro Trp Thr Phe Gly Gly Gly Thr Lys Leu Glu Ile Arg
            115                 120                 125
```

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

```
Lys Ala Ser Asp His Ile Lys Asn Trp Leu Ala
1               5                   10
```

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

```
Gly Ala Thr Ser Leu Glu Ala
1               5
```

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

```
Gln Gln Tyr Trp Ser Thr Pro Trp Thr
1               5
```

<210> SEQ ID NO 217
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 217

```
Val Gln Leu Val Glu Ser Gly Gly Gly Leu Val Lys Pro Ser Gln Thr
1               5                   10                  15

Leu Ser Leu Thr Cys Thr Val Ser Gly Phe Ser Leu Thr Ser Phe His
                20                  25                  30
```

Val Ser Trp Val Arg Gln Pro Pro Gly Lys Gly Leu Glu Trp Ile Ala
            35                  40                  45

Thr Ile Ser Ser Gly Gly Gly Thr Tyr Tyr Asn Pro Ser Leu Lys Ser
        50                  55                  60

Arg Val Thr Ile Ser Arg Asp Thr Ser Lys Asn Gln Val Ser Leu Lys
65                  70                  75                  80

Leu Ser Ser Val Thr Ala Ala Asp Thr Ala Val Tyr Tyr Cys Ala Arg
                85                  90                  95

Ile Ser Gly Trp Gly His Tyr Tyr Val Met Asp Val Trp Gly Gln Gly
            100                 105                 110

Thr Leu Val Thr Val Ser Ser
        115

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Phe Ser Leu Thr Ser Phe
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Ser Gly Gly Gly
1               5

<210> SEQ ID NO 220
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ile Ser Gly Trp Gly His Tyr Tyr Val Met Asp Val
1               5                   10

<210> SEQ ID NO 221
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Gly
            20                  25                  30

Leu Ala Trp Tyr Gln Gln Lys Pro Gly Lys Ser Pro Lys Leu Leu Ile
        35                  40                  45

```
Tyr Gly Ala Gly Ser Leu Gln Asp Gly Val Pro Ser Arg Phe Ser Gly
        50                  55                  60

Ser Gly Ser Gly Thr His Tyr Thr Leu Thr Ile Ser Ser Leu Gln Pro
 65                  70                  75                  80

Glu Asp Phe Ala Thr Tyr Phe Cys Gln Gln Gly Leu Lys Phe Pro Leu
                85                  90                  95

Thr Phe Gly Gln Gly Thr Lys Val Glu Ile Lys Arg Thr
            100                 105

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Ala Ser Glu Asp Ile Tyr Ser Gly Leu Ala
 1               5                  10

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Ala Gly Ser Leu Gln Asp
 1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln Gln Gly Leu Lys Phe Pro Leu Thr
 1               5

<210> SEQ ID NO 225
<211> LENGTH: 662
<212> TYPE: PRT
<213> ORGANISM: Homo sapiens

<400> SEQUENCE: 225

Met Arg Pro Gln Ile Leu Leu Leu Leu Ala Leu Leu Thr Leu Gly Leu
 1               5                  10                  15

Ala Ala Gln His Gln Asp Lys Val Pro Cys Lys Met Val Asp Lys Lys
                20                  25                  30

Val Ser Cys Gln Val Leu Gly Leu Leu Gln Val Pro Ser Val Leu Pro
            35                  40                  45

Pro Asp Thr Glu Thr Leu Asp Leu Ser Gly Asn Gln Leu Arg Ser Ile
        50                  55                  60

Leu Ala Ser Pro Leu Gly Phe Tyr Thr Ala Leu Arg His Leu Asp Leu
 65                  70                  75                  80

Ser Thr Asn Glu Ile Ser Phe Leu Gln Pro Gly Ala Phe Gln Ala Leu
```

```
                    85                  90                  95
Thr His Leu Glu His Leu Ser Leu Ala His Asn Arg Leu Ala Met Ala
                100                 105                 110

Thr Ala Leu Ser Ala Gly Gly Leu Gly Pro Leu Pro Arg Val Thr Ser
                115                 120                 125

Leu Asp Leu Ser Gly Asn Ser Leu Tyr Ser Gly Leu Leu Glu Arg Leu
    130                 135                 140

Leu Gly Glu Ala Pro Ser Leu His Thr Leu Ser Leu Ala Glu Asn Ser
145                 150                 155                 160

Leu Thr Arg Leu Thr Arg His Thr Phe Arg Asp Met Pro Ala Leu Glu
                165                 170                 175

Gln Leu Asp Leu His Ser Asn Val Leu Met Asp Ile Glu Asp Gly Ala
                180                 185                 190

Phe Glu Gly Leu Pro Arg Leu Thr His Leu Asn Leu Ser Arg Asn Ser
                195                 200                 205

Leu Thr Cys Ile Ser Asp Phe Ser Leu Gln Gln Leu Arg Val Leu Asp
    210                 215                 220

Leu Ser Cys Asn Ser Ile Glu Ala Phe Gln Thr Ala Ser Gln Pro Gln
225                 230                 235                 240

Ala Glu Phe Gln Leu Thr Trp Leu Asp Leu Arg Glu Asn Lys Leu Leu
                245                 250                 255

His Phe Pro Asp Leu Ala Ala Leu Pro Arg Leu Ile Tyr Leu Asn Leu
                260                 265                 270

Ser Asn Asn Leu Ile Arg Leu Pro Thr Gly Pro Pro Gln Asp Ser Lys
    275                 280                 285

Gly Ile His Ala Pro Ser Glu Gly Trp Ser Ala Leu Pro Leu Ser Ala
    290                 295                 300

Pro Ser Gly Asn Ala Ser Gly Arg Pro Leu Ser Gln Leu Leu Asn Leu
305                 310                 315                 320

Asp Leu Ser Tyr Asn Glu Ile Glu Leu Ile Pro Asp Ser Phe Leu Glu
                325                 330                 335

His Leu Thr Ser Leu Cys Phe Leu Asn Leu Ser Arg Asn Cys Leu Arg
                340                 345                 350

Thr Phe Glu Ala Arg Arg Leu Gly Ser Leu Pro Cys Leu Met Leu Leu
                355                 360                 365

Asp Leu Ser His Asn Ala Leu Glu Thr Leu Glu Leu Gly Ala Arg Ala
    370                 375                 380

Leu Gly Ser Leu Arg Thr Leu Leu Leu Gln Gly Asn Ala Leu Arg Asp
385                 390                 395                 400

Leu Pro Pro Tyr Thr Phe Ala Asn Leu Ala Ser Leu Gln Arg Leu Asn
                405                 410                 415

Leu Gln Gly Asn Arg Val Ser Pro Cys Gly Gly Pro Asp Glu Pro Gly
                420                 425                 430

Pro Ser Gly Cys Val Ala Phe Ser Gly Ile Thr Ser Leu Arg Ser Leu
                435                 440                 445

Ser Leu Val Asp Asn Glu Ile Glu Leu Leu Arg Ala Gly Ala Phe Leu
    450                 455                 460

His Thr Pro Leu Thr Glu Leu Asp Leu Ser Ser Asn Pro Gly Leu Glu
465                 470                 475                 480

Val Ala Thr Gly Ala Leu Gly Gly Leu Glu Ala Ser Leu Glu Val Leu
                485                 490                 495

Ala Leu Gln Gly Asn Gly Leu Met Val Leu Gln Val Asp Leu Pro Cys
                500                 505                 510
```

```
Phe Ile Cys Leu Lys Arg Leu Asn Leu Ala Glu Asn Arg Leu Ser His
            515                 520                 525
Leu Pro Ala Trp Thr Gln Ala Val Ser Leu Glu Val Leu Asp Leu Arg
        530                 535                 540
Asn Asn Ser Phe Ser Leu Leu Pro Gly Ser Ala Met Gly Gly Leu Glu
545                 550                 555                 560
Thr Ser Leu Arg Arg Leu Tyr Leu Gln Gly Asn Pro Leu Ser Cys Cys
                565                 570                 575
Gly Asn Gly Trp Leu Ala Ala Gln Leu His Gln Gly Arg Val Asp Val
            580                 585                 590
Asp Ala Thr Gln Asp Leu Ile Cys Arg Phe Ser Ser Gln Glu Glu Val
        595                 600                 605
Ser Leu Ser His Val Arg Pro Glu Asp Cys Leu Lys Gly Gly Leu Lys
    610                 615                 620
Asn Ile Asn Leu Ile Ile Ile Leu Thr Phe Ile Leu Val Ser Ala Ile
625                 630                 635                 640
Leu Leu Thr Thr Leu Ala Ala Cys Cys Cys Val Arg Arg Gln Lys Phe
                645                 650                 655
Asn Gln Gln Tyr Lys Ala
            660

<210> SEQ ID NO 226
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp His
            20                  25                  30
Ala Ile His Trp Val Arg Gln Ala Pro Gly Gln Arg Leu Glu Trp Met
        35                  40                  45
Gly Tyr Phe Ser Pro Gly Asn Asp Asp Phe Lys Tyr Ser Gln Lys Phe
    50                  55                  60
Gln Gly Arg Val Thr Ile Thr Ala Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Trp Ile Met Gln Tyr Trp Gly Gln Gly Thr Leu Val Thr
            100                 105                 110
Val Ser Ser
        115

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Tyr Thr Phe Thr Asp His Ala Ile His
1               5                   10
```

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Phe Ser Pro Gly Asn Asp Asp Phe Lys Tyr Ser Gln Lys Phe Gln
1               5                   10                  15

Gly

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Trp Ile Met Gln Tyr
1               5

<210> SEQ ID NO 230
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gln Gly Thr Lys Val Glu Ile
            100                 105                 110

Lys

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Lys Ser Ser Gln Ser Val Leu Tyr Ser Ser Asn Asn Lys Asn Tyr Leu
1               5                   10                  15

Ala

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Trp Ala Ser Thr Arg Glu Ser
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gln Gln Tyr Tyr Ser Tyr Pro Leu Thr
1               5

<210> SEQ ID NO 234
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Trp Ser Trp Trp Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Phe Asp Tyr Trp Gly Gln Gly Thr Thr Leu Thr Val
            100                 105                 110

Ser Ser

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Phe Ser Leu Thr Ser Tyr Gly
1               5

```
<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ile Trp Gly Asp Gly Ser Thr
1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Lys Gly Gly Tyr Phe Asp Tyr
1               5

<210> SEQ ID NO 238
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Ile Val Leu Thr Gln Ser Pro Ala Val Met Ser Ala Ser Pro Gly
1               5                   10                  15

Glu Lys Val Ala Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gly Gly Thr Lys Leu Glu Ile Lys
            100                 105

<210> SEQ ID NO 239
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Ser Val Ser Tyr
1               5

<210> SEQ ID NO 240
<211> LENGTH: 3
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 240

Ser Thr Ser
1

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gln Gln Arg Ser Ser Tyr Pro Trp Thr
1               5

<210> SEQ ID NO 242
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Met Asp Leu Met Cys Lys Lys Met Lys His Leu Trp Phe Phe Leu Leu
1               5                   10                  15

Leu Val Ala Ala Pro Arg Trp Val Leu Ser Gln Leu Gln Val Gln Glu
            20                  25                  30

Ser Gly Pro Gly Leu Val Lys Pro Ser Glu Thr Leu Ser Leu Ile Cys
        35                  40                  45

Thr Val Ser Gly Gly Ser Ile Arg Thr Ser Gly Tyr Tyr Trp Gly Trp
    50                  55                  60

Phe Arg Gln Pro Pro Gly Lys Gly Leu Glu Trp Ile Gly Thr Ser His
65                  70                  75                  80

Asn Ser Gly Ser Thr Tyr Tyr Asn Pro Ser Leu Lys Ser Arg Val Thr
                85                  90                  95

Ile Ser Val Asp Thr Ser Lys Asn Gln Phe Ser Leu Lys Leu Asn Ser
            100                 105                 110

Val Thr Ala Ala Asp Thr Ala Val Tyr Tyr Cys Ala Arg Gln Gly Tyr
        115                 120                 125

Asp Phe Lys Val Asn Ile Asp Val Trp Gly Gln Gly Thr Thr Val Thr
    130                 135                 140

Val Ser Ser Ala Ser
145

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Gly Ser Ile Arg Thr Ser Gly Tyr
1               5

<210> SEQ ID NO 244

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

His Asn Ser Gly Ser
1               5

<210> SEQ ID NO 245
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Gly Tyr Asp Phe Lys Val Asn Ile Asp Val
1               5                   10

<210> SEQ ID NO 246
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Leu Thr Phe Gly Gly Gly Thr Lys Val Glu Ile Lys Arg
        115                 120                 125

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Arg Ala Ser Gln Ser Val Ser Ser Tyr Leu Ala
1               5                   10

<210> SEQ ID NO 248
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 248

Asp Ala Ser Asn Arg Ala Thr
1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gln Arg Ser Asn Trp Pro Leu Thr
1               5

<210> SEQ ID NO 250
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
                20                  25                  30

Trp Met Asn Trp Val Arg Gln Ala Pro Gly Gln Gly Leu Glu Trp Ile
            35                  40                  45

Gly Arg Ile Tyr Pro Gly Asp Gly Glu Thr Asn Tyr Asn Gly Lys Phe
        50                  55                  60

Lys Asp Arg Val Ile Ala Asp Lys Ser Ser Ala Tyr Met Glu Leu Ser
65                  70                  75                  80

Ser Leu Arg Ser Glu Asp Thr Ala Val Tyr Tyr Cys Ala Arg Ile Tyr
                85                  90                  95

Gly Asn Val Tyr Phe Asp Val Trp Gly Gln Gly Thr Thr Val Thr Val
                100                 105                 110

Ser Ser

<210> SEQ ID NO 251
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gly Ser Trp Met Asn
1               5

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 252

Arg Ile Tyr Pro Gly Asp Gly Glu Thr Asn Tyr Asn Gly Lys Phe Lys
1               5                   10                  15

Asp

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ile Tyr Gly Asn Val Tyr Phe Asp Val
1               5

<210> SEQ ID NO 254
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Asp Ile Gln Leu Thr Gln Ser Pro Ser Phe Leu Ser Ala Ser Val Gly
1               5                   10                  15

Asp Arg Val Ile Cys Ser Ala Arg Ser Ser Ile Ser Phe Met Tyr Trp
            20                  25                  30

Tyr Gln Gln Lys Pro Gly Lys Ala Pro Lys Leu Leu Ile Tyr Asp Thr
        35                  40                  45

Ser Asn Leu Ala Ser Gly Val Pro Ser Arg Phe Ser Gly Ser Gly Ser
    50                  55                  60

Gly Thr Glu Phe Thr Leu Ile Ser Ser Leu Glu Ala Glu Asp Ala Ala
65                  70                  75                  80

Thr Tyr Tyr Cys Gln Gln Trp Ser Ser Tyr Pro Leu Thr Phe Gly Gln
                85                  90                  95

Gly Thr Lys Leu Glu Ile Lys
            100

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Ala Arg Ser Ser Ile Ser Phe Met Tyr
1               5                   10

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asp Thr Ser Asn Leu Ala Ser
1               5

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gln Gln Trp Ser Ser Tyr Pro Leu Thr
1               5

<210> SEQ ID NO 258
<211> LENGTH: 319
<212> TYPE: PRT
<213> ORGANISM: Homo sapiens

<400> SEQUENCE: 258

Met Val Gly Lys Met Trp Pro Val Leu Trp Thr Leu Cys Ala Val Arg
1               5                   10                  15

Val Thr Val Asp Ala Ile Ser Val Glu Thr Pro Gln Asp Val Leu Arg
                20                  25                  30

Ala Ser Gln Gly Lys Ser Val Thr Leu Pro Cys Thr Tyr His Thr Ser
            35                  40                  45

Thr Ser Ser Arg Glu Gly Leu Ile Gln Trp Asp Lys Leu Leu Leu Thr
        50                  55                  60

His Thr Glu Arg Val Val Ile Trp Pro Phe Ser Asn Lys Asn Tyr Ile
65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
        115                 120                 125

Thr Lys Ser Arg Val Arg Leu Leu Val Leu Val Pro Pro Ser Lys Pro
    130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
        195                 200                 205

Tyr Ile Cys Thr Ser Ser Asn Glu Glu Gly Thr Gln Phe Cys Asn Ile
    210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Gly Ile Ile Ile
                245                 250                 255

Tyr Cys Cys Cys Cys Arg Gly Lys Asp Asp Asn Thr Glu Asp Lys Glu
            260                 265                 270

Asp Ala Arg Pro Asn Arg Glu Ala Tyr Glu Glu Pro Pro Glu Gln Leu
        275                 280                 285

Arg Glu Leu Ser Arg Glu Arg Glu Glu Asp Asp Tyr Arg Gln Glu
            290                 295                 300

Glu Gln Arg Ser Thr Gly Arg Glu Ser Pro Asp His Leu Asp Gln
305                 310                 315

<210> SEQ ID NO 259
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Glu Val Gln Leu Val Glu Ser Gly Gly Asp Phe Val Gln Pro Gly Gly
1               5                   10                  15

Ser Leu Arg Val Ser Cys Ala Ala Ser Gly Phe Ala Phe Ser His Tyr
            20                  25                  30

Ala Met Ser Trp Val Arg Gln Ala Pro Gly Lys Gly Leu Glu Trp Val
        35                  40                  45

Ala Tyr Ile Ser Ser Gly Gly Ser Gly Thr Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Arg Ser Leu Arg Ala Glu Asp Ser Ala Val Tyr Phe Cys
                85                  90                  95

Thr Arg Val Lys Leu Gly Thr Tyr Tyr Phe Asp Ser Trp Gly Gln Gly
            100                 105                 110

Thr Leu Leu Thr Val Ser Ser
        115

<210> SEQ ID NO 260
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

His Tyr Ala Met Ser
1               5

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Tyr Ile Ser Ser Gly Gly Ser Gly Thr Tyr Tyr Ser Asp Ser Val Lys
1               5                   10                  15

Gly

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic

```
                             peptide

<400> SEQUENCE: 262

Val Lys Leu Gly Thr Tyr Tyr Phe Asp Ser
1               5                   10

<210> SEQ ID NO 263
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Asp Ile Gln Met Thr Gln Ser Pro Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Asp Lys Ala Pro Lys Leu Leu Ile
            35                  40                  45

Phe Tyr Ser Ser Asn Leu His Ser Gly Val Pro Ser Arg Phe Ser Gly
        50                  55                  60

Gly Gly Ser Gly Thr Asp Tyr Thr Leu Thr Ile Ser Ser Leu Gln Pro
65                  70                  75                  80

Glu Asp Ile Ala Thr Tyr Phe Cys His Gln Tyr Ser Lys Leu Pro Trp
                85                  90                  95

Thr Phe Gly Gln Gly Thr Lys Val Glu Ile Lys Arg
            100                 105

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Ala Ser Gln Asp Ile Ser Asn Tyr Leu Asn
1               5                   10

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Tyr Ser Ser Asn Leu His Ser
1               5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

His Gln Tyr Ser Lys Leu Pro Trp Thr
```

<210> SEQ ID NO 267
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Glu Trp Val
        35                  40                  45

Ala Tyr Ile Ser Ser Gly Gly Ser Ser Ile Asn Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95

Thr Arg Gly Gly Thr Gly Thr Arg Ser Leu Tyr Tyr Phe Asp Tyr Trp
            100                 105                 110

Gly Gln Gly Ala Thr Leu Ile Val Ser Ser
        115                 120

<210> SEQ ID NO 268
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asn Phe Gly Met His
1               5

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Tyr Ile Ser Ser Gly Gly Ser Ser Ile Asn Tyr Ala Asp Thr Val
1               5                   10                  15

<210> SEQ ID NO 270
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Gly Thr Gly Thr Arg Ser Leu Tyr Tyr Phe Asp Tyr
1               5                   10

<210> SEQ ID NO 271
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Lys Thr Leu Pro Tyr
                85                  90                  95

Thr Phe Gly Gly Gly Thr Lys Val Glu Ile Lys
            100                 105

<210> SEQ ID NO 272
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Arg Ala Ser Gln Asp Ile Gly Asn Phe Leu Asn
1               5                   10

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Tyr Thr Ser Arg Leu Gln Ser
1               5

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Gln Gly Lys Thr Leu Pro Tyr Thr
1               5

<210> SEQ ID NO 275
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Tyr Ile Tyr Pro Asn Asn Gly Gly Thr Gly Tyr Asn Gln Lys Phe
    50                  55                  60

Lys Ser Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Thr Tyr Gly His Tyr Tyr Gly Tyr Met Phe Ala Tyr Trp Gly Gln
            100                 105                 110

Gly Thr Leu Val Thr Val Ser Ala
        115                 120

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Asp Tyr Asn Met Asp
1               5

<210> SEQ ID NO 277
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Tyr Ile Tyr Pro Asn Asn Gly Gly Thr Gly Tyr Asn Gln Lys Phe Lys
1               5                   10                  15

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Tyr Gly His Tyr Tyr Gly Tyr Met Phe Ala Tyr
1               5                   10

<210> SEQ ID NO 279
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 279

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Ile Lys Arg
            100                 105

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ser Ala Ser Ser Ser Val Ser Tyr Met His
1               5                   10

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ser Thr Ser Asn Leu Ala Ser
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Gln Arg Ser Ser Tyr Pro Tyr Thr
1               5

<210> SEQ ID NO 283
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gln Val Gln Leu Gln Gln Ser Gly Ala Glu Leu Val Lys Pro Gly Ala

```
                1               5                   10                  15
Ser Val Arg Leu Ser Cys Lys Thr Ser Gly Tyr Thr Phe Thr Thr His
                20                  25                  30

Tyr Val Ser Trp Val Lys Gln Lys Pro Gly Gln Gly Leu Glu Trp Ile
                35                  40                  45

Gly Trp Ile Phe Gly Gly Ser Ala Arg Thr Asn Tyr Asn Gln Lys Phe
            50                  55                  60

Gln Gly Lys Ala Thr Leu Thr Val Asp Thr Ser Ser Thr Ala Tyr
65                  70                  75                  80

Met Asp Leu Arg Ser Leu Thr Ser Asp Ser Ala Val Tyr Phe Cys
                85                  90                  95

Val Arg Gln Val Gly Trp Asp Asp Ala Leu Asp Phe Trp Gly Gln Gly
                100                 105                 110

Thr Gln Val Thr Val Ser Ser
        115
```

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

```
Gln Val Gly Trp Asp Asp Ala Leu Asp Phe
1               5                   10
```

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

```
Trp Ile Phe Gly Gly Ser Ala Arg Thr Asn Tyr Asn Gln Lys Phe Gln
1               5                   10                  15

Gly
```

<210> SEQ ID NO 286
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

```
Thr His Tyr Val Ser
1               5
```

<210> SEQ ID NO 287
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

```
Asp Ile Val Met Thr Gln Ser Pro Ser Ser Leu Ala Val Ser Ala Gly
```

```
                1               5                  10                  15

Asp Thr Val Thr Ile Asn Cys Arg Ser Ser Gln Ser Leu Phe Ser Gly
                               20                  25                  30

Asn Tyr Asn Tyr Leu Ala Trp Tyr Gln Gln Lys Thr Gly Gln Thr Pro
            35                  40                  45

Lys Leu Leu Ile Ser Tyr Ala Ser Thr Arg His Thr Gly Val Pro Asp
        50                  55                  60

Arg Phe Val Gly Ser Gly Ser Gly Thr Asp Phe Ile Leu Thr Ile Tyr
65                  70                  75                  80

Asn Phe Gln Thr Glu Asp Leu Gly Asp Tyr Tyr Cys Gln Gln His Tyr
                    85                  90                  95

Ser Ser Pro Arg Thr Phe Gly Pro Gly Thr Lys Leu Lys Ile Lys
                100                 105                 110
```

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

```
Gln Gln His Tyr Ser Ser Pro Arg Thr
1               5
```

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

```
Tyr Ala Ser Thr Arg His Thr
1               5
```

<210> SEQ ID NO 290
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

```
Arg Ser Ser Gln Ser Leu Phe Ser Gly Asn Tyr Asn Tyr Leu Ala
1               5                   10                  15
```

<210> SEQ ID NO 291
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30
```

```
Trp Leu His Trp Val Arg Gln Ala Pro Gly Lys Gly Leu Glu Trp Val
            35                  40                  45

Gly Met Ile Asp Pro Ser Asn Ser Asp Thr Arg Phe Asn Pro Asn Phe
 50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala
        115                 120

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Tyr Thr Phe Thr Ser Tyr
 1               5

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asp Pro Ser Asn Ser Asp Thr Arg Phe Asn Pro
 1               5                  10

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Tyr Arg Ser Tyr Val Thr Pro Leu Asp Tyr
 1               5                  10

<210> SEQ ID NO 295
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Asp Ile Gln Met Thr Gln Ser Pro Ser Ser Leu Ser Ala Ser Val Gly
 1               5                  10                  15

Asp Arg Val Thr Ile Thr Cys Lys Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45
```

Ala Pro Lys Leu Leu Ile Tyr Trp Ala Ser Thr Arg Glu Ser Gly Val
            50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg

<210> SEQ ID NO 296
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gln Ser Leu Leu Tyr Thr Ser Ser Gln Lys Asn Tyr Leu Ala
1               5                   10

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Trp Ala Ser Thr Arg Glu Ser
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gln Gln Tyr Tyr Ala Tyr Pro Trp Thr
1               5

<210> SEQ ID NO 299
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Arg Val Asn Pro Asn Arg Arg Gly Thr Thr Tyr Asn Gln Lys Phe
        50                  55                  60

Glu Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Ala Asn Trp Leu Asp Tyr Trp Gly Gln Gly Thr Thr Val Thr
        100                 105                 110

Val Ser Ser Ala
        115

<210> SEQ ID NO 300
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Tyr Thr Phe Thr Asp Tyr
1               5

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asn Pro Asn Arg Arg Gly
1               5

<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ala Asn Trp Leu Asp Tyr
1               5

<210> SEQ ID NO 303
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
            20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln

```
                    65                  70                  75                  80
Pro Glu Asp Phe Ala Thr Tyr Tyr Cys Gln Val Tyr Ser Gly Tyr Pro
                85                  90                  95
Leu Thr Phe Gly Gly Gly Thr Lys Val Glu Ile Lys Arg
            100                 105
```

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

```
Ser Ser Val Ser Ser Ile Tyr Leu His
1               5
```

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

```
Ser Thr Ser Asn Leu Ala Ser
1               5
```

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

```
Gln Val Tyr Ser Gly Tyr Pro Leu Thr
1               5
```

<210> SEQ ID NO 307
<211> LENGTH: 1390
<212> TYPE: PRT
<213> ORGANISM: Homo sapiens

<400> SEQUENCE: 307

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110
```

```
Lys Asp Asn Ile Asn Met Ala Leu Val Val Asp Thr Tyr Asp Asp
            115                 120                 125
Gln Leu Ile Ser Cys Gly Ser Val Asn Arg Gly Thr Cys Gln Arg His
        130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                165                 170                 175
Val Ser Ala Leu Gly Ala Lys Val Leu Ser Ser Val Lys Asp Arg Phe
                180                 185                 190
Ile Asn Phe Phe Val Gly Asn Thr Ile Asn Ser Ser Tyr Phe Pro Asp
            195                 200                 205
His Pro Leu His Ser Ile Ser Val Arg Arg Leu Lys Glu Thr Lys Asp
210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
                260                 265                 270
Thr Phe His Thr Arg Ile Ile Arg Phe Cys Ser Ile Asn Ser Gly Leu
        275                 280                 285
His Ser Tyr Met Glu Met Pro Leu Glu Cys Ile Leu Thr Glu Lys Arg
        290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
        370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
        450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
            515                 520                 525
Cys Leu Ser Ala Pro Pro Phe Val Gln Cys Gly Trp Cys His Asp Lys
```

```
            530                 535                 540
Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                    565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                    645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                    725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
        770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                    805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                    885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
        930                 935                 940

Leu Leu Leu Leu Leu Gly Phe Phe Leu Trp Leu Lys Lys Arg Lys Gln
945                 950                 955                 960
```

-continued

```
Ile Lys Asp Leu Gly Ser Glu Leu Val Arg Tyr Asp Ala Arg Val His
            965                 970                 975
Thr Pro His Leu Asp Arg Leu Val Ser Ala Arg Ser Val Ser Pro Thr
            980                 985                 990
Thr Glu Met Val Ser Asn Glu Ser Val Asp Tyr Arg Ala Thr Phe Pro
            995                1000                1005
Glu Asp Gln Phe Pro Asn Ser Ser Gln Asn Gly Ser Cys Arg Gln
       1010                1015                1020
Val Gln Tyr Pro Leu Thr Asp Met Ser Pro Ile Leu Thr Ser Gly
       1025                1030                1035
Asp Ser Asp Ile Ser Ser Pro Leu Leu Gln Asn Thr Val His Ile
       1040                1045                1050
Asp Leu Ser Ala Leu Asn Pro Glu Leu Val Gln Ala Val Gln His
       1055                1060                1065
Val Val Ile Gly Pro Ser Ser Leu Ile Val His Phe Asn Glu Val
       1070                1075                1080
Ile Gly Arg Gly His Phe Gly Cys Val Tyr His Gly Thr Leu Leu
       1085                1090                1095
Asp Asn Asp Gly Lys Lys Ile His Cys Ala Val Lys Ser Leu Asn
       1100                1105                1110
Arg Ile Thr Asp Ile Gly Glu Val Ser Gln Phe Leu Thr Glu Gly
       1115                1120                1125
Ile Ile Met Lys Asp Phe Ser His Pro Asn Val Leu Ser Leu Leu
       1130                1135                1140
Gly Ile Cys Leu Arg Ser Glu Gly Ser Pro Leu Val Val Leu Pro
       1145                1150                1155
Tyr Met Lys His Gly Asp Leu Arg Asn Phe Ile Arg Asn Glu Thr
       1160                1165                1170
His Asn Pro Thr Val Lys Asp Leu Ile Gly Phe Gly Leu Gln Val
       1175                1180                1185
Ala Lys Gly Met Lys Tyr Leu Ala Ser Lys Lys Phe Val His Arg
       1190                1195                1200
Asp Leu Ala Ala Arg Asn Cys Met Leu Asp Glu Lys Phe Thr Val
       1205                1210                1215
Lys Val Ala Asp Phe Gly Leu Ala Arg Asp Met Tyr Asp Lys Glu
       1220                1225                1230
Tyr Tyr Ser Val His Asn Lys Thr Gly Ala Lys Leu Pro Val Lys
       1235                1240                1245
Trp Met Ala Leu Glu Ser Leu Gln Thr Gln Lys Phe Thr Thr Lys
       1250                1255                1260
Ser Asp Val Trp Ser Phe Gly Val Leu Leu Trp Glu Leu Met Thr
       1265                1270                1275
Arg Gly Ala Pro Pro Tyr Pro Asp Val Asn Thr Phe Asp Ile Thr
       1280                1285                1290
Val Tyr Leu Leu Gln Gly Arg Arg Leu Leu Gln Pro Glu Tyr Cys
       1295                1300                1305
Pro Asp Pro Leu Tyr Glu Val Met Leu Lys Cys Trp His Pro Lys
       1310                1315                1320
Ala Glu Met Arg Pro Ser Phe Ser Glu Leu Val Ser Arg Ile Ser
       1325                1330                1335
Ala Ile Phe Ser Thr Phe Ile Gly Glu His Tyr Val His Val Asn
       1340                1345                1350
```

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385            1390

<210> SEQ ID NO 308
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Tyr Glu Asp Phe Asp Ser Trp Gly Gln Gly Thr
            100                 105                 110

Thr Val Thr Val Ser Ser Ala
        115

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Tyr Thr Phe Thr Gly Tyr
1               5

<210> SEQ ID NO 310
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Tyr Pro Gly Ser Gly Asn
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

Gly Gly Tyr Tyr Glu Asp Phe Asp Ser
1               5

<210> SEQ ID NO 312
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gly Gln Tyr Ala Asn Tyr Pro Tyr
                85                  90                  95

Thr Phe Gly Gln Gly Thr Lys Leu Glu Ile Lys Arg
            100                 105

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gln Gly Ile Ile Ser Tyr Leu Ala
1               5

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ala Ala Ser Ser Leu Gln Ser
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Gln Tyr Ala Asn Tyr Pro Tyr Thr

<210> SEQ ID NO 316
<211> LENGTH: 983
<212> TYPE: PRT
<213> ORGANISM: Homo sapiens

<400> SEQUENCE: 316

```
Met Asp Cys Gln Leu Ser Ile Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
                35                  40                  45

Ser His Gly Trp Glu Glu Ile Ser Gly Val Asp Glu His Tyr Thr Pro
        50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125

Asp Asp His Gly Val Lys Phe Arg Glu His Gln Phe Thr Lys Ile Asp
    130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
    210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
        275                 280                 285

Lys Cys Pro Pro His Ser Ser Thr Gln Glu Asp Gly Ser Met Asn Cys
    290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
                325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
        355                 360                 365
```

```
Asn Ile Lys Gln Cys Glu Pro Cys Ser Pro Asn Val Arg Phe Leu Pro
370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
            405                 410                 415

Glu Leu Ser Ser Pro Pro Arg Gln Phe Ala Ala Val Ser Ile Thr Thr
            420                 425                 430

Asn Gln Ala Ala Pro Ser Pro Val Leu Thr Ile Lys Lys Asp Arg Thr
                435                 440                 445

Ser Arg Asn Ser Ile Ser Leu Ser Trp Gln Glu Pro Glu His Pro Asn
450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
            485                 490                 495

Ser Ser Leu Lys Pro Asp Thr Ile Tyr Val Phe Gln Ile Arg Ala Arg
                500                 505                 510

Thr Ala Ala Gly Tyr Gly Thr Asn Ser Arg Lys Phe Glu Phe Glu Thr
            515                 520                 525

Ser Pro Asp Ser Phe Ser Ile Ser Gly Glu Ser Ser Gln Val Val Met
530                 535                 540

Ile Ala Ile Ser Ala Ala Val Ala Ile Ile Leu Leu Thr Val Val Ile
545                 550                 555                 560

Tyr Val Leu Ile Gly Arg Phe Cys Gly Tyr Lys Ser Lys His Gly Ala
                565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Thr Gln Ala
            595                 600                 605

Val His Glu Phe Ala Lys Glu Leu Asp Ala Thr Asn Ile Ser Ile Asp
                610                 615                 620

Lys Val Val Gly Ala Gly Glu Phe Gly Glu Val Cys Ser Gly Arg Leu
625                 630                 635                 640

Lys Leu Pro Ser Lys Lys Glu Ile Ser Val Ala Ile Lys Thr Leu Lys
                645                 650                 655

Val Gly Tyr Thr Glu Lys Gln Arg Arg Asp Phe Leu Gly Glu Ala Ser
            660                 665                 670

Ile Met Gly Gln Phe Asp His Pro Asn Ile Ile Arg Leu Glu Gly Val
            675                 680                 685

Val Thr Lys Ser Lys Pro Val Met Ile Val Thr Glu Tyr Met Glu Asn
690                 695                 700

Gly Ser Leu Asp Ser Phe Leu Arg Lys His Asp Ala Gln Phe Thr Val
705                 710                 715                 720

Ile Gln Leu Val Gly Met Leu Arg Gly Ile Ala Ser Gly Met Lys Tyr
                725                 730                 735

Leu Ser Asp Met Gly Tyr Val His Arg Asp Leu Ala Ala Arg Asn Ile
            740                 745                 750

Leu Ile Asn Ser Asn Leu Val Cys Lys Val Ser Asp Phe Gly Leu Ser
                755                 760                 765

Arg Val Leu Glu Asp Asp Pro Glu Ala Ala Tyr Thr Thr Arg Gly Gly
770                 775                 780

Lys Ile Pro Ile Arg Trp Thr Ser Pro Glu Ala Ile Ala Tyr Arg Lys
```

```
                785                 790                 795                 800
Phe Thr Ser Ala Ser Asp Val Trp Ser Tyr Gly Ile Val Leu Trp Glu
                805                 810                 815

Val Met Ser Tyr Gly Glu Arg Pro Tyr Trp Glu Met Ser Asn Gln Asp
            820                 825                 830

Val Ile Lys Ala Val Asp Gly Tyr Arg Leu Pro Pro Met Asp
            835                 840                 845

Cys Pro Ala Ala Leu Tyr Gln Leu Met Leu Asp Cys Trp Gln Lys Asp
            850                 855                 860

Arg Asn Asn Arg Pro Lys Phe Glu Gln Ile Val Ser Ile Leu Asp Lys
865                 870                 875                 880

Leu Ile Arg Asn Pro Gly Ser Leu Lys Ile Ile Thr Ser Ala Ala Ala
                885                 890                 895

Arg Pro Ser Asn Leu Leu Leu Asp Gln Ser Asn Val Asp Ile Thr Thr
            900                 905                 910

Phe Arg Thr Thr Gly Asp Trp Leu Asn Gly Val Trp Thr Ala His Cys
            915                 920                 925

Lys Glu Ile Phe Thr Gly Val Glu Tyr Ser Ser Cys Asp Thr Ile Ala
        930                 935                 940

Lys Ile Ser Thr Asp Asp Met Lys Lys Val Gly Val Thr Val Val Gly
945                 950                 955                 960

Pro Gln Lys Lys Ile Ile Ser Ser Ile Lys Ala Leu Glu Thr Gln Ser
                965                 970                 975

Lys Asn Gly Pro Val Pro Val
            980

<210> SEQ ID NO 317
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Glu Val Gln Leu Val Gln Ser Gly Ala Glu Val Lys Met Pro Gly Ala
1               5                   10                  15

Ser Val Lys Leu Ser Cys Arg Val Ser Gly Asp Thr Phe Thr Ala Tyr
            20                  25                  30

Phe Ile His Trp Val Arg Gln Ala Pro Gly Gln Gly Leu Glu Trp Met
        35                  40                  45

Gly Trp Phe Asn Pro Ile Ser Gly Thr Ala Gly Ser Ala Glu Lys Phe
    50                  55                  60

Arg Gly Arg Val Ala Met Thr Arg Asp Thr Ser Ile Ser Thr Ala Tyr
65                  70                  75                  80

Met Glu Leu Asn Arg Leu Thr Phe Asp Asp Thr Ala Val Tyr Tyr Cys
                85                  90                  95

Ala Arg Gln His Arg Gly Asn Thr Phe Asp Pro Trp Gly Gln Gly Thr
            100                 105                 110

Leu Val Thr Val Ser Ser
        115

<210> SEQ ID NO 318
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 318

Asp Thr Phe Thr Ala Tyr Phe Ile His
1               5

<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Trp Phe Asn Pro Ile Ser Gly Thr Ala Gly Ser Ala Glu Lys Phe Arg
1               5                   10                  15

Gly

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln His Arg Gly Asn Thr Phe Asp Pro
1               5

<210> SEQ ID NO 321
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Ser Ala Leu Thr Gln Pro Ala Ser Val Ser Gly Ser Pro Gly Gln Ser
1               5                   10                  15

Ile Thr Ile Ser Cys Thr Gly Thr Ser Ser Asp Ile Gly Ala Tyr Lys
            20                  25                  30

Tyr Val Ser Trp Tyr Gln Gln His Pro Gly Lys Ala Pro Lys Leu Val
        35                  40                  45

Ile Tyr Glu Val Ser Asn Arg Pro Ser Gly Val Ser Ser Arg Phe Ser
    50                  55                  60

Gly Ser Lys Ser Gly Gln Thr Ala Ser Leu Thr Ile Ser Gly Leu Gln
65                  70                  75                  80

Ala Asp Asp Glu Ala Asp Tyr Tyr Cys Asn Ser Tyr Gln Gly Tyr Asn
                85                  90                  95

Thr Trp Val Phe Gly Gly Gly Thr Lys Val Thr Val Leu Gly
            100                 105                 110

<210> SEQ ID NO 322
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Thr Gly Thr Ser Ser Asp Ile Gly Ala Tyr Lys Tyr Val Ser
1               5                   10

<210> SEQ ID NO 323
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Glu Val Ser Asn Arg Pro Ser
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ser Tyr Gln Gly Tyr Asn Thr Trp Val
1               5

<210> SEQ ID NO 325
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Leu Gly Val Ala Ala Ala Ser Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 326
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 326

Gly Asp Ser Val Ser Ser Asn Ser Ala Ala
1               5                   10

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Thr Tyr Tyr Arg Ser Lys Trp Tyr Asn
1               5

<210> SEQ ID NO 328
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ala Arg Asp Leu Gly Val Ala Ala Ala Asp Ser Tyr Tyr Tyr Tyr Gly
1               5                   10                  15

Met Asp Val Trp
            20

<210> SEQ ID NO 329
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Gln Pro Val Leu Thr Gln Pro Pro Ser Ala Ser Ala Thr Pro Gly Gln
1               5                   10                  15

Arg Val Thr Ile Ser Cys Ser Gly Ser Ser Ser Asn Ile Gly Ser Asn
                20                  25                  30

Thr Leu Asp Trp Phe Gln Gln Leu Pro Gly Thr Ala Pro Lys Leu Leu
            35                  40                  45

Ile Phe Asp Thr Asn Arg Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ala Glu Asp Glu Ala Val Tyr Phe Cys Ala Thr Trp Asp Asn Ser Leu
                85                  90                  95

Asn Gly Ala Val Phe Gly Gly Gly Thr Lys Leu Ser Val Pro
            100                 105                 110

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330
```

Ser Ser Asn Ile Gly Ser Asn Thr
1               5

<210> SEQ ID NO 331
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asp Thr Asn
1

<210> SEQ ID NO 332
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ala Thr Trp Asp Asn Ser Leu Asn Gly Ala Val Phe
1               5                   10

<210> SEQ ID NO 333
<211> LENGTH: 468
<212> TYPE: PRT
<213> ORGANISM: Homo sapiens

<400> SEQUENCE: 333

Met Ala Pro Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala Ala
                20                  25                  30

Thr Pro Ser Lys Val Trp Gly Ser Ala Gly Arg Ile Glu Pro Arg
            35                  40                  45

Gly Gly Gly Arg Gly Ala Leu Pro Thr Ser Met Gly Gln His Gly Pro
50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
                100                 105                 110

Leu His Asp Gln Ser Ile Gly Thr Gln Gln Trp Glu His Ser Pro Leu
            115                 120                 125

Gly Glu Leu Cys Pro Pro Gly Ser His Arg Ser Glu His Pro Gly Ala
        130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Arg Gly Cys Pro Arg Gly Met Val Lys Val Lys Asp Cys Thr Pro Trp

```
                210                 215                 220
Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
                260                 265                 270

Lys Cys Met Asp Arg Val Cys Phe Trp Arg Leu Gly Leu Leu Arg Gly
                275                 280                 285

Pro Gly Ala Glu Asp Asn Ala His Asn Glu Ile Leu Ser Asn Ala Asp
                290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Arg Leu Leu
                340                 345                 350

Val Pro Ala Asn Gly Ala Asp Pro Thr Glu Thr Leu Met Leu Phe Phe
                355                 360                 365

Asp Lys Phe Ala Asn Ile Val Pro Phe Asp Ser Trp Asp Gln Leu Met
                370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
                420                 425                 430

Glu Arg Met Glu Arg His Ala Arg Glu Lys Ile Gln Asp Leu Leu
                435                 440                 445

Val Asp Ser Gly Lys Phe Ile Tyr Leu Glu Asp Gly Thr Gly Ser Ala
                450                 455                 460

Val Ser Leu Glu
465

<210> SEQ ID NO 334
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Gly Ile Thr Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Asp Pro Gly Thr Thr Val Ile Met Ser Trp Phe Asp Pro Trp
            100                 105                 110

Gly Gln Gly Thr Leu Val Thr Val Ser Ser
        115                 120

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gly Phe Thr Phe Ser Ser Tyr
1               5

<210> SEQ ID NO 336
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Thr Gly Ser Gly Gly Ser
1               5

<210> SEQ ID NO 337
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asp Pro Gly Thr Thr Val Ile Met Ser Trp Phe Asp Pro
1               5                   10

<210> SEQ ID NO 338
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys
            100                 105
```

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gln Ser Val Arg Gly Arg Tyr Leu Ala
1               5

<210> SEQ ID NO 340
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Ala Ser Ser Arg Ala Thr
1               5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gln Gln Tyr Gly Ser Ser Pro Arg Thr
1               5

<210> SEQ ID NO 342
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Asp Trp Val
        35                  40                  45

Thr Val Ile Ser Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Gly Pro Glu Asp Thr Ala Val Tyr Tyr Cys
                85                  90                  95

Ala Lys Ser Leu Ser Gly Thr Tyr Trp Gly Tyr Gly Met Asp Val Trp
            100                 105                 110

Gly Gln Gly Thr Thr Val Thr Val Ser
        115                 120

```
<210> SEQ ID NO 343
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gly Phe Thr Phe Ser Gly Tyr Gly
1               5

<210> SEQ ID NO 344
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ile Ser Tyr Asp Gly Ser Asn Lys
1               5

<210> SEQ ID NO 345
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Cys Ala Lys Ser Leu Ser Gly Thr Tyr Trp Gly Tyr Gly Met Asp Val
1               5                   10                  15

<210> SEQ ID NO 346
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Asp Asp Phe Ala Thr Tyr Tyr Cys Gln Gln Tyr Asn Arg Tyr Ser Trp
                85                  90                  95

Thr Phe Gly Gln Gly Thr Lys Val Glu Ile Lys
            100                 105

<210> SEQ ID NO 347
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 347

Gln Asn Ile Ser Ser Trp
1               5

<210> SEQ ID NO 348
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Lys Ala Ser
1

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gln Gln Tyr Asn Arg Tyr Ser Trp Thr
1               5

<210> SEQ ID NO 350
<211> LENGTH: 317
<212> TYPE: PRT
<213> ORGANISM: Homo sapiens

<400> SEQUENCE: 350

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
                20                  25                  30

Pro Pro Pro Pro Ala Pro His Gln Pro Pro Ala Ala Ser Arg Ser Met
            35                  40                  45

Phe Val Ala Leu Leu Gly Leu Gly Leu Gly Gln Val Val Cys Ser Val
        50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

-continued

Trp Ala Lys Ile Ser Asn Met Thr Phe Ser Asn Gly Lys Leu Ile Val
            195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
    275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315

<210> SEQ ID NO 351
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Ser Ala
        115                 120

<210> SEQ ID NO 352
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Tyr Thr Phe Thr Asn Tyr
1               5

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asn Pro Asn Thr Gly Glu Pro Thr Phe Asp Asp
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ser Arg Gly Lys Asn Glu Ala Trp Phe Ala Tyr
1               5                   10

<210> SEQ ID NO 355
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
            100                 105                 110

Arg

<210> SEQ ID NO 356
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gln Ser Leu Val His Arg Asn Gly Asn Thr Tyr Leu His
1               5                   10

<210> SEQ ID NO 357
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Thr Val Ser Asn Arg Phe Ser
1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ser Gln Ser Ser His Val Pro Pro Thr
1               5

<210> SEQ ID NO 359
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Glu Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ile Arg Ala Tyr Gly Ser Gly Ser Tyr Ser Arg Tyr Tyr
                100                 105                 110

Tyr Tyr Gly Met Asp Val Trp Gly Gln Gly Thr Thr Val Thr Val Ser
            115                 120                 125

Ser

<210> SEQ ID NO 360
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Tyr Thr Phe Thr Ser Tyr Gly Ile Ser
1               5                   10

<210> SEQ ID NO 361
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 361

Trp Ile Ser Ala Tyr Asn Gly Asn Thr Asn Tyr Ala Gln Lys Leu Gln
1               5                   10                  15

<210> SEQ ID NO 362
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Asp Ile Arg Ala Tyr Gly Ser Gly Ser Tyr Ser Arg Tyr Tyr Tyr Tyr
1               5                   10                  15

Gly Met Asp Val
            20

<210> SEQ ID NO 363
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Leu Glu Ile Val Leu Thr Gln Ser Pro Ala Thr Leu Ser Val Ser Pro
1               5                   10                  15

Gly Glu Arg Ala Thr Leu Ser Cys Arg Ala Ser Gln Asn Ile Gly Ser
            20                  25                  30

Ile Leu Ala Trp Tyr Gln His Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Asp Asp Phe Ala Val Tyr Tyr Cys Gln Gln Tyr Leu Tyr Trp Pro
                85                  90                  95

Phe Thr Phe Gly Gly Gly Thr Lys Val Glu Ile Lys
            100                 105

<210> SEQ ID NO 364
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Arg Ala Ser Gln Asn Ile Gly Ser Ile Leu Ala
1               5                   10

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365
```

Gly Ala Ser Thr Arg Ala Thr
1               5

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gln Gln Tyr Leu Tyr Trp Pro Phe Thr
1               5

<210> SEQ ID NO 367
<211> LENGTH: 296
<212> TYPE: PRT
<213> ORGANISM: Homo sapiens

<400> SEQUENCE: 367

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Val Leu Thr Lys Cys Gln Glu Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285

Gln Asp Leu Gly Pro Val Pro Met
    290                 295

<210> SEQ ID NO 368
<211> LENGTH: 160
<212> TYPE: PRT
<213> ORGANISM: Homo sapiens

<400> SEQUENCE: 368

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Ser His Trp Asn Trp Arg Thr Arg Leu Leu Gly Trp Val
145                 150                 155                 160

<210> SEQ ID NO 369
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Glu Val Gln Leu Gln Gln Ser Gly Pro Glu Leu Val Lys Pro Gly Ala
1               5                   10                  15

Ser Met Lys Ile Ser Cys Lys Ser Ser Gly Tyr Ser Phe Thr Arg Tyr
            20                  25                  30

Thr Met Asn Trp Val Lys Gln Ser His Gly Lys Asn Leu Glu Trp Ile
        35                  40                  45

Gly Val Ile Asn Pro Tyr Asn Gly Gly Thr Val Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Thr Asp Tyr Asp Gly Tyr Ala Met Asp Tyr Trp Gly Gln Gly
            100                 105                 110

Thr Ser Val Thr Val Ser Ser Ala Lys Thr
        115                 120

<210> SEQ ID NO 370

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Tyr Ser Phe Thr Arg Tyr Thr Met Asn
1               5                   10

<210> SEQ ID NO 371
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Val Ile Asn Pro Tyr Asn Gly Gly Thr Val Tyr Asn Gln Lys Phe Lys
1               5                   10                  15

Gly

<210> SEQ ID NO 372
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Thr Asp Tyr Asp Gly Tyr Ala Met Asp Tyr
1               5                   10

<210> SEQ ID NO 373
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Asp Val Gln Ile Thr Gln Ser Pro Ser Tyr Leu Ala Ala Ser Pro Gly
1               5                   10                  15

Glu Thr Ile Thr Ile Asn Cys Arg Ala Thr Lys Ser Ile Ser Lys Tyr
            20                  25                  30

Leu Ala Trp Tyr Gln Glu Gln Pro Gly Lys Thr Asn Asn Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Ser Gly Thr Lys Leu Glu Ile Lys
            100                 105

<210> SEQ ID NO 374
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 374

Arg Ala Thr Lys Ser Ile Ser Lys Tyr Leu Ala
1               5                   10

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ser Gly Ser Thr Leu Gln Ser
1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gln Gln His Asn Glu Tyr Pro Tyr Thr
1               5

<210> SEQ ID NO 377
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Glu Val Gln Leu Gln Gln Ser Gly Pro Glu Leu Val Lys Pro Gly Ala
1               5                   10                  15

Ser Met Arg Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Val Tyr Asn Pro Tyr Asn Gly Gly Thr Val Tyr Asn Gln Lys Phe
    50                  55                  60

Lys Gly Lys Ala Thr Leu Thr Val Asp Lys Ser Ser Thr Thr Tyr
65                  70                  75                  80

Met Glu Leu Leu Ser Leu Thr Ser Glu Asp Ser Ala Val Tyr Tyr Cys
                85                  90                  95

Ala Arg Thr Asp Ser Gly Gly Tyr Ala Met Asp Cys Trp Gly Gln Gly
            100                 105                 110

Thr Ser Val Thr Val Ser Ser Ala Lys Thr
        115                 120

<210> SEQ ID NO 378
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 378

Gly Tyr Ser Phe Thr Gly Tyr Thr Met Asn
1               5                   10

<210> SEQ ID NO 379
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Val Tyr Asn Pro Tyr Asn Gly Gly Thr Val Tyr Asn Gln Lys Phe Lys
1               5                   10                  15

Gly

<210> SEQ ID NO 380
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Thr Asp Ser Gly Gly Tyr Ala Met Asp Cys
1               5                   10

<210> SEQ ID NO 381
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Asp Val Gln Ile Thr Gln Ser Pro Ser Tyr Leu Asp Ala Ser Pro Gly
1               5                   10                  15

Glu Thr Ile Thr Ile Asn Cys Arg Ala Ser Lys Thr Ile Ser Lys Tyr
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Ser Gly Thr Lys Leu Glu Ile Lys
            100                 105

<210> SEQ ID NO 382
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

```
Arg Ala Ser Lys Thr Ile Ser Lys Tyr Leu Ala
1               5                   10

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ser Gly Ser Thr Leu Gln Ser
1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gln Gln His Asn Glu Tyr Pro Tyr Thr
1               5

<210> SEQ ID NO 385
<211> LENGTH: 661
<212> TYPE: PRT
<213> ORGANISM: Homo sapiens

<400> SEQUENCE: 385

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
                20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
        50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205
```

```
Ile Thr Asp Gln Val Pro Phe Ser Val Ser Val Ser Gln Leu Arg Ala
210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
            245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser Ser His Trp Leu Arg Leu
```

```
                625                 630                 635                 640
Pro Arg Ile Phe Cys Ser Cys Pro Ile Gly Glu Asn Ser Pro Leu Leu
                    645                 650                 655

Ser Gly Gln Gln Val
            660

<210> SEQ ID NO 386
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gly Gly Gly Gly Ser Gly Gly Gly Gly Ser Gly Gly Gly Gly Ser Gly
1               5                   10                  15

Gly Gly Gly Ser
            20

<210> SEQ ID NO 387
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Tyr Ser Met Asn
1               5

<210> SEQ ID NO 388
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
        115                 120

<210> SEQ ID NO 389
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 389

Ala Arg Gly Ala Pro Ile Gly Ala Ala Ala Gly Trp Phe Asp Pro
1               5                   10                  15

<210> SEQ ID NO 390
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gly Ala Pro Ile Gly Ala Ala Ala Gly Trp Phe Asp Pro
1               5                   10

<210> SEQ ID NO 391
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Gln Gly Ala Ala Ala Gly Trp Phe Asp Pro Trp
            100                 105                 110

Gly Gln Gly Thr Leu Val Thr Val Ser Ser
        115                 120

<210> SEQ ID NO 392
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Arg Gly Ala Pro Gln Gly Ala Ala Ala Gly Trp Phe Asp Pro
1               5                   10                  15

<210> SEQ ID NO 393
<211> LENGTH: 13
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 393

Gly Ala Pro Gln Gly Ala Ala Ala Gly Trp Phe Asp Pro
1               5                   10

<210> SEQ ID NO 394
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Leu Gly Ala Ala Ala Gly Trp Phe Asp Pro Trp
            100                 105                 110

Gly Gln Gly Thr Leu Val Thr Val Ser Ser
        115                 120

<210> SEQ ID NO 395
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Ala Arg Gly Ala Pro Leu Gly Ala Ala Ala Gly Trp Phe Asp Pro
1               5                   10                  15

<210> SEQ ID NO 396
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gly Ala Pro Leu Gly Ala Ala Ala Gly Trp Phe Asp Pro
1               5                   10

<210> SEQ ID NO 397
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
        115                 120
```

<210> SEQ ID NO 398
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 398

```
Ala Arg Gly Ala Pro Phe Gly Ala Ala Ala Gly Trp Phe Asp Pro
1               5                   10                  15
```

<210> SEQ ID NO 399
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 399

```
Gly Ala Pro Phe Gly Ala Ala Ala Gly Trp Phe Asp Pro
1               5                   10
```

<210> SEQ ID NO 400
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 400

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

-continued

Leu Gln Met Asn Ser Leu Arg Ala Glu Asp Thr Ala Val Tyr Tyr Cys
                85                  90                  95

Ala Arg Gly Ala Pro Val Gly Ala Ala Gly Trp Phe Asp Pro Trp
            100                 105                 110

Gly Gln Gly Thr Leu Val Thr Val Ser Ser
        115                 120

<210> SEQ ID NO 401
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Ala Arg Gly Ala Pro Val Gly Ala Ala Gly Trp Phe Asp Pro
1               5                   10                  15

<210> SEQ ID NO 402
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gly Ala Pro Val Gly Ala Ala Ala Gly Trp Phe Asp Pro
1               5                   10

<210> SEQ ID NO 403
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (102)..(102)
<223> OTHER INFORMATION: Met, Leu, Ile, Val, Gln or Phe

<400> SEQUENCE: 403

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Xaa Gly Ala Ala Ala Gly Trp Phe Asp Pro Trp
            100                 105                 110

Gly Gln Gly Thr Leu Val Thr Val Ser Ser
        115                 120

<210> SEQ ID NO 404

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Met, Leu, Ile, Val, Gln or Phe

<400> SEQUENCE: 404

Ala Arg Gly Ala Pro Xaa Gly Ala Ala Ala Gly Trp Phe Asp Pro
1               5                   10                  15

<210> SEQ ID NO 405
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Met, Leu, Ile, Val, Gln or Phe

<400> SEQUENCE: 405

Gly Ala Pro Xaa Gly Ala Ala Ala Gly Trp Phe Asp Pro
1               5                   10

<210> SEQ ID NO 406
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Asp Pro Ser Asn Ser Asp
1               5

<210> SEQ ID NO 407
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Lys Ser Ser Gln Ser Leu Leu Tyr Thr Ser Ser Gln Lys Asn Tyr Leu
1               5                   10                  15

Ala

<210> SEQ ID NO 408
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Asp Thr Gly Glu Tyr Tyr Asp Thr Asp Asp His Gly Met Asp Val
1               5                   10                  15
```

```
<210> SEQ ID NO 409
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Ser Tyr Ala Met Ser
1               5

<210> SEQ ID NO 410
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ser Val Ser Ser Ser Val Ser Ser Ile Tyr Leu His
1               5                  10

<210> SEQ ID NO 411
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Asp Gly Gly Tyr Tyr Asp Ser Gly Ala Gly Asp Tyr
1               5                  10

<210> SEQ ID NO 412
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Ala Pro Met Gly Ala Ala Ala Gly Trp Phe Asp Pro
1               5                  10

<210> SEQ ID NO 413
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45

Gly Trp Ile Lys Pro Asn Asn Gly Leu Ala Asn Tyr Ala Gln Lys Phe
    50                  55                  60

Gln Gly Arg Val Thr Met Thr Arg Asp Thr Ser Ile Ser Thr Ala Tyr
```

```
                65                  70                  75                  80
Met Glu Leu Ser Arg Leu Arg Ser Asp Asp Thr Ala Val Tyr Tyr Cys
                    85                  90                  95

Ala Arg Ser Glu Ile Thr Thr Glu Phe Asp Tyr Trp Gly Gln Gly Thr
            100                 105                 110

Leu Val Thr Val Ser Ser
        115
```

```
<210> SEQ ID NO 414
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Gly Tyr Ile Phe Thr Ala Tyr
1               5

<210> SEQ ID NO 415
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Lys Pro Asn Asn Gly Leu
1               5

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Ser Glu Ile Thr Thr Glu Phe Asp Tyr
1               5

<210> SEQ ID NO 417
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80
```

Ser Leu Gln Ala Glu Asp Val Ala Val Tyr Tyr Cys Gln Gln Ser Lys
            85                  90                  95

Glu Asp Pro Leu Thr Phe Gly Gly Gly Thr Lys Val Glu Ile Lys
        100                 105                 110

<210> SEQ ID NO 418
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Lys Ser Ser Glu Ser Val Asp Ser Tyr Ala Asn Ser Phe Leu His
1               5                   10                  15

<210> SEQ ID NO 419
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Arg Ala Ser Thr Arg Glu Ser
1               5

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gln Gln Ser Lys Glu Asp Pro Leu Thr
1               5

<210> SEQ ID NO 421
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Ser Tyr Tyr Met His
1               5

<210> SEQ ID NO 422
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Glu Gly Ala Gly Phe Ala Tyr Gly Met Asp Tyr Tyr Met Asp Val
1               5                   10                  15

<210> SEQ ID NO 423
<211> LENGTH: 451

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 423

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 424
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 425
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Tyr Thr Phe Thr Ser Tyr
             20                  25                  30
Trp Leu His Trp Val Arg Gln Ala Pro Gly Lys Gly Leu Glu Trp Val
         35                  40                  45
Gly Met Ile Asp Pro Ser Asn Ser Asp Thr Arg Phe Asn Pro Asn Phe
 50                  55                  60
Lys Asp Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
             85                  90                  95
Ala Thr Tyr Arg Ser Tyr Val Thr Pro Leu Asp Tyr Trp Gly Gln Gly
             100                 105                 110
Thr Leu Val Thr Val Ser Ser Ala Ser Thr Lys Gly Pro Ser Val Phe
         115                 120                 125
Pro Leu Ala Pro Ser Ser Lys Ser Thr Ser Gly Gly Thr Ala Ala Leu
 130                 135                 140
Gly Cys Leu Val Lys Asp Tyr Phe Pro Glu Pro Val Thr Val Ser Trp
 145                 150                 155                 160
Asn Ser Gly Ala Leu Thr Ser Gly Val His Thr Phe Pro Ala Val Leu
             165                 170                 175
Gln Ser Ser Gly Leu Tyr Ser Leu Ser Ser Val Val Thr Val Pro Ser
             180                 185                 190
Ser Ser Leu Gly Thr Gln Thr Tyr Ile Cys Asn Val Asn His Lys Pro
         195                 200                 205
Ser Asn Thr Lys Val Asp Lys Lys Val Glu Pro Lys Ser Cys Asp Lys
 210                 215                 220
Thr His Thr Cys Pro Pro Cys Pro Ala Pro Glu Leu Leu Gly Gly Pro
 225                 230                 235                 240
Ser Val Phe Leu Phe Pro Pro Lys Pro Lys Asp Thr Leu Met Ile Ser
             245                 250                 255
Arg Thr Pro Glu Val Thr Cys Val Val Val Asp Val Ser His Glu Asp
             260                 265                 270
Pro Glu Val Lys Phe Asn Trp Tyr Val Asp Gly Val Glu Val His Asn
         275                 280                 285
Ala Lys Thr Lys Pro Arg Glu Glu Gln Tyr Asn Ser Thr Tyr Arg Val
 290                 295                 300
Val Ser Val Leu Thr Val Leu His Gln Asp Trp Leu Asn Gly Lys Glu
 305                 310                 315                 320
Tyr Lys Cys Lys Val Ser Asn Lys Ala Leu Pro Ala Pro Ile Glu Lys
             325                 330                 335
Thr Ile Ser Lys Ala Lys Gly Gln Pro Arg Glu Pro Gln Val Tyr Thr
             340                 345                 350
Leu Pro Pro Ser Arg Asp Glu Leu Thr Lys Asn Gln Val Ser Leu Thr
         355                 360                 365
Cys Leu Val Lys Gly Phe Tyr Pro Ser Asp Ile Ala Val Glu Trp Glu
 370                 375                 380
Ser Asn Gly Gln Pro Glu Asn Asn Tyr Lys Thr Thr Pro Pro Val Leu
 385                 390                 395                 400
Asp Ser Asp Gly Ser Phe Leu Leu Tyr Ser Lys Leu Thr Val Asp Lys
             405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 426
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 427
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Thr Thr Tyr Asn Gln Lys Phe
 50                  55                  60

Glu Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Leu Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 428
<211> LENGTH: 215
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 428

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Ser Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 429
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 429

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45

Gly Trp Ile Lys Pro Asn Asn Gly Leu Ala Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr

```
                100                 105                 110
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Leu Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 430
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Asp Ile Val Met Thr Gln Ser Pro Asp Ser Leu Ala Val Ser Leu Gly
1               5                   10                  15
```

-continued

```
Glu Arg Ala Thr Ile Asn Cys Lys Ser Ser Glu Ser Val Asp Ser Tyr
             20                  25                  30

Ala Asn Ser Phe Leu His Trp Tyr Gln Gln Lys Pro Gly Gln Pro Pro
         35                  40                  45

Lys Leu Leu Ile Tyr Arg Ala Ser Thr Arg Glu Ser Gly Val Pro Asp
     50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                 85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 431
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

```
Ser Tyr Ala Ile Ser
1               5
```

<210> SEQ ID NO 432
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

```
Gly Asp Ser Ser Ile Arg His Ala Tyr Tyr Tyr Gly Met Asp Val
1               5                   10                  15
```

<210> SEQ ID NO 433
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

```
Ser Ser Ser Tyr Tyr Trp Gly
```

```
<210> SEQ ID NO 434
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Gly Ser Asp Arg Phe His Pro Tyr Phe Asp Tyr
1               5                   10

<210> SEQ ID NO 435
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Ser Tyr Tyr Met His
1               5

<210> SEQ ID NO 436
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Gly Ala Pro Asn Tyr Gly Asp Thr Thr His Asp Tyr Tyr Tyr Met Asp
1               5                   10                  15

Val

<210> SEQ ID NO 437
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gly Tyr Tyr Met His
1               5
```